United States Patent
Kim et al.

(10) Patent No.: US 11,690,287 B2
(45) Date of Patent: Jun. 27, 2023

(54) ORGANIC LIGHT-EMITTING DEVICE AND DISPLAY APPARATUS INCLUDING THE SAME

(71) Applicant: Samsung Display Co., Ltd., Yongin-si (KR)

(72) Inventors: Kyungsik Kim, Yongin-si (KR); Seulong Kim, Yongin-si (KR); Sungsoo Bae, Yongin-si (KR); Dongchan Lee, Yongin-si (KR); Jaeweon Hur, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 585 days.

(21) Appl. No.: 16/444,485

(22) Filed: Jun. 18, 2019

(65) Prior Publication Data
US 2020/0203621 A1    Jun. 25, 2020

(30) Foreign Application Priority Data
Dec. 19, 2018    (KR) .................. 10-2018-0165469

(51) Int. Cl.
*H01L 51/00* (2006.01)
*C07D 209/86* (2006.01)
(Continued)

(52) U.S. Cl.
CPC ........ *H01L 51/0067* (2013.01); *C07D 209/86* (2013.01); *C07D 401/14* (2013.01);
(Continued)

(58) Field of Classification Search
CPC ............ H01L 51/0067; H01L 27/3248; H01L 51/0061; H01L 51/0072; H01L 51/008;
(Continued)

(56) References Cited

U.S. PATENT DOCUMENTS

| 9,905,779 B2 | 2/2018 | Ogiwara et al. |
| 11,043,638 B2 | 6/2021 | Ogiwara et al. |

(Continued)

FOREIGN PATENT DOCUMENTS

| EP | 2 402 351 A1 | 1/2012 |
| JP | 2015-144224 A | 8/2015 |

(Continued)

OTHER PUBLICATIONS

Partial English Translation of relevant parts of JP 2018-125504 A dated Aug. 9, 2018, listed above.

(Continued)

*Primary Examiner* — Alexander C Kollias
(74) *Attorney, Agent, or Firm* — Lewis Roca Rothgerber Christie LLP

(57) ABSTRACT

An organic light-emitting device includes a first electrode; a second electrode; and an organic layer between the first electrode and the second electrode. The organic layer includes an emission layer. The emission layer includes a first compound, a second compound, and a third compound. The first compound is represented by Formula 1, the second compound is represented by Formula 2, the third compound is represented by Formula 3, and the first compound and the second compound are different from each other.

$$(Y_{11})_{c11}\text{——}(L_{11})_{a11}\text{——}(Y_{12})_{c12}$$    Formula 1

$$(Y_{21})_{c21}\text{——}(L_{21})_{a21}\text{——}(Y_{22})_{c22}$$    Formula 2

(Continued)

Formula 3

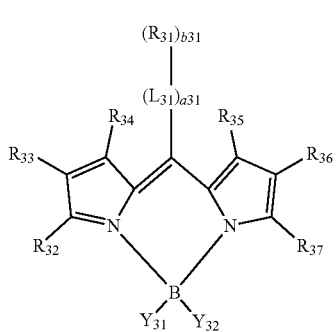

21 Claims, 2 Drawing Sheets

(51) Int. Cl.
  *C07D 401/14* (2006.01)
  *C07D 403/10* (2006.01)
  *C07D 403/14* (2006.01)
  *C07D 487/04* (2006.01)
  *C07F 5/02* (2006.01)
  *C09K 11/06* (2006.01)
  *H01L 27/32* (2006.01)
  *H01L 51/50* (2006.01)

(52) U.S. Cl.
  CPC ......... *C07D 403/10* (2013.01); *C07D 403/14* (2013.01); *C07D 487/04* (2013.01); *C07F 5/022* (2013.01); *C09K 11/06* (2013.01); *H01L 27/3248* (2013.01); *H01L 51/008* (2013.01); *H01L 51/0061* (2013.01); *H01L 51/0072* (2013.01); *C09K 2211/1018* (2013.01); *H01L 51/5012* (2013.01); *H01L 51/5056* (2013.01)

(58) Field of Classification Search
  CPC ............. H01L 51/5012; H01L 51/5056; H01L 2251/5384; H01L 51/5024; H01L 27/3244; H01L 51/005; H01L 51/0071; H01L 51/50; C07D 209/86; C07D 401/14; C07D 403/10; C07D 403/14; C07D 487/04; C07F 5/022; C09K 11/06; C09K 2211/1018
  See application file for complete search history.

(56) References Cited

U.S. PATENT DOCUMENTS

| | | | |
|---|---|---|---|
| 2012/0049192 A1* | 3/2012 | Shin | H01L 27/1285 257/59 |
| 2016/0190469 A1* | 6/2016 | Ogiwara | H01L 51/0067 257/40 |
| 2016/0190478 A1 | 6/2016 | Nakanotani et al. | |
| 2016/0329512 A1* | 11/2016 | Nishide | H01L 51/504 |
| 2017/0288147 A1* | 10/2017 | Fujita | C07F 7/0816 |
| 2018/0053901 A1 | 2/2018 | Yoshida et al. | |
| 2018/0151810 A1 | 5/2018 | Adachi et al. | |
| 2019/0044073 A1 | 2/2019 | Ogiwara et al. | |

FOREIGN PATENT DOCUMENTS

| | | |
|---|---|---|
| JP | 2018-125504 A | 8/2018 |
| KR | 10-2016-0044522 A | 4/2016 |
| KR | 10-2017-0085434 A | 7/2017 |
| KR | 10-2017-0113975 A | 10/2017 |
| KR | 10-2017-0134163 A | 12/2017 |
| KR | 10-2018-0099657 A | 9/2018 |
| WO | WO 2016/056559 A1 | 4/2016 |
| WO | WO 2016/158540 A1 | 10/2016 |

OTHER PUBLICATIONS

Partial English Translation of relevant parts of KR 10-2017-0134163 A dated Dec. 6, 2017, listed above.

* cited by examiner

ORGANIC LIGHT-EMITTING DEVICE AND DISPLAY APPARATUS INCLUDING THE SAME

CROSS-REFERENCE TO RELATED APPLICATION

This application claims priority to and the benefit of Korean Patent Application No. 10-2018-0165469, filed on Dec. 19, 2018, in the Korean Intellectual Property Office, the disclosure of which is incorporated herein in its entirety by reference.

BACKGROUND

1. Field

One or more embodiments relate to an organic light-emitting device and a display apparatus including the same.

2. Description of the Related Art

Organic light-emitting devices are self-emission devices, have wide viewing angles, high contrast ratios, short response times, as well as excellent characteristics in terms of brightness, driving voltage, and response speed, and produce full-color images.

An example of such organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state, thereby generating light.

SUMMARY

An aspect according to one or more embodiments of the present disclosure is directed toward an organic light-emitting device and a display apparatus including the same.

Additional aspects will be set forth in part in the description which follows and, in part, will be apparent from the description, or may be learned by practice of the presented embodiments.

According to an embodiment of the present disclosure, an organic light-emitting device includes: a first electrode; a second electrode; and an organic layer between the first electrode and the second electrode, wherein the organic layer includes an emission layer, the emission layer includes a first compound, a second compound, and a third compound, the first compound is represented by Formula 1, the second compound is represented by Formula 2, the third compound is represented by Formula 3, and the first compound and the second compound are different from each other:

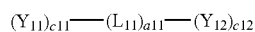

Formula 1

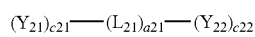

Formula 2

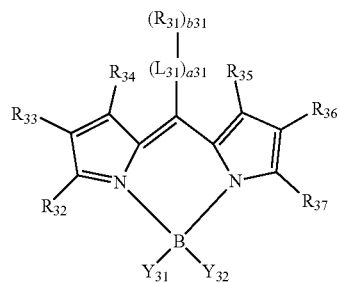

Formula 3

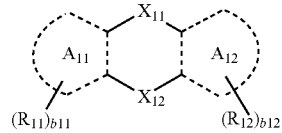

Formula 1A

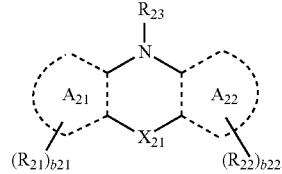

Formula 2A

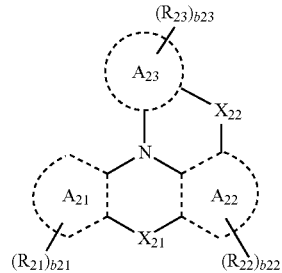

Formula 2B

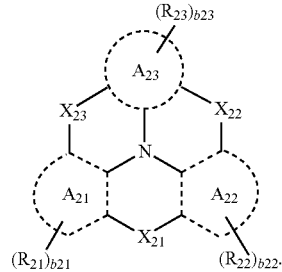

Formula 2C

In Formulae 1 to 3, 1A, and 2A to 2C, $L_{11}$ may be selected from:

a π electron-depleted nitrogen-free cyclic group; and a π electron-depleted nitrogen-free cyclic group substituted with at least one selected from deuterium, a $C_1$-$C_{60}$ alkyl group, a π electron-depleted nitrogen-free cyclic group, and —Si($Q_{31}$)($Q_{32}$)($Q_{33}$), a11 may be selected from 0, 1, 2, and 3, $Y_{11}$ may be a group represented by Formula 1A, $Y_{12}$ may be selected from:

—F, a cyano group, and a π electron-depleted nitrogen-containing cyclic group;

a $C_1$-$C_{60}$ alkyl group, a π electron-depleted nitrogen-containing cyclic group, and a π electron-depleted nitrogen-free cyclic group, each substituted with at least one selected from —F and a cyano group; and a π electron-depleted nitrogen-containing cyclic group substituted with at least one selected from deuterium, a $C_1$-$C_{60}$ alkyl group, a π electron-depleted nitrogen-containing cyclic group, and a π electron-depleted nitrogen-free cyclic group, c11 and c12 may each independently be selected from 1, 2, and 3, $X_{11}$ may be selected from a single bond, $N(R_{13})$, O, and S, $X_{12}$ may be selected from a single bond, $N(R_{14})$, O, and S, $X_{11}$ and $X_{12}$ may not be a single bond at the same time, $A_{11}$ and $A_{12}$ may each independently be a n electron-depleted nitrogen-free cyclic group, $R_{11}$ to $R_{14}$ may each independently be selected from:

a binding site, hydrogen, deuterium, a $C_1$-$C_{60}$ alkyl group, a π electron-depleted nitrogen-free cyclic group, and —Si$(Q_1)(Q_2)(Q_3)$;

a π electron-depleted nitrogen-free cyclic group substituted with deuterium, a $C_1$-$C_{60}$ alkyl group, a π electron-depleted nitrogen-free cyclic group, and —Si$(Q_{31})(Q_{32})(Q_{33})$; and a π electron-depleted nitrogen-free cyclic group substituted with a π electron-depleted nitrogen-free cyclic group that is substituted with at least one selected from deuterium, a $C_1$-$C_{60}$ alkyl group, a π electron-depleted nitrogen-free cyclic group, and —Si$(Q_{21})(Q_{22})(Q_{23})$, wherein one selected from $R_{11}$ to $R_{14}$ may be a binding site, b11 and b12 may each independently be selected from 1, 2, 3, 4, 5, and 6, $L_{21}$ may be selected from a substituted or unsubstituted $C_5$-$C_{60}$ carbocyclic group and a substituted or unsubstituted $C_1$-$C_{60}$ heterocyclic group, a21 may be selected from 0, 1, 2, and 3, $Y_{21}$ may be a group represented by one selected from Formulae 2A to 2C, $Y_{22}$ may be selected from:

—F, a cyano group, and a π electron-depleted nitrogen-containing cyclic group;

a $C_1$-$C_{60}$ alkyl group, a π electron-depleted nitrogen-containing cyclic group, and a π electron-depleted nitrogen-free cyclic group, each substituted with at least one selected from —F and a cyano group; and a π electron-depleted nitrogen-containing cyclic group substituted with at least one selected from deuterium, a $C_1$-$C_{60}$ alkyl group, a π electron-depleted nitrogen-containing cyclic group, and a π electron-depleted nitrogen-free cyclic group, c21 and c22 may each independently be selected from 1, 2, 3, 4, 5, and 6, $X_{21}$ may be selected from a single bond, $N(R_{24})$, O, and S, $X_{22}$ may be selected from a single bond, $N(R_{25})$, O, and S, $X_{23}$ may be selected from a single bond, $N(R_{26})$, O, and S, $A_{21}$ to $A_{23}$ may each independently be a π electron-depleted nitrogen-free cyclic group, $R_{21}$ to $R_{26}$ may each independently be selected from:

a binding site, hydrogen, deuterium, a $C_1$-$C_{60}$ alkyl group, a π electron-depleted nitrogen-free cyclic group, —N$(Q_1)(Q_2)$, and —Si$(Q_1)(Q_2)(Q_3)$;

a π electron-depleted nitrogen-free cyclic group substituted with at least one selected from deuterium, a $C_1$-$C_{60}$ alkyl group, a π electron-depleted nitrogen-free cyclic group, —N$(Q_{31})(Q_{32})$, and —Si$(Q_{31})(Q_{32})(Q_{33})$; and a π electron-depleted nitrogen-free cyclic group substituted with a T electron-depleted nitrogen-free cyclic group that is substituted with at least one selected from deuterium, a $C_1$-$C_{60}$ alkyl group, a π electron-depleted nitrogen-free cyclic group, —N$(Q_{21})(Q_{22})$, and —Si$(Q_{21})(Q_{22})(Q_{23})$, wherein one selected from $R_{21}$ to $R_{24}$ in Formula 2A may be a binding site, one selected from $R_{21}$ to $R_{25}$ in Formula 2B may be a binding site, and one selected from $R_{21}$ to $R_{26}$ in Formula 2C may be a binding site, b21 to b23 may each independently be selected from 1, 2, 3, 4, 5, and 6, $L_{31}$ may be selected from a substituted or unsubstituted $C_5$-$C_{60}$ carbocyclic group and a substituted or unsubstituted $C_1$-$C_{60}$ heterocyclic group, a31 may be selected from 0, 1, 2, and 3, $R_{31}$ to $R_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —B$(Q_1)(Q_2)$, —N$(Q_1)(Q_2)$, —P$(Q_1)(Q_2)$, —C(=O)$(Q_1)$, —S(=O)$(Q_1)$, —S(=O)$_2(Q_1)$, —P(=O)$(Q_1)(Q_2)$, and —P(=S)$(Q_1)(Q_2)$, wherein $R_{31}$ to $R_{37}$ may optionally be linked to form a substituted or unsubstituted $C_5$-$C_{60}$ carbocyclic group or a substituted or unsubstituted $C_1$-$C_{60}$ heterocyclic group, b31 may be selected from 1, 2, 3, 4, 5, and 6, $Y_{31}$ and $Y_{32}$ may each independently be selected from —F, —Cl, —Br, —I, a substituted or unsubstituted $C_1$-$C_{60}$ alkyl group, a substituted or unsubstituted $C_1$-$C_{60}$ alkoxy group, a substituted or unsubstituted $C_6$-$C_{60}$ aryl group, and a substituted or unsubstituted $C_6$-$C_{60}$ aryloxy group, wherein $Y_{31}$ and $Y_{32}$ may optionally be linked to form a substituted or unsubstituted $C_5$-$C_{60}$ carbocyclic group or a substituted or unsubstituted $C_1$-$C_{60}$ heterocyclic group, $Q_1$ to $Q_3$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, a biphenyl group, and a terphenyl group, and

* indicates a binding site to a neighboring atom.

According to an embodiment of the present disclosure, a display apparatus includes a thin film transistor (including a source electrode, a drain electrode, and an active layer); and the organic light-emitting device described above, wherein the first electrode of the organic light-emitting device is electrically connected to one selected from the source electrode and the drain source of the thin film transistor.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
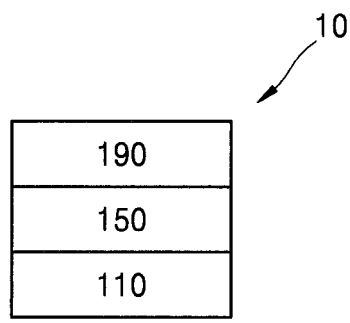
FIG. 1 is a schematic cross-sectional view of an organic light-emitting device according to an embodiment.

The present disclosure will now be described more fully with reference to exemplary embodiments. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. Enhancements and features of the present invention, and how to achieve them will become apparent by reference to the embodiment that will be described later in more detail, together with the accompanying drawings. This invention may, however, be embodied in many different forms and should not be limited to the exemplary embodiments.

Hereinafter, embodiments are described in more detail by referring to the attached drawings, and in the drawings, like reference numerals denote like elements, and a redundant explanation thereof will not be provided herein.

As used herein, the singular forms "a," "an" and "the" are intended to include the plural forms as well, unless the context clearly indicates otherwise.

It will be further understood that the terms "comprises" and/or "comprising" as used herein specify the presence of stated features or components, but do not preclude the presence or addition of one or more other features or components.

It will be understood that when a layer, region, or component is referred to as being "on" or "onto" another layer, region, or component, it may be directly or indirectly formed on the other layer, region, or component. That is, for example, intervening layers, regions, or components may be present.

Sizes of components in the drawings may be exaggerated for convenience of explanation. In other words, because sizes and thicknesses of components in the drawings are arbitrarily illustrated for convenience of explanation, the following embodiments of the present disclosure are not limited thereto.

The term "organic layer" as used herein refers to a single layer and/or a plurality of layers disposed between the first electrode and the second electrode of the organic light-emitting device. A material included in the "organic layer" is not limited to an organic material.

An organic light-emitting device according to an embodiment may include: a first electrode; a second electrode; and an organic layer between the first electrode and the second electrode, wherein the organic layer may include an emission layer, the emission layer may include a first compound, a second compound, and a third compound, the first compound may be represented by Formula 1, the second compound may be represented by Formula 2, the third compound may be represented by Formula 3, and the first compound and the second compound may be different from each other:

$$(Y_{11})_{c11}\text{---}(L_{11})_{a11}\text{---}(Y_{12})_{c12}$$ Formula 1

$$(Y_{21})_{c21}\text{---}(L_{21})_{a21}\text{---}(Y_{22})_{c22}$$ Formula 2

Formula 3

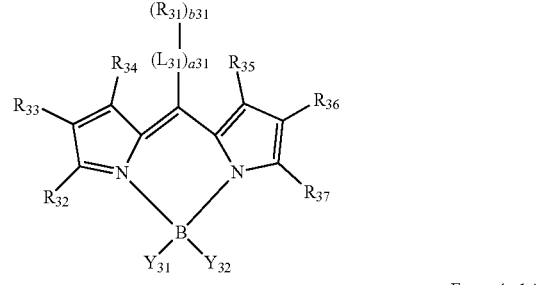

Formula 1A

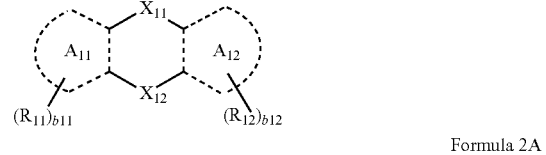

Formula 2A

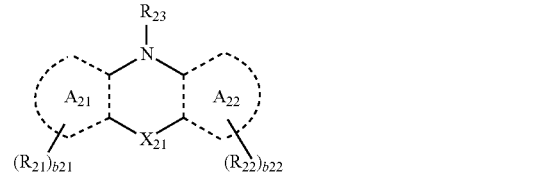

Formula 2B

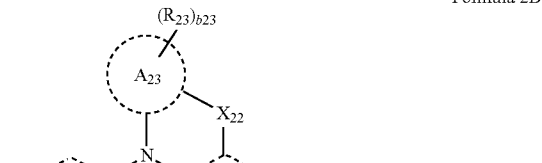

Formula 2C

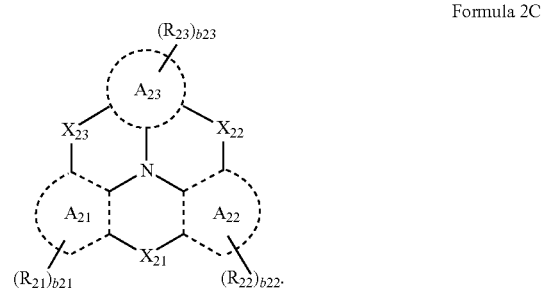

In Formula 1 to 3, 1A and 2A to 2C, $L_{11}$ may be selected from:

a π electron-depleted nitrogen-free cyclic group; and a π electron-depleted nitrogen-free cyclic group substituted with at least one selected from deuterium, a $C_1$-$C_{60}$ alkyl group, a π electron-depleted nitrogen-free cyclic group, and —Si($Q_{31}$)($Q_{32}$)($Q_{33}$), a11 may be selected from 0, 1, 2, and 3, $Y_{11}$ may be a group represented by Formula 1A, $Y_{12}$ may be selected from:

—F, a cyano group, and a π electron-depleted nitrogen-containing cyclic group;

a $C_1$-$C_{60}$ alkyl group, a π electron-depleted nitrogen-containing cyclic group, and a π electron-depleted nitrogen-free cyclic group, each substituted with at least one selected from —F and a cyano group; and a π electron-depleted nitrogen-containing cyclic group substituted with at least one selected from deuterium, a $C_1$-$C_{60}$ alkyl group, a π electron-depleted nitrogen-containing cyclic group, and a π electron-depleted nitrogen-free cyclic group, c11 and c12 may each independently be selected from 1, 2, and 3, $X_{11}$ may be selected from a single bond, N($R_{13}$), O, and S, $X_{12}$ may be selected from a single bond, N($R_{14}$), O, and S, $X_{11}$ and $X_{12}$ may not be a single bond at the same time, $A_{11}$ and $A_{12}$ may each independently be a π electron-depleted nitrogen-free cyclic group, $R_{11}$ to $R_{14}$ may each independently be selected from:

a binding site (e.g., to $L_{11}$), hydrogen, deuterium, a $C_1$-$C_{60}$ alkyl group, and a π electron-depleted nitrogen-free cyclic group and —Si($Q_1$)($Q_2$)($Q_3$);

a π electron-depleted nitrogen-free cyclic group substituted with at least one selected from deuterium, a $C_1$-$C_{60}$ alkyl group, a π electron-depleted nitrogen-free cyclic group, and —Si($Q_{31}$)($Q_{32}$)($Q_{33}$); and a π electron-depleted nitrogen-free cyclic group substituted with a π electron-depleted nitrogen-free cyclic group that is substituted with at least one selected from deuterium, a $C_1$-$C_{60}$ alkyl group, a π electron-depleted nitrogen-free cyclic group, and —Si($Q_{21}$)($Q_{22}$)($Q_{23}$), wherein one selected from $R_{11}$ to $R_{14}$ may be a binding site (e.g., to $L_{11}$), b11 and b12 may each independently be selected from 1, 2, 3, 4, 5, and 6, $L_{21}$ may be selected from a substituted or unsubstituted $C_5$-$C_{60}$ carbocyclic group and a substituted or unsubstituted $C_1$-$C_{60}$ heterocyclic group, a21 may be selected from 0, 1, 2, and 3, $Y_{21}$ may be a group represented by one selected from Formulae 2A to 2C, $Y_{22}$ may be selected from:

—F, a cyano group, and a π electron-depleted nitrogen-containing cyclic group;

a $C_1$-$C_{60}$ alkyl group, a π electron-depleted nitrogen-containing cyclic group, and a π electron-depleted nitrogen-free cyclic group, each substituted with at least one selected from —F and a cyano group; and a π electron-depleted nitrogen-containing cyclic group substituted with at least one selected from deuterium, a $C_1$-$C_{60}$ alkyl group, a π electron-depleted nitrogen-containing cyclic group, and a π electron-depleted nitrogen-free cyclic group, c21 and c22 may each independently be selected from 1, 2, 3, 4, 5, and 6, $X_{21}$ may be selected from a single bond, N($R_{24}$), O, and S, $X_{22}$ may be selected from a single bond, N($R_{25}$), O, and S, $X_{23}$ may be selected from a single bond, N($R_{26}$), O, and S, $A_{21}$ to $A_{23}$ may each independently be a π electron-depleted nitrogen-free cyclic group, $R_{21}$ to $R_{26}$ may each independently be selected from:

a binding site (e.g., to $L_{21}$), hydrogen, deuterium, a $C_1$-$C_{60}$ alkyl group, a π electron-depleted nitrogen-free cyclic group, —N($Q_1$)($Q_2$), and —Si($Q_1$)($Q_2$)($Q_3$);

a π electron-depleted nitrogen-free cyclic group substituted with at least one selected from deuterium, a $C_1$-$C_{60}$ alkyl group, a π electron-depleted nitrogen-free cyclic group, —N($Q_{31}$)($Q_{32}$), and —Si($Q_{31}$)($Q_{32}$)($Q_{33}$); and a π electron-depleted nitrogen-free cyclic group substituted with a π electron-depleted nitrogen-free cyclic group that is substituted with at least one selected from deuterium, a $C_1$-$C_{60}$ alkyl group, a π electron-depleted nitrogen-free cyclic group, —N($Q_{21}$)($Q_{22}$), and —Si($Q_{21}$)($Q_{22}$)($Q_{23}$), wherein one selected from $R_{21}$ to $R_{24}$ in Formula 2A may be a binding site (e.g., to $L_{21}$), one selected from $R_{21}$ to $R_{25}$ in Formula 2B may be a binding site (e.g., to $L_{21}$), and one selected from $R_{21}$ to $R_{26}$ in Formula 2C may be a binding site (e.g., to $L_{21}$);

b21 to b23 may each independently be selected from 1, 2, 3, 4, 5, and 6, $L_{31}$ may be selected from a substituted or unsubstituted $C_5$-$C_{60}$ carbocyclic group and a substituted or unsubstituted $C_1$-$C_{60}$ heterocyclic group, a31 may be selected from 0, 1, 2, and 3; and $R_{31}$ to $R_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), $R_{31}$ to $R_{37}$ may optionally be linked (e.g., to a neighboring group) to form a substituted or unsubstituted $C_5$-$C_{60}$ carbocyclic group or a substituted or unsubstituted $C_1$-$C_{60}$ heterocyclic group, b31 may be selected from 1, 2, 3, 4, 5, and 6, $Y_{31}$ and $Y_{32}$ may each independently be selected from —F, —Cl, —Br, —I, a substituted or unsubstituted $C_1$-$C_{60}$ alkyl group, a substituted or unsubstituted $C_1$-$C_{60}$ alkoxy group, a substituted or unsubstituted $C_6$-$C_{60}$ aryl group, and a substituted or unsubstituted $C_6$-$C_{60}$ aryloxy group, wherein $Y_{31}$ and $Y_{32}$ may optionally be linked to form a substituted or unsubstituted $C_5$-$C_{60}$ carbocyclic group or a substituted or unsubstituted $C_1$-$C_{60}$ heterocyclic group, $Q_1$ to $Q_3$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, a biphenyl group, and a terphenyl group, and

* indicates a binding site to a neighboring atom.

For example, $L_{11}$ in Formula 1 may be selected from:

a benzene group, a naphthalene group, a phenalene group, an anthracene group, a fluoranthene group, a triphenylene group, a phenanthrene group, a pyrene group, a chrysene group, a perylene group, a fluorene group, a carbazole group, a dibenzofuran group, and a dibenzothiophene group; and a benzene group, a naphthalene group, a phenalene group, an anthracene group, a fluoranthene group, a triphenylene group, a phenanthrene group, a pyrene group, a chrysene group, a perylene group, a fluorene group, a carbazole group, a dibenzofuran group, and a dibenzothiophene group, each substituted with at least one selected from deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, but embodiments of the present disclosure are not limited thereto.

For example, $L_{21}$ and $L_{31}$ in Formulae 2 and 3 may each independently be selected from:

a benzene group, a naphthalene group, a phenalene group, an anthracene group, a fluoranthene group, a triphenylene group, a phenanthrene group, a pyrene group, a chrysene group, a perylene group, a pyridine group, a pyrimidine group, a pyrazine group, a pyridazine group, a triazine group, a quinoline group, an isoquinoline group, a benzoquinoline group, a benzoisoquinoline group, a phthalazine group, a naphthyridine group, a quinoxaline group, a benzoquinoxaline group, a quinazoline group, a benzoquinazoline group, a fluorene group, a carbazole group, a dibenzofuran group, and a dibenzothiophene group; and a benzene group, a naphthalene group, a phenalene group, an anthracene group, a fluoranthene group, a triphenylene group, a phenanthrene group, a pyrene group, a chrysene group, a perylene group, a pyridine group, a pyrimidine group, a pyrazine group, a pyridazine group, a triazine group, a quinoline group, an isoquinoline group, a benzoquinoline group, a benzoisoquinoline group, a phthalazine group, a naphthyridine group, a quinoxaline group, a benzoquinoxaline group, a quinazoline group, a benzoquinazoline group, a fluorene group, a carbazole group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, but embodiments of the present disclosure are not limited thereto.

For example, a11, a21, and a31 in Formulae 1 to 3 may each independently be selected from 0 and 1, but embodiments of the present disclosure are not limited thereto.

For example, in Formula 1A, $X_{11}$ may be selected from $N(R_{13})$, O, and S, and $X_{12}$ may be a single bond, but embodiments of the present disclosure are not limited thereto.

For example, in Formula 1A, $A_{11}$ and $A_{12}$ may each independently be selected from a benzene group, a naphthalene group, a fluorene group, a carbazole group, a dibenzofuran group, a dibenzothiophene group, a benzofluorene group, a benzocarbazole group, a benzonaphthofuran group, a benzonaphthothiophene group, an indolofluorene group, an indolocarbazole group, an indolodibenzofuran group, an indolodibenzothiophene group, an indenofluorene group, an indenocarbazole group, an indenodibenzofuran group, an indenodibenzothiophene group, a benzofuranofluorene group, a benzofuranocarbazole group, a benzofuranodibenzofuran group, a benzofuranodibenzothiophene group, a benzothienofluorene group, a benzothienocarbazole group, a benzothienodibenzofuran group, and a benzothienodibenzothiophene group, but embodiments of the present disclosure are not limited thereto.

For example, in Formula 1A, $R_{11}$ to $R_{14}$ may each independently be selected from:

a binding site, hydrogen, deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, and —$Si(Q_1)(Q_2)(Q_3)$;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, each substituted with at least one selected from deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, and —$Si(Q_{31})(Q_{32})(Q_{33})$; and a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, each substituted with at least one selected from a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group that are each substituted with at least one selected from deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, and —Si($Q_{21}$)($Q_{22}$)($Q_{23}$), one selected from $R_{11}$ to $R_{14}$ may be a binding site, $Q_1$ to $Q_3$, $Q_{21}$ to $Q_{23}$, and $Q_{31}$ to $Q_{33}$ may each independently be selected from a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, but embodiments of the present disclosure are not limited thereto.

In one embodiment, in Formula 1A, $R_{11}$ to $R_{14}$ may each independently be selected from:

a binding site, hydrogen, deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, and —Si($Q_1$)($Q_2$)($Q_3$);

a phenyl group, a biphenyl group, a terphenyl group, a naphthyl group, a phenanthrenyl group, a fluorenyl group, a carbazolyl group, a dibenzofuranyl group, and a dibenzothiophenyl group, each substituted with at least one selected from deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, and —Si($Q_{31}$)($Q_{32}$)($Q_{33}$); and a phenyl group, a biphenyl group, a terphenyl group, a naphthyl group, a phenanthrenyl group, a fluorenyl group, a carbazolyl group, a dibenzofuranyl group, and a dibenzothiophenyl group, each substituted with at least one selected from a phenyl group, a biphenyl group, a terphenyl group, a naphthyl group, a phenanthrenyl group, a fluorenyl group, a carbazolyl group, a dibenzofuranyl group, and a dibenzothiophenyl group, that are each substituted with at least one selected from deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, and —Si($Q_{21}$)($Q_{22}$)($Q_{23}$), one selected from $R_{11}$ to $R_{14}$ may be a binding site, $Q_1$ to $Q_3$, $Q_{21}$ to $Q_{23}$, and $Q_{31}$ to $Q_{33}$ may each independently be selected from a $C_1$-$C_{20}$ alkyl group, a phenyl group, a biphenyl group, a terphenyl group, a naphthyl group, a phenanthrenyl group, a fluorenyl group, a carbazolyl group, a dibenzofuranyl group, and a dibenzothiophenyl group, but embodiments of the present disclosure are not limited thereto.

For example, in Formula 1, $Y_{12}$ may be selected from:

—F, a cyano group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group;

a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from —F and a cyano group; and a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, but embodiments of the present disclosure are not limited thereto.

In one embodiment, $Y_{12}$ in Formula 1 may be selected from:

—F, a cyano group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, and a quinazolinyl group;

a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, and a quinazolinyl group, each substituted with at least one selected from —F and a cyano group; and a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, and a quinazolinyl group, each substituted with at least one selected from deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, and a quinazolinyl group, but embodiments of the present disclosure are not limited thereto.

For example, in Formula 1, c11 and c12 may each independently be 1, but embodiments of the present disclosure are not limited thereto.

For example, in Formulae 2A to 2C, $X_{21}$ may be a single bond, $X_{22}$ may be a single bond, and $X_{23}$ may be a single bond, but embodiments of the present disclosure are not limited thereto.

For example, in Formulae 2A to 2C, $A_{21}$ to $A_{23}$ may each independently be selected from a benzene group, a naphthalene group, a fluorene group, a carbazole group, a dibenzofuran group, a dibenzothiophene group, an indolofluorene group, an indolocarbazole group, an indolodibenzofuran group, an indolodibenzothiophene group, an indenofluorene group, an indenocarbazole group, an indenodibenzofuran group, an indenodibenzothiophene group, a benzofuranofluorene group, a benzofuranocarbazole group, a benzofuranodibenzofuran group, a benzofuranodibenzothiophene group, a benzothienofluorene group, a benzothienocarbazole group, a benzothienodibenzofuran group, and a benzothienodibenzothiophene group, but embodiments of the present disclosure are not limited thereto.

In one embodiment, in Formula 2, $Y_{21}$ may be a group represented by Formula 2A, but embodiments of the present disclosure are not limited thereto.

For example, in Formulae 2A to 2C, $R_{21}$ to $R_{26}$ may each independently be selected from:

a binding site, hydrogen, deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, —$N(Q_1)(Q_2)$, and —$Si(Q_1)(Q_2)(Q_3)$;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, each substituted with at least one selected from deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, —$N(Q_{31})(Q_{32})$, and —$Si(Q_{31})(Q_{32})(Q_{33})$; and a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, each substituted with at least one selected from a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group that are each independently substituted with at least one selected from deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, —$N(Q_{21})(Q_{22})$, and —$Si(Q_{21})(Q_{22})(Q_{23})$, one selected from $R_{21}$ to $R_{24}$ in Formula 2A may be a binding site, one selected from $R_{21}$ to $R_{25}$ in Formula 2B may be a binding site, one selected from $R_{21}$ to $R_{26}$ in Formula 2C may be a binding site, and $Q_1$ to $Q_3$, $Q_{21}$ to $Q_{23}$, and $Q_{31}$ to $Q_{33}$ may each independently be selected from a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, but embodiments of the present disclosure are not limited thereto.

In one embodiment, in Formulae 2A to 2C, $R_{21}$ to $R_{26}$ may each independently be selected from:

a binding site, hydrogen, deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, —N($Q_1$)($Q_2$), and —Si($Q_1$)($Q_2$)($Q_3$);

a phenyl group, a biphenyl group, a terphenyl group, a naphthyl group, a phenanthrenyl group, a fluorenyl group, a carbazolyl group, a dibenzofuranyl group, and a dibenzothiophenyl group, each substituted with at least one selected from deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, —N($Q_{31}$)($Q_{32}$), and —Si($Q_{31}$)($Q_{32}$)($Q_{33}$); and a phenyl group, a biphenyl group, a terphenyl group, a naphthyl group, a phenanthrenyl group, a fluorenyl group, a carbazolyl group, a dibenzofuranyl group, and a dibenzothiophenyl group, each substituted with at least one selected from a phenyl group, a biphenyl group, a terphenyl group, a naphthyl group, a phenanthrenyl group, a fluorenyl group, a carbazolyl group, a dibenzofuranyl group, and a dibenzothiophenyl group that are each substituted with at least one selected from deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, —N($Q_{21}$)($Q_{22}$), and —Si($Q_{21}$)($Q_{22}$)($Q_{23}$), one selected from $R_{21}$ to $R_{24}$ in Formula 2A may be a binding site, one selected from $R_{21}$ to $R_{25}$ in Formula 2B may be a binding site, one selected from $R_{21}$ to $R_{26}$ in Formula 2C may be a binding site, and $Q_1$ to $Q_3$, $Q_{21}$ to $Q_{23}$, and $Q_{31}$ to $Q_{33}$ may each independently be selected from a $C_1$-$C_{20}$ alkyl group, a phenyl group, a biphenyl group, a terphenyl group, a naphthyl group, a phenanthrenyl group, a fluorenyl group, a carbazolyl group, a dibenzofuranyl group, and a dibenzothiophenyl group, but embodiments of the present disclosure are not limited thereto.

For example, in Formula 2, $Y_{22}$ may be selected from:

—F, a cyano group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group;

a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from —F and a cyano group; and a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, but embodiments of the present disclosure are not limited thereto.

In one embodiment, in Formula 2, $Y_{22}$ may be selected from:

—F, a cyano group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, and a quinazolinyl group;

a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, and a quinazolinyl group, each substituted with at least one selected from —F and a cyano group; and a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, and a quinazolinyl group, each substituted with at least one selected from deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a fluorenyl group, a carbazolyl group, a dibenzofuranyl group, a dibenzothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, and a quinazolinyl group, but embodiments of the present disclosure are not limited thereto.

For example, in Formula 2, c21 and c22 may each independently be selected from 1, 2, and 3, but embodiments of the present disclosure are not limited thereto.

For example, in Formula 3, $R_{31}$ to $R_{37}$ may each independently be selected from:

hydrogen, deuterium, —F, —Cl, —Br, —I, a cyano group, a $C_1$-$C_{20}$ alkyl group, and a $C_1$-$C_{20}$ alkoxy group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from deuterium, —F, —Cl, —Br, —I, a cyano group, a $C_1$-$C_{20}$ alkyl group, a $C_1$-$C_{20}$ alkoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group; and —$B(Q_1)(Q_2)$ and —$N(Q_1)(Q_2)$, and $Q_1$ and $Q_2$ may each independently be selected from:

hydrogen, deuterium, and a $C_1$-$C_{20}$ alkyl group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group; and a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, but embodiments of the present disclosure are not limited thereto.

In one embodiment, in Formula 3, $R_{31}$ to $R_{37}$ may each independently be selected from:

hydrogen, deuterium, —F, —Cl, —Br, —I, a cyano group, a methyl group, an ethyl group, an n-propyl group, an isopropyl group, an n-butyl group, an isobutyl group, a sec-butyl group, a tert-butyl group, a methoxy group, an ethoxy group, a propoxy group, and a butoxy group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group, each substituted with at least one selected from deuterium, —F, —Cl, —Br, —I, a cyano group, a methyl group, an ethyl group, an n-propyl group, an isopropyl group, an n-butyl group, an isobutyl group, a sec-butyl group, a tert-butyl group, a methoxy group, an ethoxy group, a propoxy group, a butoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group; and —B($Q_1$)($Q_2$) and —N($Q_1$)($Q_2$), and $Q_1$ and $Q_2$ may each independently be selected from:

hydrogen, deuterium, a methyl group, an ethyl group, an n-propyl group, an isopropyl group, an n-butyl group, an isobutyl group, a sec-butyl group, and a tert-butyl group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group; and a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group, each substituted with at least one selected from deuterium, a methyl group, an ethyl group, an n-propyl group, an isopropyl group, an n-butyl group, an isobutyl group, a sec-butyl group, a tert-butyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group, but embodiments of the present disclosure are not limited thereto.

For example, in Formula 3, $Y_{31}$ and $Y_{32}$ may each independently be selected from —F, —Cl, —Br, —I, a $C_1$-$C_{20}$ alkyl group, and a $C_1$-$C_{20}$ alkoxy group, but embodiments of the present disclosure are not limited thereto.

In one embodiment, in Formula 3, $Y_{31}$ and $Y_{32}$ may each independently be selected from —F, a methyl group, an ethyl group, an n-propyl group, an isopropyl group, an n-butyl group, an isobutyl group, a sec-butyl group, a tert-butyl group, a methoxy group, an ethoxy group, a propoxy group, and a butoxy group, but embodiments of the present disclosure are not limited thereto.

In one embodiment, the first compound may be selected from compounds of Group I:

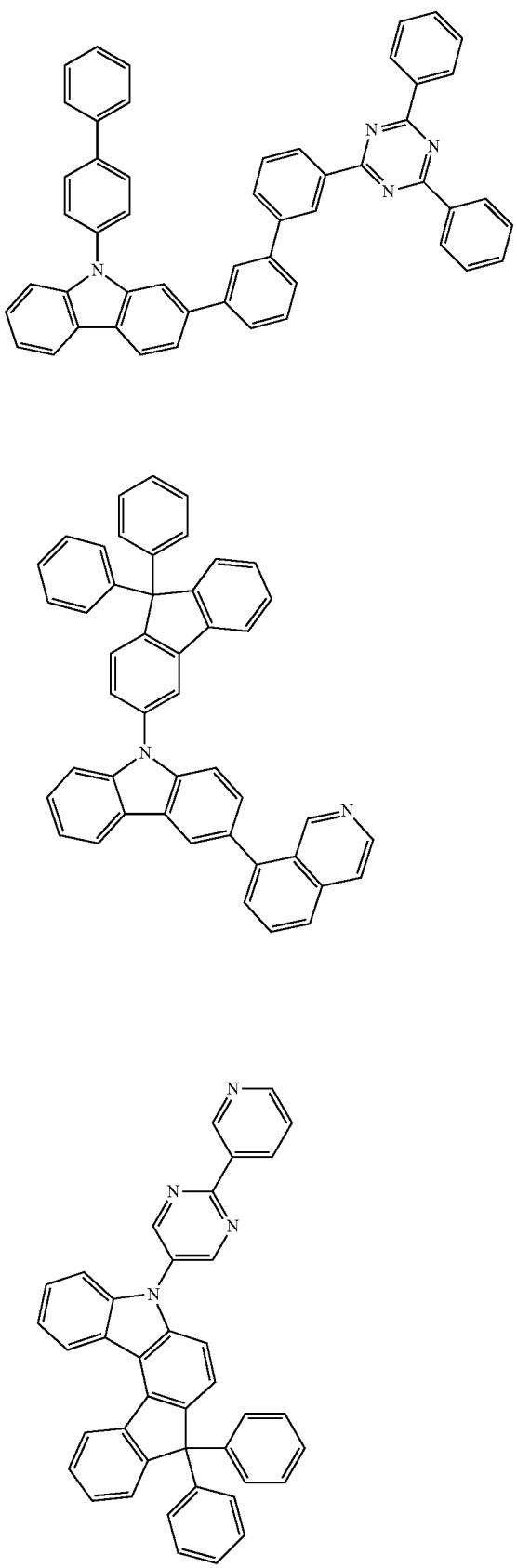

<Group I>

-continued
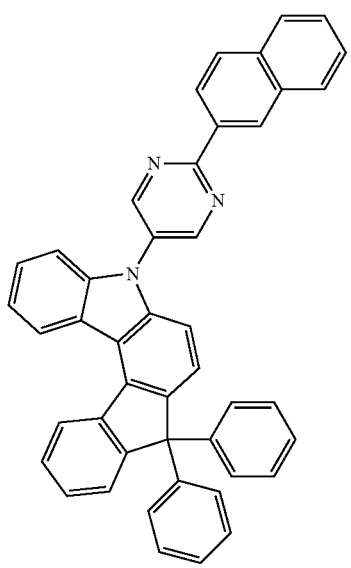
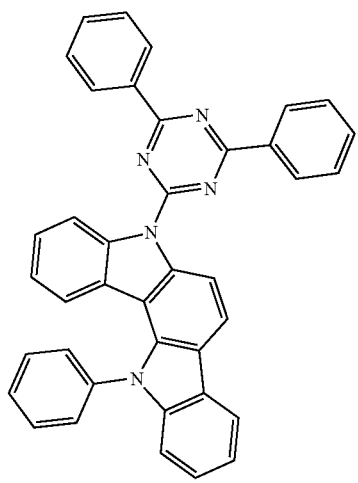
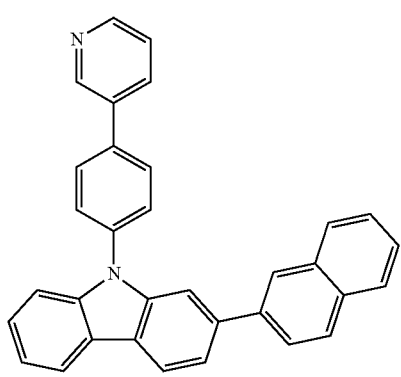
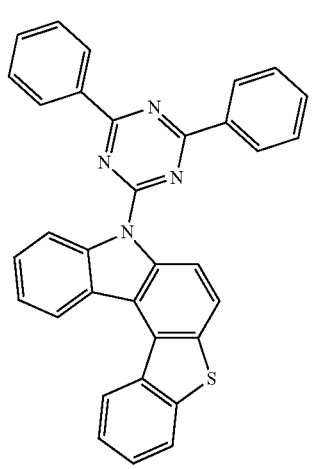
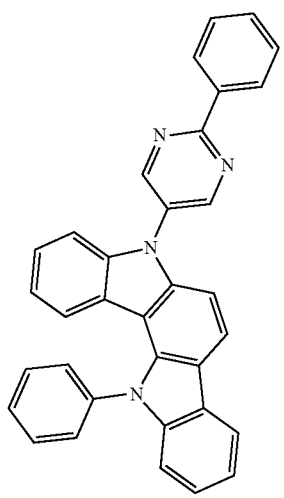
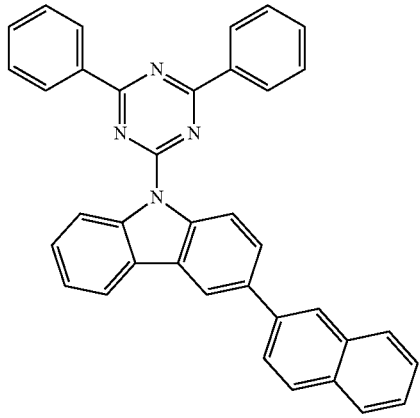

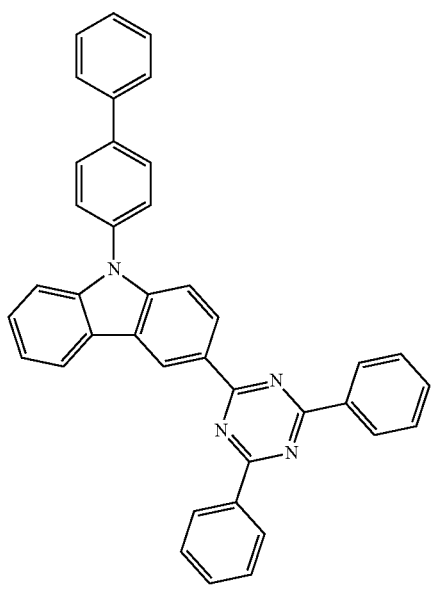
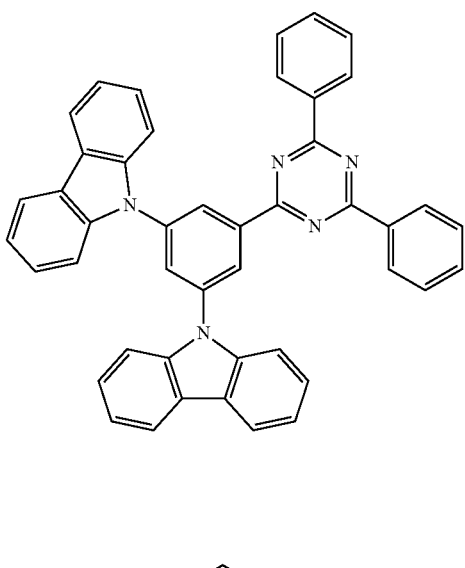
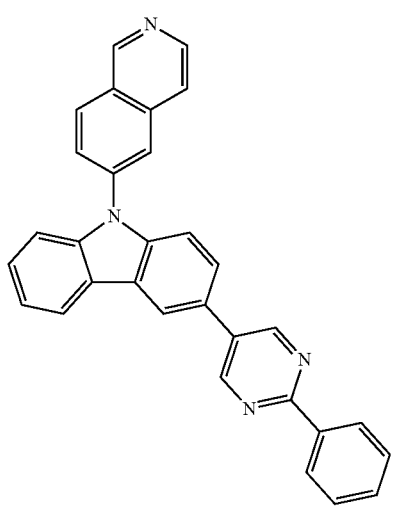
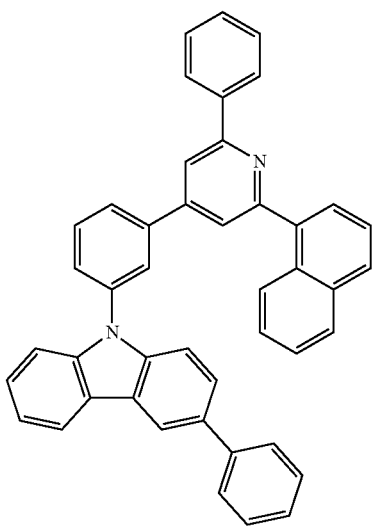
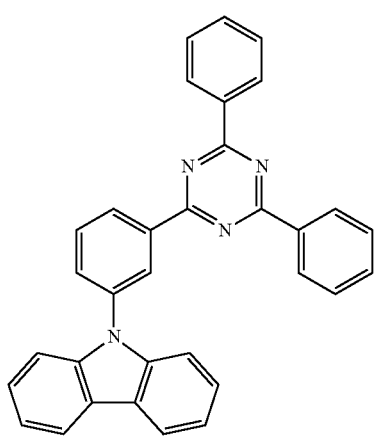
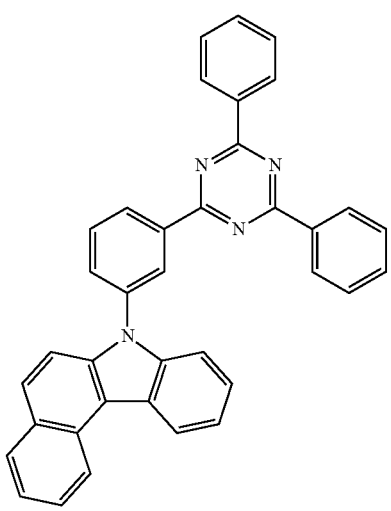

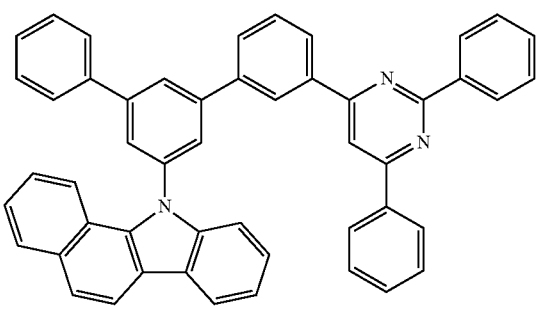
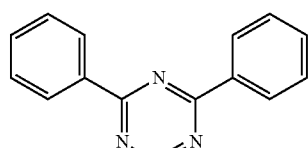
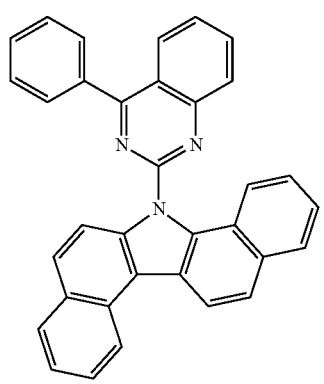
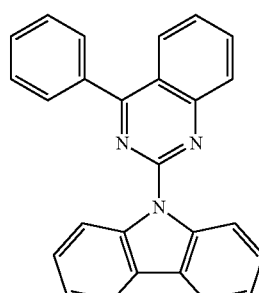
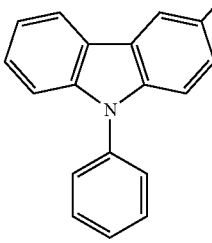
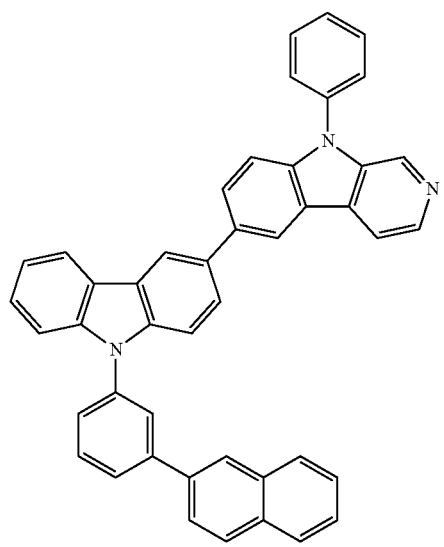
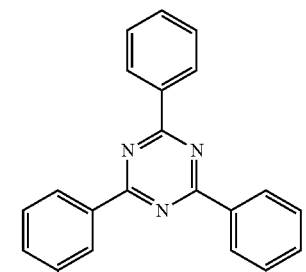
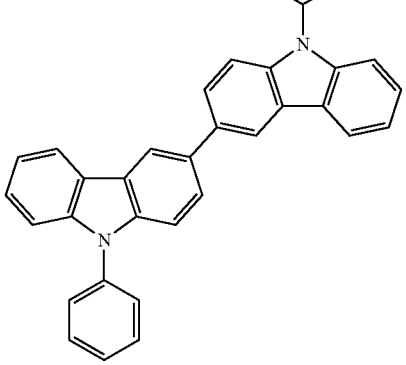

27
-continued
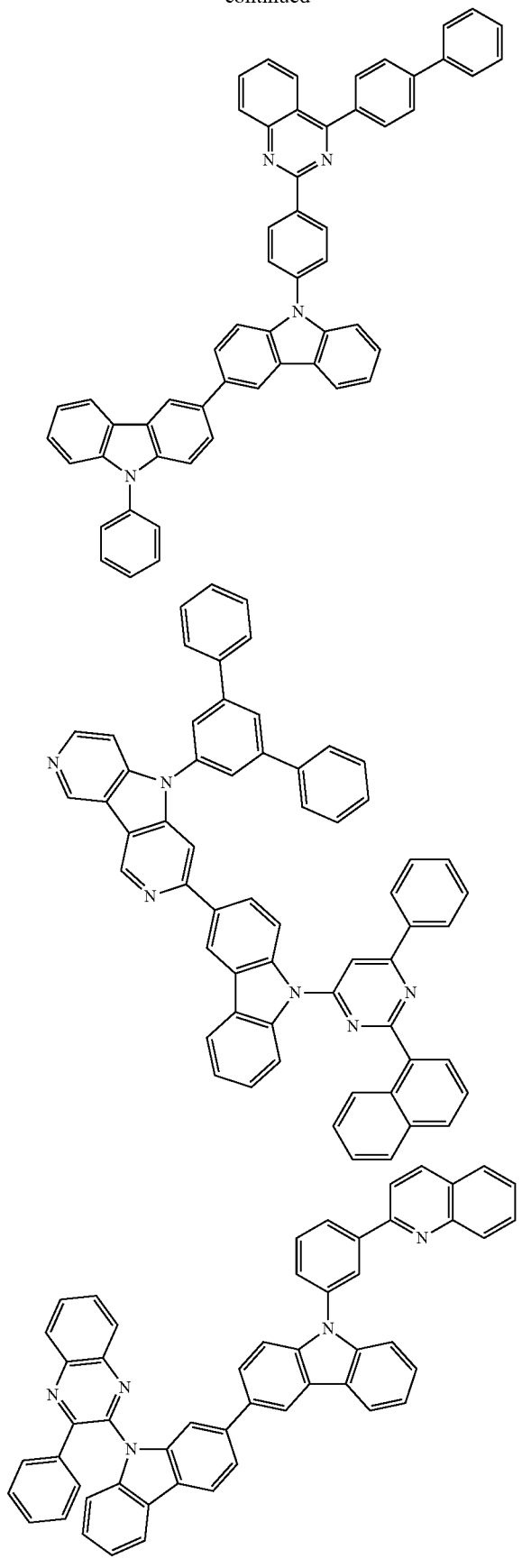
28
-continued
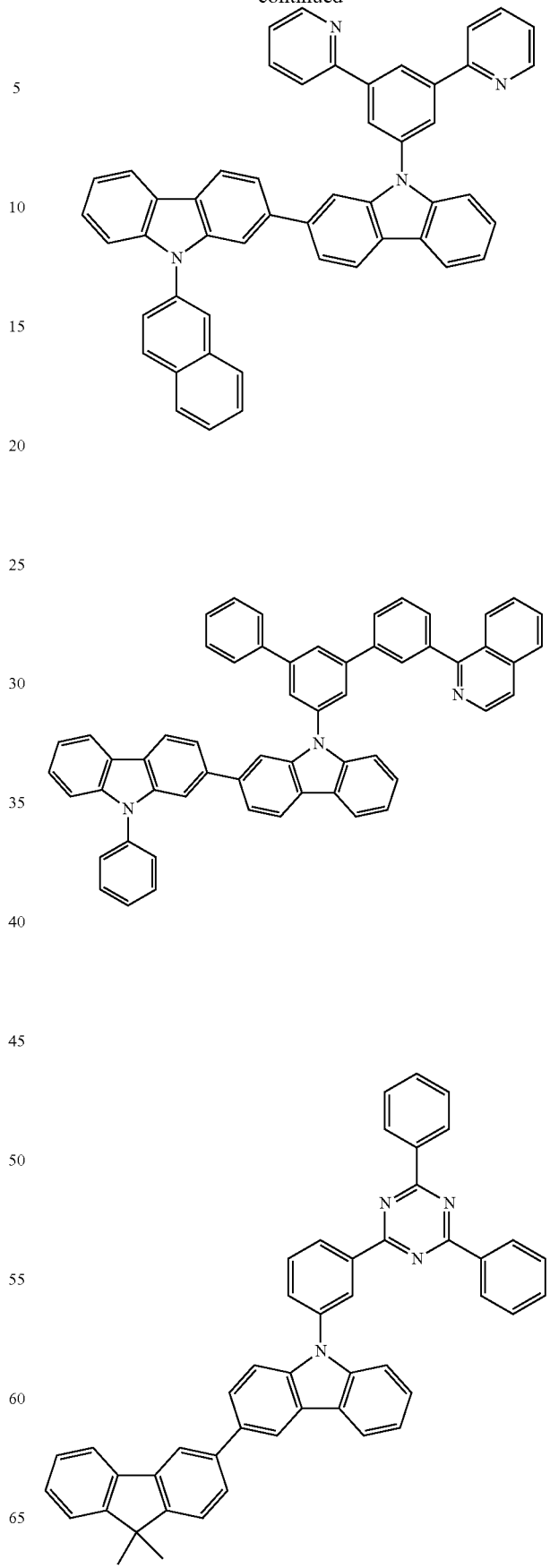

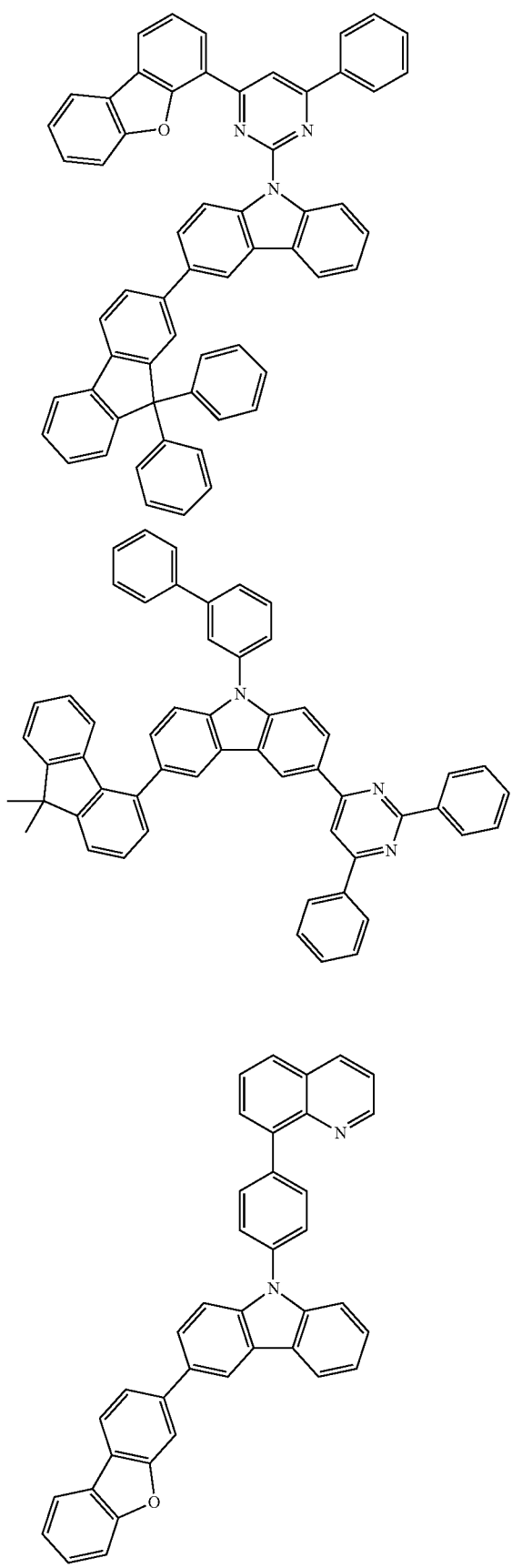
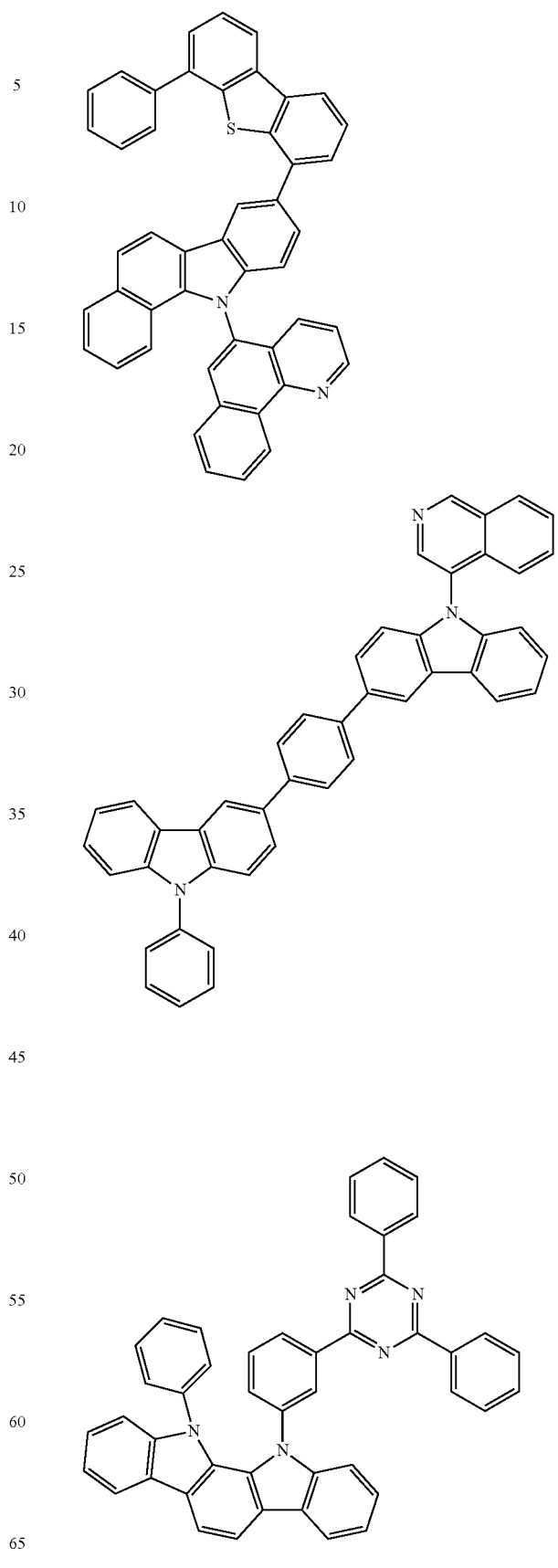

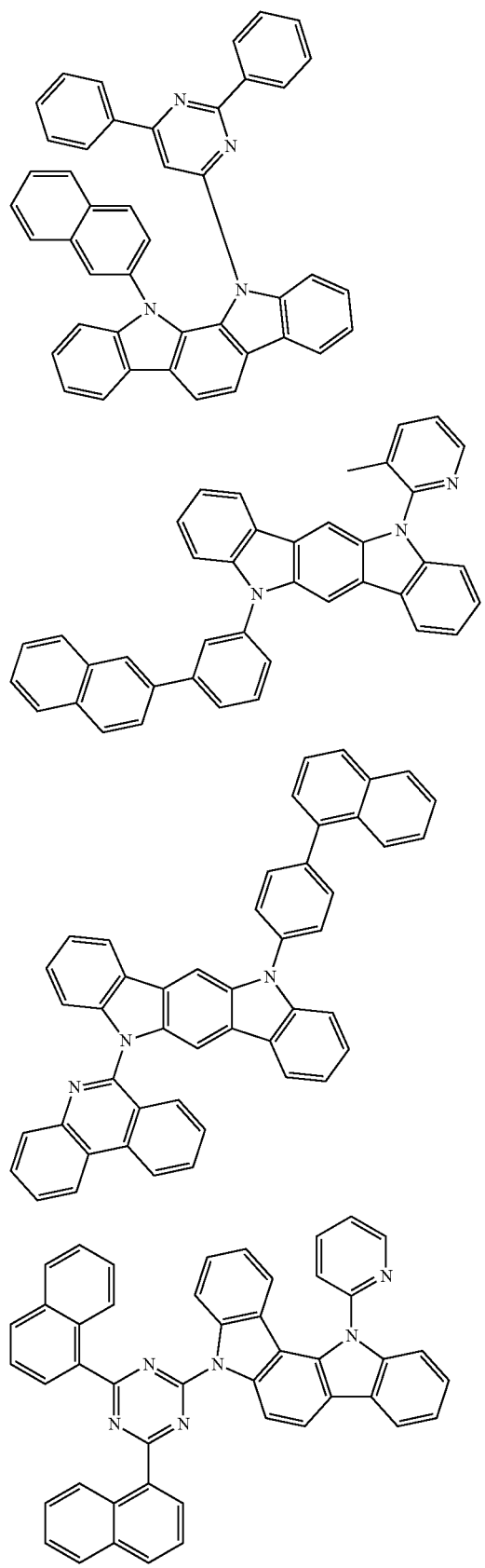
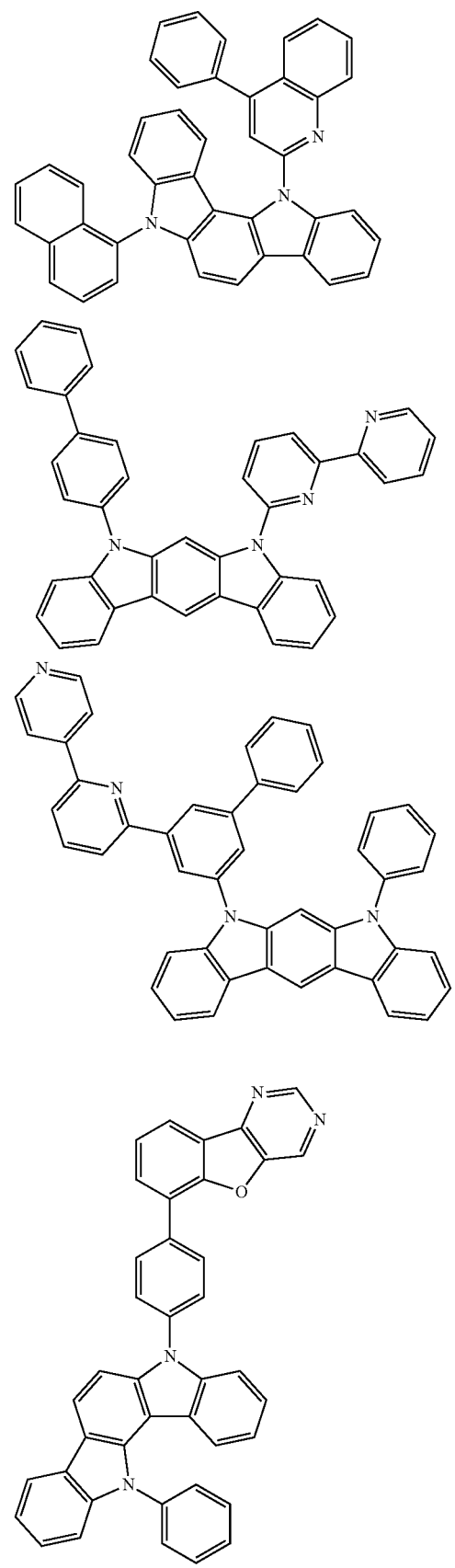

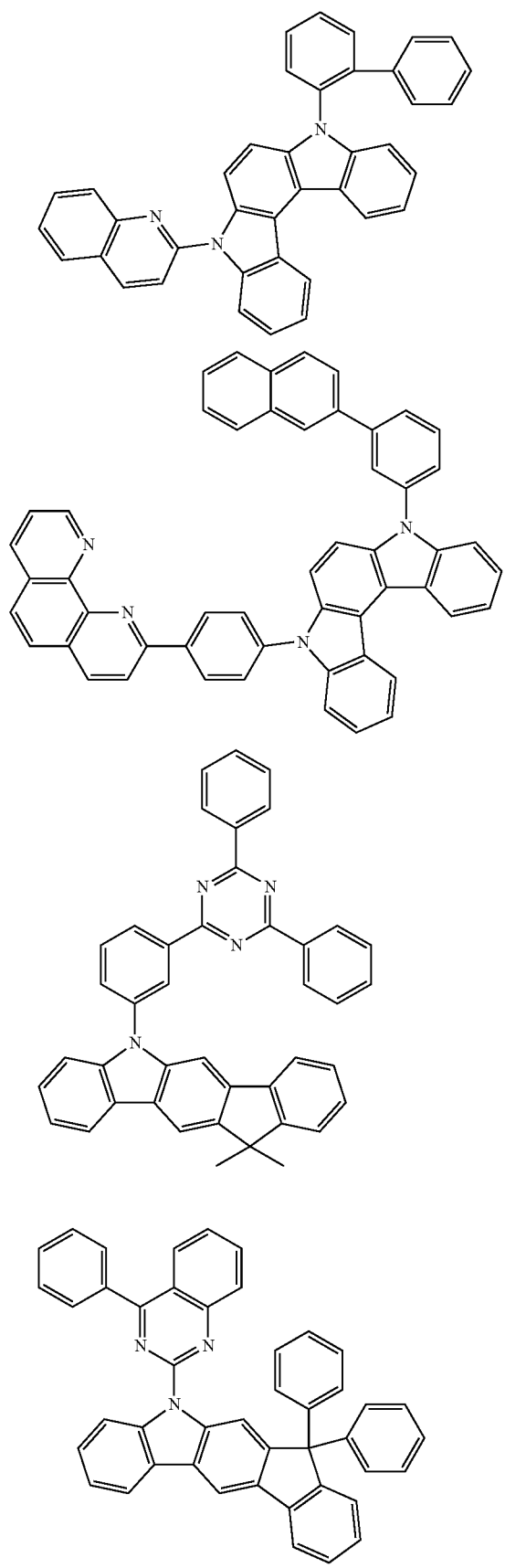
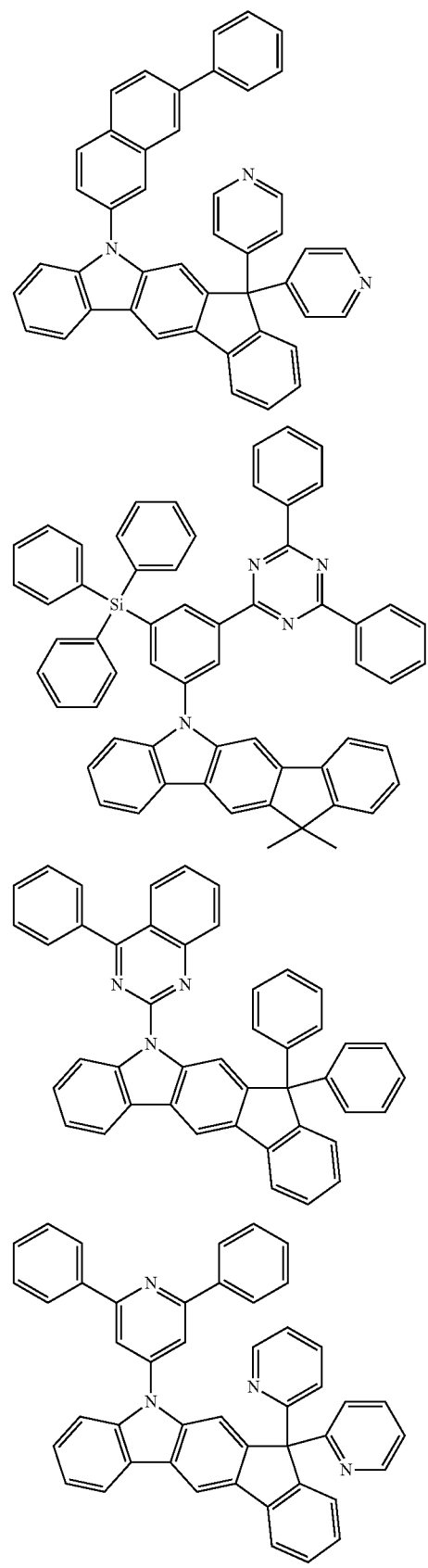

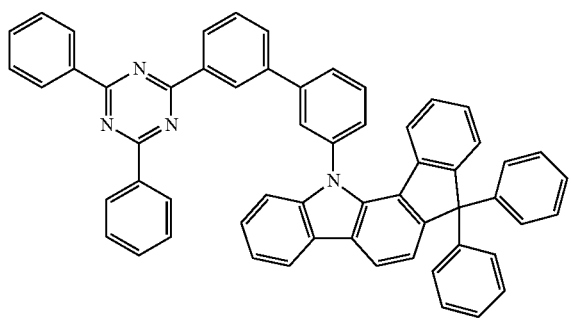
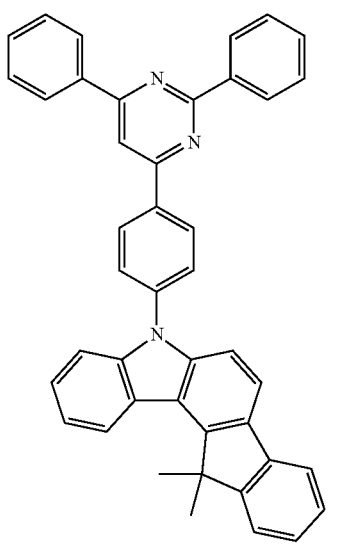
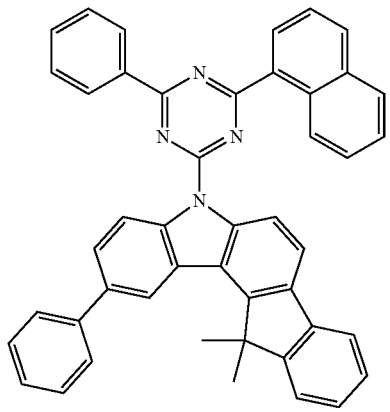
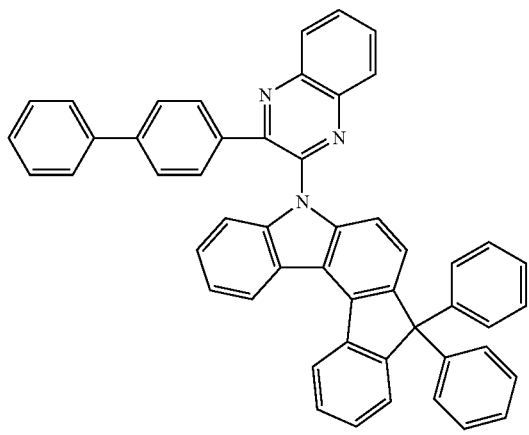
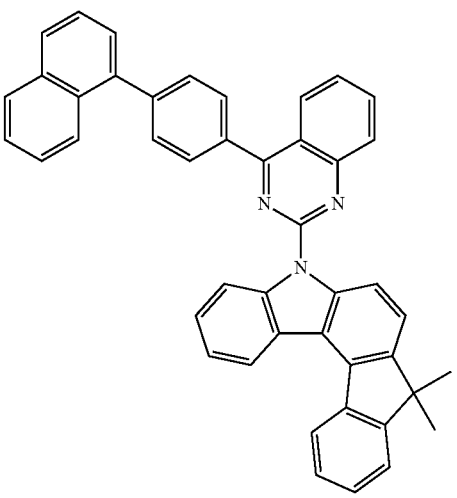
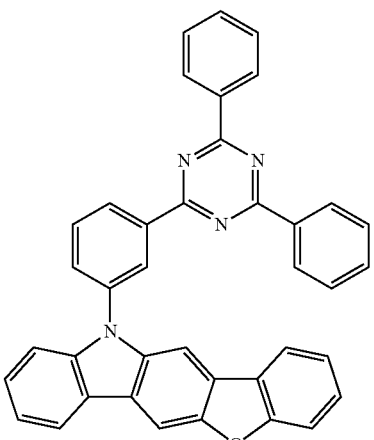
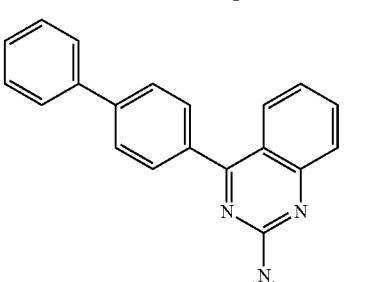
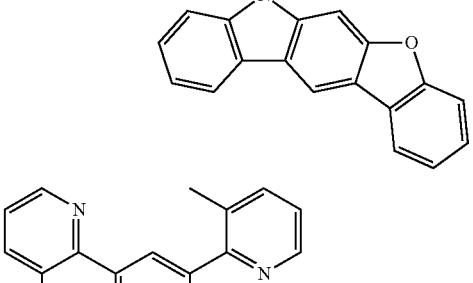
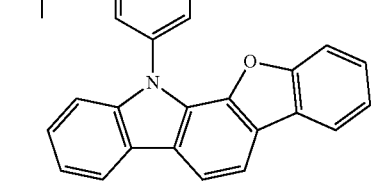

37
-continued
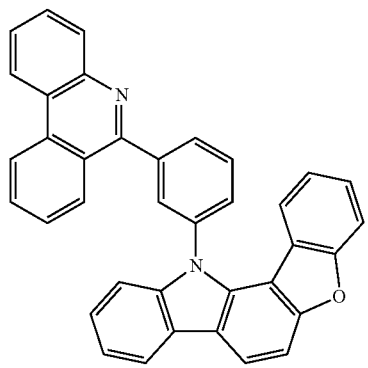
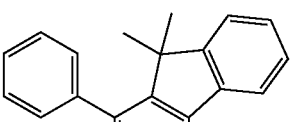
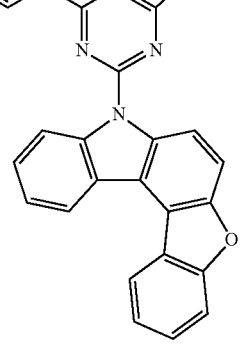
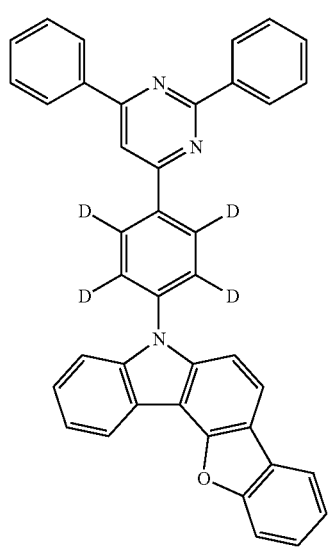
38
-continued
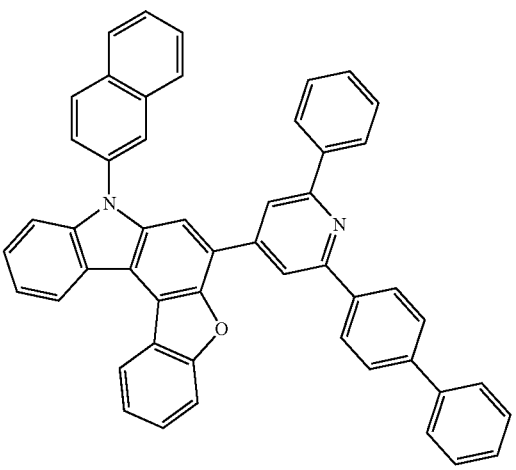
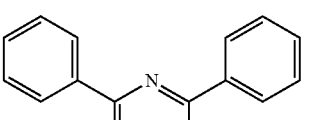
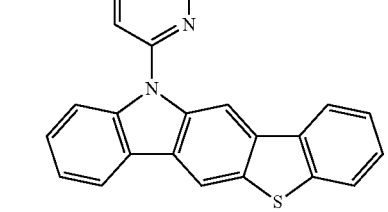
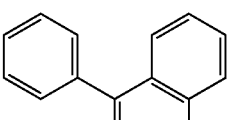
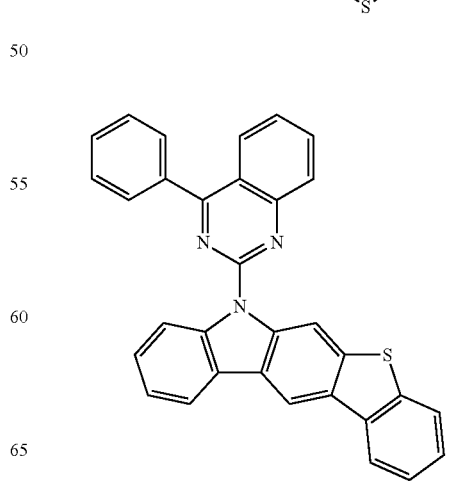

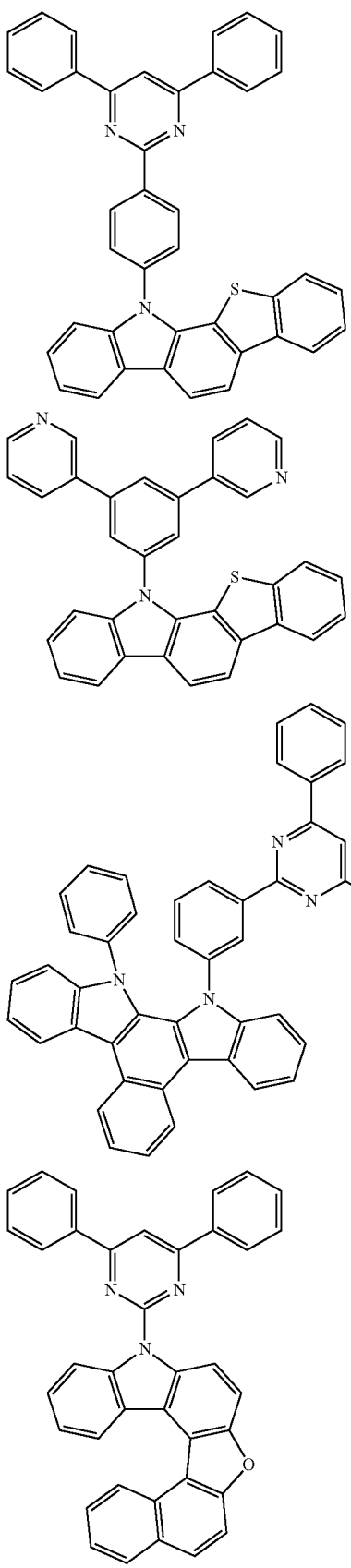
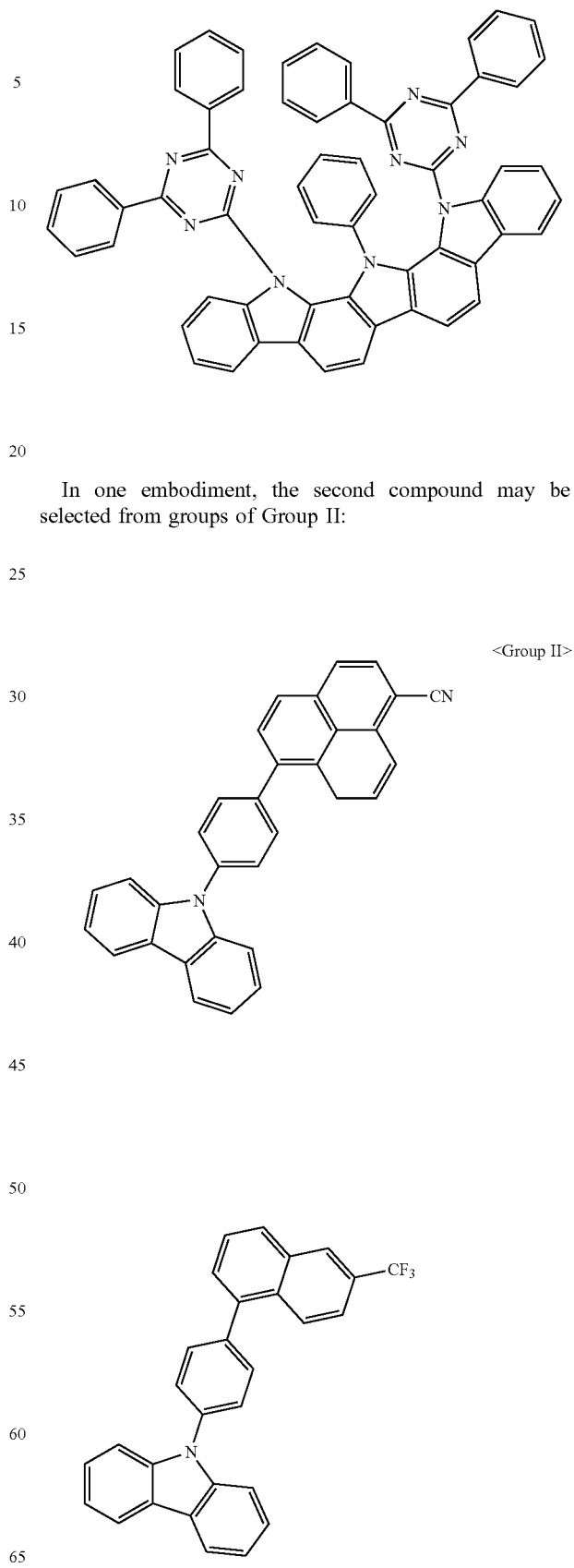
In one embodiment, the second compound may be selected from groups of Group II:
<Group II>

41
-continued
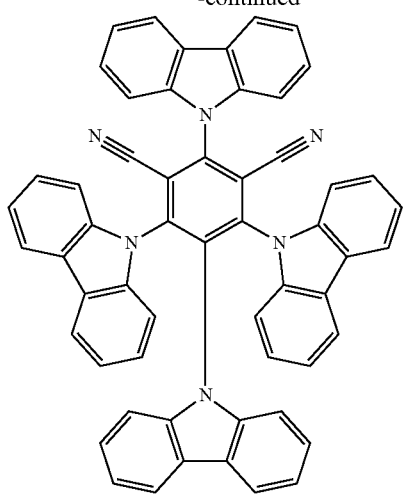
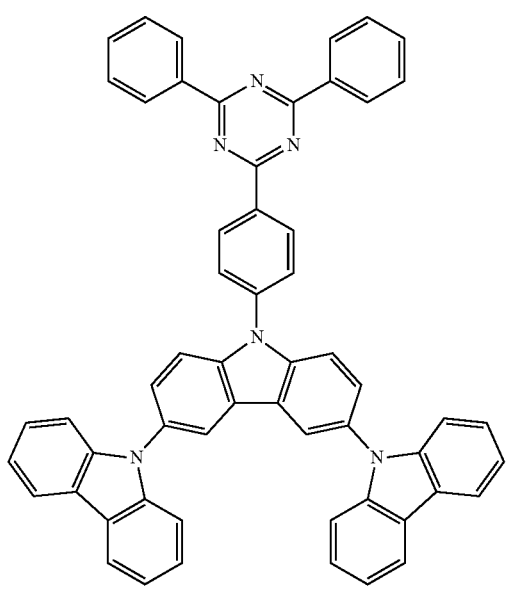
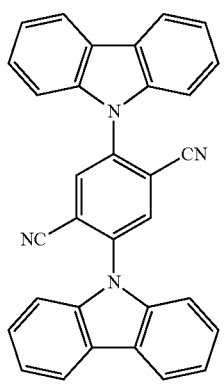
42
-continued
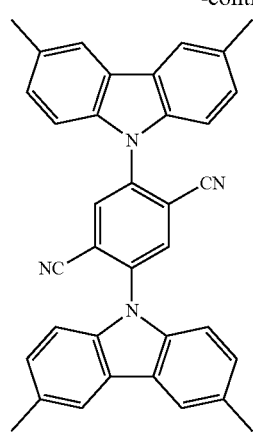
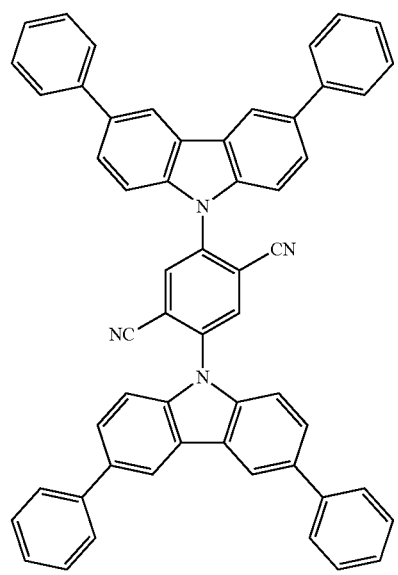
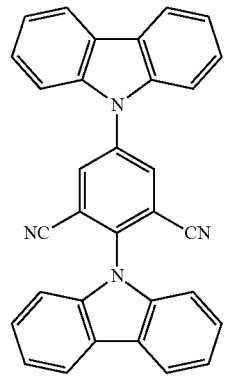

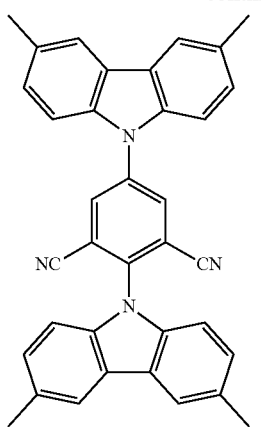
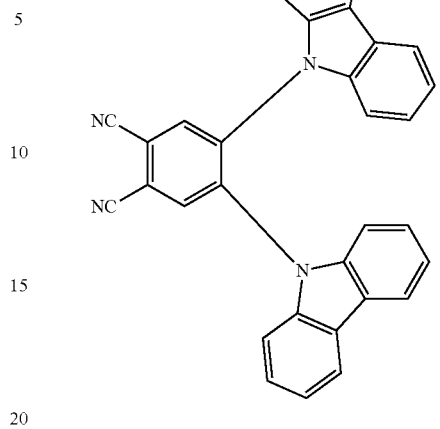
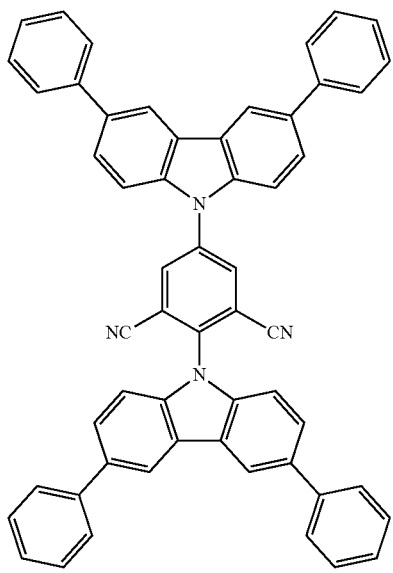
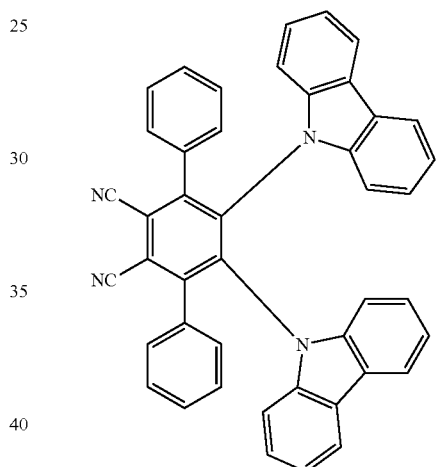
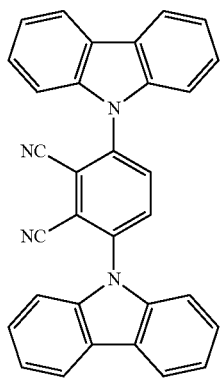
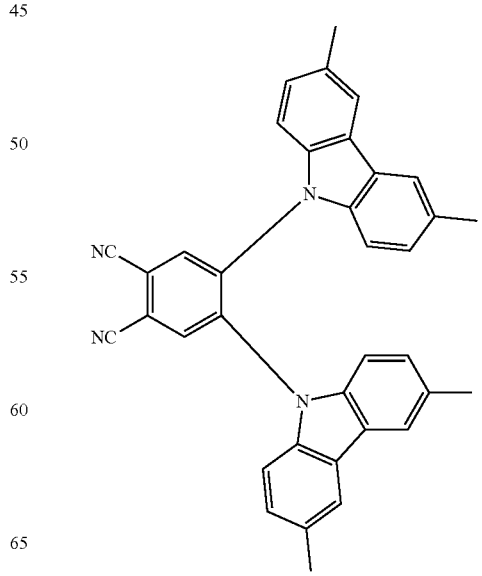

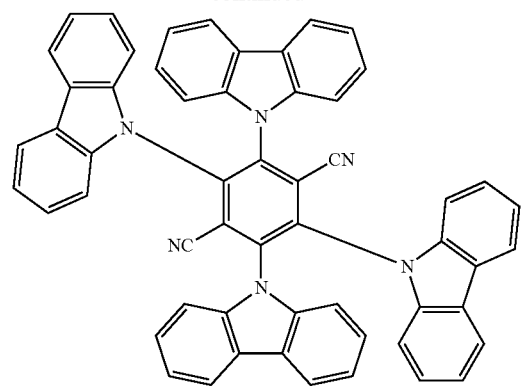
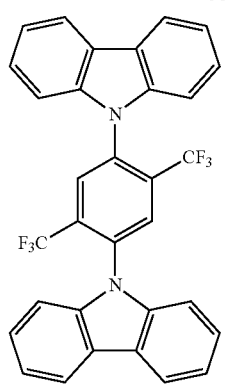
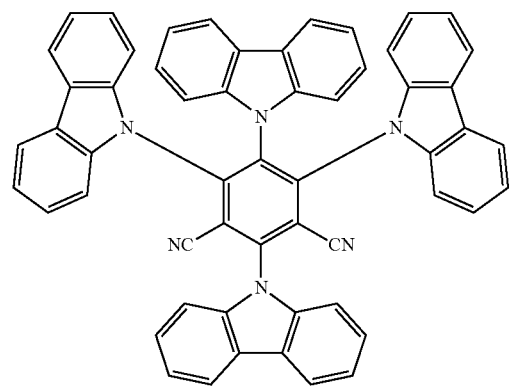
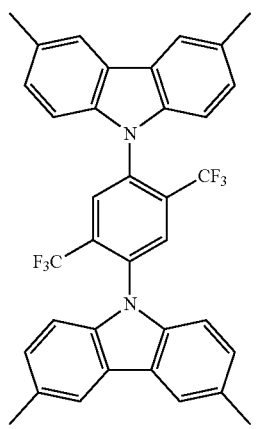
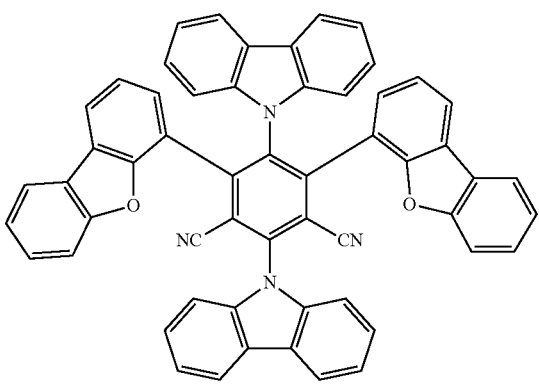
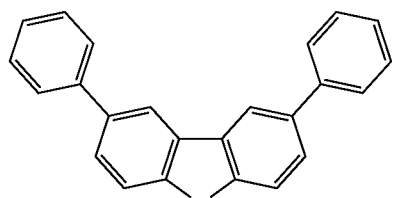
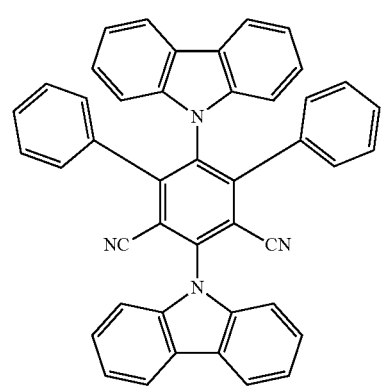
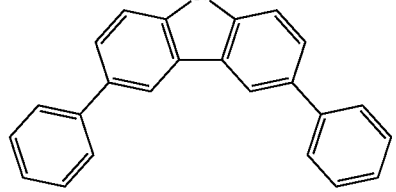

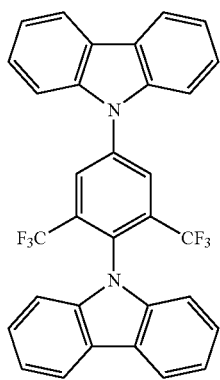
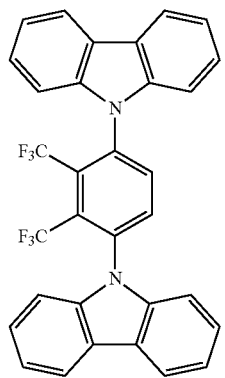
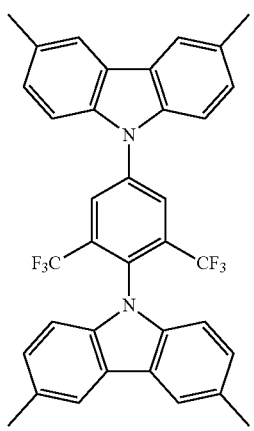
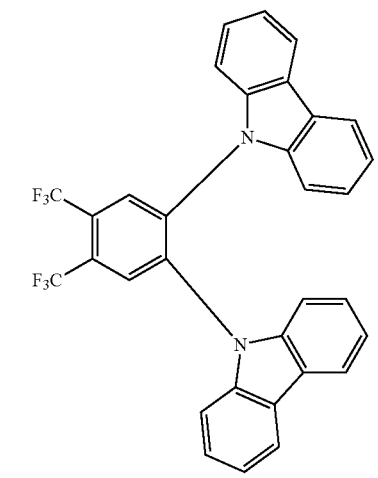
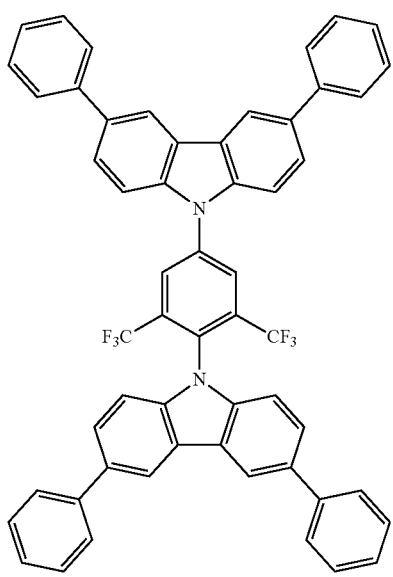
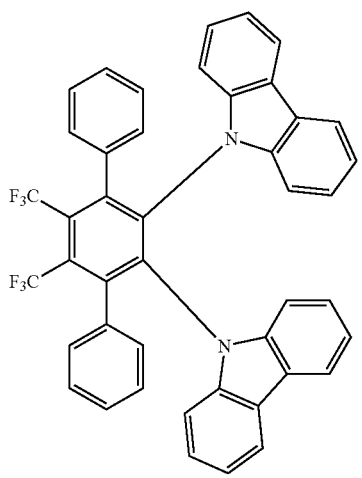

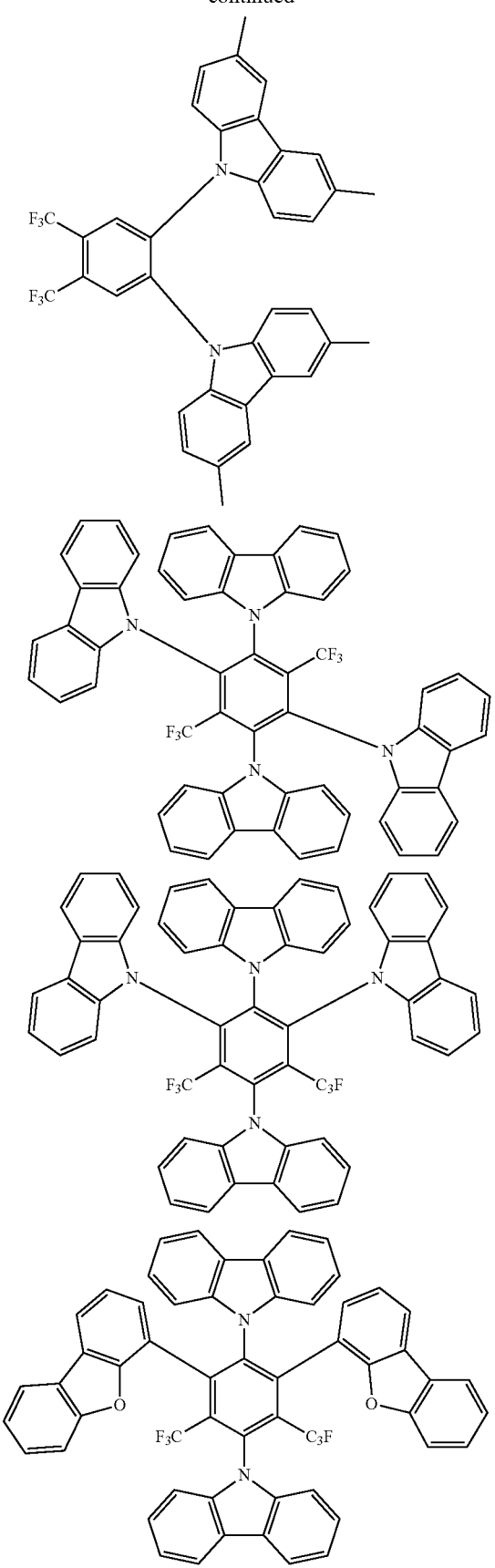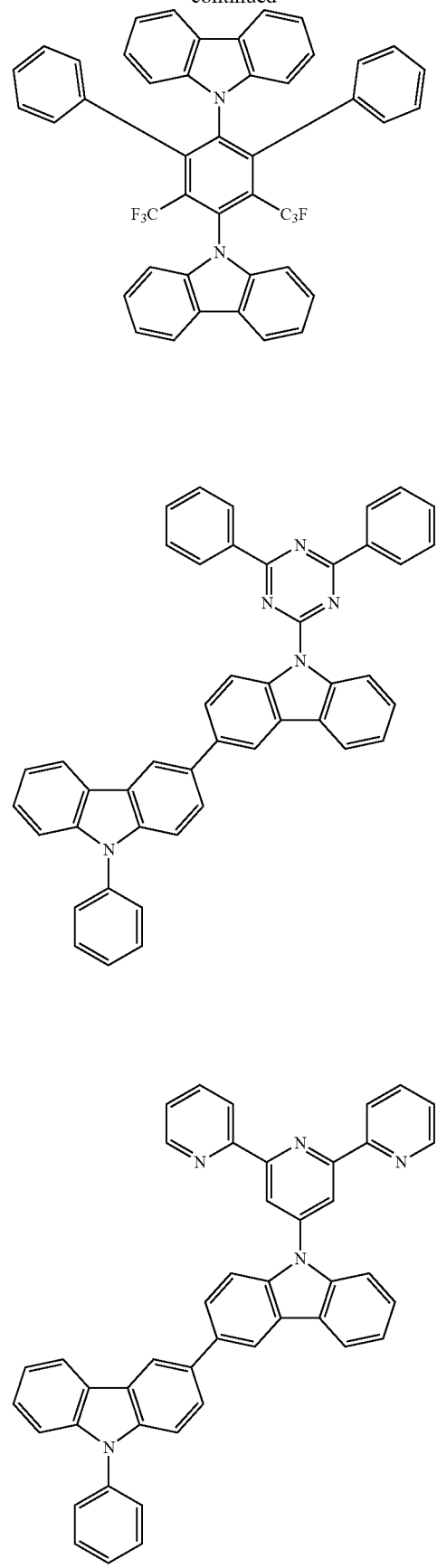

-continued
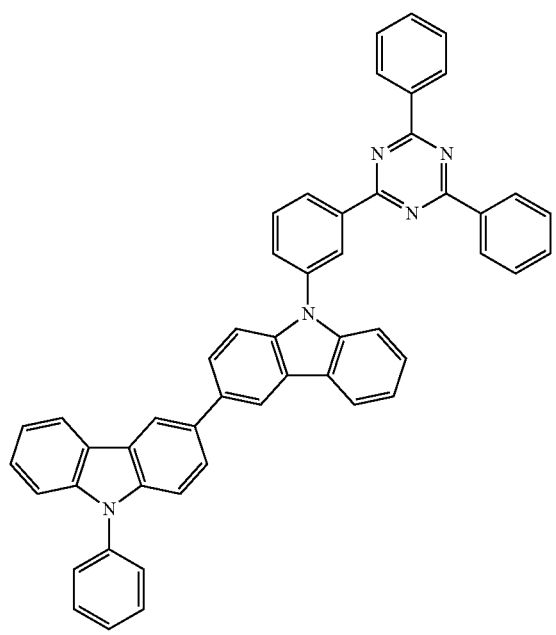
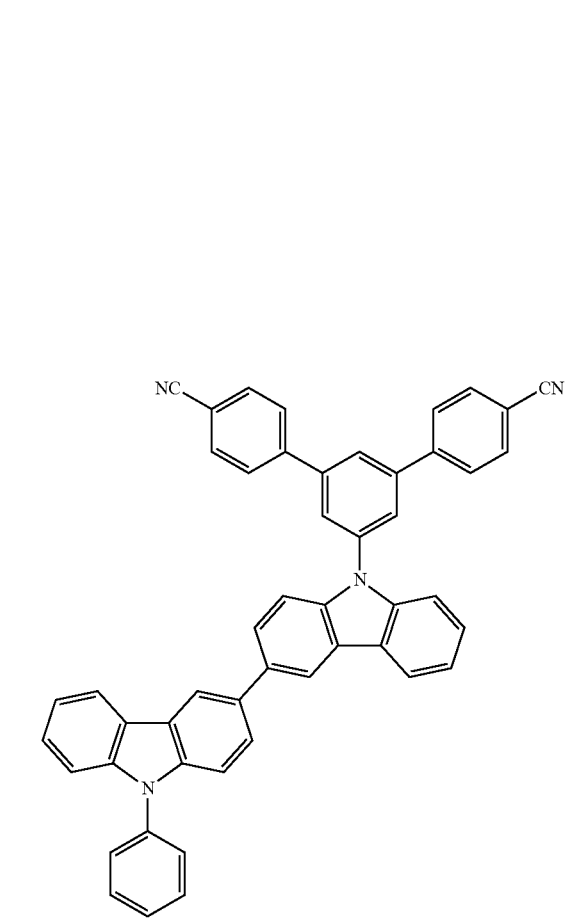
-continued
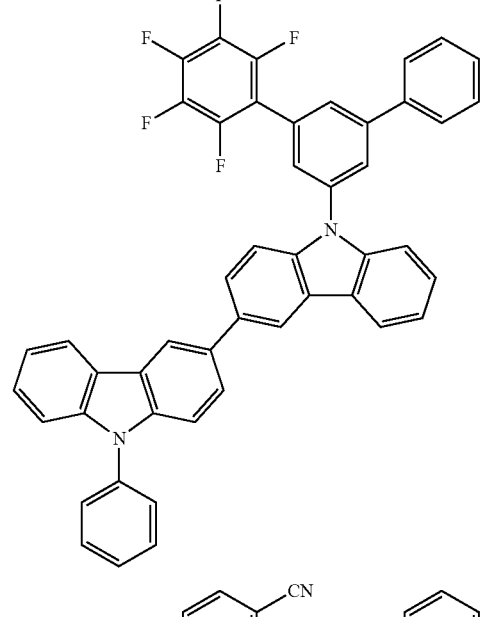
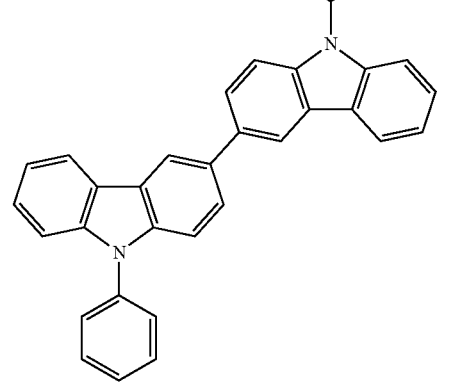
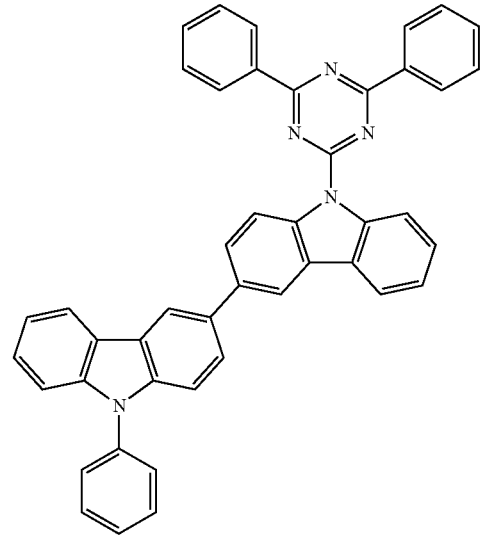

53
-continued
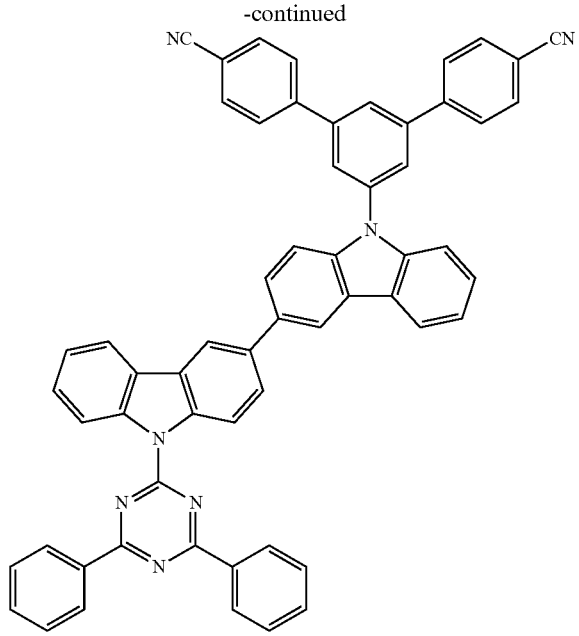
54
-continued
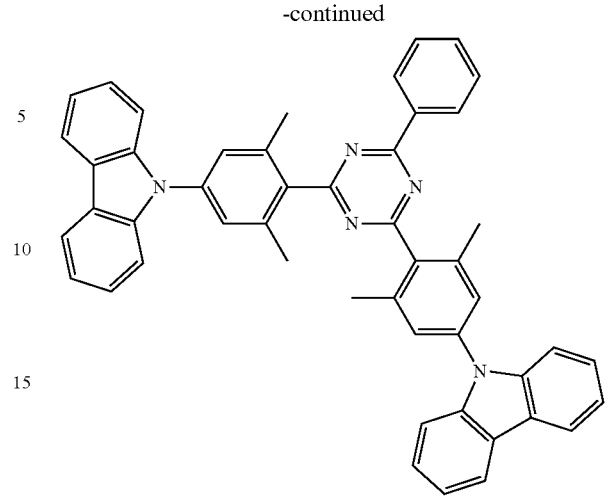
In one embodiment, the third compound may be selected from groups of Group III:
<Group III>
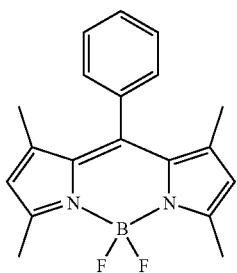
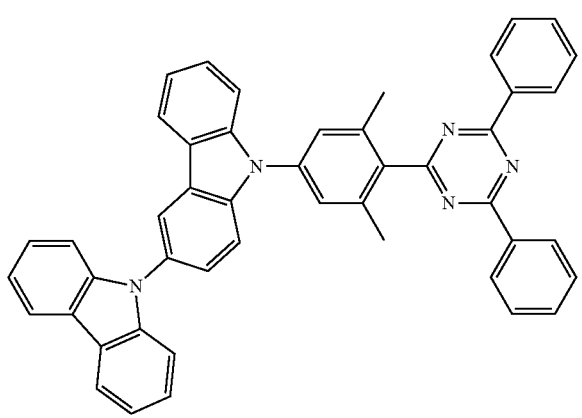
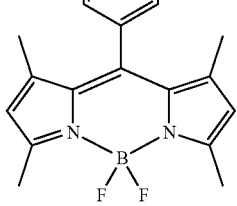
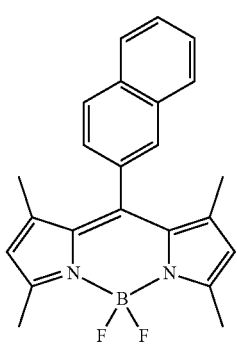

55
-continued
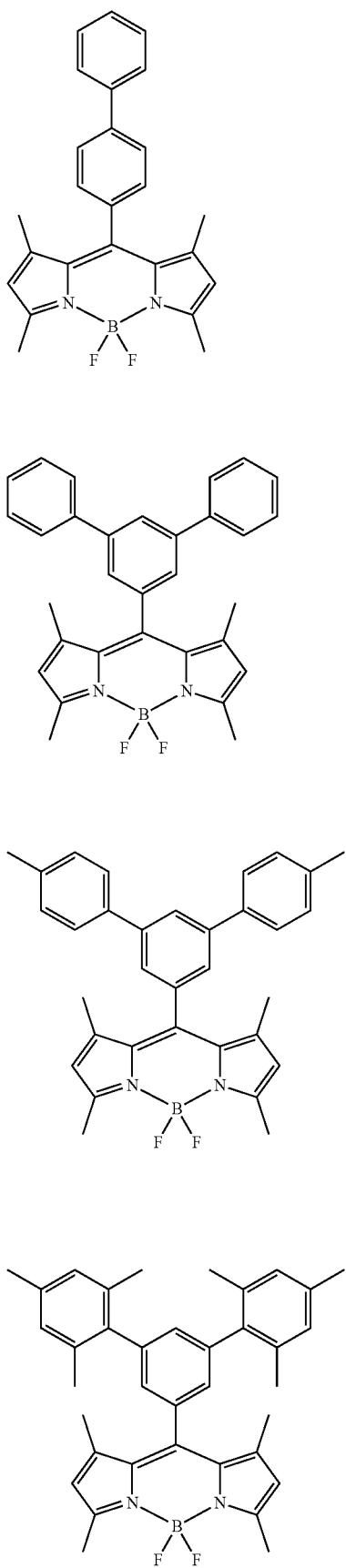
56
-continued
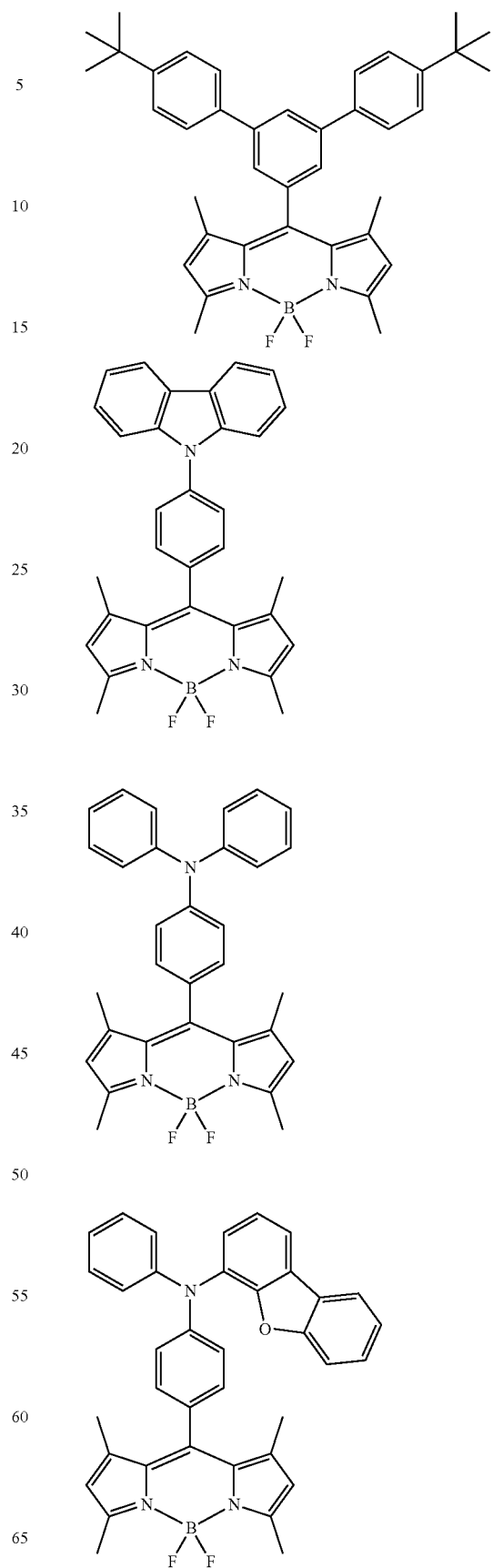

57
-continued
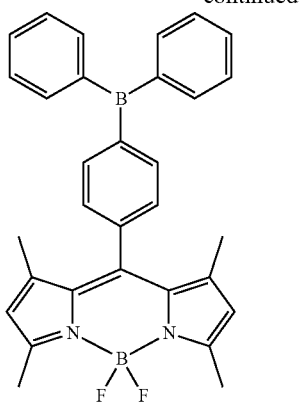
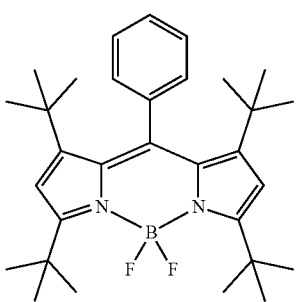
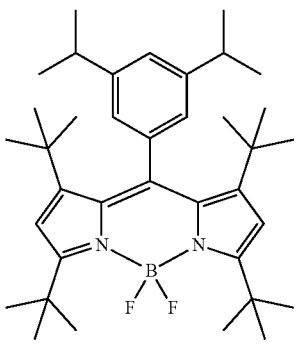
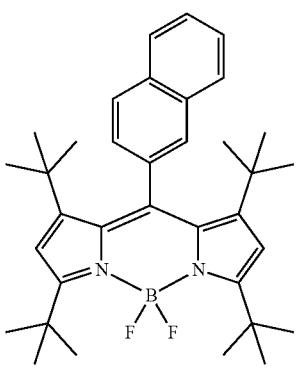
58
-continued
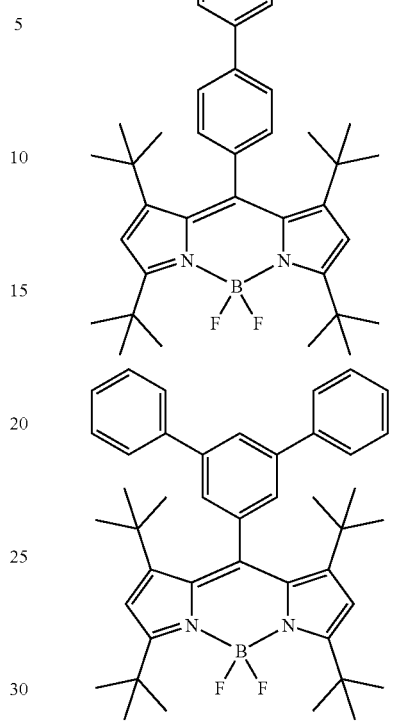
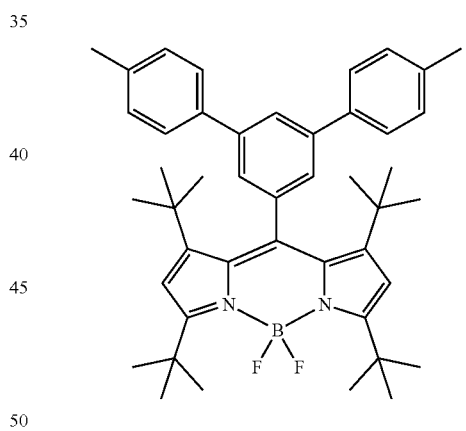
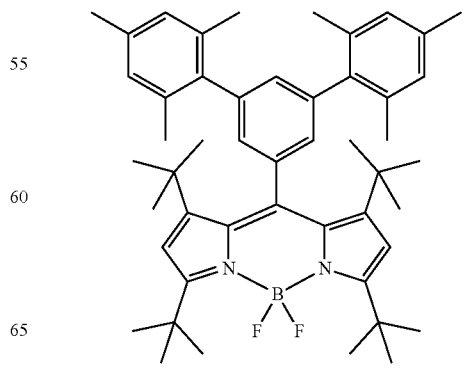

59
-continued
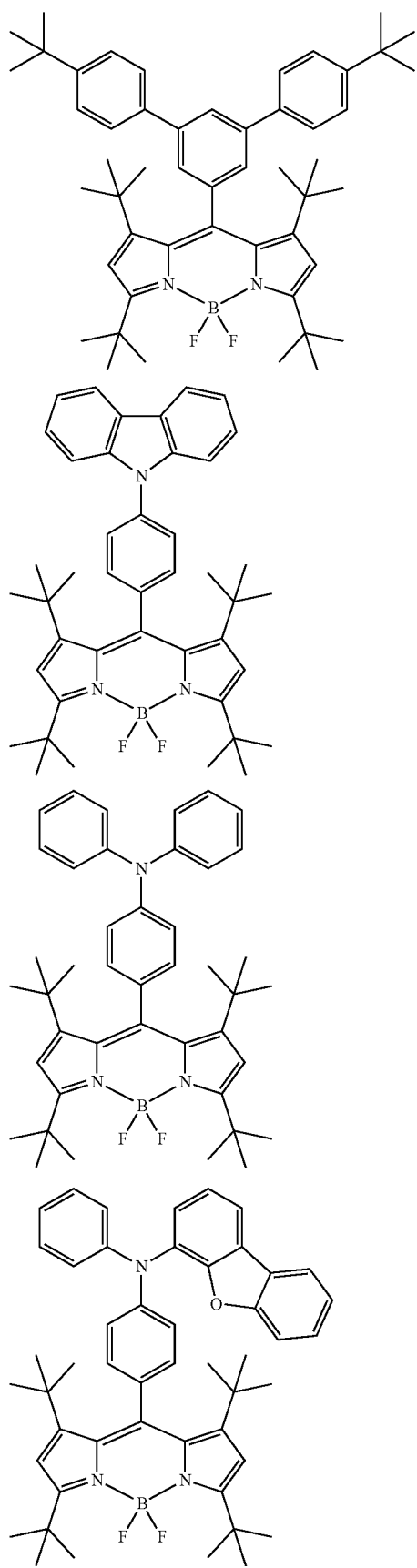
60
-continued
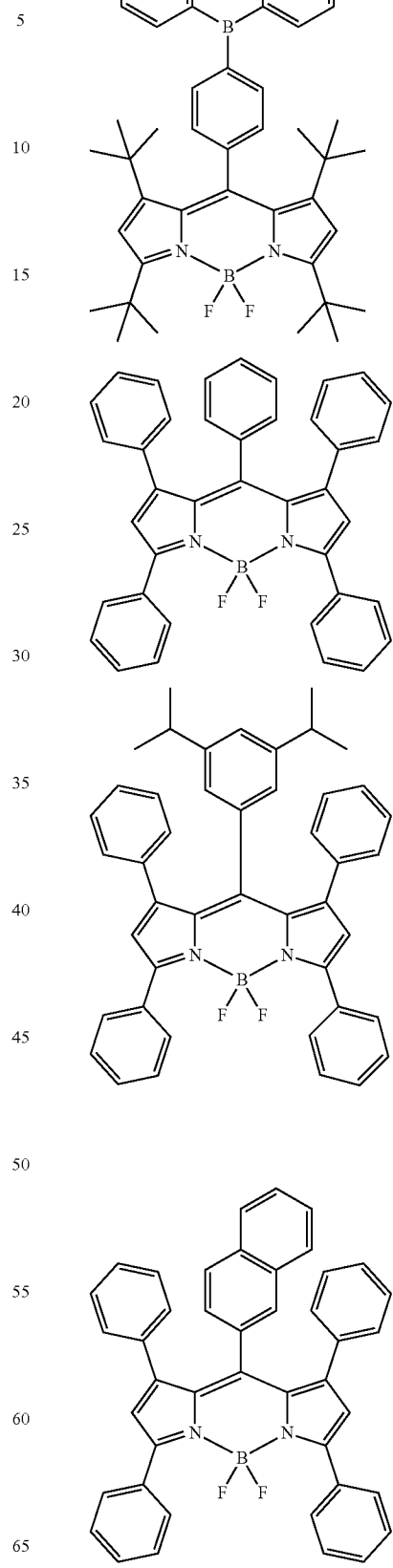

61
-continued
62
-continued
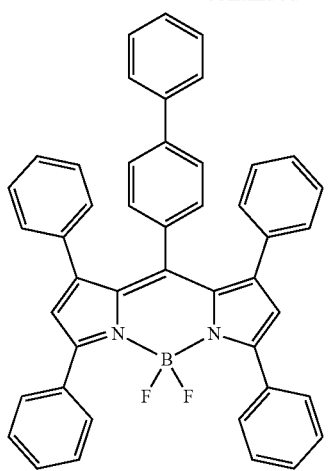
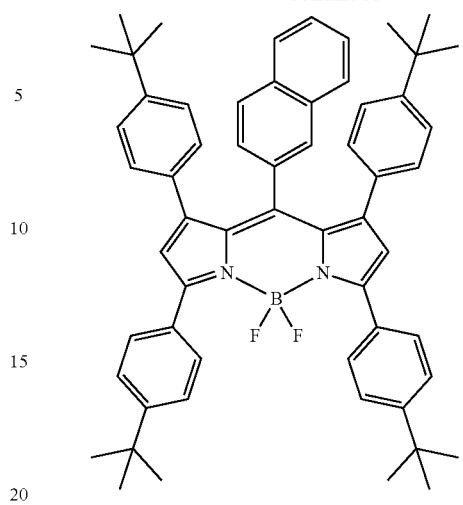
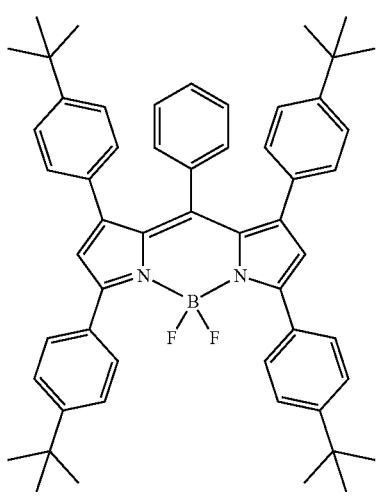
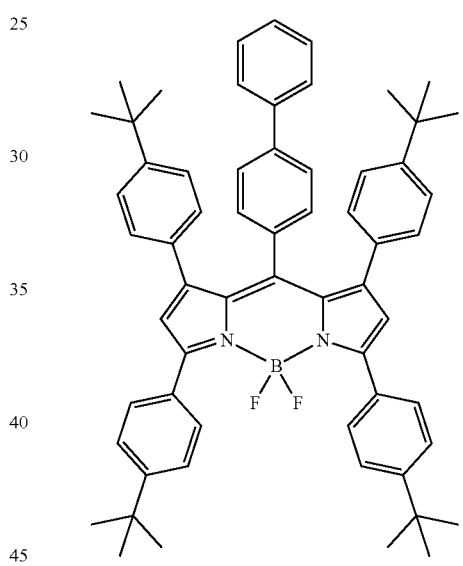
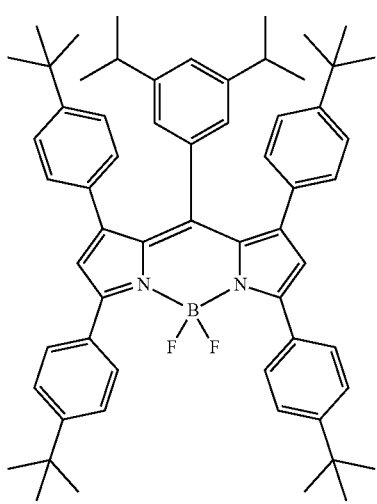
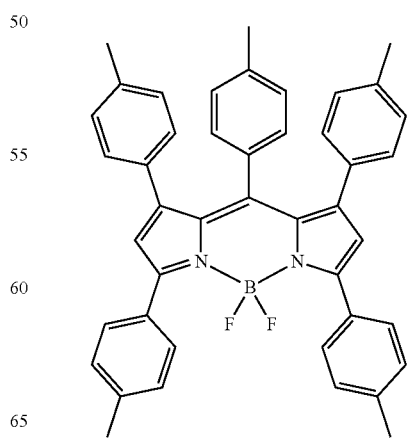

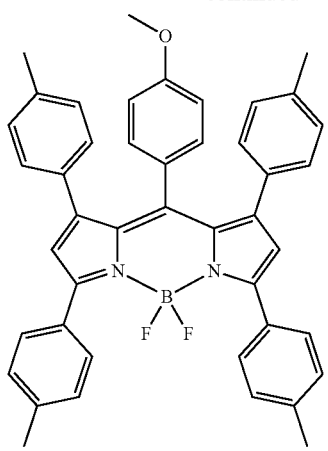
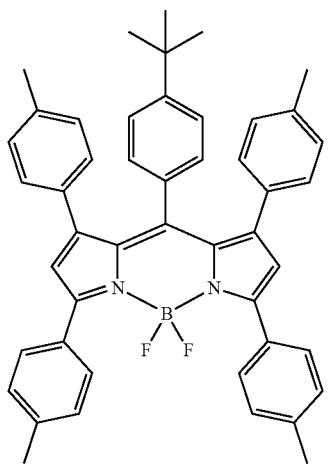
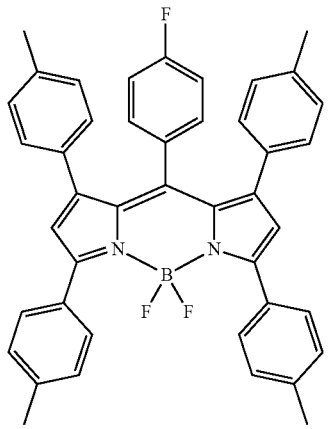
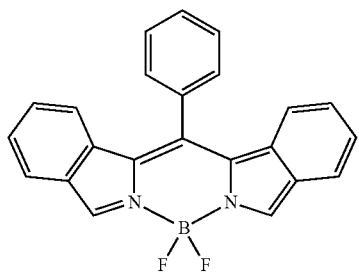
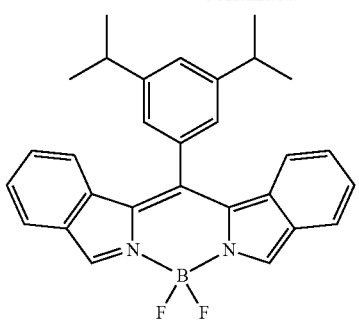
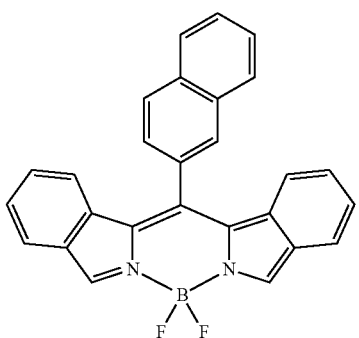
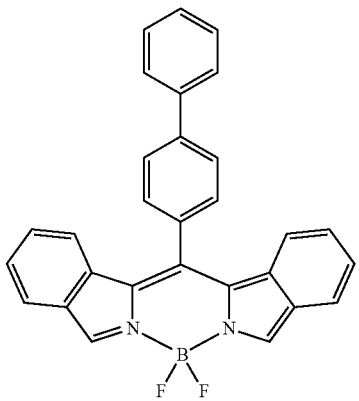
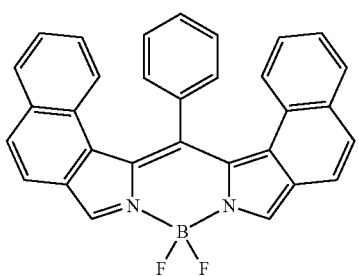
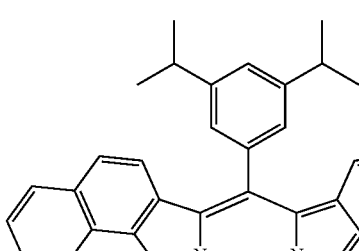

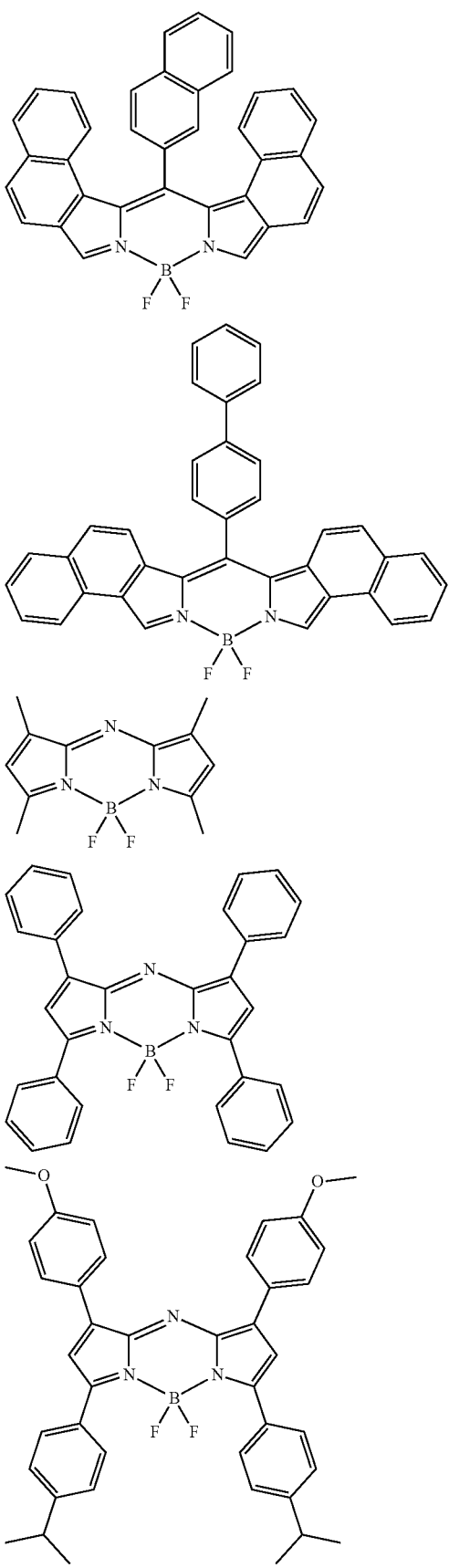

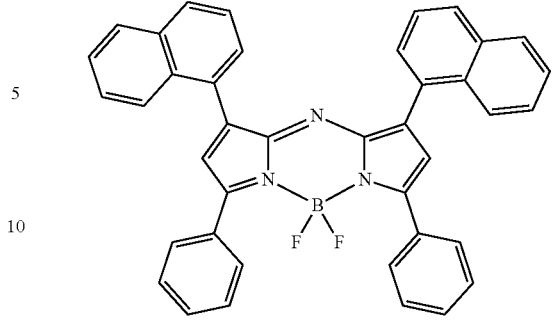

Because the first compound is a compound including both the electron transport moiety and the hole transport moiety, an organic light-emitting device including the first compound may improve charge balance of electrons and holes. Therefore, the organic light-emitting device may provide improved efficiency and/or improved lifespan.

The second compound may satisfy Condition 1:

$$\Delta E_{ST}(C2) \leq 0.3 \text{ eV}. \quad \text{Condition 1}$$

In Condition 1, $\Delta E_{ST}(C2)$ represents a difference between a lowest excitation singlet energy level of the second compound ($E_{S1}(C2)$) and a lowest excitation triplet energy level of the second compound ($E_{T1}(C2)$).

$E_{S1}(C2)$ and $E_{T1}(C2)$ may be evaluated by utilizing a density functional theory (DFT) method of Gaussian program structurally optimized at a level of B3LYP/6-31G(d,p).

When the second compound satisfies Condition 1, the second compound may have suitable (e.g., sufficiently high) reverse intersystem crossing (RISC) efficiency at room temperature.

The third compound may have a maximum emission wavelength in a range of about 520 nm to about 780 nm, but embodiments of the present disclosure are not limited thereto. For example, the third compound in the emission layer does not directly participate in the formation of excitons, and receives energy from formed excitons and emits red fluorescence.

The organic light-emitting device may emit fluorescence in a range of about 520 nm to about 780 nm, but embodiments of the present disclosure are not limited thereto.

Because the organic light-emitting device has an energy level enough to emit fluorescence from the third compound, the organic light-emitting device may have suitable (e.g., high) color purity. In addition, because the second compound has suitable (e.g., sufficiently high) RISC efficiency at room temperature, all the triplet energy of the first compound that may not participate in light emission may be transmitted to the third compound. Because it is possible to reduce or minimize excitons that disappear without participating in light emission, the efficiency of the organic light-emitting device may be improved.

The amount of the first compound in the emission layer may be in a range of about 60 wt % to about 90 wt % based on the total weight of the emission layer, but embodiments of the present disclosure are not limited thereto.

The amount of the second compound in the emission layer may be in a range of about 10 wt % to about 40 wt % based on the total weight of the emission layer, but embodiments of the present disclosure are not limited thereto.

The amount of the third compound in the emission layer may be in a range of about 0.5 wt % to about 5 wt % based on the total weight of the emission layer, but embodiments of the present disclosure are not limited thereto.

When the first compound, the second compound, and the third compound are within these ranges, an organic light-emitting device having both improved efficiency and improved lifespan may be provided.

In one embodiment, the emission layer may include or consist of (i.e., include only) the first compound, the second compound, and the third compound, but embodiments of the present disclosure are not limited thereto.

In one embodiment, the organic layer may further include a hole transport region; the hole transport region may be disposed between the first electrode and the emission layer; the hole transport region may include a first hole transport layer and a second hole transport layer; the first hole transport layer may include a first hole transport material; the second hole transport layer may include a second hole transport material; and the first hole transport material and the second hole transport material may be different from each other.

Because the organic light-emitting device includes the first hole transport layer and the second hole transport layer, hole injection from the anode may be facilitated, and the lifespan and the efficiency of the organic light-emitting device may be improved.

For example, the first hole transport material may be represented by Formula 201:

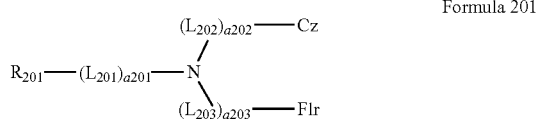

Formula 201

In Formula 201, $L_{201}$ to $L_{203}$ may each independently be selected from a substituted or unsubstituted $C_5$-$C_{60}$ carbocyclic group, and a substituted or unsubstituted $C_1$-$C_{60}$ heterocyclic group, a201 to a203 may each independently be selected from 0, 1, 2, and 3, Cz may be a substituted or unsubstituted carbazolyl group, Flr may be selected from a substituted or unsubstituted fluorenyl group and a substituted or unsubstituted a spiro-bifluorenyl group, and $R_{201}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 201, $L_{201}$ to $L_{203}$ may each independently be selected from a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

For example, in Formula 201, a201 to a203 may each independently be selected from 0, 1, and 2, but embodiments of the present disclosure are not limited thereto.

For example, in Formula 201, Cz may be selected from:
a carbazolyl group; and
a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ are the same as described above with respect to $L_{201}$ to $L_{203}$, but embodiments of the present disclosure are not limited thereto.

In one embodiment, in Formula 201, Cz may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

For example, in Formula 201, FIr may be selected from:

a fluorenyl group and a spiro-bifluorenyl group; and a fluorenyl group and a spiro-bifluorenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ are the same as described above with respect to $L_{201}$ to $L_{203}$, but embodiments of the present disclosure are not limited thereto.

In one embodiment, in Formula 201, FIr may be selected from:

a fluorenyl group and a spiro-bifluorenyl group; and a fluorenyl group and a spiro-bifluorenyl group, each substituted with at least one selected from a fluorenyl group and a spiro-bifluorenyl group deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

For example, in Formula 201, $R_{201}$ may be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, $—Si(Q_{31})(Q_{32})(Q_{33})$, and $—N(Q_{31})(Q_{32})$, and $Q_{31}$ to $Q_{33}$ are the same as described above with respect to $L_{201}$ to $L_{203}$.

In one embodiment, the first hole transport material may be selected from groups of Group IV, but embodiments of the present disclosure are not limited thereto:

<Group IV>

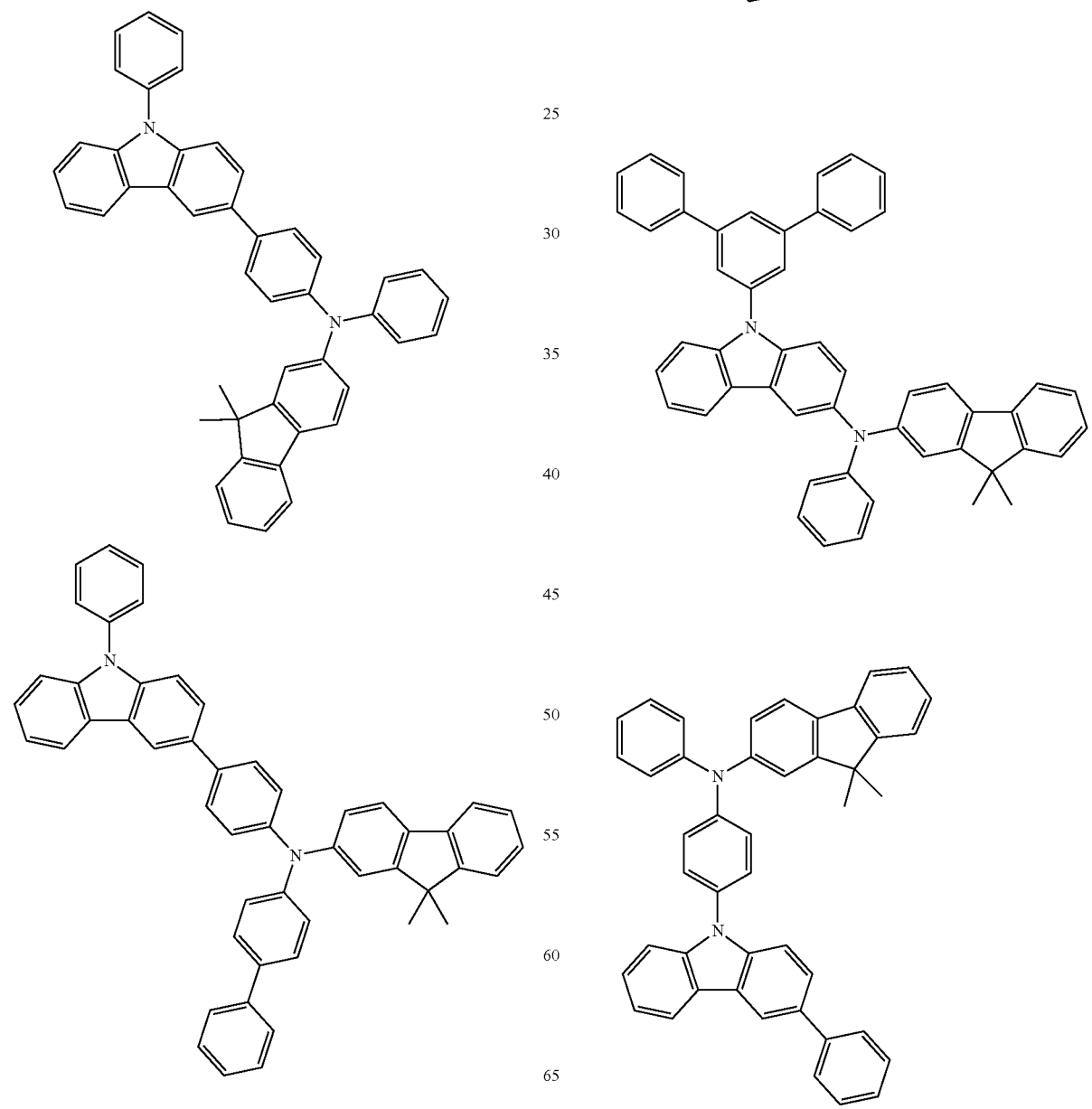

73
-continued
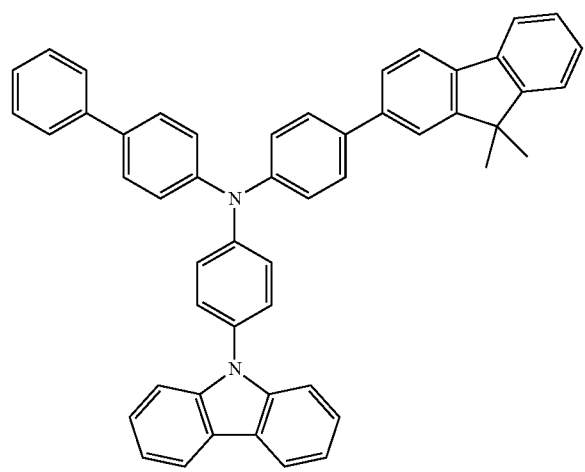
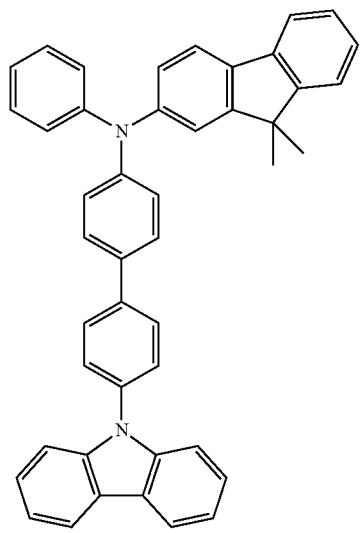
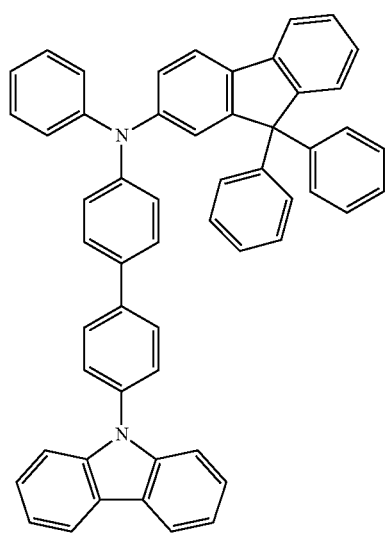
74
-continued
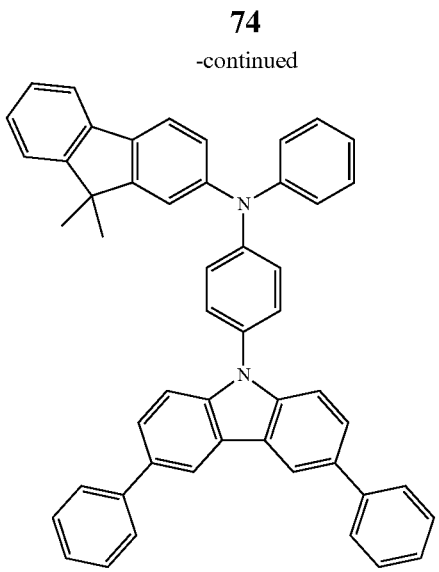
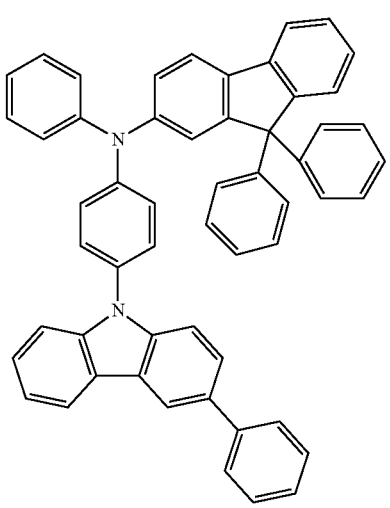
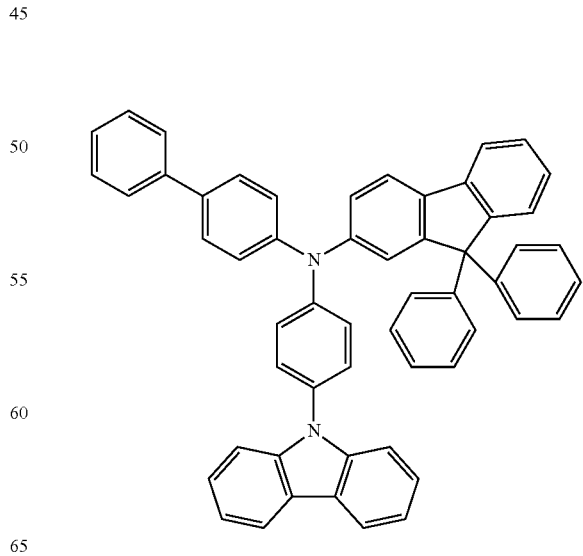

75
-continued
76
-continued
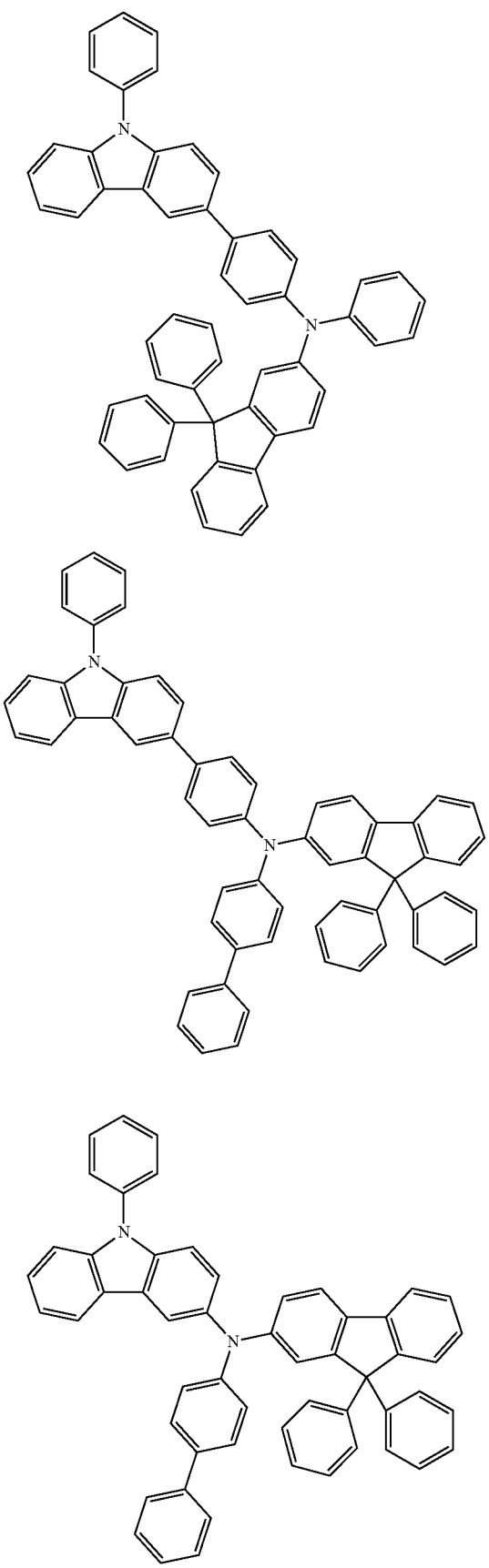
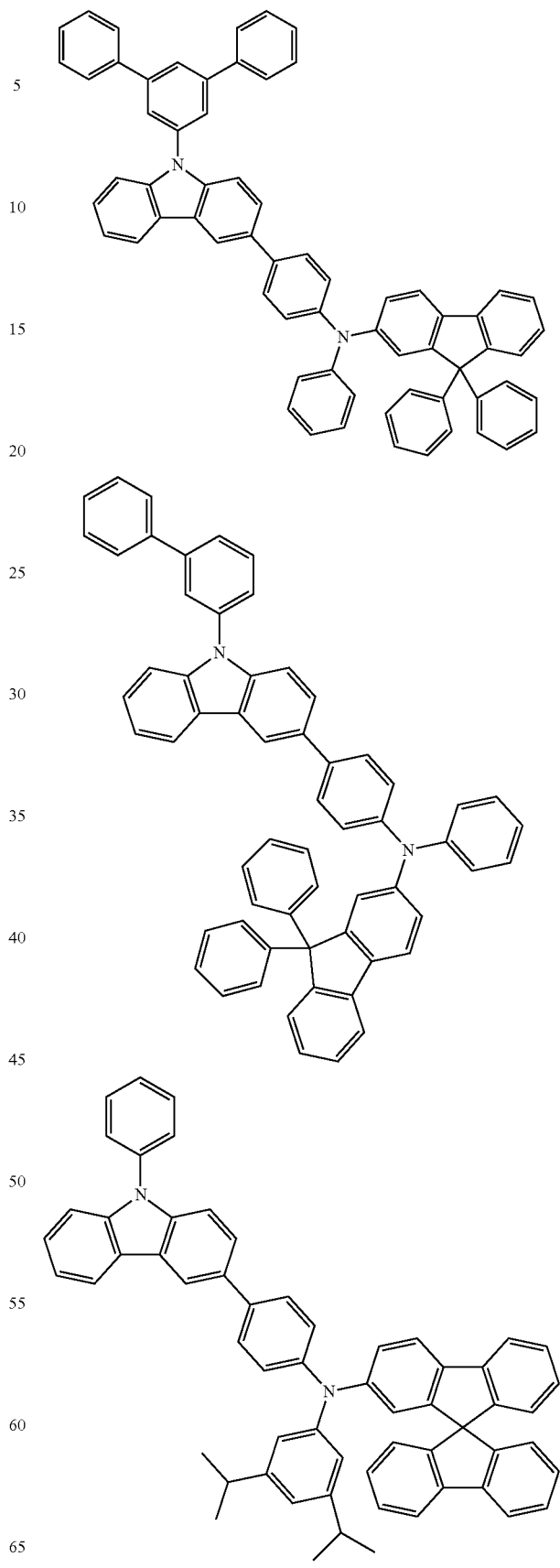

77
-continued
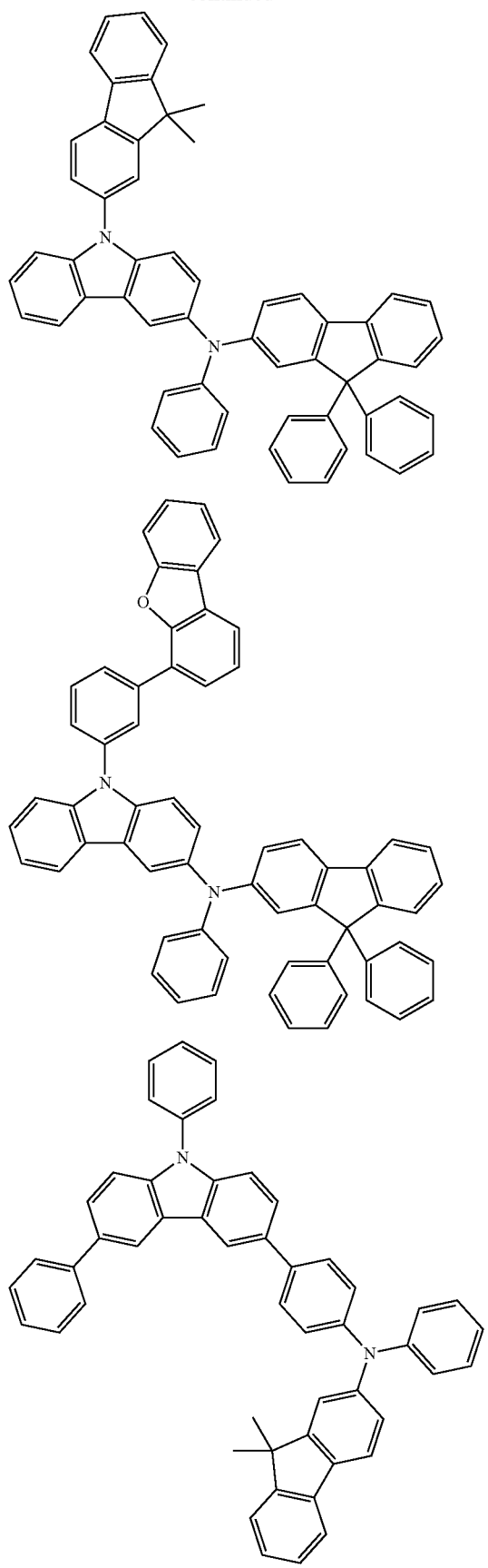
78
-continued
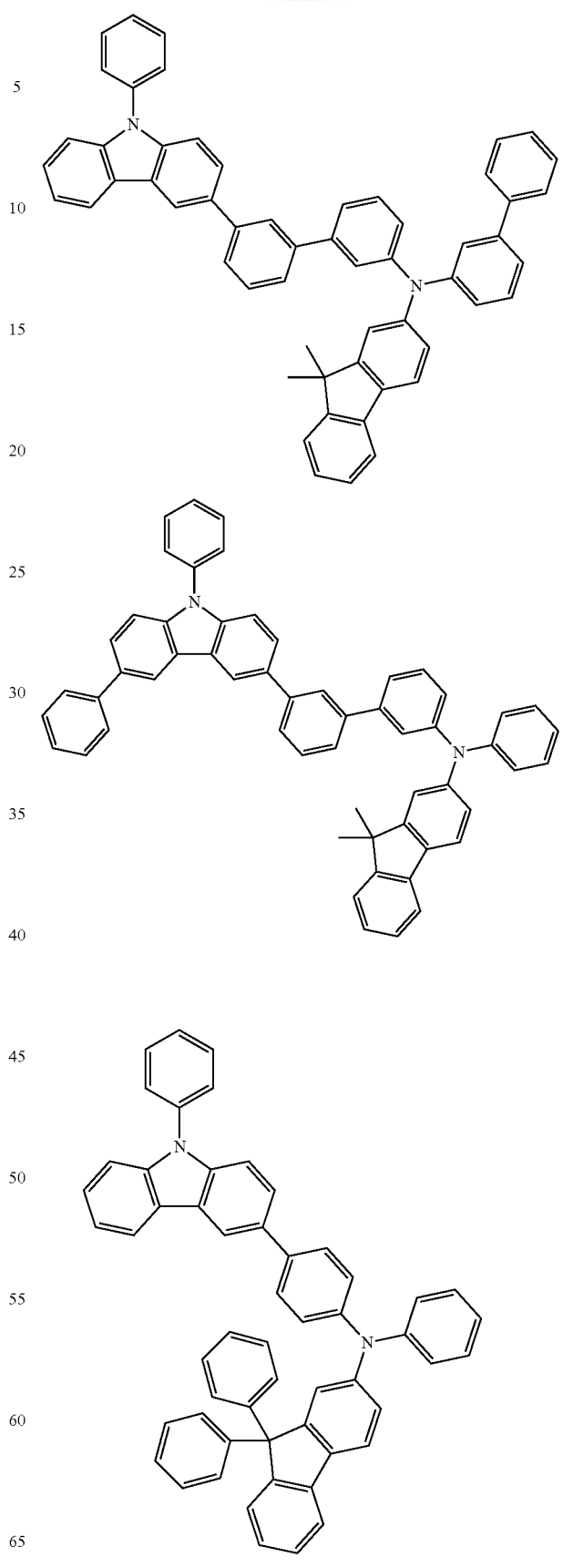

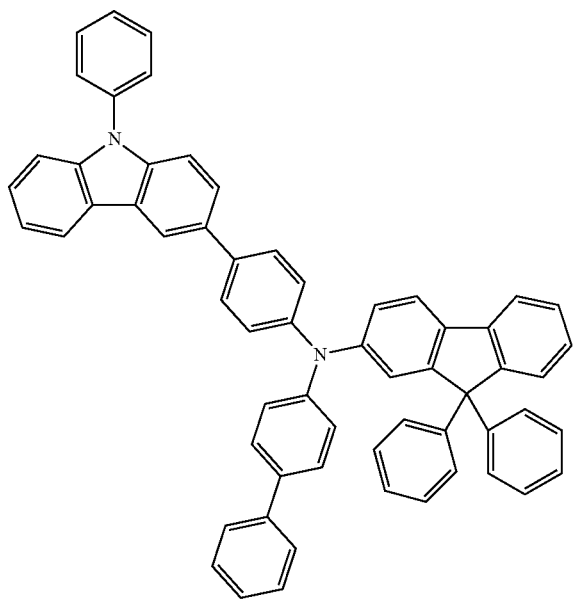
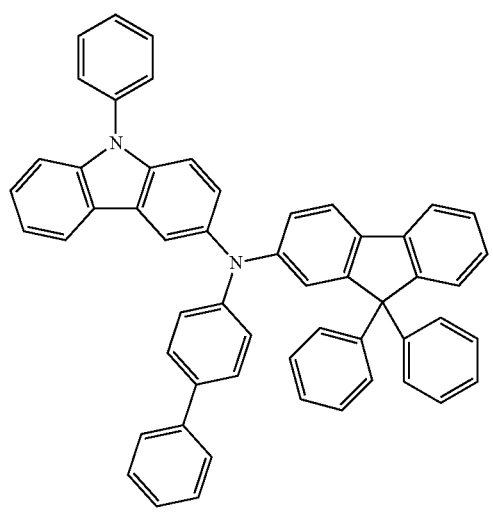
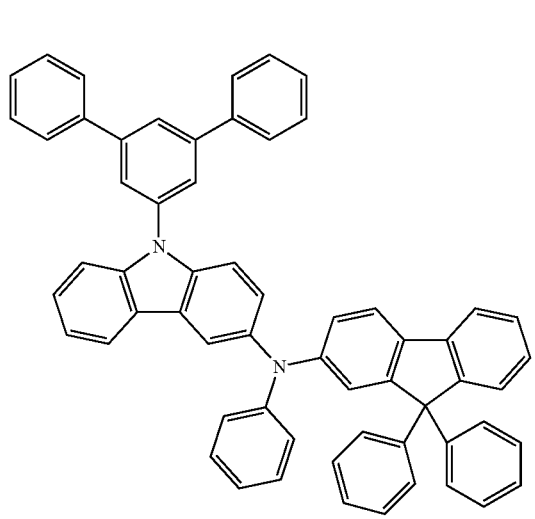
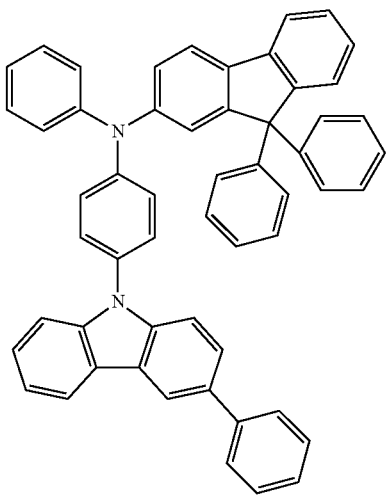
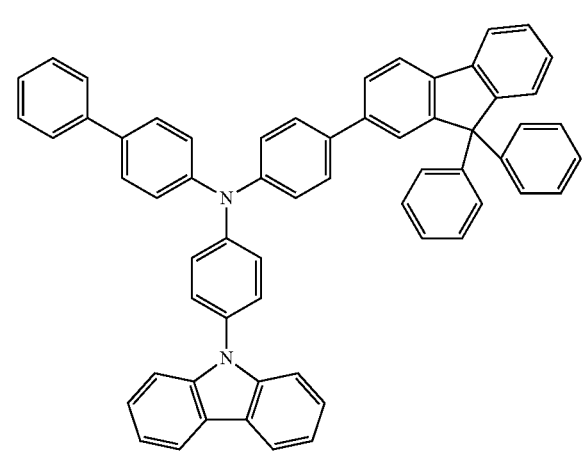
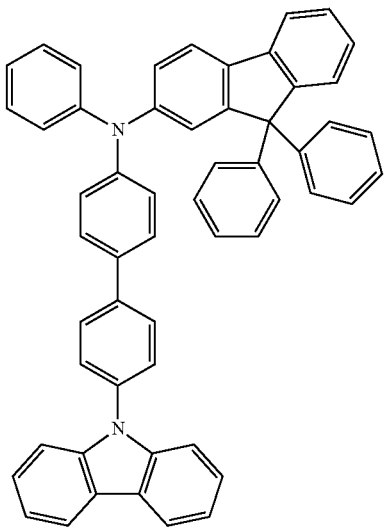

81
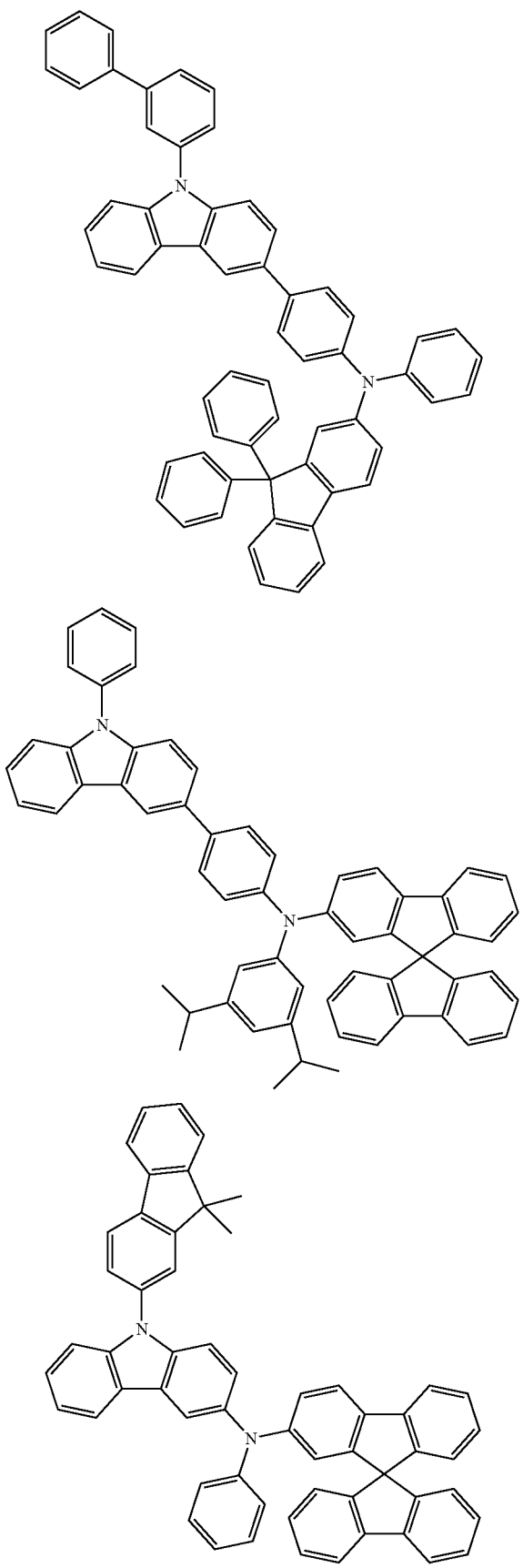 [SMILES: c1ccc(-c2cccc(-n3c4ccccc4c4cc(-c5ccc(N(c6ccccc6)c6ccc7c(c6)C(c6ccccc6)(c6ccccc6)c6ccccc6-7)cc5)ccc43)c2)cc1 ; CC(C)c1cc(C(C)C)cc(N(c2ccc(-c3ccc4c(c3)c3ccccc3n4-c3ccccc3)cc2)c2ccc3c(c2)C2(c4ccccc4-c4ccccc42)c2ccccc2-3)c1 ; CC1(C)c2ccccc2-c2ccc(-n3c4ccccc4c4cc(N(c5ccccc5)c5ccc6c(c5)C(c5ccccc5)(c5ccccc5)c5ccccc5-6)ccc43)cc21]
82
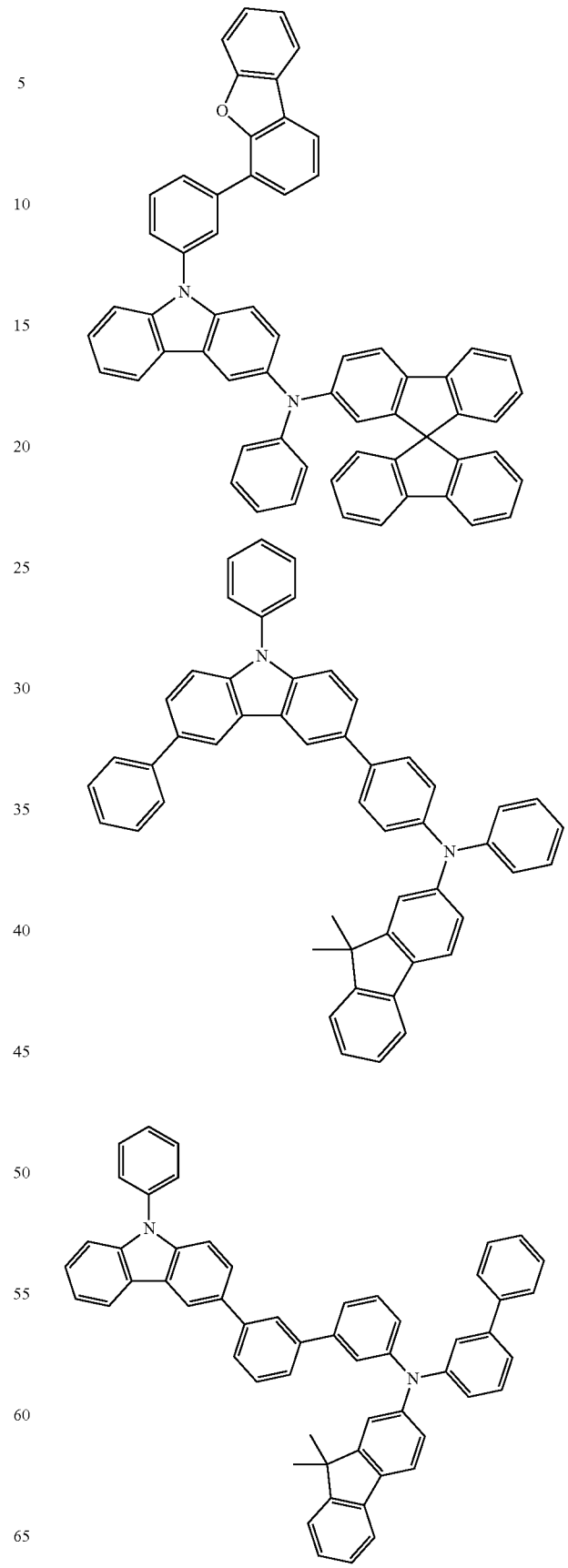

-continued

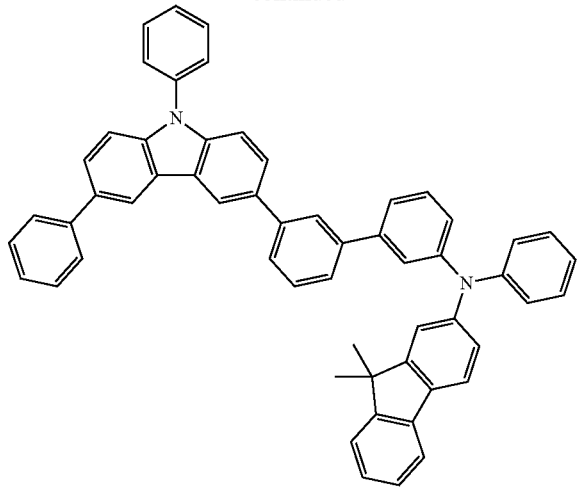

For example, the second hole transport material may be represented by Formula 202:

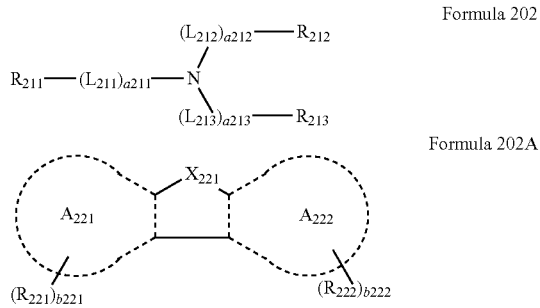

Formula 202

Formula 202A

In Formulae 202 and 202A, $L_{211}$ to $L_{213}$ may each independently be selected from a substituted or unsubstituted $C_5$-$C_{60}$ carbocyclic group, and a substituted or unsubstituted $C_1$-$C_{60}$ heterocyclic group a211 to a213 may each independently be selected from 0, 1, 2, and 3, $R_{211}$ to $R_{213}$ may each independently be selected from a group represented by Formula 202A, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from $R_{211}$ to $R_{213}$ may be a group represented by Formula 202A, $X_{221}$ may be selected from $N(R_{223})$, $C(R_{223})(R_{224})$, O, and S, $A_{221}$ and $A_{222}$ may each independently be selected from i) a 6-membered ring, ii) a condensed ring in which two or more 6-membered rings are condensed with each other, and iii) a condensed ring in which at least one 6-membered ring and at least one 5-membered ring are condensed with each other, $R_{221}$ to $R_{224}$ may each independently be selected from a binding site (e.g., to a respective $L_{211}$ to $L_{213}$), hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{00}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein one selected from $R_{221}$ to $R_{224}$ may be a binding site, and b221 and b222 may each independently be selected from 1, 2, 3, 4, 5, and 6.

For example, $L_{211}$ to $L_{213}$ in Formula 202 may each independently be the same as defined in connection with $L_{201}$.

For example, a211 to a213 in Formula 202 may each independently be the same as defined in connection with a201.

For example, in Formula 202, $R_{211}$ to $R_{213}$ may each independently be selected from:

a group represented by Formula 202A, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spirobifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), at least one selected from $R_{211}$ to $R_{213}$ may be a group represented by Formula 202A, and $Q_{31}$ to $Q_{33}$ are the same as described above with respect to $L_{201}$ to $L_{203}$.

For example, in Formula 202A, $X_{221}$ may be selected from C($R_{223}$)($R_{224}$) and O.

For example, in Formula 202A, the 6-membered ring may be selected from a benzene group, a pyridine group, a pyrimidine group, a pyridazine group, and a triazine group, and the 5-membered ring may be selected from a furan group, a thiophene group, a pyrrole group, and a cyclopentadiene group, but embodiments of the present disclosure are not limited thereto.

In one embodiment, in Formula 202A, $A_{221}$ and $A_{222}$ may each independently be selected from a benzene group, a naphthalene group, a pyridine group, a pyrimidine group, a pyridazine group, a triazine group, a quinoline group, an isoquinoline group, a fluorene group, a carbazole group, a dibenzothiophene group, and a dibenzofuran group, but embodiments of the present disclosure are not limited thereto.

For example, in Formula 202, $R_{221}$ to $R_{224}$ may each independently be selected from:

a binding site, hydrogen, deuterium, —F, —Cl, —Br, —I, a cyano group, a $C_1$-$C_{20}$ alkyl group, and a $C_1$-$C_{20}$ alkoxy group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group; and a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from deuterium, —F, —Cl, —Br, —I, a cyano group, a $C_1$-$C_{20}$ alkyl group, a $C_1$-$C_{20}$ alkoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, and one selected from $R_{221}$ to $R_{224}$ may be a binding site, but embodiments of the present disclosure are not limited thereto.

In one embodiment, in Formula 202, $R_{221}$ to $R_{224}$ may each independently be selected from:

a binding site, hydrogen, deuterium, —F, —Cl, —Br, —I, a cyano group, a methyl group, an ethyl group, an n-propyl group, an isopropyl group, an n-butyl group, an isobutyl group, a sec-butyl group, a tert-butyl group, a methoxy group, an ethoxy group, a propoxy group, and a butoxy group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group; and a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group, each substituted with at least one selected from deuterium, —F, —Cl, —Br, —I, a cyano group, a methyl group, an ethyl group, an n-propyl group, an isopropyl group, an n-butyl group, an isobutyl group, a sec-butyl group, a tert-butyl group, a methoxy group, an ethoxy group, a propoxy group, a butoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, and a dibenzothiophenyl group, and one selected from $R_{221}$ to $R_{224}$ may be a binding site, but embodiments of the present disclosure are not limited thereto.
In embodiment, the second hole transport material may be selected from groups of Group V, but embodiments of the present disclosure are not limited thereto:
<Group V>
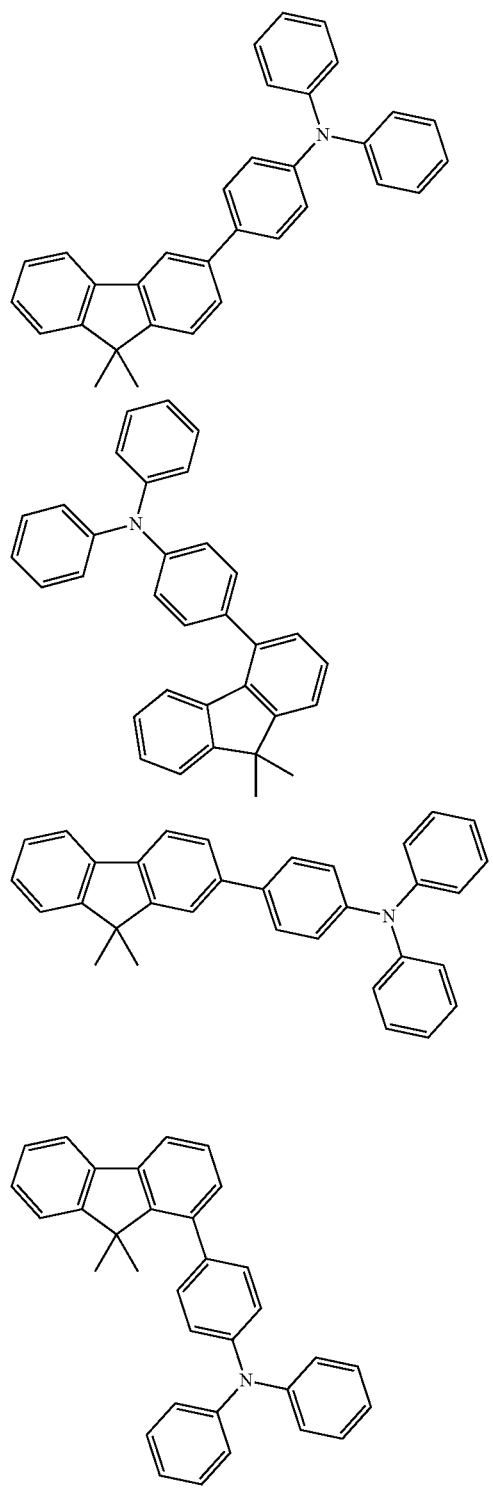
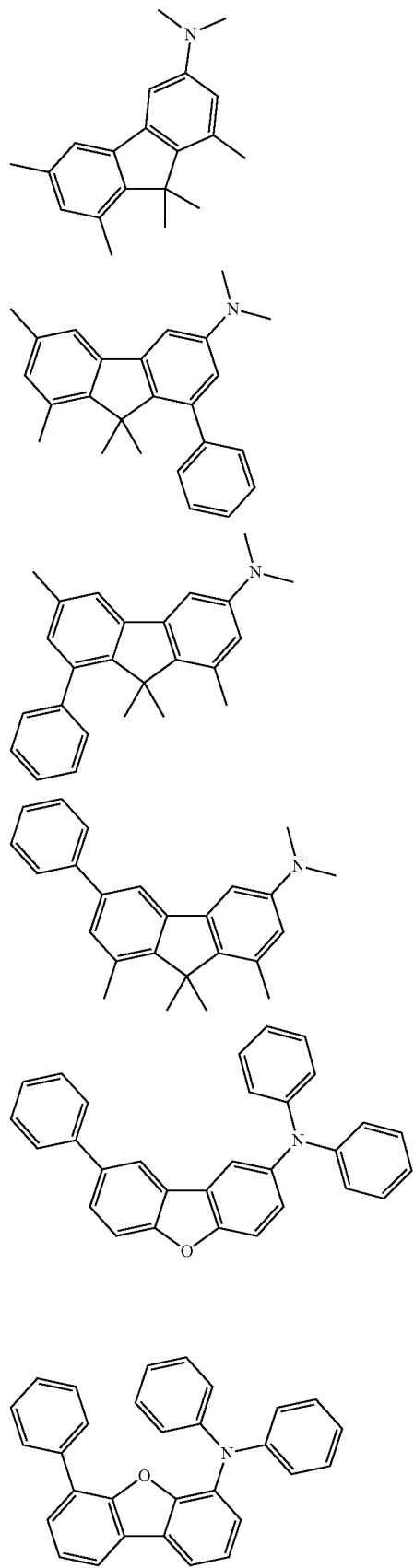

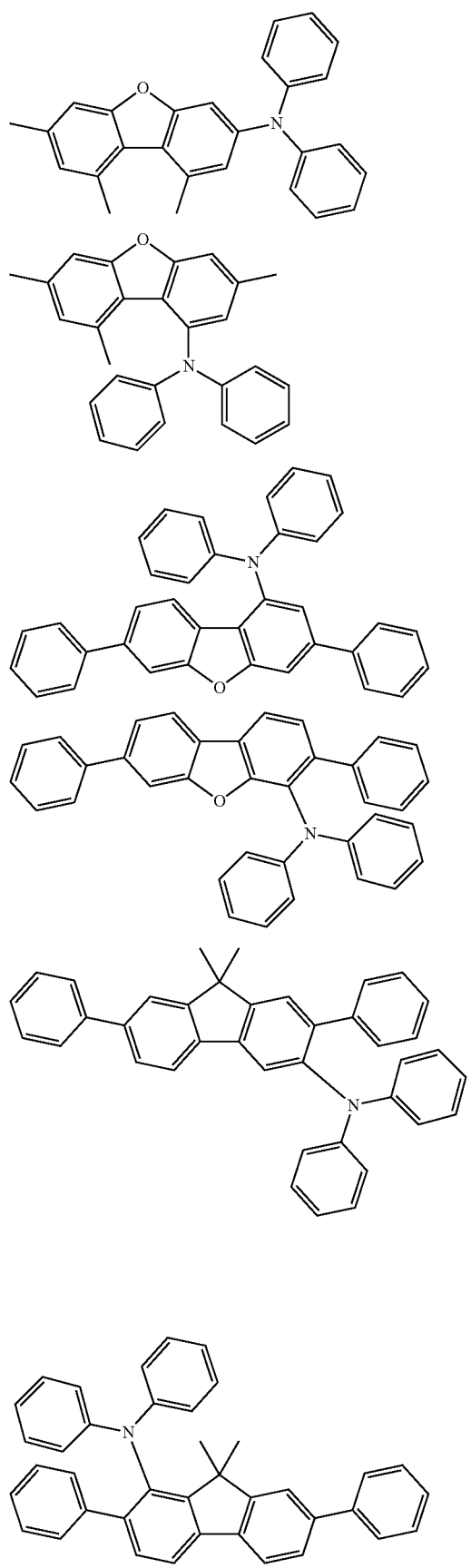
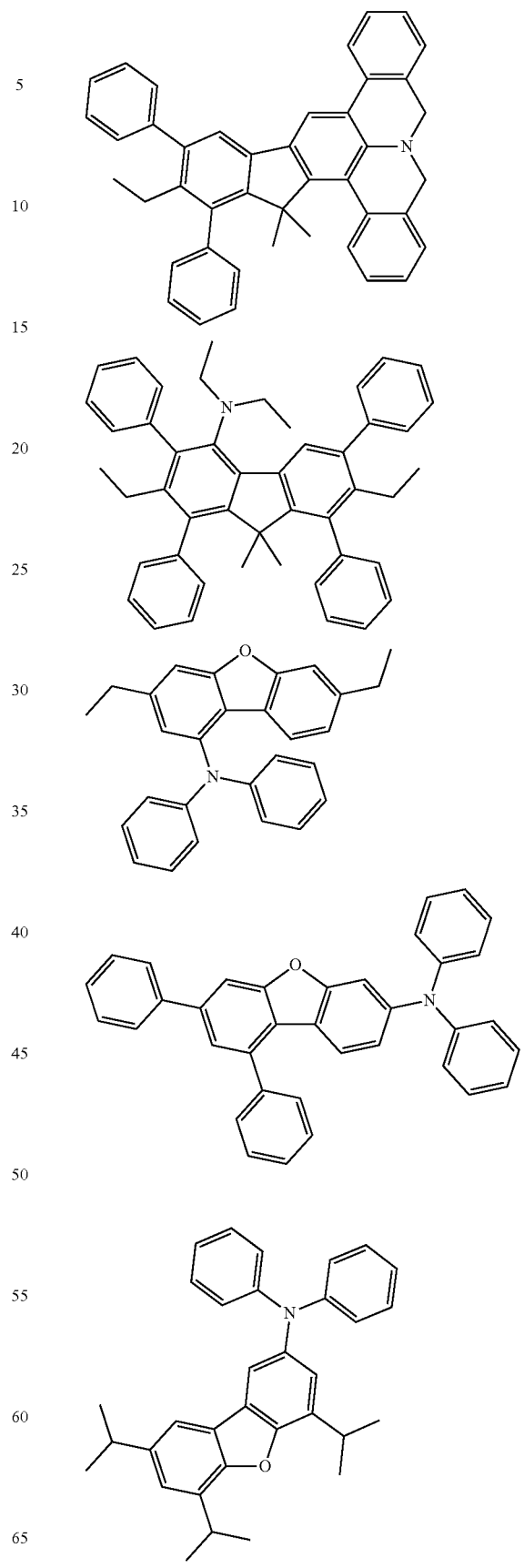

91
-continued
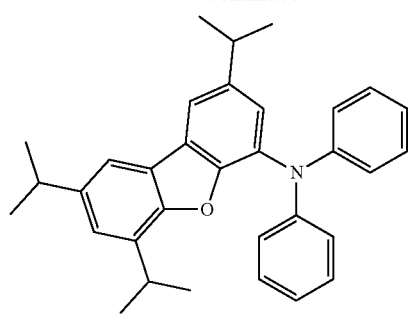
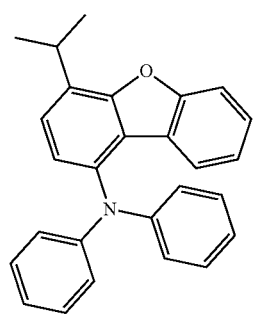
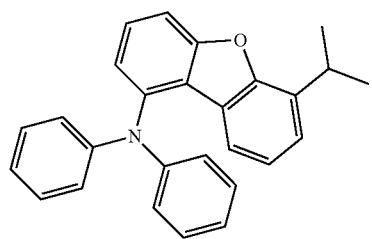
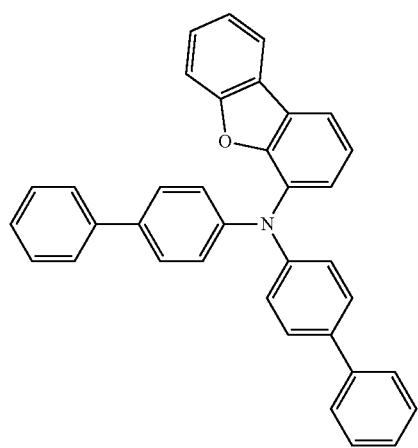
92
-continued
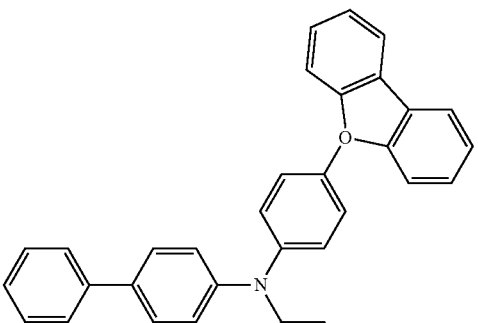
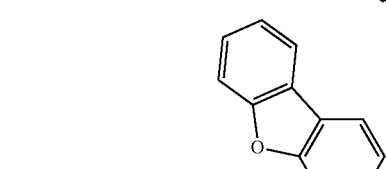
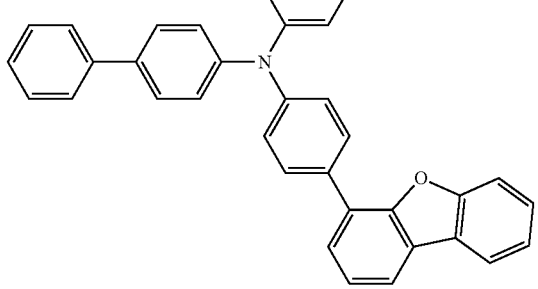

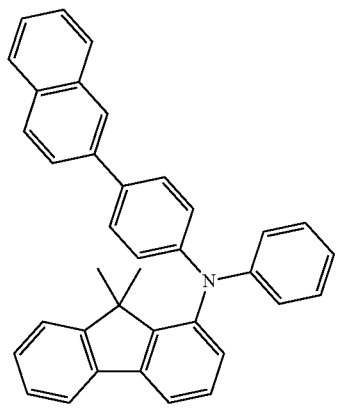
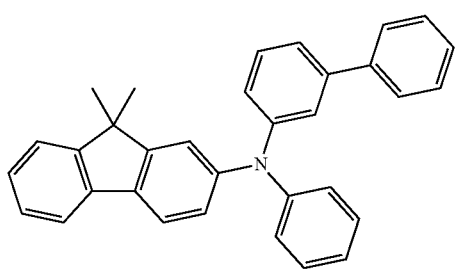
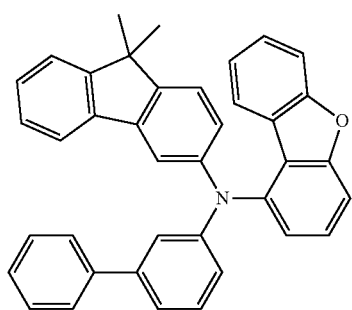
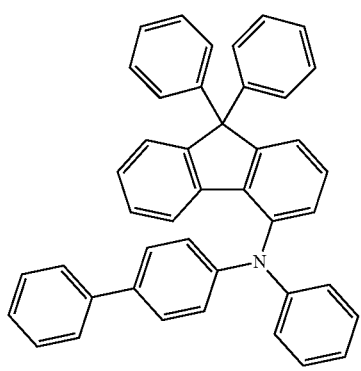
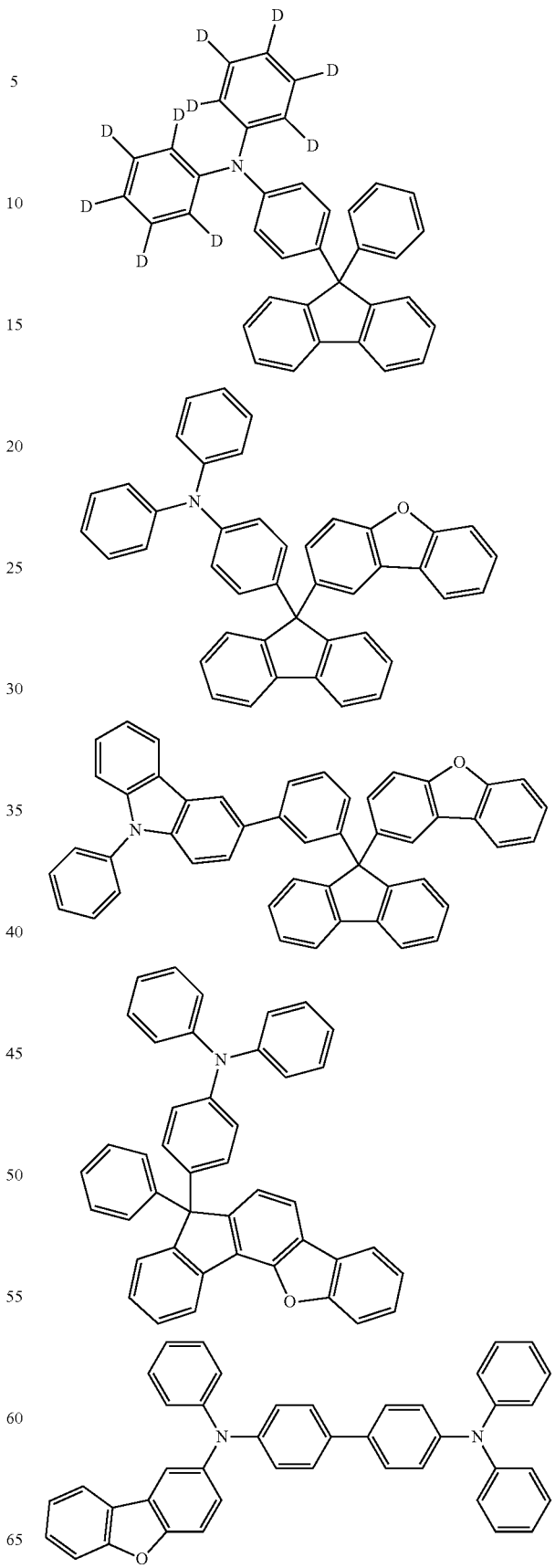

95
-continued
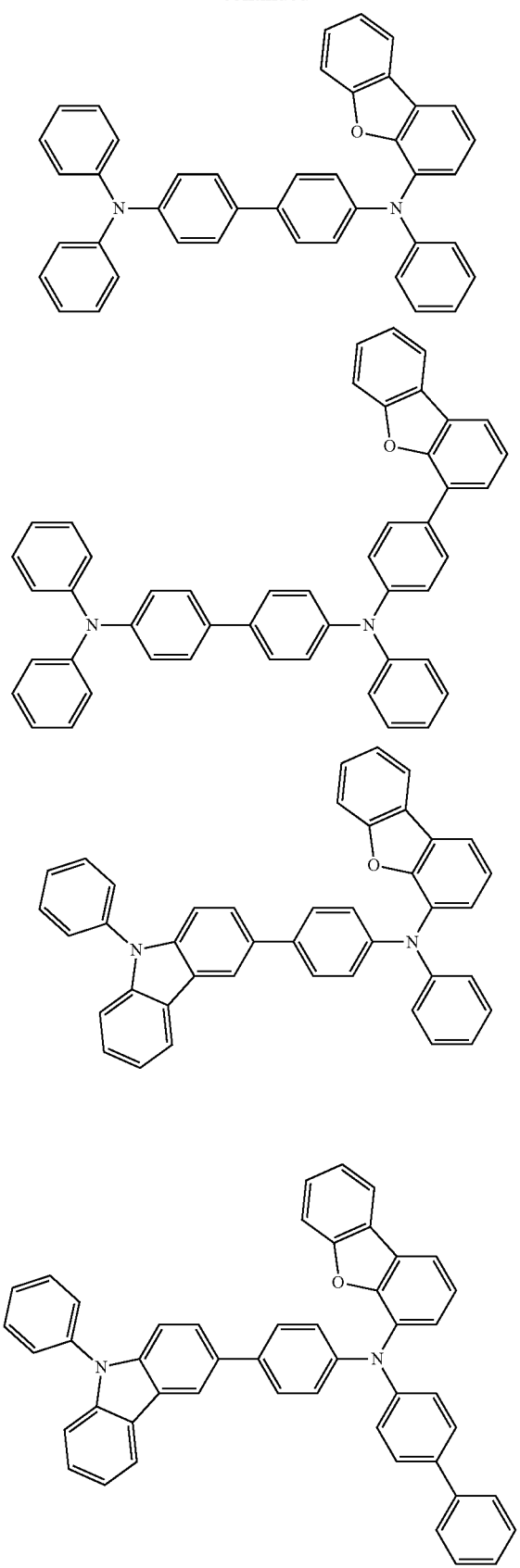
96
-continued
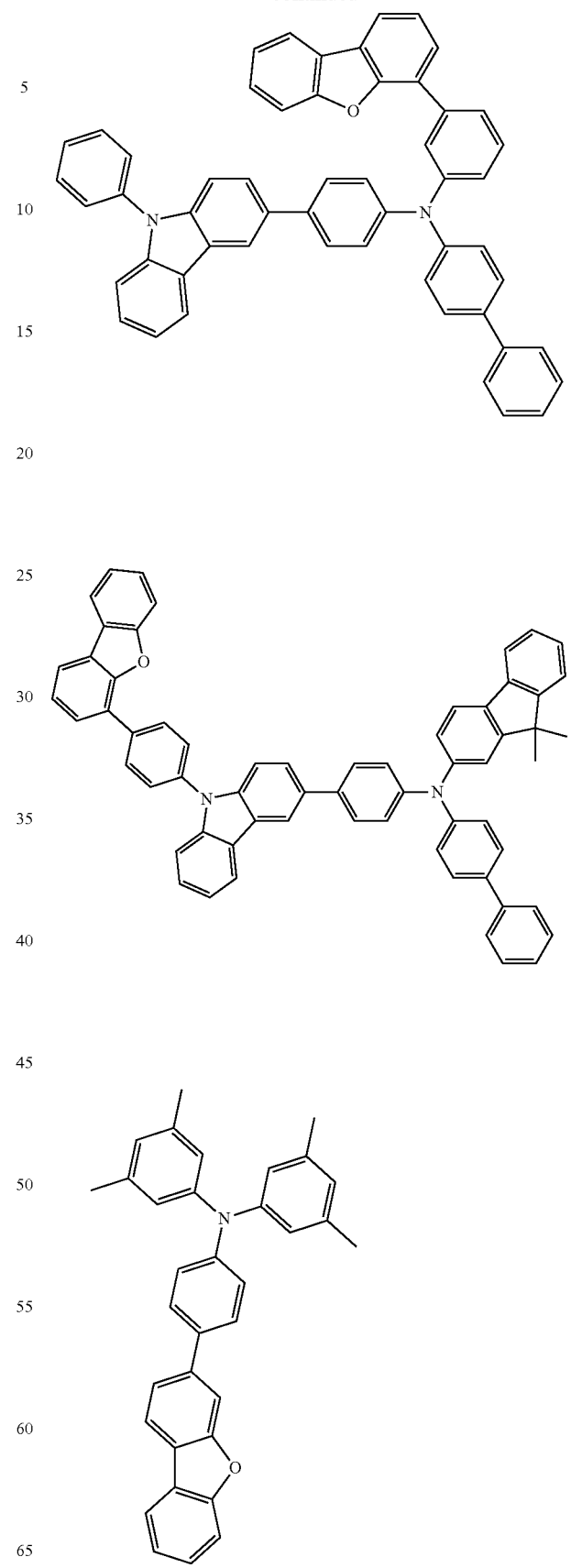

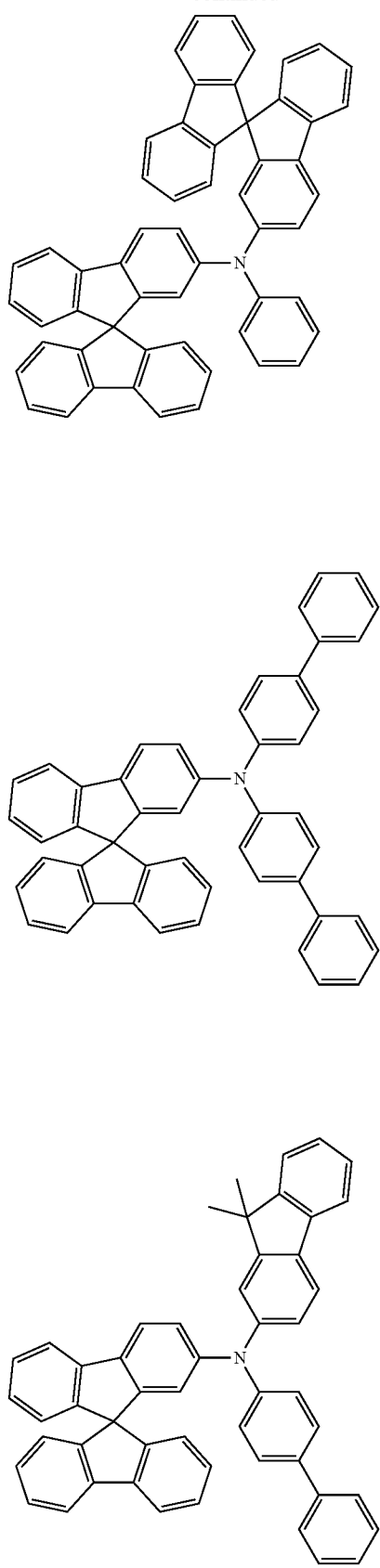

99
-continued
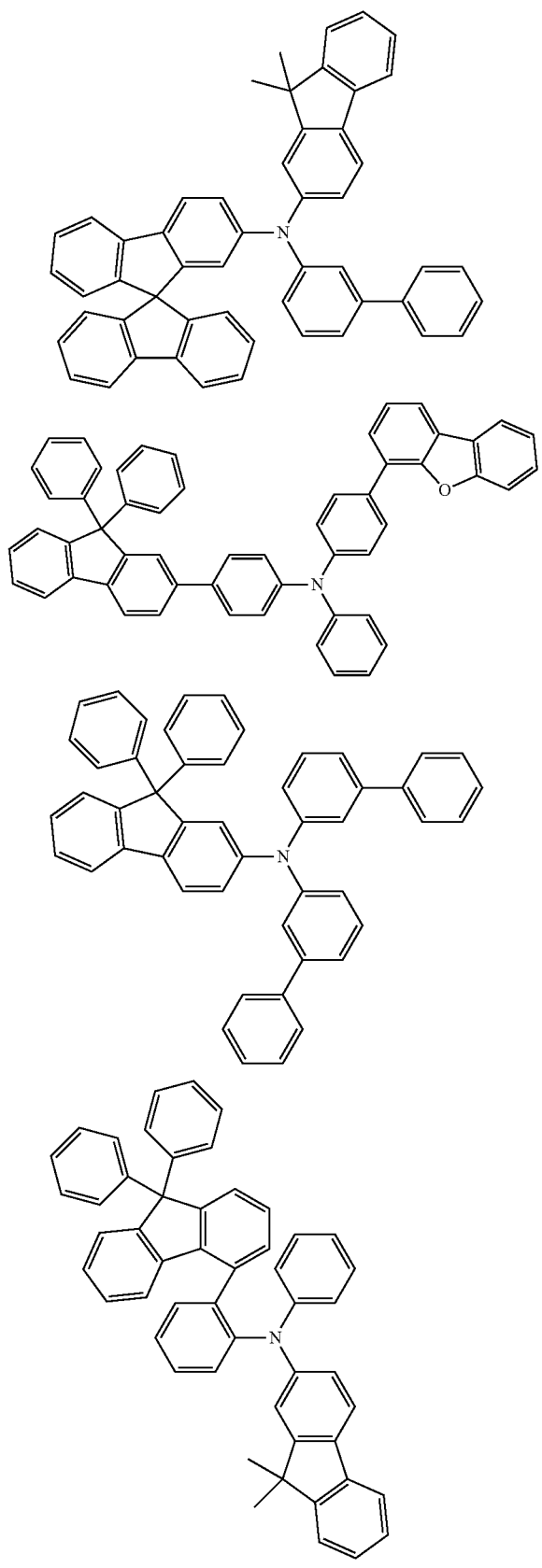
100
-continued
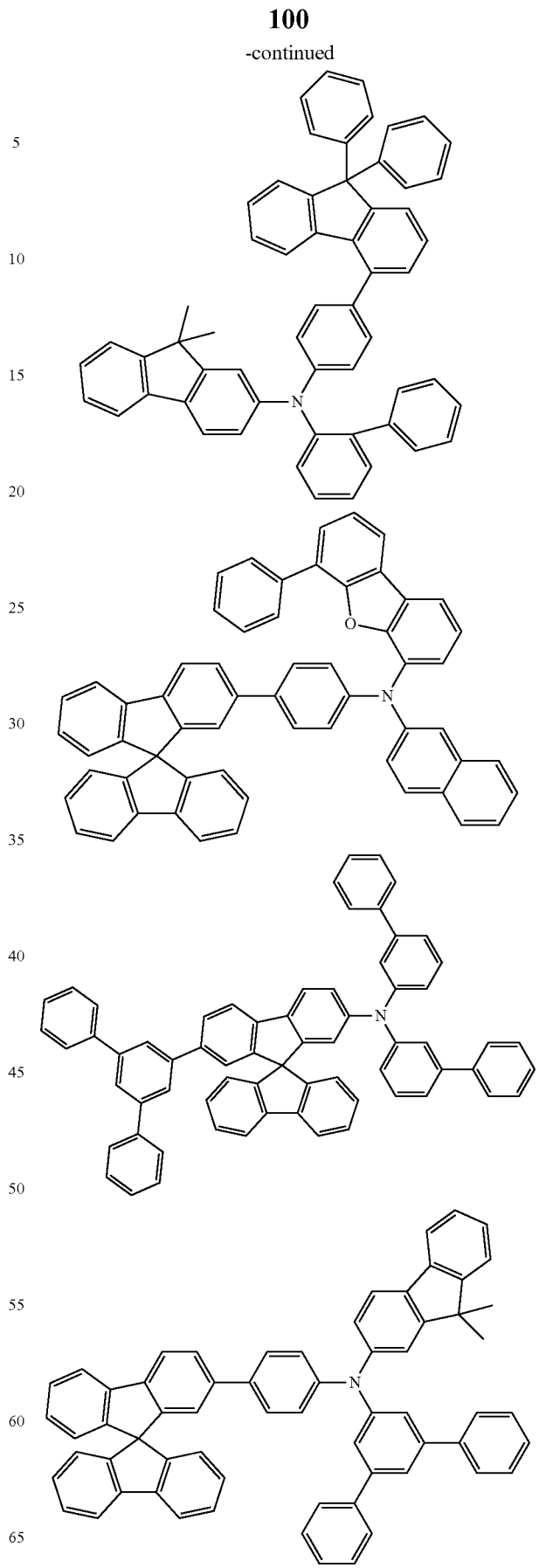

101
-continued
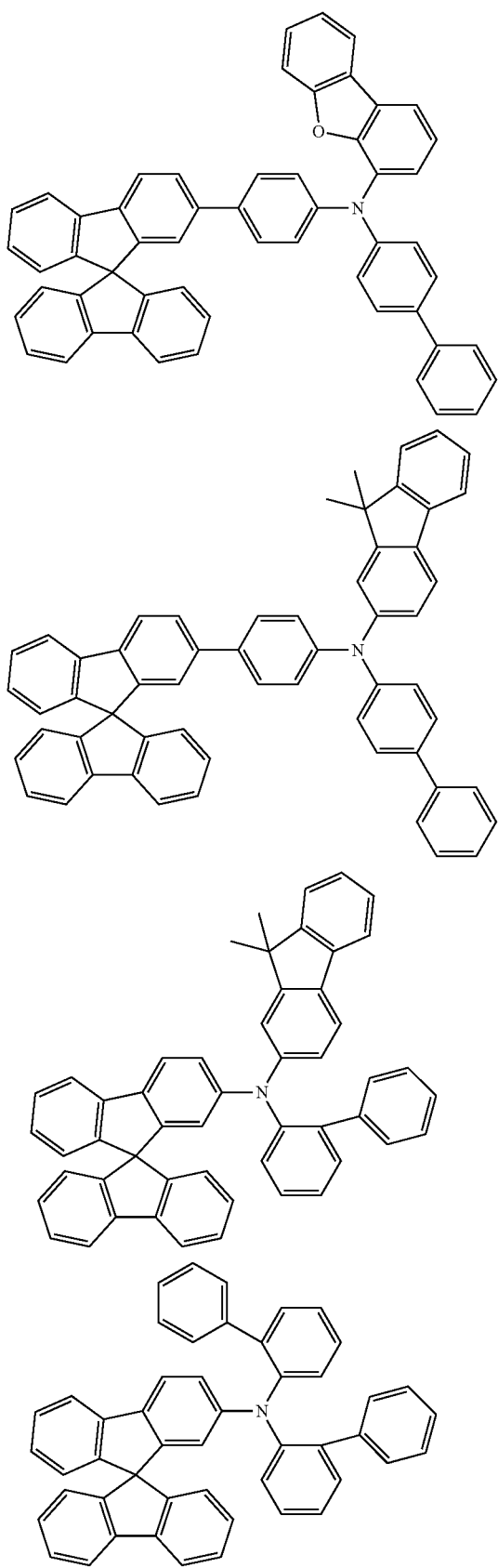
102
-continued
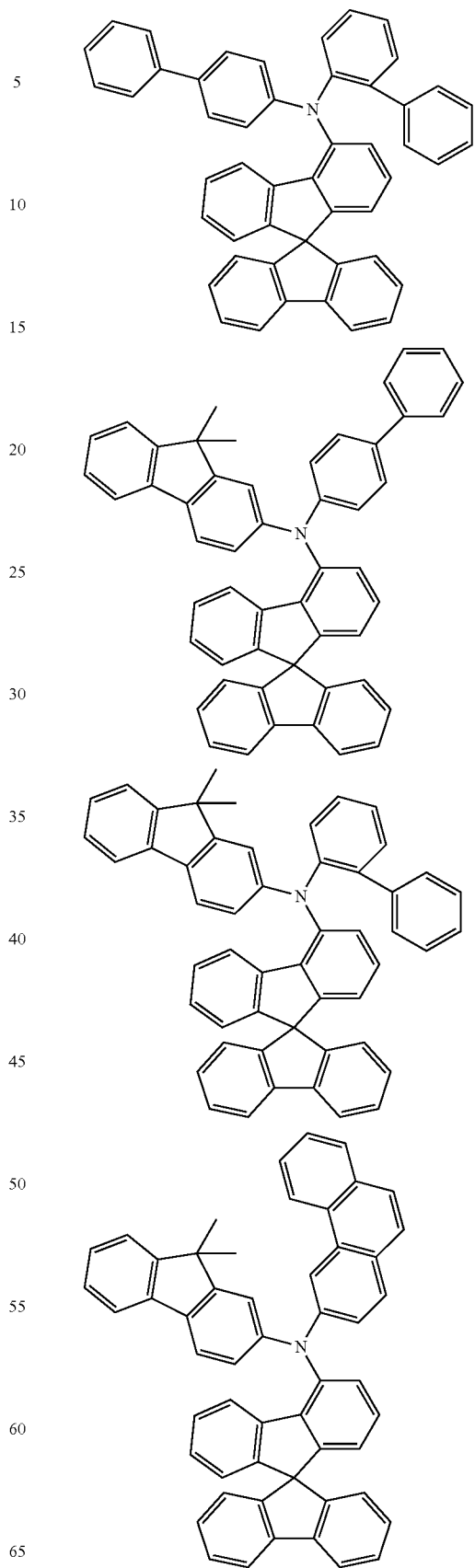

103
-continued
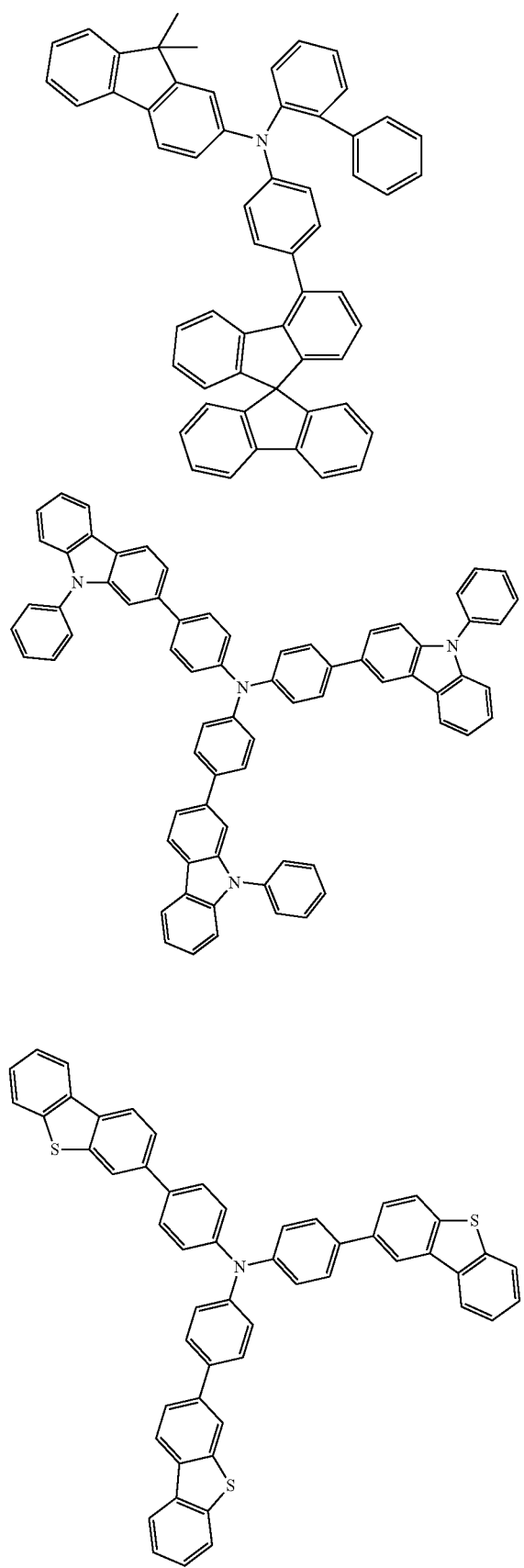
104
-continued
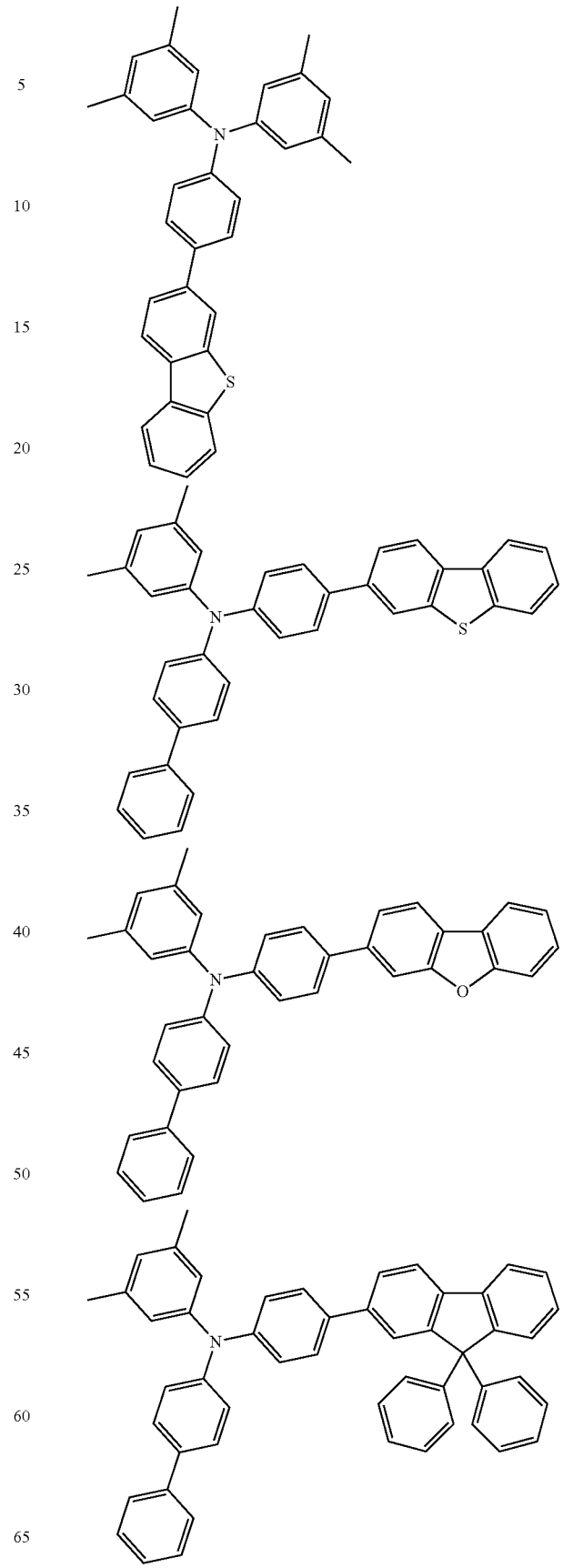

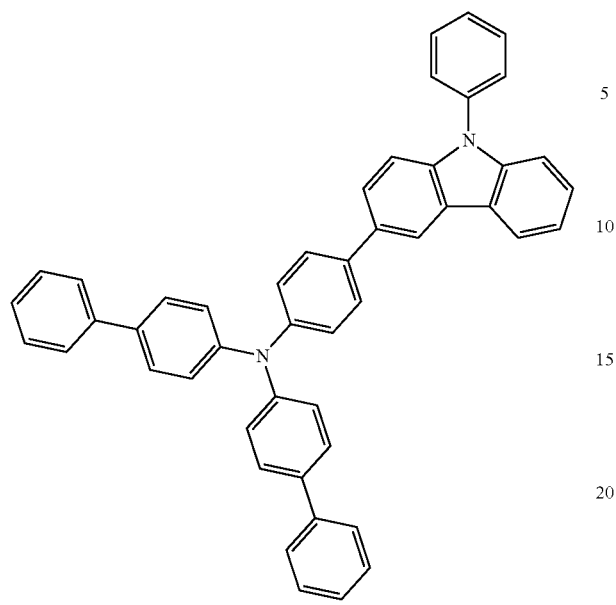
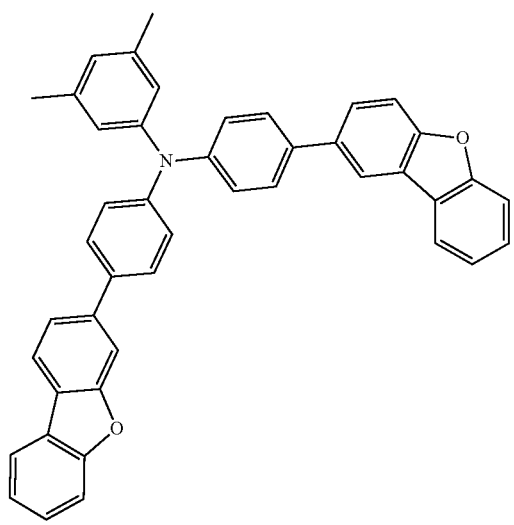
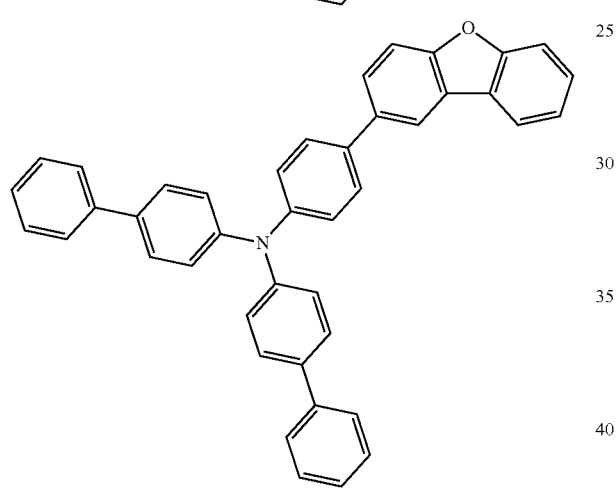
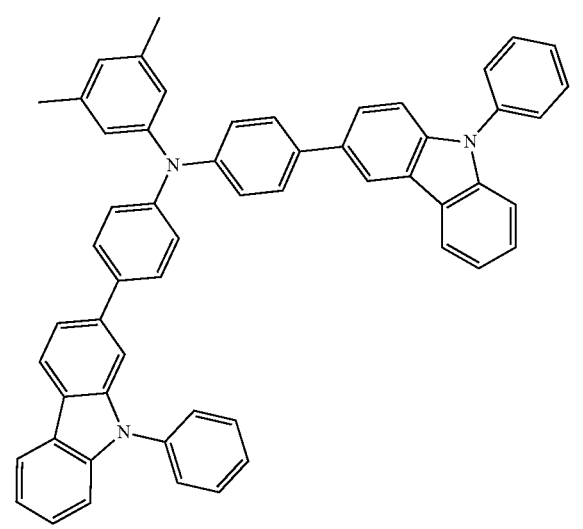
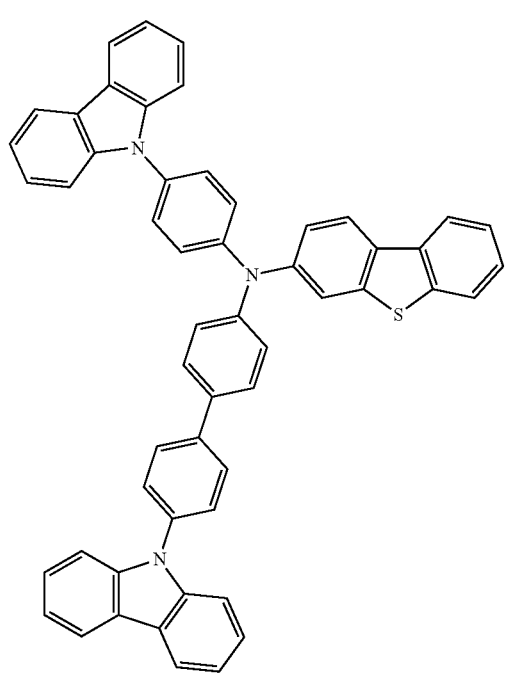

107
-continued

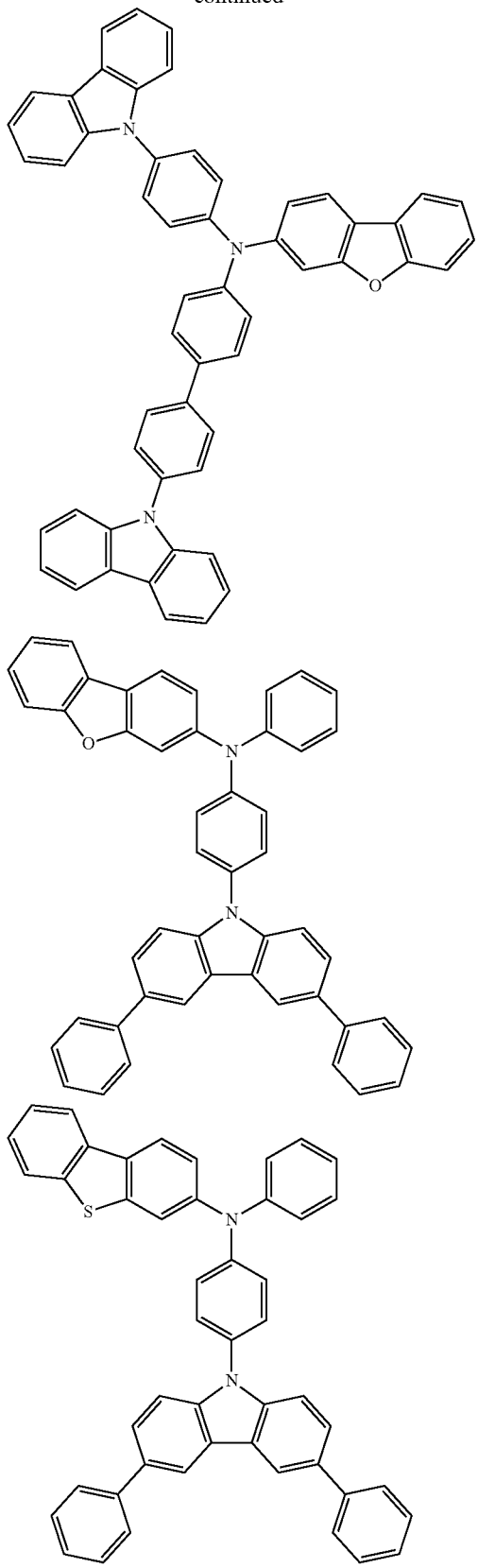

In one embodiment, the organic layer may further include an electron transport region, the electron transport region may be disposed between the emission layer and the second electrode, and the electron transport region may include a hole blocking layer, an electron transport layer, an electron injection layer, or any combination thereof, but embodiments of the present disclosure are not limited thereto.

Description of FIG. 1

FIG. 1 is a schematic view of an organic light-emitting device 10 according to an embodiment. The organic light-emitting device 10 includes a first electrode 110, an organic layer 150, and a second electrode 190.

Hereinafter, the structure of the organic light-emitting device 10 according to an embodiment and a method of manufacturing the organic light-emitting device 10 will be described in connection with FIG. 1.

First Electrode 110

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and/or water resistance.

The first electrode 110 may be formed by depositing or sputtering a material for forming the first electrode 110 on the substrate. When the first electrode 110 is an anode, the material for the first electrode may be selected from materials with a high work function to facilitate hole injection.

The first electrode 110 may be a reflective electrode, a semi-transmissive electrode, or a transmissive electrode. When the first electrode 110 is a transmissive electrode, a material for forming the first electrode may be selected from indium tin oxide (ITO), indium zinc oxide (IZO), tin oxide ($SnO_2$), zinc oxide (ZnO), and any combinations thereof, but embodiments of the present disclosure are not limited thereto. In one or more embodiments, when the first electrode 110 is a semi-transmissive electrode or a reflectable electrode, a material for forming the first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but embodiments of the present disclosure are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 is disposed on the first electrode 110. The organic layer 150 may include an emission layer.

The organic layer 150 may further include a hole transport region between the first electrode 110 and the emission layer, and an electron transport region between the emission layer and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked (e.g., laminated) from the first electrode 110 in the stated order, but the structure of the hole transport region is not limited thereto.

The hole transport region may include at least one selected from m-MTDATA, TDATA, 2-TNATA, NPB (NPD), β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201-1, and a compound represented by Formula 202-1.

For example, when the hole transport region includes the first hole transport material and the second hole transport material, the hole transport region may further include a compound represented by Formula 201-1 and/or a compound represented by Formula 202-1, wherein the compound represented by Formula 201-1 and the compound represented by Formula 202-1 are different from the first hole transport material and the second hole transport material:

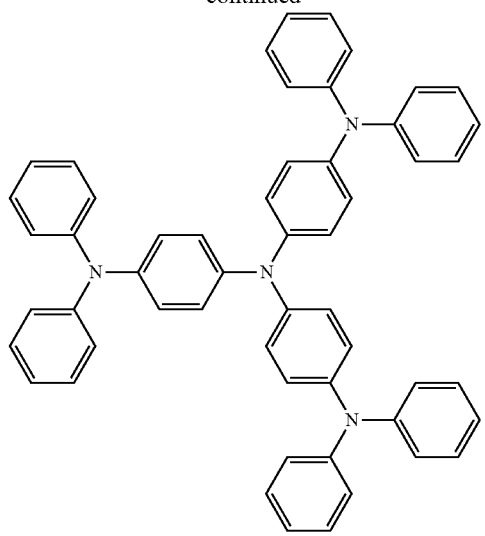

TDATA

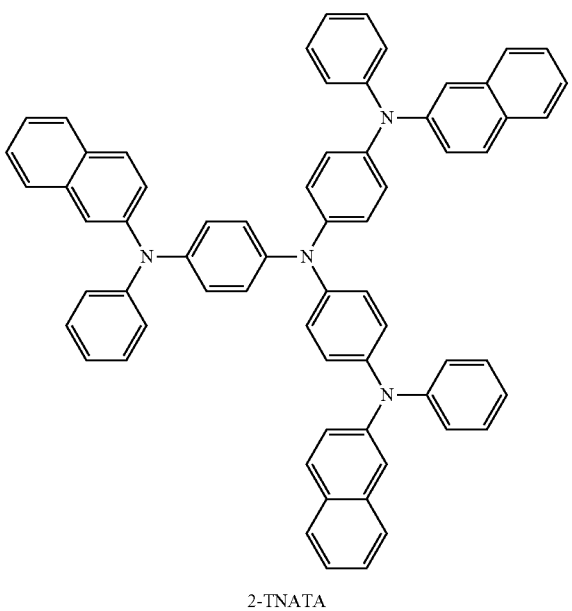

2-TNATA

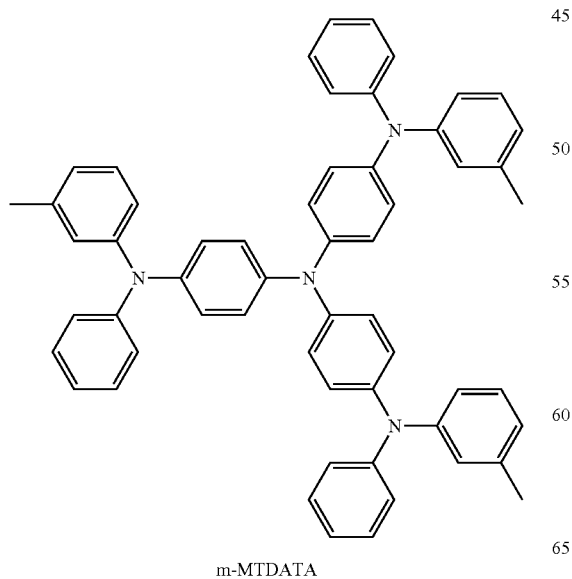

m-MTDATA

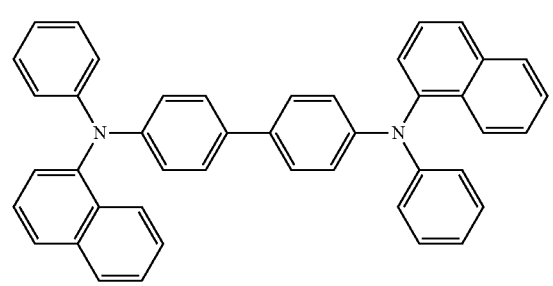

NPB

-continued

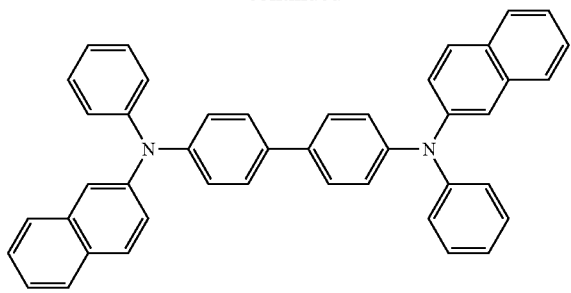

β-NPB

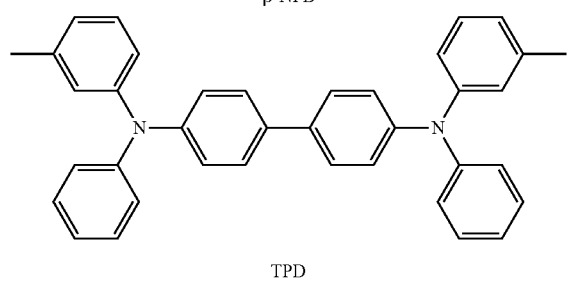

TPD

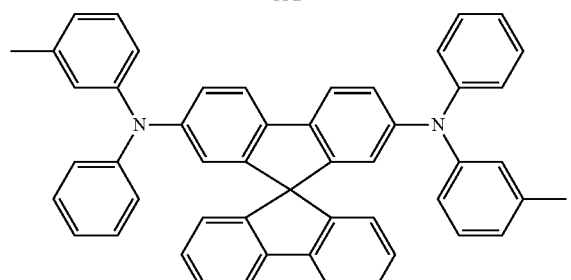

Spiro-TPD

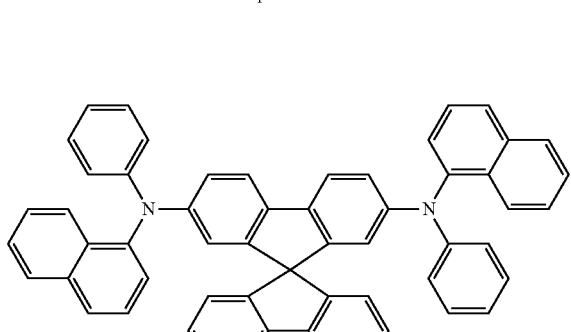

Spiro-NPB

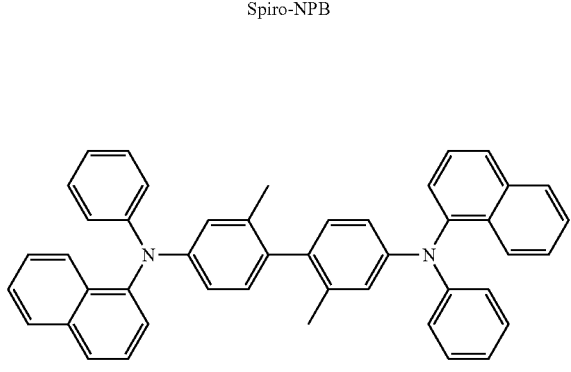

methylated NPB

-continued

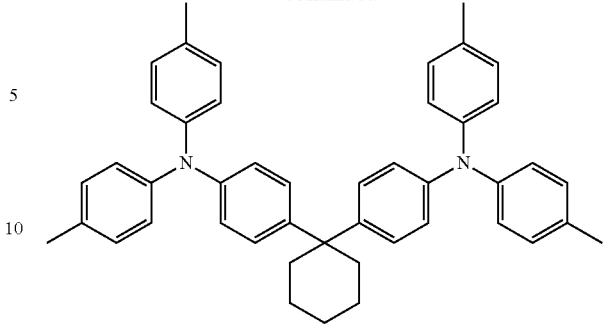

TAPC

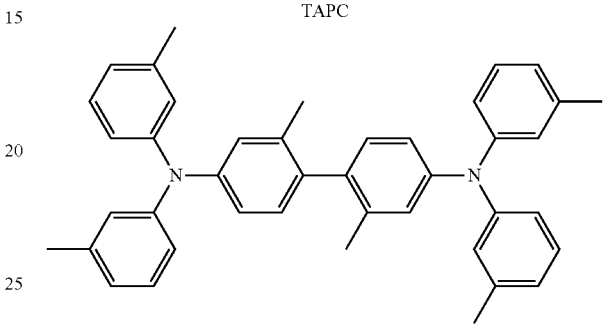

HMTPD

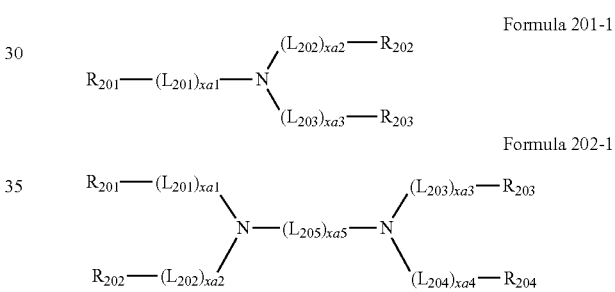

Formula 201-1

Formula 202-1

In Formulae 201-1 and 202-1, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$L_{205}$ may be selected from *—O—*', *—S—*', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer of 0 to 3, xa5 may be an integer of 1 to 10, and $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{00}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In one embodiment, in Formula 202-1, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In one embodiment, in Formulae 201-1 and 202-1, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more embodiments, xa1 to xa4 may each independently be 0, 1, or 2.

In one or more embodiments, xa5 may be 1, 2, 3, or 4.

In one or more embodiments, $R_{201}$ to $R_{204}$ and $Q_{201}$ may each independently be selected from:

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$), and $Q_{31}$ to $Q_{33}$ are the same as described above with respect to $L_{201}$ to $L_{205}$.

In one or more embodiments, in Formula 201-1, at least one selected from $R_{201}$ to $R_{203}$ may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

In one or more embodiments, in Formula 202-1, i) $R_{201}$ and $R_{202}$ may be linked via a single bond, and/or ii) $R_{203}$ and $R_{204}$ may be linked via a single bond.

In one or more embodiments, in Formula 202-1, at least one selected from $R_{201}$ to $R_{204}$ may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but embodiments of the present disclosure are not limited thereto.

The compound represented by Formula 201-1 may be represented by Formula 201A:

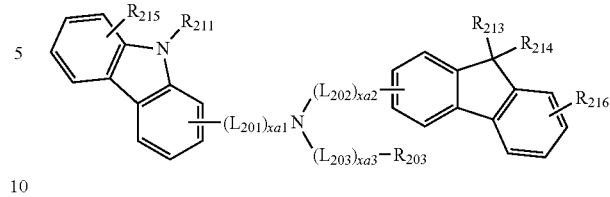

Formula 201A

In one embodiment, the compound represented by Formula 201-1 may be represented by Formula 201A(1), but embodiments of the present disclosure are not limited thereto:

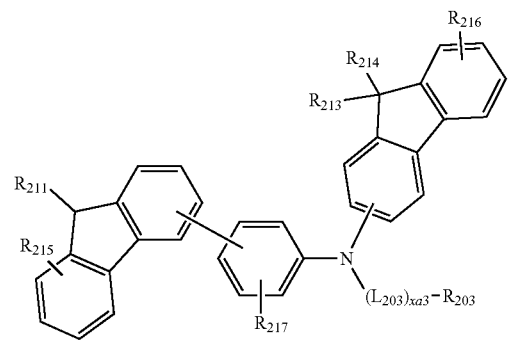

Formula 201A(1)

In one embodiment, the compound represented by Formula 201-1 may be represented by Formula 201A-1, but embodiments of the present disclosure are not limited thereto:

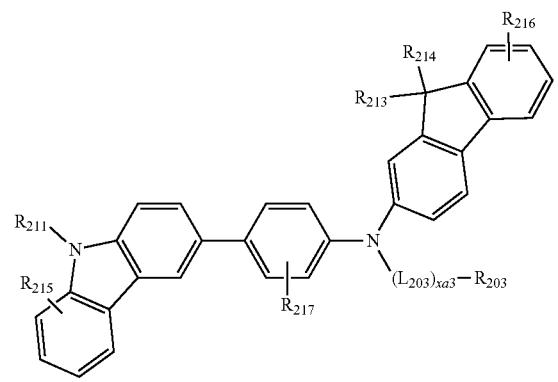

Formula 201A-1

In one embodiment, the compound represented by Formula 202-1 may be represented by Formula 202AA:

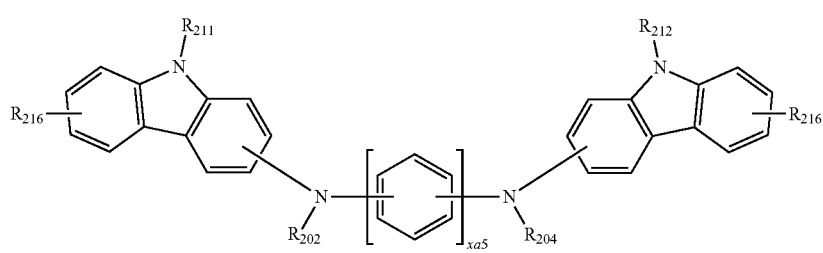

Formula 202AA

In one embodiment, the compound represented by Formula 202-1 may be represented by Formula 202A-1:

Formula 202A-1

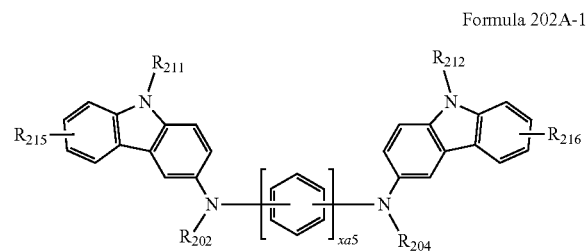

In Formulae 201A, 201A(1), 201A-1, 202AA, and 202A-1, $L_{201}$ to $L_{203}$, xa1 to xa3, xa5, and $R_{202}$ to $R_{204}$ are the same as described above with respect to Formulae 201-1 and 202-1, $R_{211}$ and $R_{212}$ may each independently be the same as defined in connection with $R_{203}$ of Formulae 201-1 and 202-1

$R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but embodiments of the present disclosure are not limited thereto:

HT1

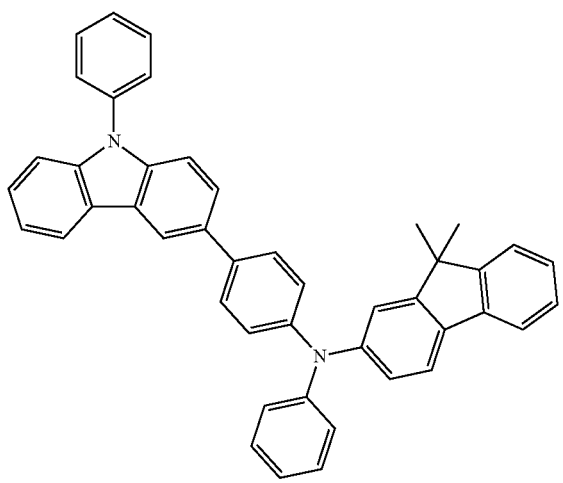

HT2

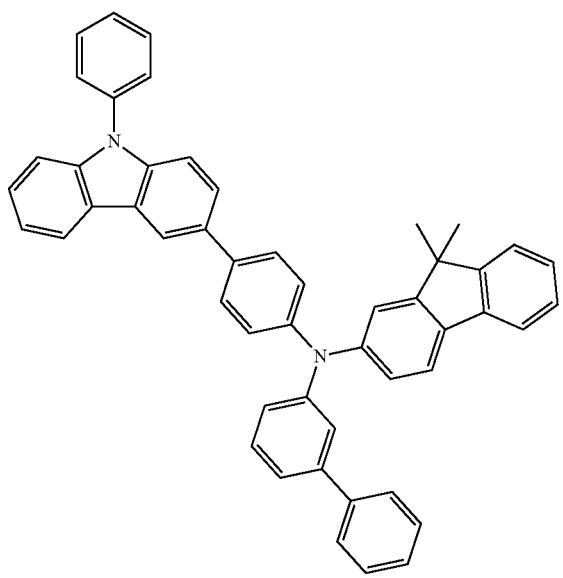

-continued
HT3
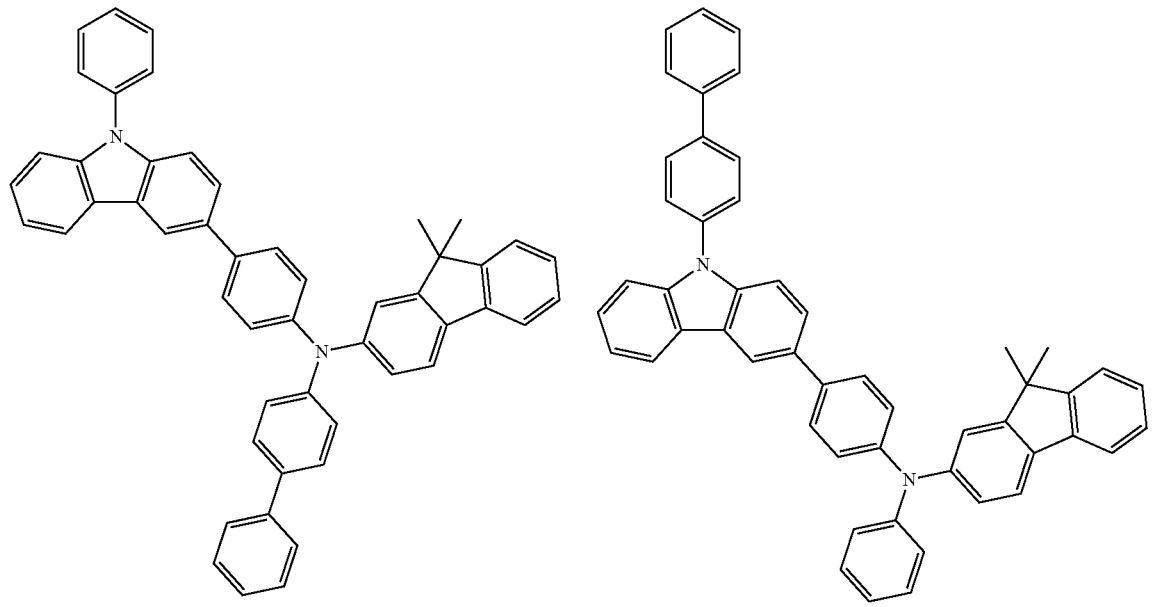
HT4
HT5
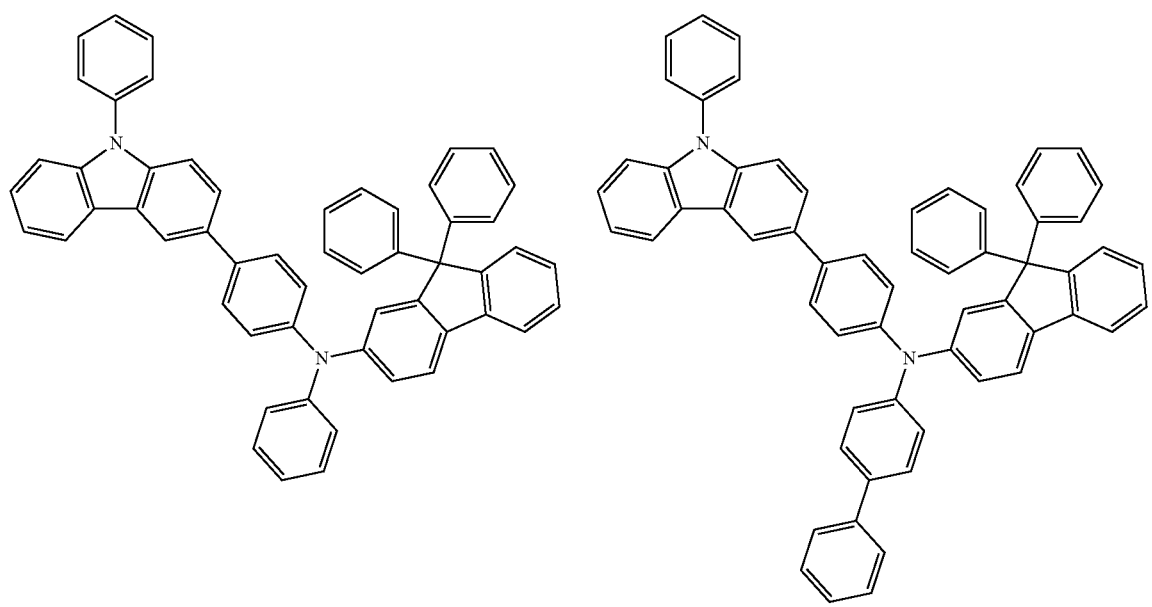
HT6

-continued
HT7
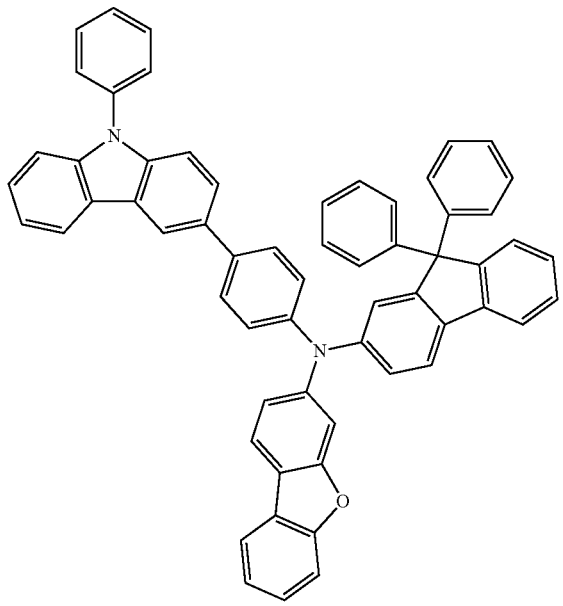
HT8
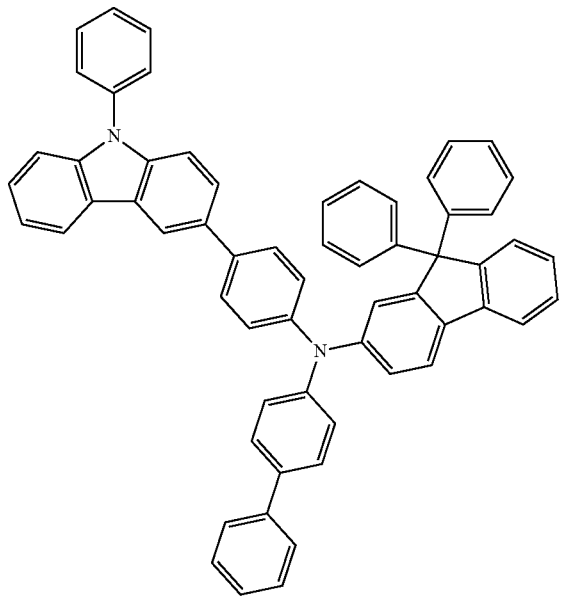
HT9
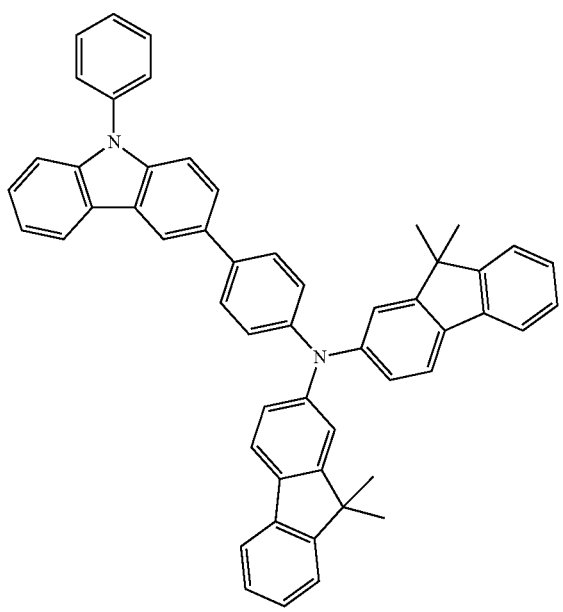
HT10
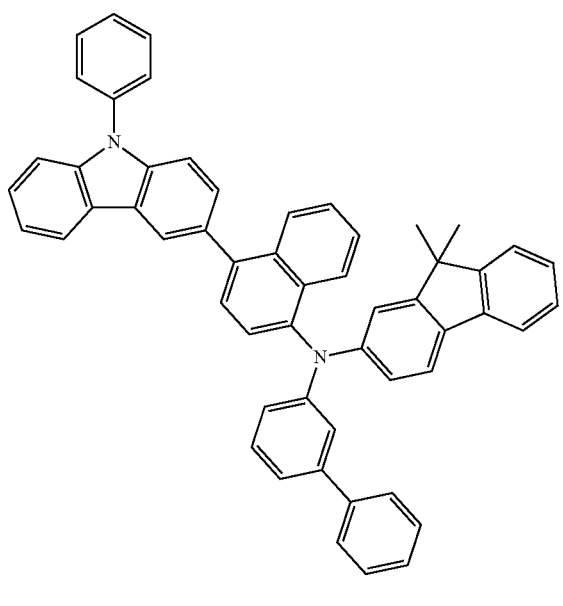

-continued
HT11
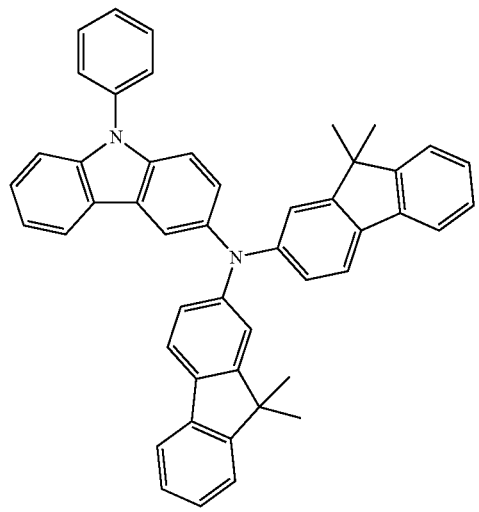
HT12
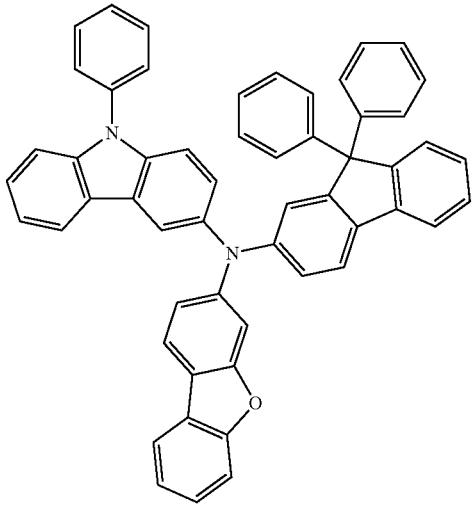
HT13
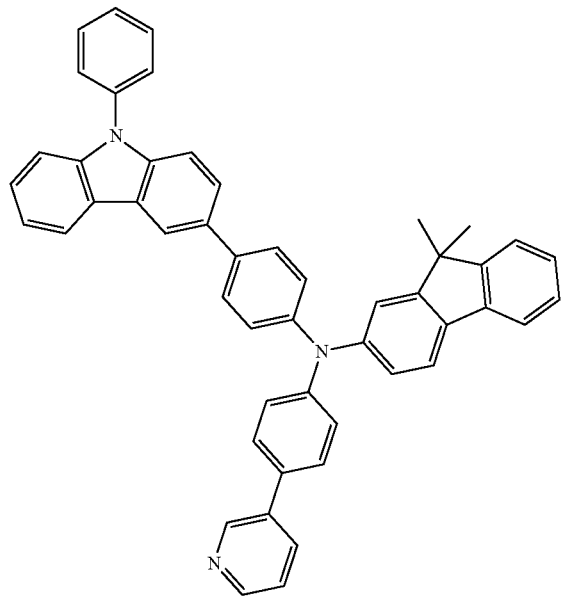
HT14
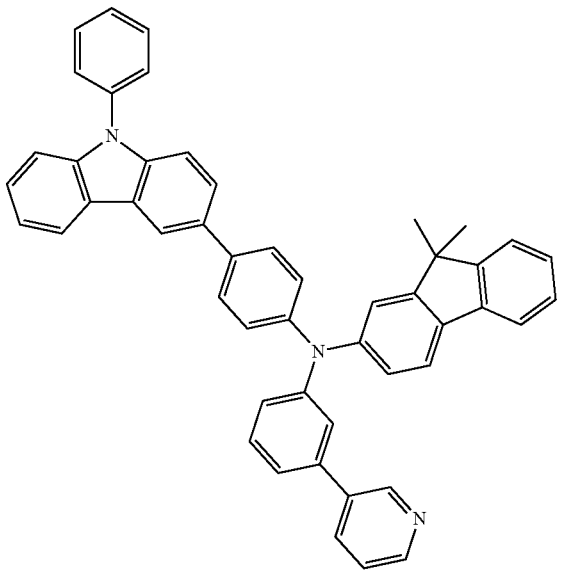
HT15
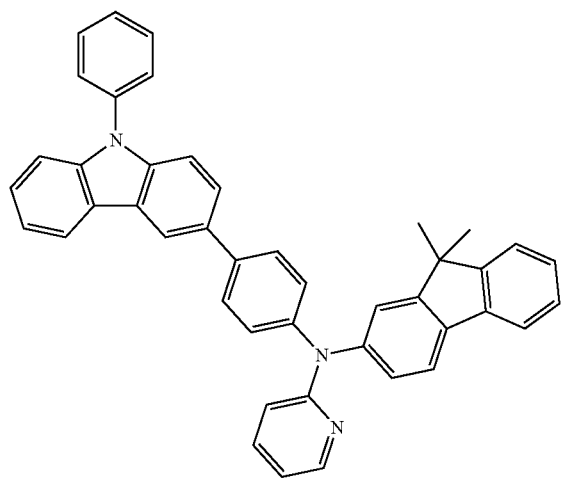
HT16
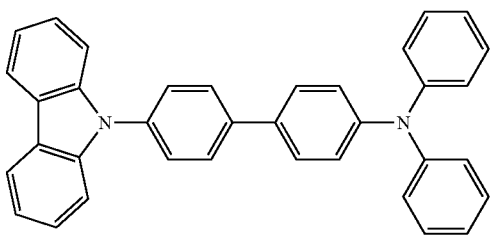

-continued
HT17
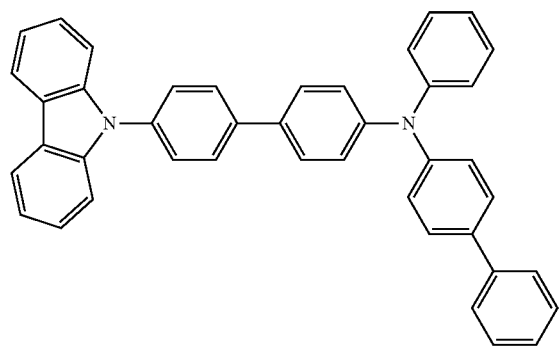
HT18
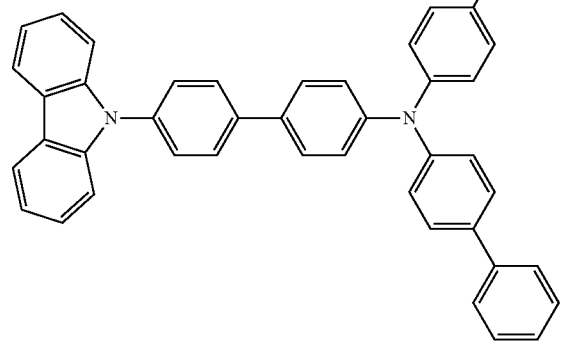
HT19
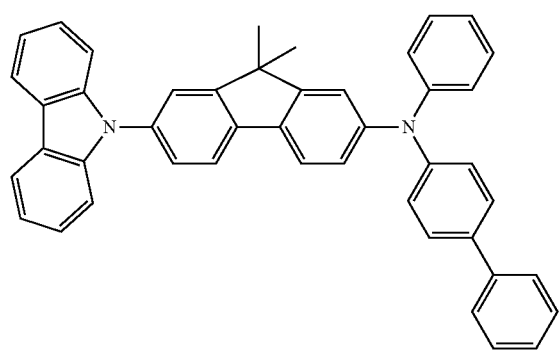
HT20
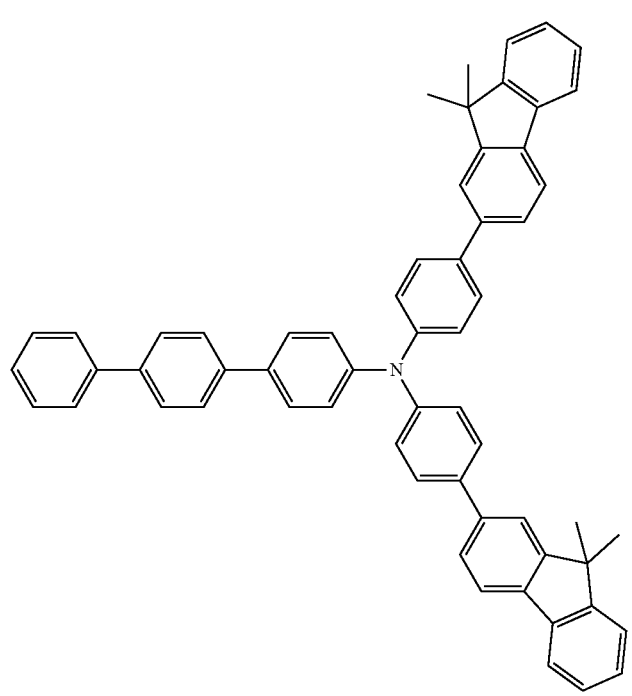

-continued
HT21
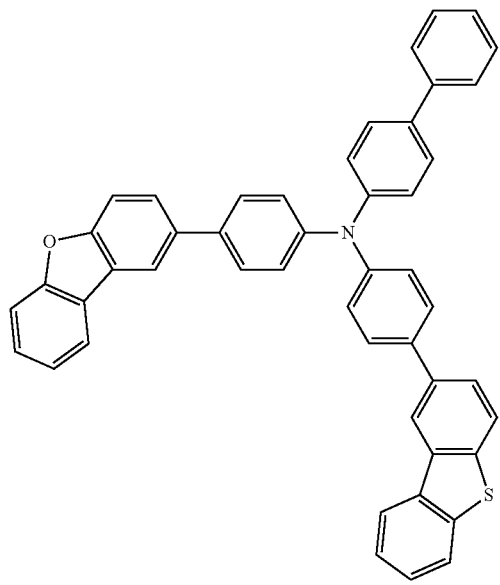
HT22
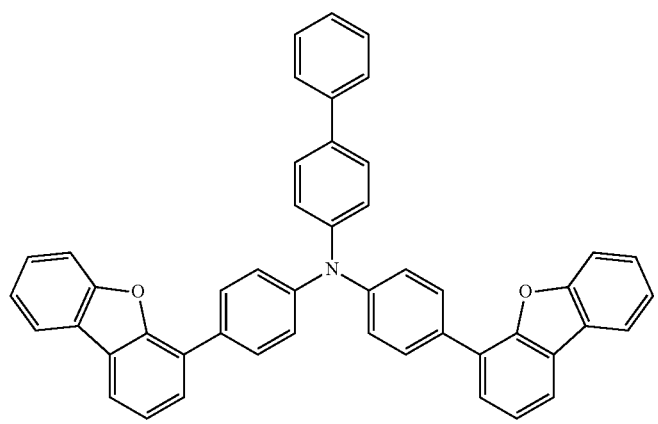
HT23
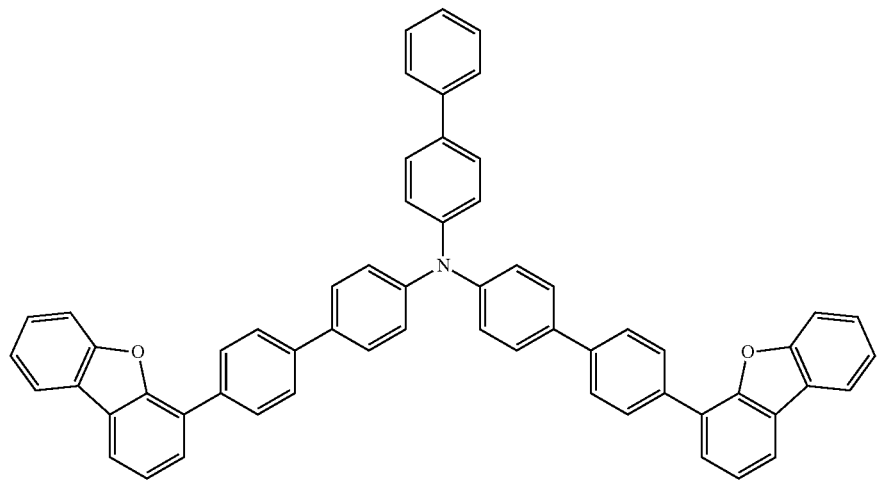

-continued
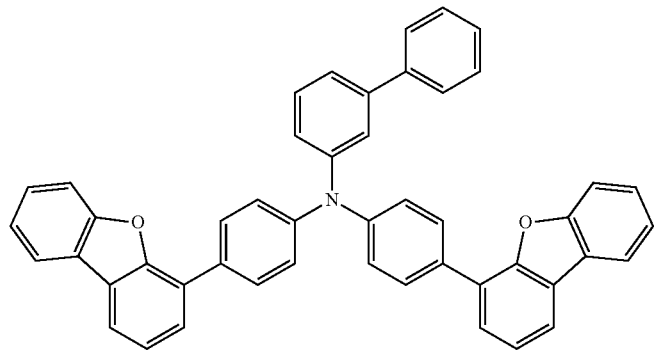
HT24
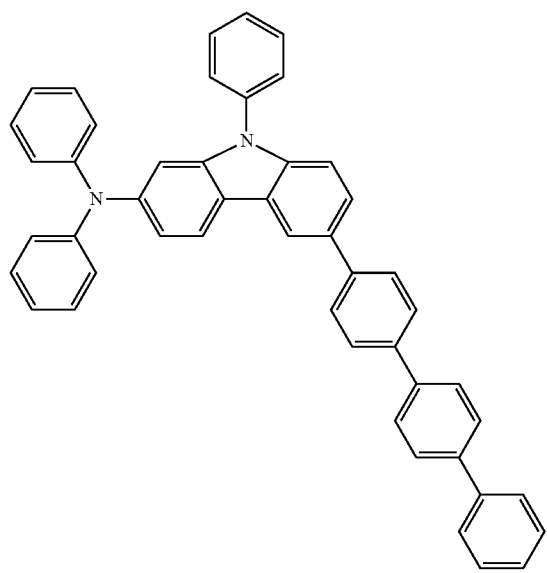
HT25
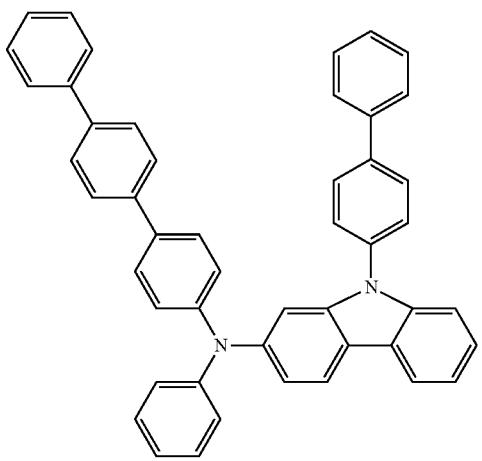
HT26
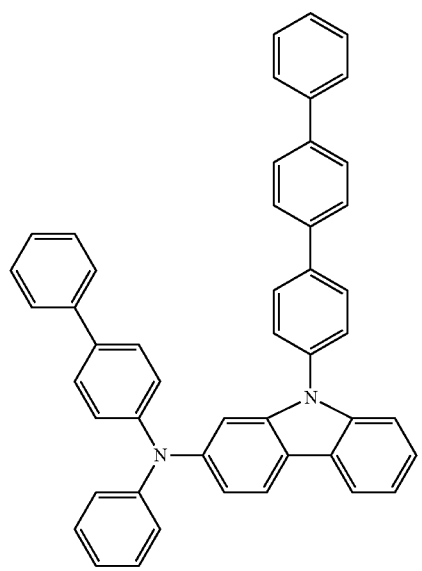
HT27

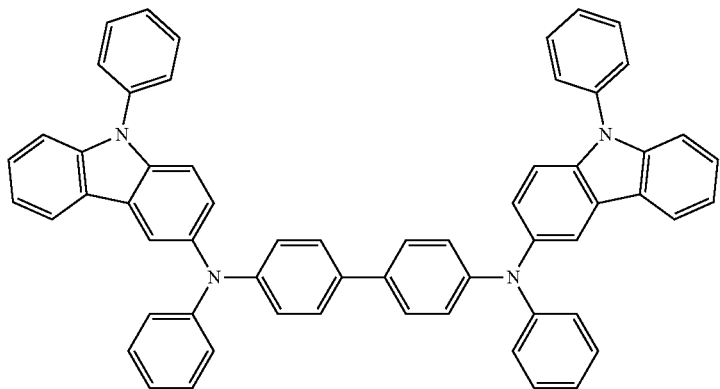
HT28
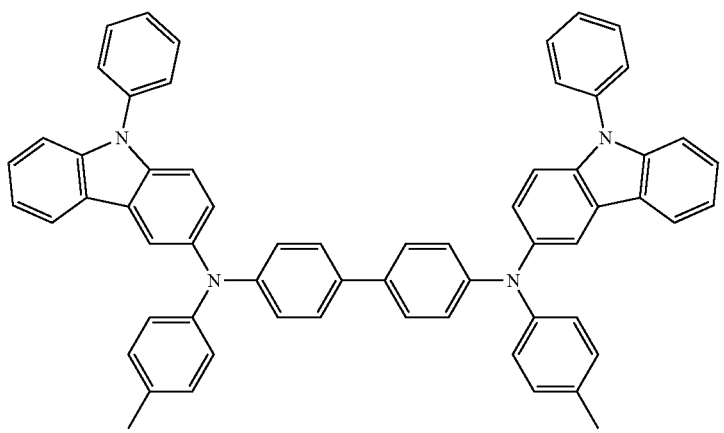
HT29
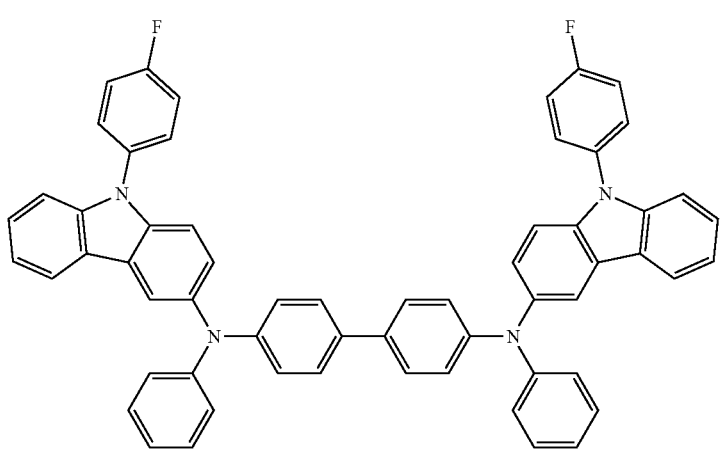
HT30

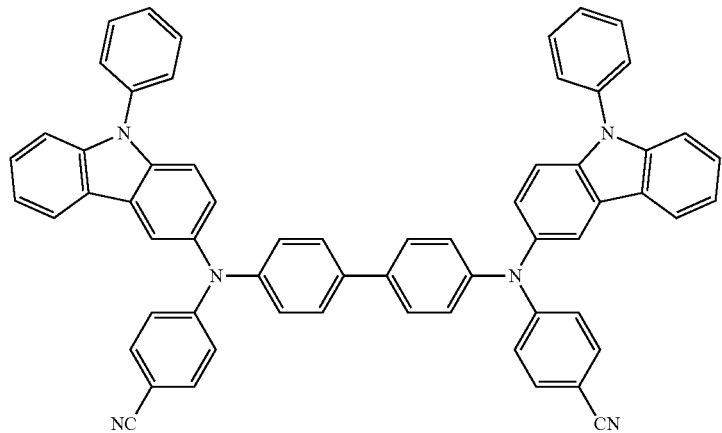
HT31
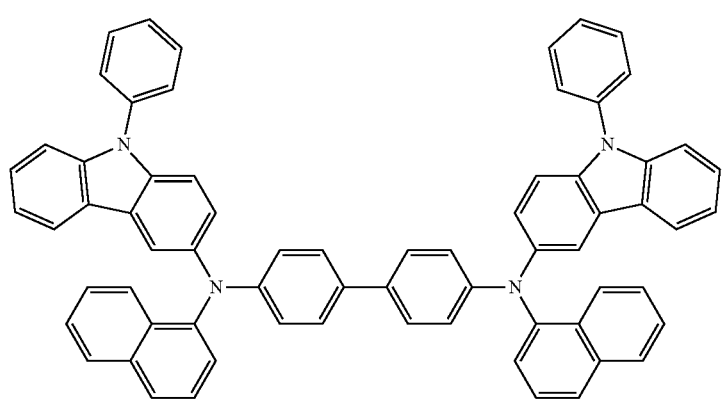
HT32
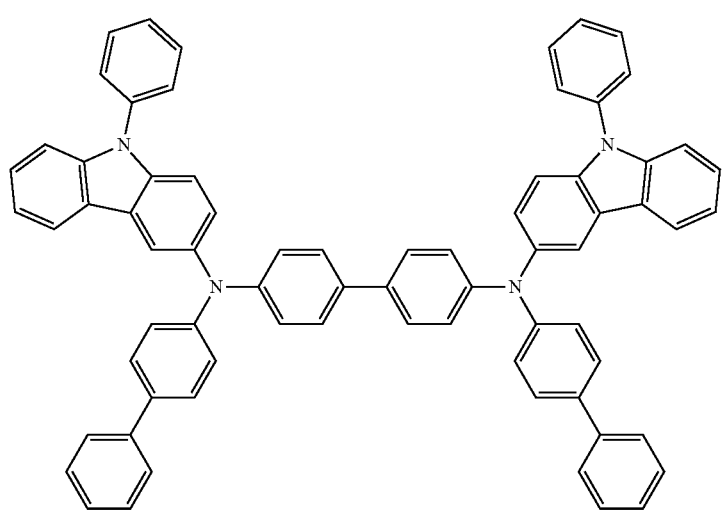
HT33

-continued

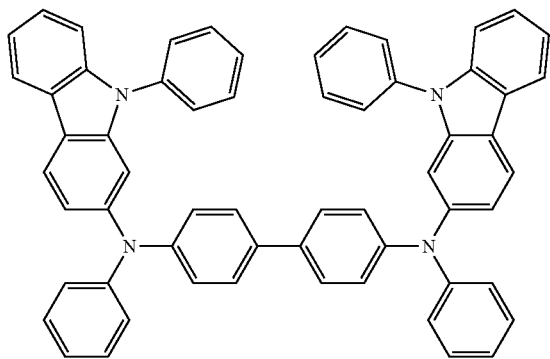
HT34

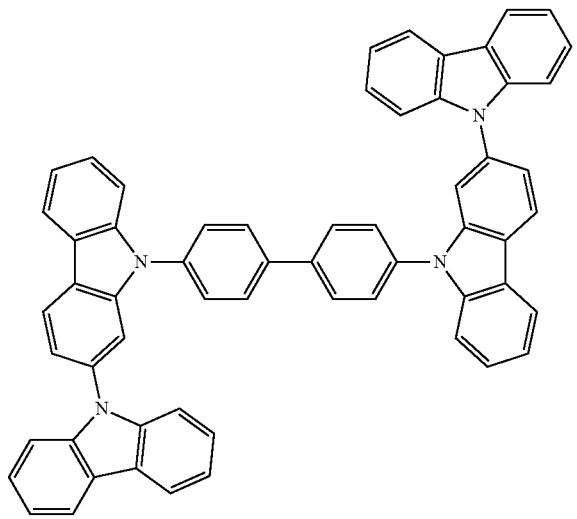
HT35

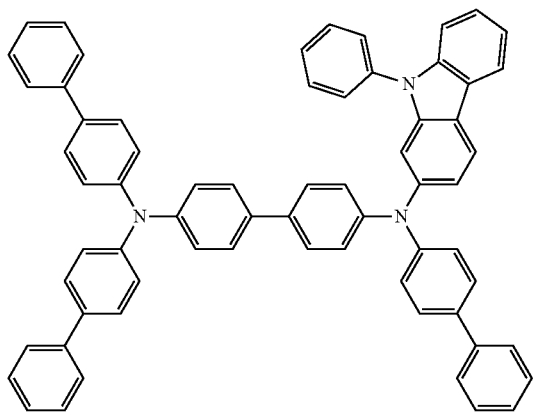
HT36

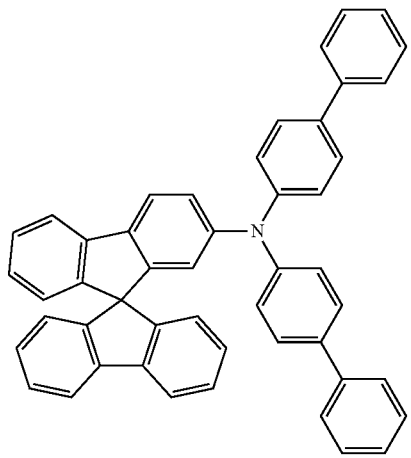
HT37

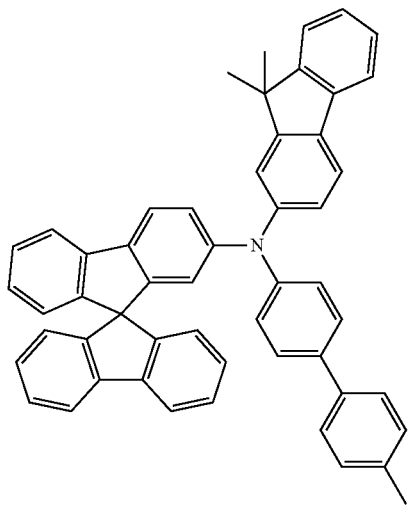
HT38

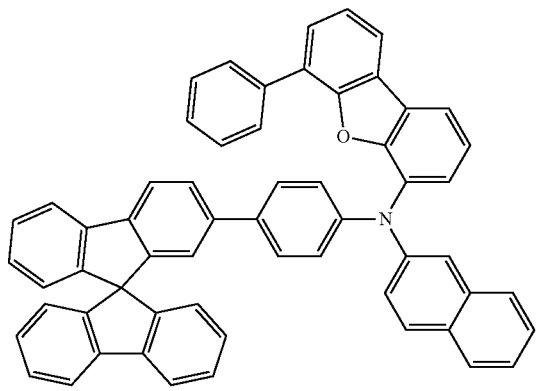
HT39

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

p-Dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In one embodiment, the p-dopant may have a lowest unoccupied molecular orbital (LUMO) level of −3.5 eV or less.

The p-dopant may include at least one selected from a quinone derivative, a metal oxide, and a cyano group-containing compound, but embodiments of the present disclosure are not limited thereto.

For example, the p-dopant may include at least one selected from:

a quinone derivative, such as tetracyanoquinodimethane (TCNQ) and/or 2,3,5,6-tetrafluoro-7,7,8,8-tetracyanoquinodimethane (F4-TCNQ);

a metal oxide, such as tungsten oxide and/or molybdenum oxide;

1,4,5,8,9,11-hexaazatriphenylene-hexacarbonitrile (HAT-CN); and a compound represented by Formula 221, but embodiments of the present disclosure are not limited thereto:

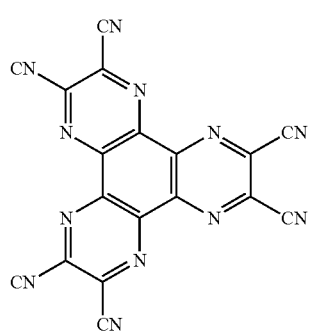

HAT-CN

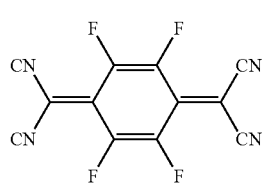

F4-TCNQ

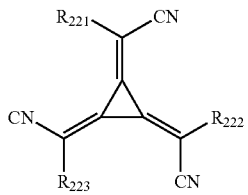

Formula 221

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one substituent selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layer in Organic Layer 150

When the organic light-emitting device 10 is a full-color organic light-emitting device, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

A thickness of the emission layer may be in a range of about 100 Å to about 1,000 Å, for example, about 200 Å to about 600 Å. When the thickness of the emission layer is within these ranges, excellent light-emission characteristics may be obtained without a substantial increase in driving voltage.

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but embodiments of the present disclosure are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked (e.g., laminated) from an emission layer. However, embodiments of the structure of the electron transport region are not limited thereto.

The electron transport region (for example, a buffer layer, a hole blocking layer, an electron control layer, and/or an electron transport layer in the electron transport region) may include a metal-free compound containing at least one π electron-depleted nitrogen-containing ring.

The term "π electron-depleted nitrogen-containing ring" as used herein refers to a $C_1$-$C_{60}$ heterocyclic group having at least one *—N=*' moiety as a ring-forming moiety.

For example, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but embodiments of the present disclosure are not limited thereto.

For example, the electron transport region may include a compound represented by Formula 601:

Formula 601

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer of 0 to 5, $R_{601}$ may be selected from a substituted or unsubstituted $C_3$-$C_{00}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{601}$)($Q_{602}$)($Q_{603}$), —C(=O)($Q_{601}$), —S(=O)$_2$($Q_{601}$), and —P(=O)($Q_{601}$)($Q_{602}$), $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer of 1 to 5.

In one embodiment, at least one of $Ar_{601}$(s) in the number of xe11 and $R_{601}$(s) in the number of xe21 may include the π electron-depleted nitrogen-containing ring.

In one embodiment, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —S(=O)$_2$($Q_{31}$), and —P(=O)($Q_{31}$)($Q_{32}$), $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more Ar601(s) may be linked via a single bond.

In one or more embodiments, $Ar_{601}$ in Formula 601 may be an anthracene group.

In one or more embodiments, a compound represented by Formula 601 may be represented by Formula 601-1:

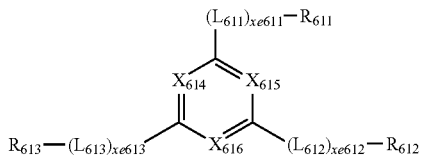

Formula 601-1

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be the same as defined in connection with $L_{601}$, xe611 to xe613 may each independently be the same as defined in connection with xe1, $R_{611}$ to $R_{613}$ may each independently be the same as defined in connection with $R_{601}$, $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one embodiment, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but embodiments of the present disclosure are not limited thereto.

In one or more embodiments, xe1 and xe611 to xe613 in Formulae 601 and 601-1 may each independently be 0, 1, or 2.

In one or more embodiments, $R_{601}$ and $R_{611}$ to $R_{613}$ in Formula 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and —S(=O)$_2$(Q$_{601}$) and —P(=O)(Q$_{601}$)(Q$_{602}$), and Q$_{601}$ and Q$_{602}$ are the same as described above with respect to Formula 601.

The electron transport region may include at least one compound selected from Compounds ET1 to ET36, but embodiments of the present disclosure are not limited thereto:

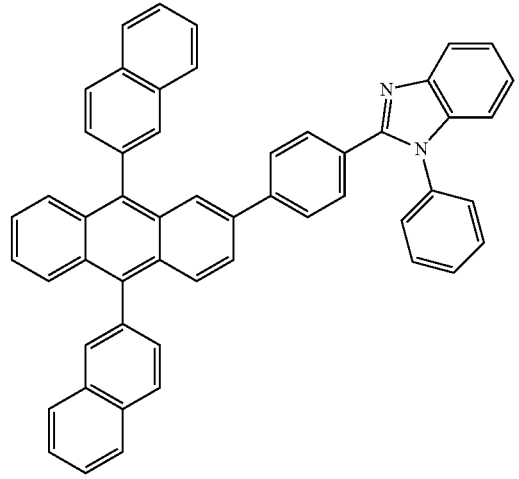

ET1

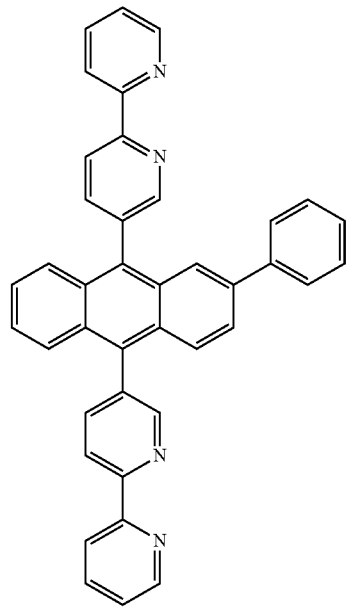

ET2

ET3
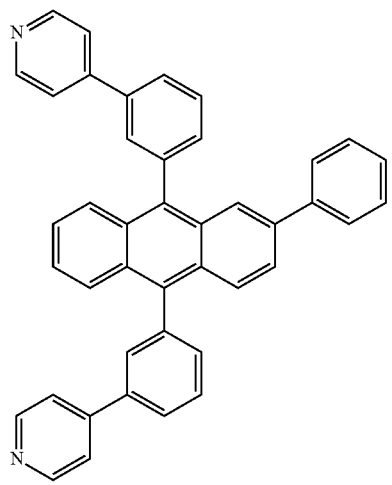
ET4
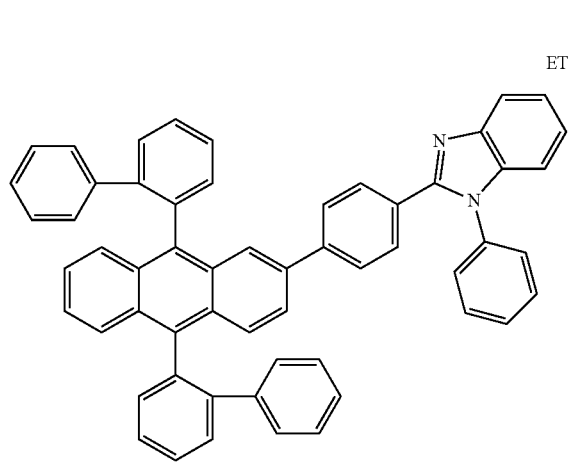
ET5
ET6
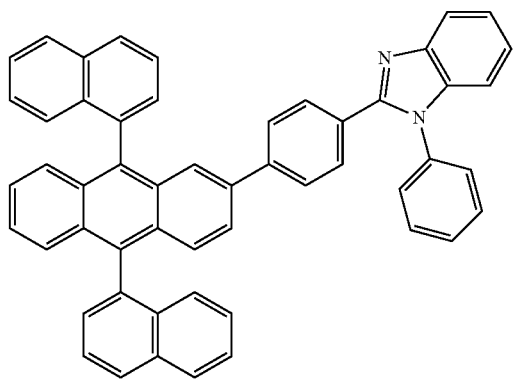
ET7
ET8
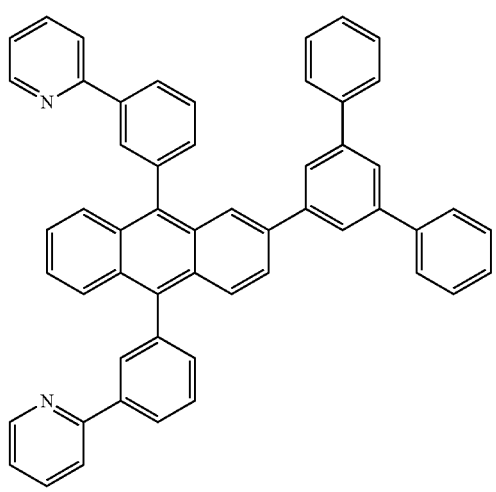

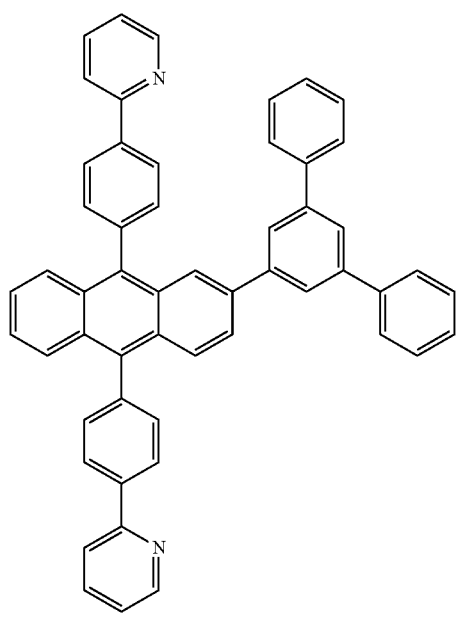
ET9
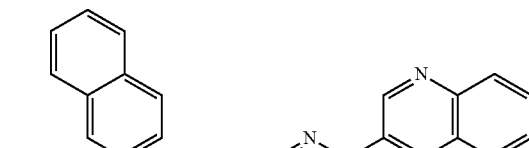
ET11
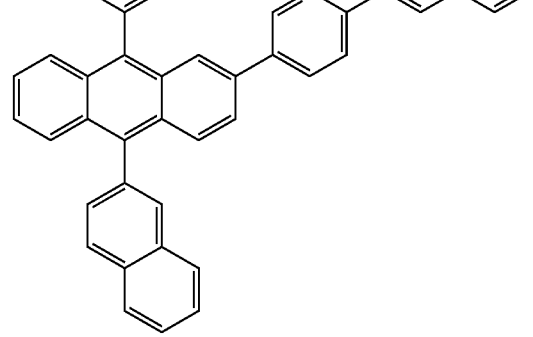
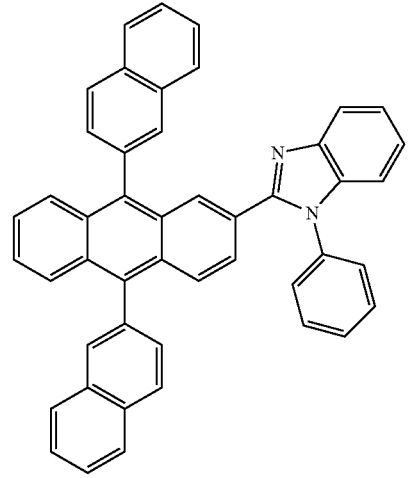
ET12
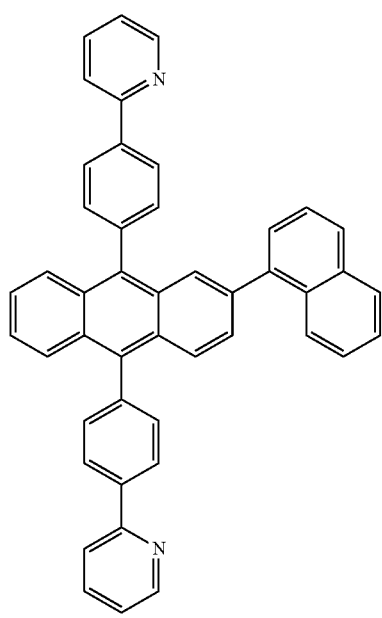
ET10
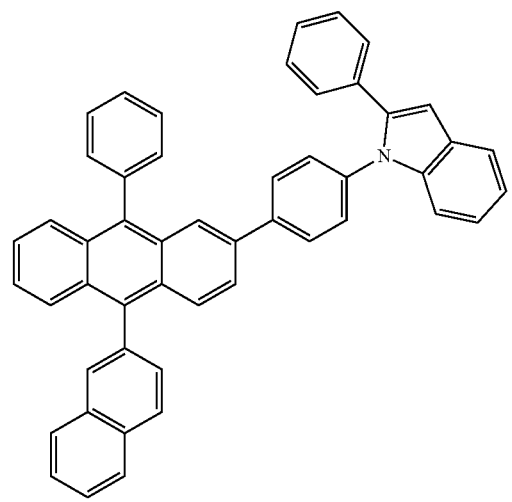
ET13

-continued
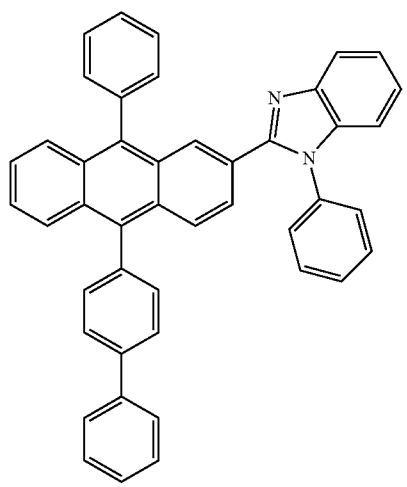
ET14
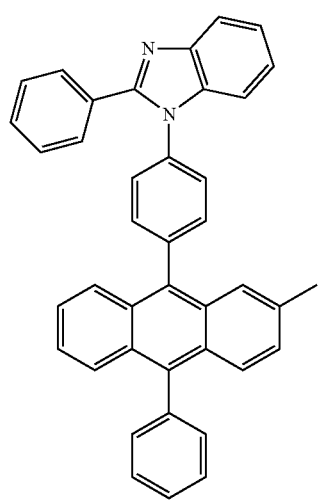
ET15
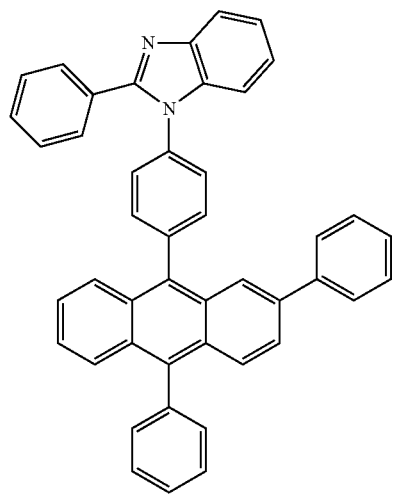
ET16
-continued
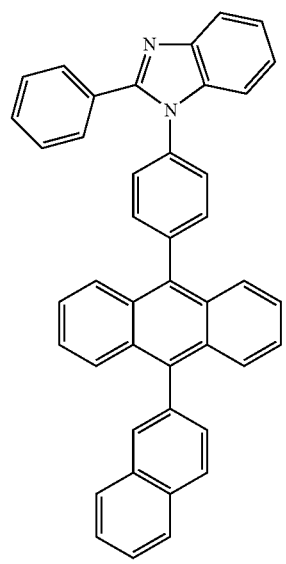
ET17
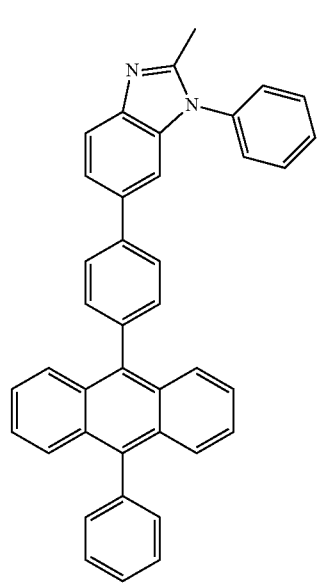
ET18
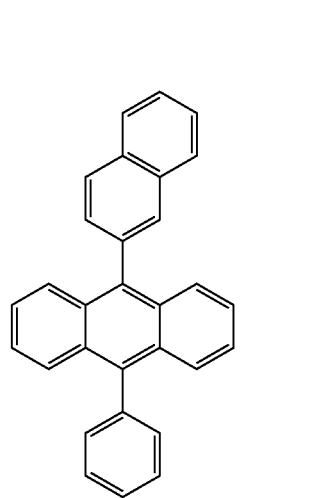
ET19

-continued
ET20
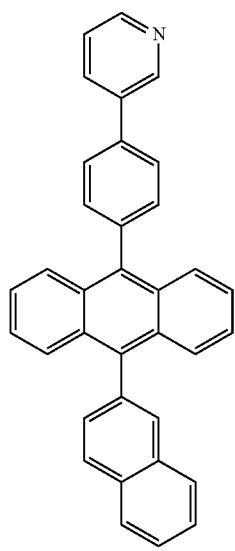
ET21
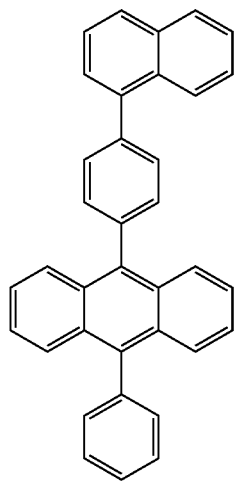
ET22
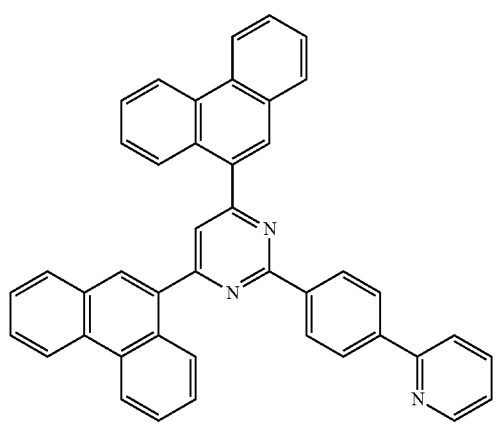
-continued
ET23
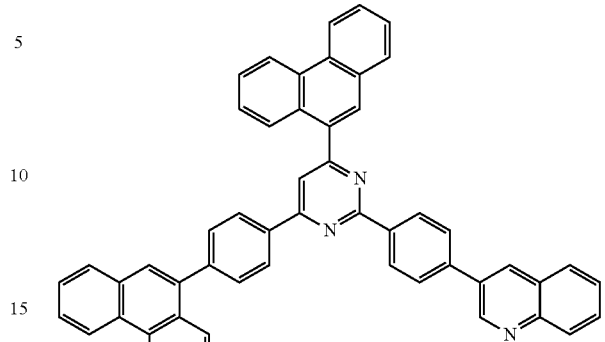
ET24
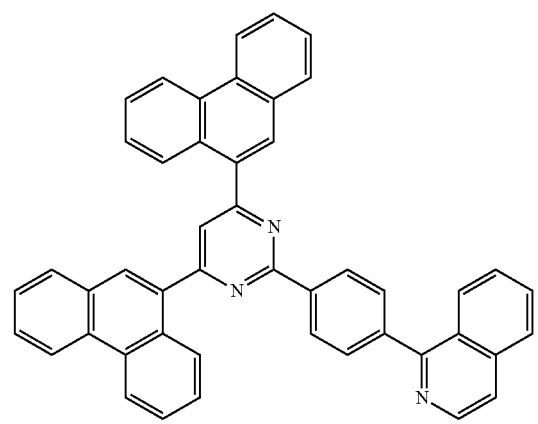
ET25
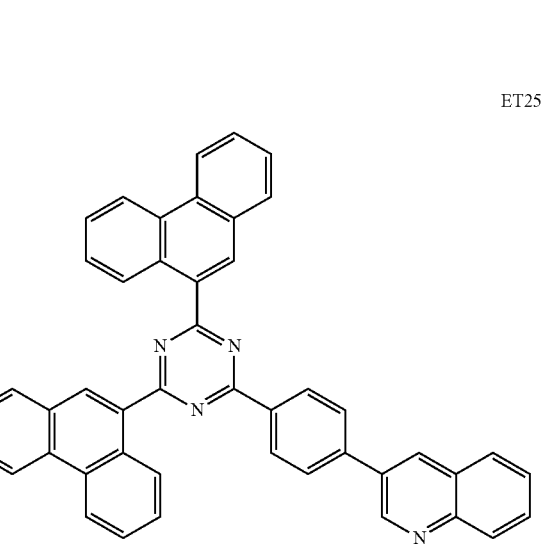

ET26
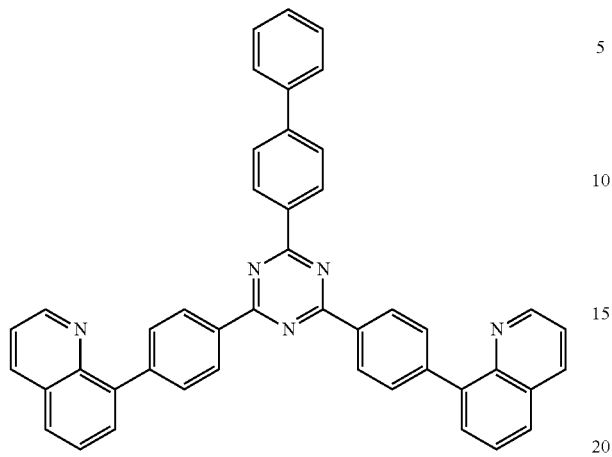
ET27
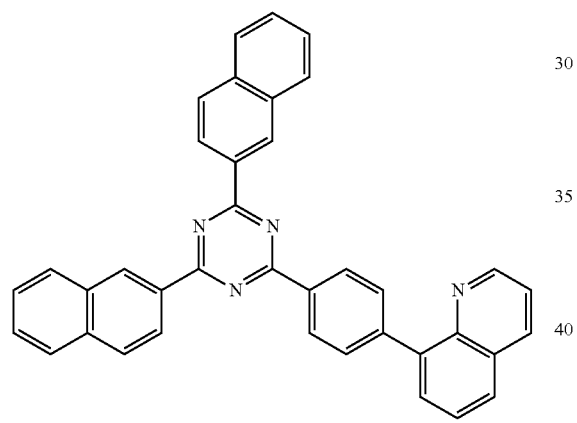
ET28
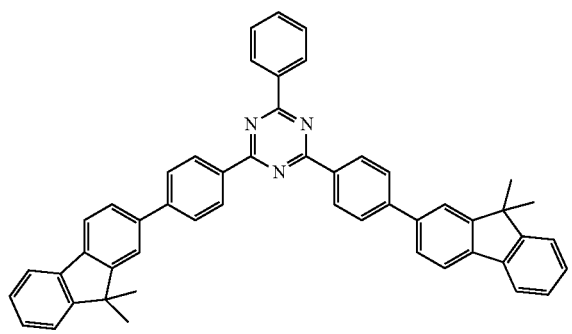
ET29
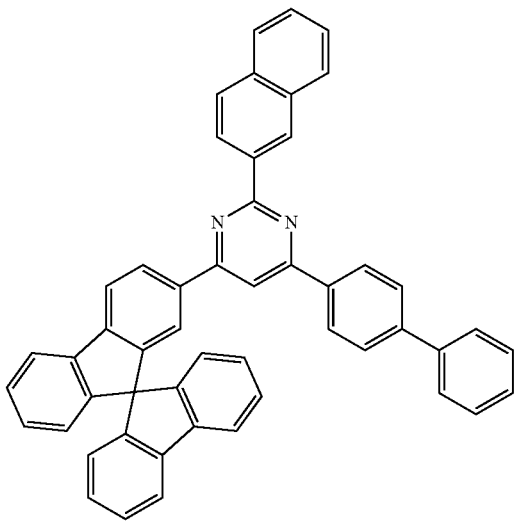
ET30
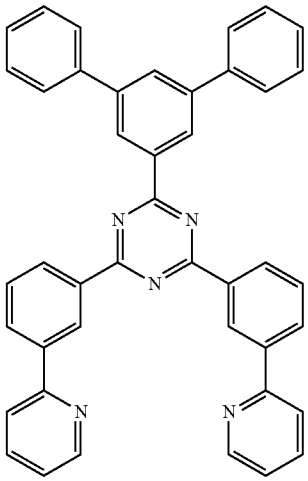
ET31
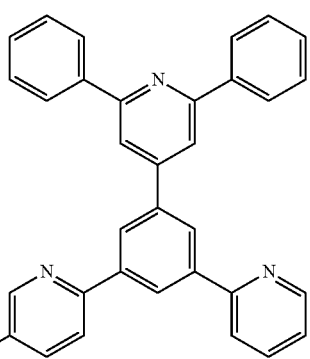

ET32
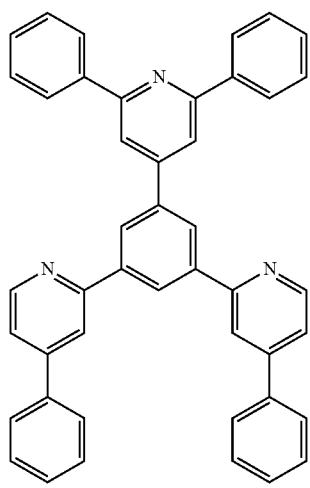
ET35
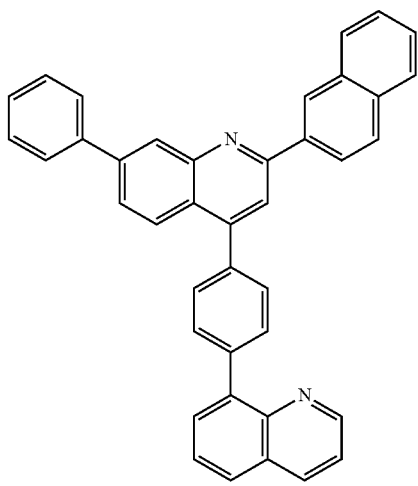
ET33
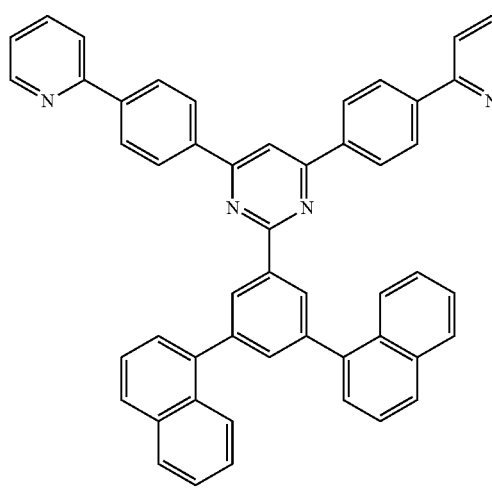
ET36
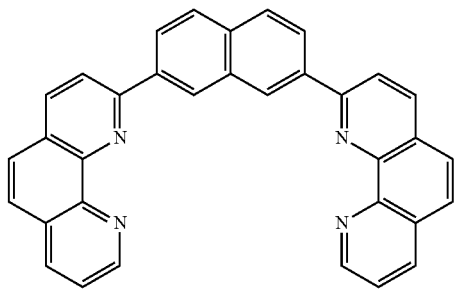
In one embodiment, the electron transport region may include at least one compound selected from 2,9-dimethyl-4,7-diphenyl-1,10-phenanthroline (BCP), 4,7-diphenyl-1,10-phenanthroline (Bphen), Alq$_3$, BAlq, 3-(biphenyl-4-yl)-5-(4-tert-butylphenyl)-4-phenyl-4H-1,2,4-triazole (TAZ), NTAZ, and diphenyl(4-(triphenylsilyl)phenyl)-phosphine oxide (TSPO1):
ET34
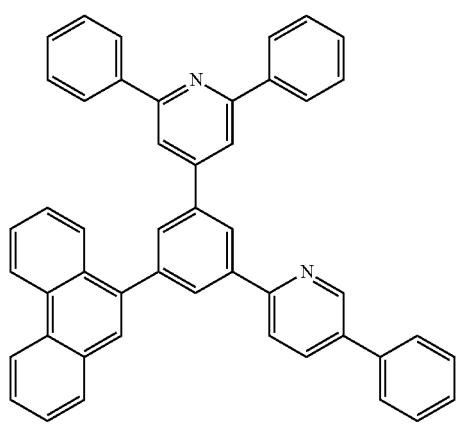
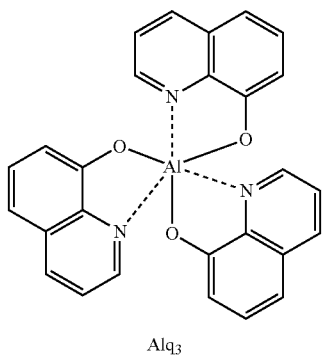
Alq$_3$

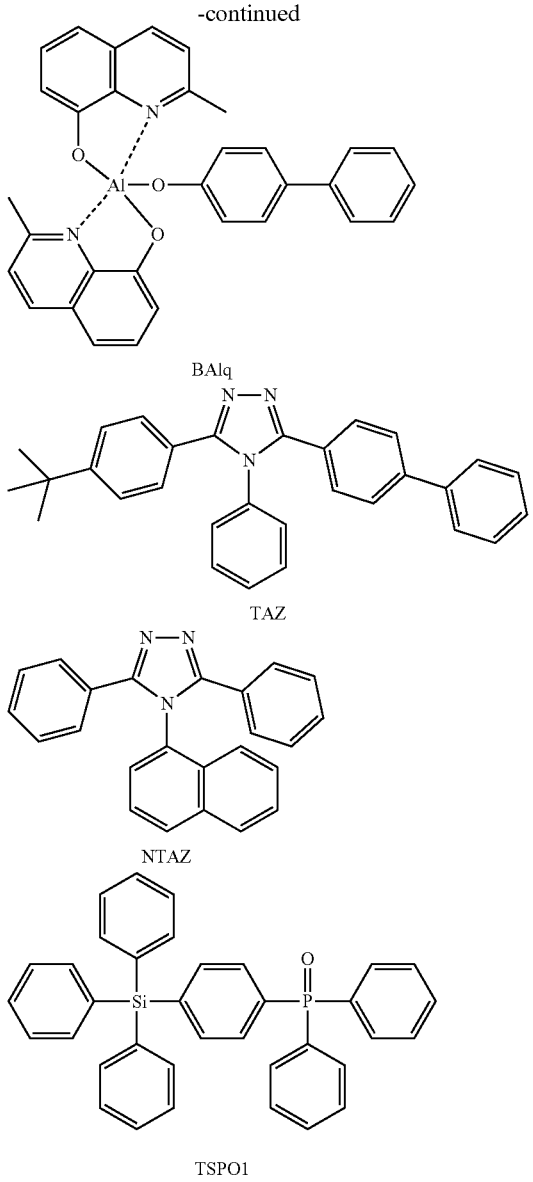

BAlq

TAZ

NTAZ

TSPO1

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, the electron blocking layer may have suitable (e.g., excellent) electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the ranges described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from alkali metal complex and alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but embodiments of the present disclosure are not limited thereto.

For example, the metal-containing material may include a Li complex. The Li complex may include, for example, Compound ET-D1 (lithium quinolate, LiQ) or ET-D2.

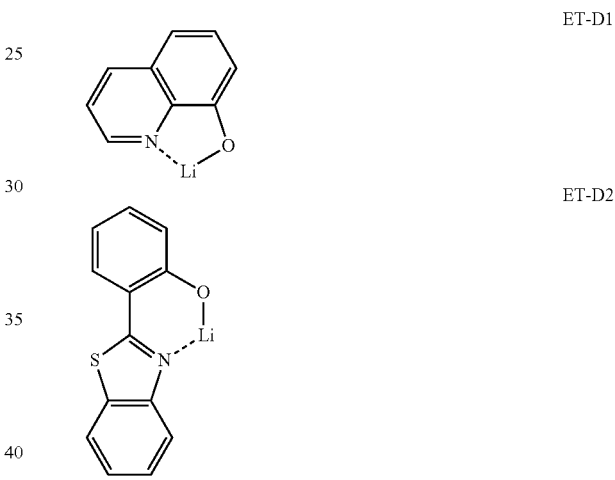

ET-D1

ET-D2

The electron transport region may include an electron injection layer that facilitates injection of electrons from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from Li, Na, K, Rb, and Cs. In one embodiment, the alkali metal may be Li, Na, and/or Cs. In one or more embodiments, the alkali metal may be Li and/or Cs, but embodiments of the present disclosure are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, and/or iodides) of the alkali metal, the alkaline earth-metal, and the rare earth metal.

The alkali metal compound may be selected from alkali metal oxides, such as $Li_2O$, $Cs_2O$, and/or $K_2O$, and alkali metal halides, such as LiF, NaF, CsF, KF, LiI, NaI, CsI, and/or KI. In one embodiment, the alkali metal compound may be selected from LiF, $Li_2O$, NaF, LiI, NaI, CsI, and KI, but embodiments of the present disclosure are not limited thereto.

The alkaline earth-metal compound may be selected from alkaline earth-metal oxides, such as BaO, SrO, CaO, $Ba_xSr_{1-x}$ O (0<x<1), and $Ba_xCa_{1-x}O$ (0<x<1). In one embodiment, the alkaline earth-metal compound may be selected from BaO, SrO, and CaO, but embodiments of the present disclosure are not limited thereto.

The rare earth metal compound may be selected from $YbF_3$, $ScF_3$, $ScO_3$, $Y_2O_3$, $Ce_2O_3$, $GdF_3$, and $TbF_3$. In one embodiment, the rare earth metal compound may be selected from $YbF_3$, $ScF_3$, $TbF_3$, $YbI_3$, $ScI_3$, and $TbI_3$, but embodiments of the present disclosure are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but embodiments of the present disclosure are not limited thereto.

The electron injection layer may include or consist of (i.e., include only) an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the ranges described above, the electron injection layer may have satisfactory electron injection characteristics without a substantial increase in driving voltage.

Second Electrode 190

The second electrode 190 may be disposed on the organic layer 150 having such a structure. The second electrode 190 may be a cathode which is an electron injection electrode, and in this regard, a material for forming the second electrode 190 may be selected from a metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode 190 may be a transmissive electrode, a semi-transmissive electrode, or a reflective electrode.

The second electrode 190 may have a single-layered structure, or a multi-layered structure including two or more layers.

Figure 2:
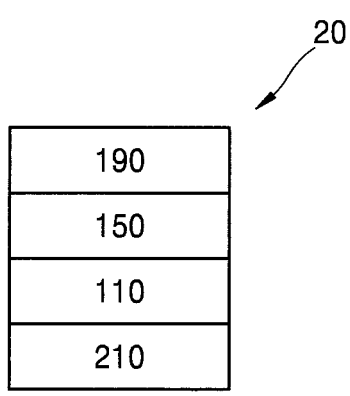
FIG. 2 is a schematic cross-sectional view of an organic light-emitting device according to an embodiment.
Figure 3:
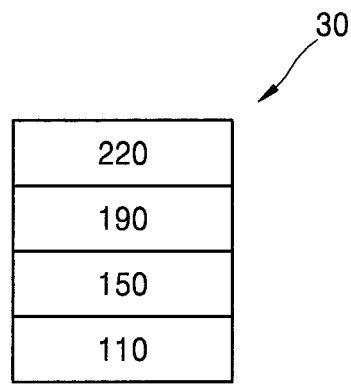
FIG. 3 is a schematic cross-sectional view of an organic light-emitting device according to an embodiment.
Figure 4:
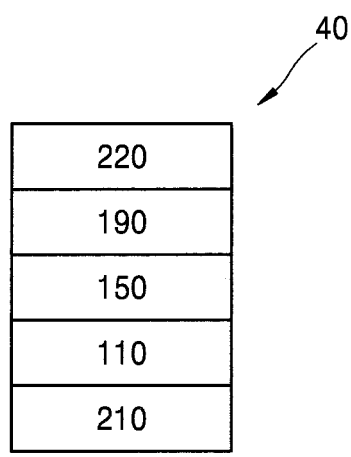
FIG. 4 is a schematic cross-sectional view of an organic light-emitting device according to an embodiment.

Description of FIGS. 2 to 4

An organic light-emitting device 20 of FIG. 2 includes a first capping layer 210, a first electrode 110, an organic layer 150, and a second electrode 190, which are sequentially stacked in this stated order; an organic light-emitting device 30 of FIG. 3 includes a first electrode 110, an organic layer 150, a second electrode 190, and a second capping layer 220, which are sequentially stacked in this stated order; and an organic light-emitting device 40 of FIG. 4 includes a first capping layer 210, a first electrode 110, an organic layer 150, a second electrode 190, and a second capping layer 220, which are sequentially stacked in this stated order.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

At least one selected from the first capping layer 210 and the second capping layer 220 may each independently include at least one material selected from carbocyclic compounds, heterocyclic compounds, amine-based compounds, porphyrine derivatives, phthalocyanine derivatives, naphthalocyanine derivatives, alkali metal complexes, and alkaline earth-based complexes. The carbocyclic compound, the heterocyclic compound, and the amine-based compound may be optionally substituted with a substituent containing (e.g., including) at least one element selected from O, N, S, Se, Si, F, Cl, Br, and I. In one embodiment, at least one selected from the first capping layer 210 and the second capping layer 220 may each independently include an amine-based compound.

In one embodiment, at least one selected from the first capping layer 210 and the second capping layer 220 may each independently include the compound represented by Formula 201 or the compound represented by Formula 202.

In one or more embodiments, at least one selected from the first capping layer 210 and the second capping layer 220 may each independently include a compound selected from Compounds HT28 to HT33 and Compounds CP1 to CP5, but embodiments of the present disclosure are not limited thereto.

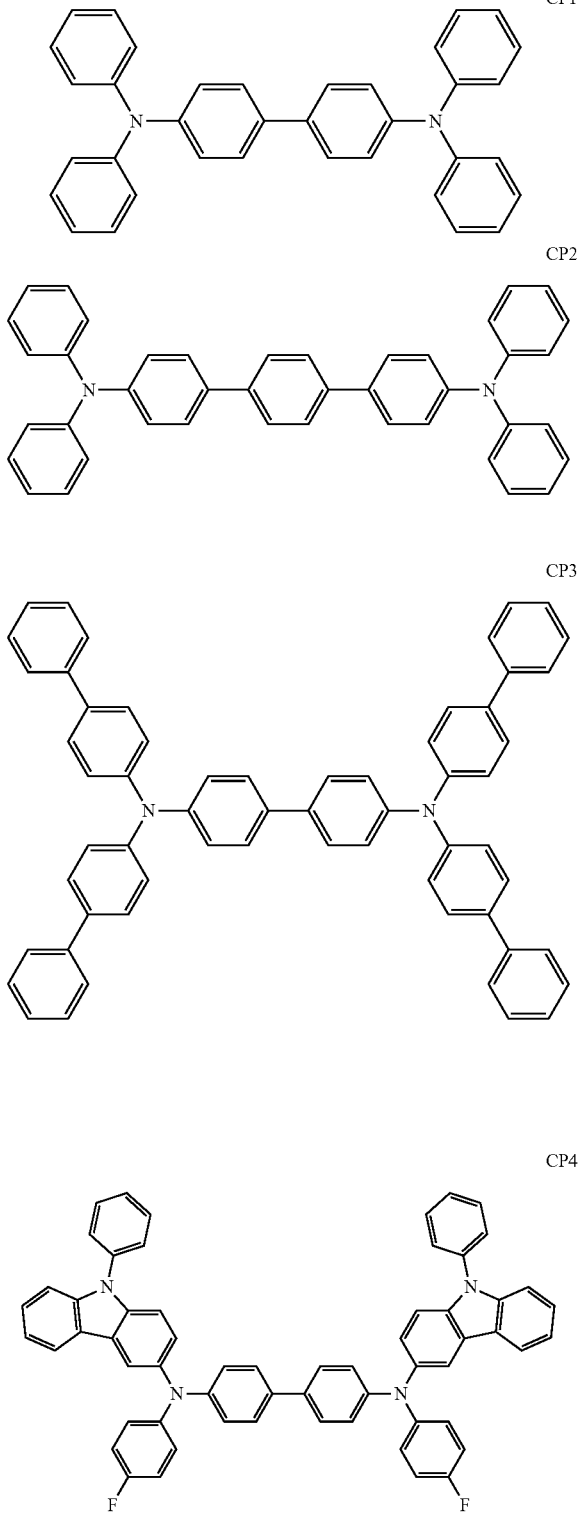

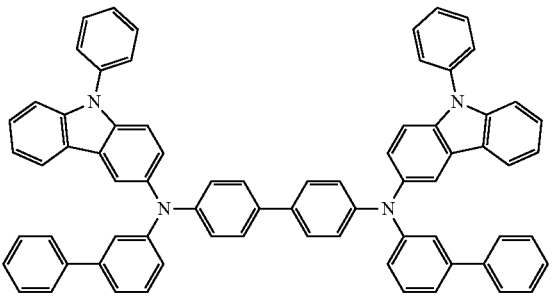

Hereinbefore, the organic light-emitting device according to an embodiment has been described in connection with FIGS. 1 to 4. However, embodiments of the present disclosure are not limited thereto.

Layers constituting the hole transport region, an emission layer, and layers constituting the electron transport region may be formed in a certain region by utilizing one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed, and the structure of a layer to be formed.

When layers constituting the hole transport region, an emission layer, and layers constituting the electron transport region are formed by spin coating, the spin coating may be performed at a coating speed of about 2000 rpm to about 5000 rpm and at a heat treatment temperature of about 80° C. to 200° C. by taking into account a material to be included in a layer to be formed, and the structure of a layer to be formed.

Display Apparatus

The organic light-emitting device according to an embodiment may be included in a display device including a thin film transistor. The thin film transistor may include a gate electrode, source and drain electrodes, a gate insulating film, and an active layer, and one of the source and drain electrodes may electrically contact a first electrode of the organic light-emitting device.

The active layer may include crystalline silicon, amorphous silicon, organic semiconductor, oxide semiconductor, and/or the like, but embodiments of the present disclosure are not limited thereto.

The display apparatus may further include a sealing member that seals the organic light-emitting device. The sealing member may enable the implementation of an image in the organic light-emitting device, and may reduce or prevent penetration of external air and moisture into the organic light-emitting device. The sealing member may be a sealing substrate made of glass and/or plastic. The sealing member may be a thin-film encapsulation layer including a plurality of organic layers and/or a plurality of inorganic layers. When the sealing member is a thin-film encapsulation layer, the whole flat display apparatus may be made flexible.

General Definition of Substituents

The term "π electron-depleted nitrogen-containing ring" as used herein refers to, for example, a cyclic group having at least one *—N=* moiety, and examples thereof include an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, s thiadiazol group, an imidazopyridine group, an imidazopyrimidine group, and an azacarbazole group, but embodiments of the present disclosure are not limited thereto.

Examples of the π electron-depleted nitrogen-free cyclic group include a benzene group, a heptalene group, an indene group, a naphthalene group, an azulene group, a heptalene group, an indacene group, acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentacene group, a rubicene group, a corozen group, an ovalene group, a pyrrole group, an isoindole group, an indole group, a furan group, a thiophene group, a benzofuran group, a benzothiophene group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group and a triindolobenzene group, but embodiments of the present disclosure are not limited thereto.

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one double bond in the middle or at the terminus of the $C_2$-$C_{60}$ alkyl group, and examples thereof include an ethenyl group, a propenyl group, and a butenyl group. The term "$C_{2-60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one triple bond in the middle or at the terminus of the $C_2$-$C_{60}$ alkyl group, and examples thereof include an ethynyl group, and a propynyl group. The term "0$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, and S as a ring-forming atom in addition to 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one double bond in its ring. Non-limiting examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein refers to a divalent group having a carbocyclic aromatic system that has at least one heteroatom selected from N, O, Si, P, and S as a ring-forming atom, in addition to 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to a group represented by —$OA_{102}$ (wherein $A_{102}$ is the $C_6$-$C_{60}$ aryl group), and the term "$C_6$-$C_{60}$ arylthio group" refers to a group represented by —$SA_{103}$ (wherein $A_{103}$ is the $C_6$-$C_{60}$ aryl group).

The term "$C_1$-$C_{60}$ heteroaryloxy group" as used herein refers to a group represented by —$OA_{104}$ (wherein $A_{104}$ is the $C_1$-$C_{60}$ heteroaryl group), and the term "$C_6$-$C_{60}$ heteroarylthio group" as used herein refers to a group represented by —$SA_{105}$ (wherein $A_{105}$ is the $C_1$-$C_{60}$ heteroaryl group).

The term "monovalent non-aromatic condensed polycyclic group" as used herein refers to a monovalent group (for example, having 8 to 60 carbon atoms) having two or more rings condensed with each other, only carbon atoms as ring-forming atoms, and no aromaticity in its entire molecular structure. An example of the monovalent non-aromatic condensed polycyclic group is a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, Si, P, and S, other than carbon atoms, as a ring-forming atom, and no aromaticity in its entire molecular structure. An example of the monovalent non-aromatic condensed heteropolycyclic group is a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which the ring-forming atoms include only carbon atoms. The $C_5$-$C_{60}$ carbocyclic group may be an aromatic carbocyclic group or a non-aromatic carbocyclic group. The $C_5$-$C_{60}$ carbocyclic group may be a ring (such as benzene), a monovalent group (such as a phenyl group), or a divalent group (such as a phenylene group). In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having the same structure as the $C_5$-$C_{60}$ carbocyclic group, except that as a ring-forming atom, at least one heteroatom selected from N, O, Si, P, and S is utilized in addition to the carbon atom (the number of carbon atoms may be in a range of 1 to 60).

In the specification, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{00}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ hetero aryloxy group, the substituted $C_1$-$C_{60}$ hetero arylthio group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, a $C_1$-$C_{60}$ alkyl group substituted with at least one selected from deuterium, —F, and a cyano group, a $C_6$-$C_{60}$ aryl group substituted with at least one selected from deuterium, —F, and a cyano group, a biphenyl group, and a terphenyl group.

The term "Ph" as used herein refers to a phenyl group, the term "Me" as used herein refers to a methyl group, the term "Et" as used herein refers to an ethyl group, the term "ter-Bu" or "But" as used herein refers to a tert-butyl group, and the term "OMe" as used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *' as used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was utilized instead of A" used in describing Synthesis Examples refers to that an identical molar equivalent of B was utilized in place of A.

EXAMPLES

Example 1

As an anode, an ITO substrate, on which ITO/Ag/ITO were deposited, was cut to a size of 50 mm×50 mm×0.7 mm, sonicated with isopropyl alcohol and pure water for 5 minutes each, and then cleaned by exposure to ultraviolet rays and ozone for 30 minutes. Then, the ITO substrate was provided to a vacuum deposition apparatus.

Compound HT3 and F4-TCNQ were vacuum-deposited on the ITO substrate at a weight ratio of 98:2 to form a hole injection layer having a thickness of 100 Å, Compound HT3 was vacuum-deposited on the hole injection layer to form a hole transport layer having a thickness of 1,200 Å, and Compounds H001, T001, and D001 were co-deposited on the hole transport layer at a weight ratio of 70:29.5:0.5 to form an emission layer having a thickness of 300 Å. Compound ET-1 and LiQ were co-deposited on the emission layer at a weight ratio of 50:50 to form an electron transport layer having a thickness of 310 Å. LiQ was deposited on the electron transport layer to form an electron injection layer having a thickness of 10 Å, and Mg and Ag (at a weight ratio of 130:10) were co-deposited on the electron injection layer to form a cathode having a thickness of 130 Å, thereby completing the manufacture of an organic light-emitting device.

Examples 2 to 11 and Comparative Examples 1 to 5

Organic light-emitting devices were manufactured in the same manner as in Example 1, except that Compounds shown in Table 1 were each utilized in forming an emission layer.

Evaluation Example

The current efficiency and lifespan of the organic light-emitting devices manufactured according to Examples 1 to 11 and Comparative Examples 1 to 5 were measured at 10 mA/cm² by utilizing Keithley SMU 236 and a luminance meter PR650, and results thereof are shown in Table 1. The lifespan represents an amount of time that lapsed when luminance was 95% of the initial luminance (100%). In addition, the lifespan was expressed with a relative value with respect to Comparative Example 1. That is, the lifespan was a relative value calculated utilizing the lifespan value of Comparative Example 1 as 100%.

TABLE 1

| | Emission layer | | | | | | |
|---|---|---|---|---|---|---|---|
| | First compound | Second compound | Third compound | Weight ratio (first compound:second compound:third compound) | Emission color | Efficiency (cd/A) | Lifespan (%) |
| Example 1 | H001 | T001 | D001 | 70:29.5:0.5 | Red | 20.2 | 180 |
| Example 2 | H001 | T001 | D001 | 80:19.5:0.5 | Red | 21.3 | 165 |
| Example 3 | H001 | T001 | D001 | 70:29:1 | Red | 19.0 | 170 |
| Example 4 | H002 | T001 | D001 | 70:29.5:0.5 | Red | 19.5 | 180 |
| Example 5 | H002 | T001 | D001 | 80:19.5:0.5 | Red | 20.1 | 170 |
| Example 6 | H003 | T001 | D001 | 70:29.5:0.5 | Red | 21.0 | 195 |
| Example 7 | H003 | T001 | D001 | 80:19.5:0.5 | Red | 22.7 | 170 |
| Example 8 | H004 | T001 | D001 | 70:29.5:0.5 | Red | 21.3 | 190 |
| Example 9 | H004 | T001 | D001 | 80:19.5:0.5 | Red | 22.0 | 185 |
| Example 10 | H001 | T002 | D001 | 70:29.5:0.5 | Red | 22.5 | 165 |
| Example 11 | H001 | T002 | D001 | 80:19.5:0.5 | Red | 23.6 | 150 |
| Comparative Example 1 | H001 | T001 | DCJTB | 70:29.5:0.5 | Red | 7.1 | 100 |
| Comparative Example 2 | H001 | T001 | — | 70:30 | yellowish green | 28 | 30 |
| Comparative Example 3 | H001 | — | DCJTB | 95:5 | Red | 2.8 | 110 |
| Comparative Example 4 | HX01 | TX01 | DX01 | 70:29.5:0.5 | Green | 32 | 70 |
| Comparative Example 5 | HX02 | TX02 | DX02 | 70:29.5:0.5 | Blue | 5.2 | 7 |

H001
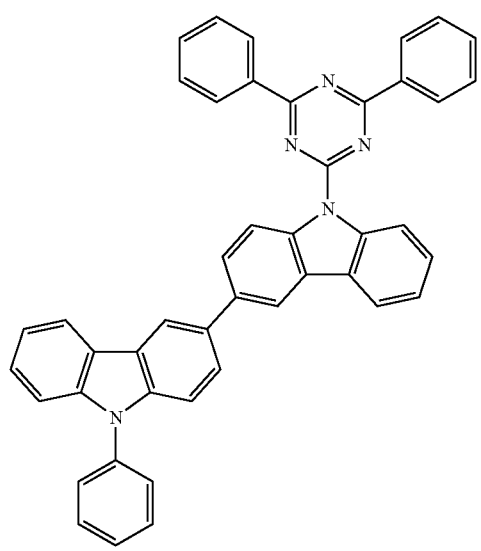
H004
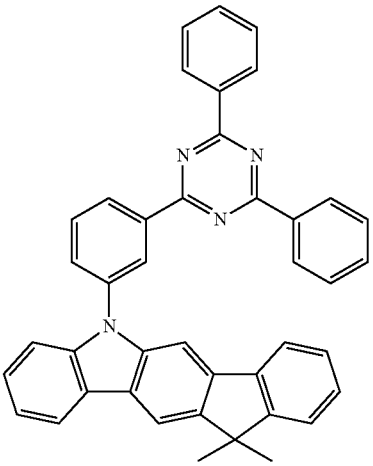
HX01
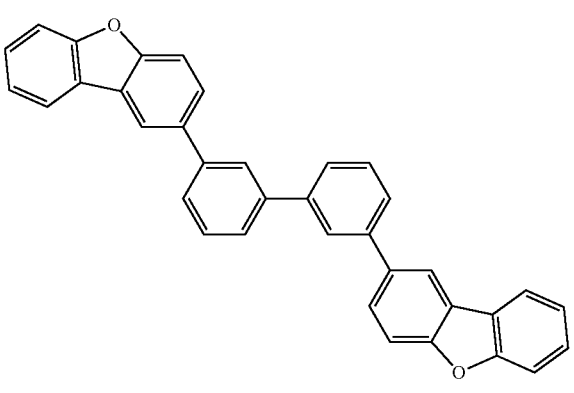
H002
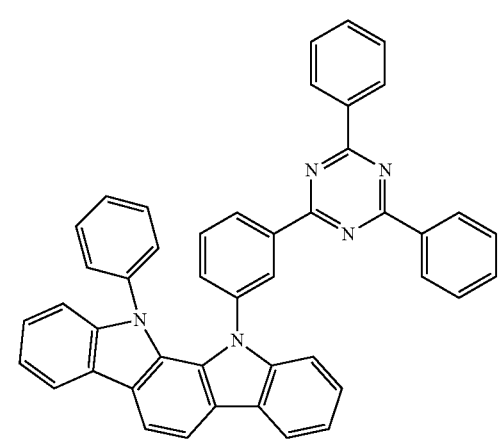
HX02
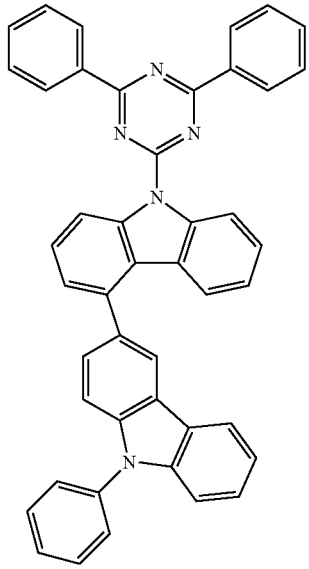
H003

-continued

T001
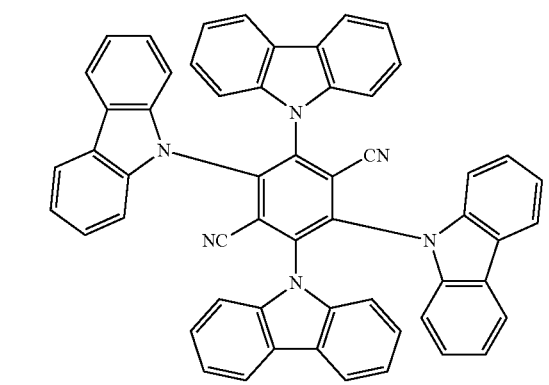

T002
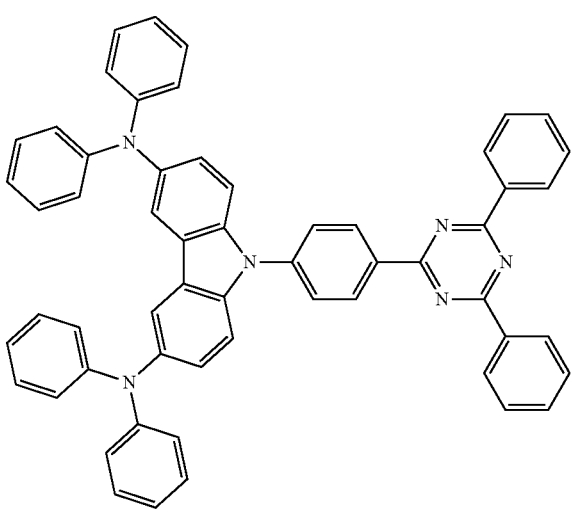

TX01
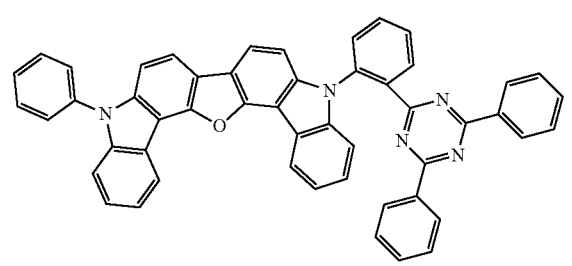

TX02
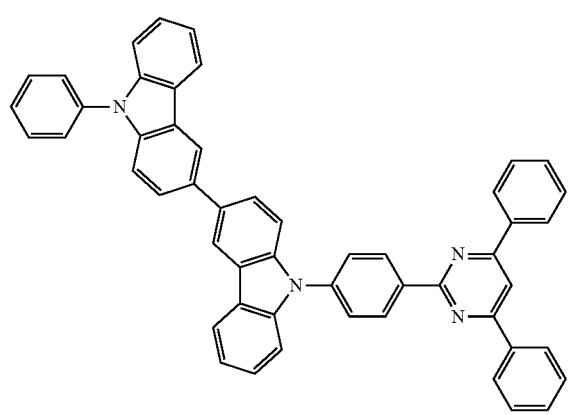

-continued

D001
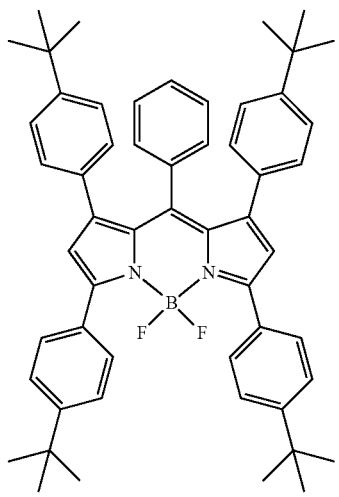

DX01
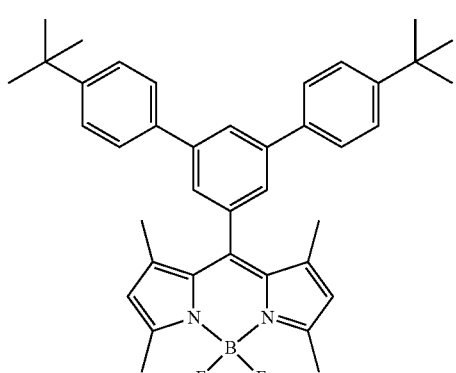

DX02
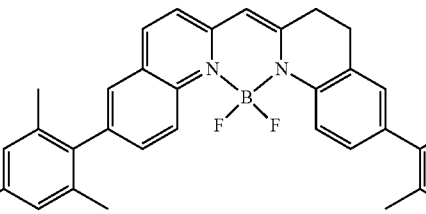

DCJTB
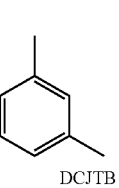

Referring to Table 1, it is confirmed that the current efficiency and lifespan of the organic light-emitting devices of Examples 1 to 11 are better (e.g., more excellent) than those of the organic light-emitting devices of Comparative Examples 1 to 5. For example, it is confirmed that the organic light-emitting devices of Examples 1 to 3 have significantly improved lifespan while maintaining a similar or improved current efficiency.

An organic light-emitting device according to an embodiment may have high efficiency and a long lifespan.

Expressions such as "at least one of," when preceding a list of elements, modify the entire list of elements and do not modify the individual elements of the list. Further, the use of "may" when describing embodiments of the present invention refers to "one or more embodiments of the present invention." Also, the term "exemplary" is intended to refer to an example or illustration.

It will be understood that when an element or layer is referred to as being "on," "connected to," or "coupled to" another element or layer, it can be directly on, connected to, or coupled to the other element or layer, or one or more intervening elements or layers may be present.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." Also, the term "exemplary" is intended to refer to an example or illustration.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. An organic light-emitting device comprising:
   a first electrode;
   a second electrode; and
   an organic layer between the first electrode and the second electrode,
   wherein the organic layer comprises an emission layer,
   the emission layer comprises a first compound, a second compound, and a third compound,
   the first compound is represented by Formula 1,
   the second compound is represented by Formula 2,
   the third compound is represented by Formula 3, and
   the first compound and the second compound are different from each other:

$(Y_{11})_{c11}$—$(L_{11})_{a11}$—$(Y_{21})_{c12}$  Formula 1

$(Y_{21})_{c21}$—$(L_{21})_{a21}$—$(Y_{22})_{c22}$  Formula 2

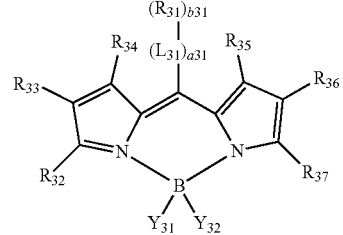

Formula 3

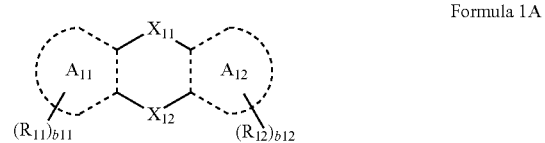

Formula 1A

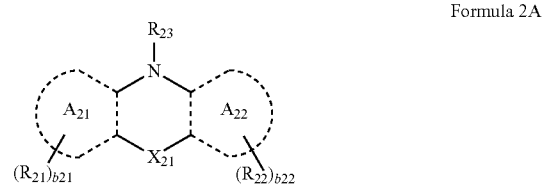

Formula 2A

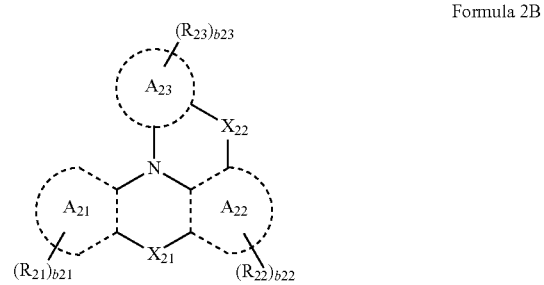

Formula 2B

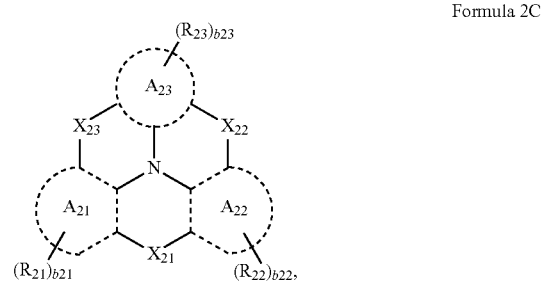

Formula 2C wherein, in Formulae 1 to 3, 1A, and 2A to 2C, $L_{11}$ is selected from the group consisting of:
a π electron-depleted nitrogen-free cyclic group; and
a π electron-depleted nitrogen-free cyclic group substituted with at least one selected from the group consisting of deuterium, a $C_1$-$C_{60}$ alkyl group, a π electron-depleted nitrogen-free cyclic group, and —Si($Q_{31}$)($Q_{32}$)($Q_{33}$), a11 is selected from the group consisting of 0, 1, 2, and 3, $Y_{11}$ is a group represented by Formula 1A, $Y_{12}$ is selected from the group consisting of:
—F, a cyano group, and a π electron-depleted nitrogen-containing cyclic group;
a $C_1$-$C_{60}$ alkyl group, a π electron-depleted nitrogen-containing cyclic group, and a π electron-depleted nitrogen-free cyclic group, each substituted with at least one selected from the group consisting of —F and a cyano group; and a π electron-depleted nitrogen-containing cyclic group substituted with at least one selected from the group consisting of deuterium, a $C_1$-$C_{60}$ alkyl group, a π electron-depleted nitrogen-containing cyclic group, and a π electron-depleted nitrogen-free cyclic group, c11 and c12 are each independently selected from the group consisting of 1, 2, and 3, $X_{11}$ is selected from the group consisting of a single bond, $N(R_{13})$, O, and S, $X_{12}$ is selected from the group consisting of a single bond, $N(R_{14})$, O, and S, $X_{11}$ and $X_{12}$ are not a single bond at the same time, $A_{11}$ and $A_{12}$ are each independently a π electron-depleted nitrogen-free cyclic group or a substituted or unsubstituted carbazole group, $R_{11}$ to $R_{14}$ are each independently selected from the group consisting of:

a binding site, hydrogen, deuterium, a $C_1$-$C_{60}$ alkyl group, a π electron-depleted nitrogen-free cyclic group, and —$Si(Q_1)(Q_2)(Q_3)$;

a π electron-depleted nitrogen-free cyclic group substituted with at least one selected from the group consisting of deuterium, a $C_1$-$C_{60}$ alkyl group, a π electron-depleted nitrogen-free cyclic group, and —$Si(Q_{31})(Q_{32})(Q_{33})$; and a π electron-depleted nitrogen-free cyclic group substituted with a π electron-depleted nitrogen-free cyclic group that is substituted with at least one selected from the group consisting of deuterium, a $C_1$-$C_{60}$ alkyl group, a π electron-depleted nitrogen-free cyclic group, and —$Si(Q_{21})(Q_{22})(Q_{23})$, wherein one selected from the group consisting of $R_{11}$ to $R_{14}$ is a binding site, b11 and b12 are each independently selected from the group consisting of 1, 2, 3, 4, 5, and 6, $L_{21}$ is selected from the group consisting of a substituted or unsubstituted $C_5$-$C_{60}$ carbocyclic group and a substituted or unsubstituted $C_1$-$C_{60}$ heterocyclic group, a21 is selected from the group consisting of 0, 1, 2, and 3, $Y_{21}$ is a group represented by one selected from the group consisting of Formulae 2A to 2C, $Y_{22}$ is selected from the group consisting of:

—F, a cyano group, and a π electron-depleted nitrogen-containing cyclic group;

a $C_1$-$C_{60}$ alkyl group, a π electron-depleted nitrogen-containing cyclic group, and a π electron-depleted nitrogen-free cyclic group, each substituted with at least one selected from the group consisting of —F and a cyano group; and a π electron-depleted nitrogen-containing cyclic group substituted with at least one selected from the group consisting of deuterium, a $C_1$-$C_{60}$ alkyl group, a π electron-depleted nitrogen-containing cyclic group, and a π electron-depleted nitrogen-free cyclic group, c21 and c22 are each independently selected from the group consisting of 1, 2, 3, 4, 5, and 6, $X_{21}$ is selected from the group consisting of a single bond, $N(R_{24})$, O, and S, $X_{22}$ is selected from the group consisting of a single bond, $N(R_{25})$, O, and S, $X_{23}$ is selected from the group consisting of a single bond, $N(R_{26})$, O, and S, $A_{21}$ to $A_{23}$ are each independently a π electron-depleted nitrogen-free cyclic group, $R_{21}$ to $R_{26}$ are each independently selected from the group consisting of:

a binding site, hydrogen, deuterium, a $C_1$-$C_{60}$ alkyl group, a π electron-depleted nitrogen-free cyclic group, —$N(Q_1)(Q_2)$, and —$Si(Q_1)(Q_2)(Q_3)$;

a π electron-depleted nitrogen-free cyclic group substituted with at least one selected from the group consisting of deuterium, a $C_1$-$C_{60}$ alkyl group, a π electron-depleted nitrogen-free cyclic group, —$N(Q_{31})(Q_{32})$, and —$Si(Q_{31})(Q_{32})(Q_{33})$; and a π electron-depleted nitrogen-free cyclic group substituted with a π electron-depleted nitrogen-free cyclic group that is substituted with at least one selected from the group consisting of deuterium, a $C_1$-$C_{60}$ alkyl group, a π electron-depleted nitrogen-free cyclic group, —$N(Q_{21})(Q_{22})$, and —$Si(Q_{21})(Q_{22})(Q_{23})$, wherein one selected from the group consisting of $R_{21}$ to $R_{24}$ in Formula 2A is a binding site, one selected from the group consisting of $R_{21}$ to $R_{25}$ in Formula 2B is a binding site, and one selected from the group consisting of $R_{21}$ to $R_{26}$ in Formula 2C is a binding site, b21 to b23 are each independently selected from the group consisting of 1, 2, 3, 4, 5, and 6, $L_{31}$ is selected from the group consisting of a substituted or unsubstituted $C_5$-$C_{60}$ carbocyclic group and a substituted or unsubstituted $C_1$-$C_{60}$ heterocyclic group, a31 is selected from the group consisting of 0, 1, 2, and 3, $R_{31}$ to $R_{37}$ are each independently selected from the group consisting of hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$B(Q_1)(Q_2)$, —$N(Q_1)(Q_2)$, —$P(Q_1)(Q_2)$, —$C(=O)(Q_1)$, —$S(=O)(Q_1)$, —$S(=O)_2(Q_1)$, —$P(=O)(Q_1)(Q_2)$, and —$P(=S)(Q_1)(Q_2)$, wherein $R_{31}$ to $R_{37}$ are optionally linked to form a substituted or unsubstituted $C_5$-$C_{60}$ carbocyclic group or a substituted or unsubstituted $C_1$-$C_{60}$ heterocyclic group, b31 is selected from the group consisting of 1, 2, 3, 4, 5, and 6, $Y_{31}$ and $Y_{32}$ are each independently selected from the group consisting of —F, —Cl, —Br, —I, a substituted or unsubstituted $C_1$-$C_{60}$ alkyl group, a substituted or unsubstituted $C_1$-$C_{60}$ alkoxy group, a substituted or unsubstituted $C_6$-$C_{60}$ aryl group, and a substituted or unsubstituted $C_6$-$C_{60}$ aryloxy group, wherein $Y_{31}$ and $Y_{32}$ are optionally linked to form a substituted or unsubstituted $C_5$-$C_{60}$ carbocyclic group or a substituted or unsubstituted $C_1$-$C_{60}$ heterocyclic group, $Q_1$ to $Q_3$, $Q_{21}$ to $Q_{23}$, and $Q_{31}$ to $Q_{33}$ are each independently selected from the group consisting of hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero arylthio group, a $C_1$-$C_{60}$ hetero arylthio group, a monovalent non-aromatic condensed polycyclic group, a monovalent non-aromatic condensed heteropolycyclic group, a biphenyl group, and a terphenyl group, and indicates a binding site to a neighboring atom, and a weight ratio among the first compound, the second compound and the third compound is 70:29:1 to 80:19.5:0.5.

2. The organic light-emitting device of claim 1, wherein $L_{11}$ is selected from the group consisting of:

a benzene group, a naphthalene group, a phenalene group, an anthracene group, a fluoranthene group, a triphenylene group, a phenanthrene group, a pyrene group, a chrysene group, a perylene group, a fluorene group, a carbazole group, a dibenzofuran group, and a dibenzothiophene group; and a benzene group, a naphthalene group, a phenalene group, an anthracene group, a fluoranthene group, a triphenylene group, a phenanthrene group, a pyrene group, a chrysene group, a perylene group, a fluorene group, a carbazole group, a dibenzofuran group, and a dibenzothiophene group, each substituted with at least one selected from the group consisting of deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, and $L_{21}$ and $L_{31}$ are each independently selected from the group consisting of:

a benzene group, a naphthalene group, a phenalene group, an anthracene group, a fluoranthene group, a triphenylene group, a phenanthrene group, a pyrene group, a chrysene group, a perylene group, a pyridine group, a pyrimidine group, a pyrazine group, a pyridazine group, a triazine group, a quinoline group, an isoquinoline group, a benzoquinoline group, a benzoisoquinoline group, a phthalazine group, a naphthyridine group, a quinoxaline group, a benzoquinoxaline group, a quinazoline group, a benzoquinazoline group, a fluorene group, a carbazole group, a dibenzofuran group, and a dibenzothiophene group; and a benzene group, a naphthalene group, a phenalene group, an anthracene group, a fluoranthene group, a triphenylene group, a phenanthrene group, a pyrene group, a chrysene group, a perylene group, a pyridine group, a pyrimidine group, a pyrazine group, a pyridazine group, a triazine group, a quinoline group, an isoquinoline group, a benzoquinoline group, a benzoisoquinoline group, a phthalazine group, a naphthyridine group, a quinoxaline group, a benzoquinoxaline group, a quinazoline group, a benzoquinazoline group, a fluorene group, a carbazole group, a dibenzofuran group, and a dibenzothiophene group, each substituted with at least one selected from the group consisting of deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group.

3. The organic light-emitting device of claim 1, wherein $X_{11}$ is selected from the group consisting of $N(R_{13})$, O, and S, and $X_{12}$ is a single bond.

4. The organic light-emitting device of claim 1, wherein $R_{11}$ to $R_{14}$ are each independently selected from the group consisting of:

a binding site, hydrogen, deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, and —Si($Q_1$)($Q_2$)($Q_3$);

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, each substituted with at least one selected from the group consisting of deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, and —Si($Q_{31}$)($Q_{32}$)($Q_{33}$); and a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group, each substituted with at least one selected from the group consisting of a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group that are each substituted with at least one selected from the group consisting of deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, and —Si($Q_{21}$)($Q_{22}$)($Q_{23}$), one selected from the group consisting of $R_{11}$ to $R_{14}$ is a binding site, and $Q_1$ to $Q_3$, $Q_{21}$ to $Q_{23}$, and $Q_{31}$ to $Q_{33}$ are each independently selected from the group consisting of a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, and a dinaphthothiophenyl group.

5. The organic light-emitting device of claim 1, wherein $Y_{12}$ is selected from the group consisting of:

—F, a cyano group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group;

a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from the group consisting of —F and a cyano group; and a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from the group consisting of deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group.

6. The organic light-emitting device of claim 1, wherein c11 and c12 are each independently 1.

7. The organic light-emitting device of claim 1, wherein $X_{21}$ is a single bond,
$X_{22}$ is a single bond, and
$X_{23}$ is a single bond.

8. The organic light-emitting device of claim 1, wherein $Y_{21}$ is a group represented by Formula 2A.

9. The organic light-emitting device of claim 1, wherein $Y_{22}$ is selected from the group consisting of:

—F, a cyano group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group;

a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from the group consisting of —F and a cyano group; and a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from the group consisting of deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group.

10. The organic light-emitting device of claim 1, wherein c21 and c22 are each independently selected from the group consisting of 1, 2, and 3.

11. The organic light-emitting device of claim 1, wherein $R_{31}$ to $R_{37}$ are each independently selected from the group consisting of:

hydrogen, deuterium, —F, —Cl, —Br, —I, a cyano group, a $C_1$-$C_{20}$ alkyl group, and a $C_1$-$C_{20}$ alkoxy group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from the group consisting of deuterium, —F, —Cl, —Br, —I, a cyano group, a $C_1$-$C_{20}$ alkyl group, a $C_1$-$C_{20}$ alkoxy group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group; and —B($Q_1$)($Q_2$) and —N($Q_1$)($Q_2$), and $Q_1$ and $Q_2$ are each independently selected from the group consisting of:

hydrogen, deuterium, and a $C_1$-$C_{20}$ alkyl group;

a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group; and a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group, each substituted with at least one selected from the group consisting of deuterium, a $C_1$-$C_{20}$ alkyl group, a phenyl group, a biphenyl group, a terphenyl group, a naphthyl group, a phenanthrenyl group, a triphenylenyl group, a chrysenyl group, a fluoranthenyl group, a fluorenyl group, a carbazolyl group, a dibenzofuranyl group, a dibenzothiophenyl group, a benzofluorenyl group, a benzocarbazolyl group, a benzonaphthofuranyl group, a benzonaphthothiophenyl group, a dibenzofluorenyl group, a dibenzocarbazolyl group, a dinaphthofuranyl group, a dinaphthothiophenyl group, a pyridinyl group, a pyrazinyl group, a pyridazinyl group, a pyrimidinyl group, a triazinyl group, a quinolinyl group, an isoquinolinyl group, a quinolinyl group, an isoquinolinyl group, a naphthyridinyl group, a quinoxalinyl group, a quinazolinyl group, an azafluorenyl group, an azacarbazolyl group, an azadibenzofuranyl group, an azadibenzothiophenyl group, a diazafluorenyl group, a diazacarbazolyl group, a diazadibenzofuranyl group, and a diazadibenzothiophenyl group.

12. The organic light-emitting device of claim 1, wherein $Y_{31}$ and $Y_{32}$ are each independently selected from the group consisting of —F, —Cl, —Br, —I, a $C_1$-$C_{20}$ alkyl group, and a $C_1$-$C_{20}$ alkoxy group.

13. The organic light-emitting device of claim 1, wherein
the first compound is selected from the group consisting of compounds of Group I,
the second compound is selected from the group consisting of compounds of Group II, and
the third compound is selected from the group consisting of compounds of Group III:

<Group I>

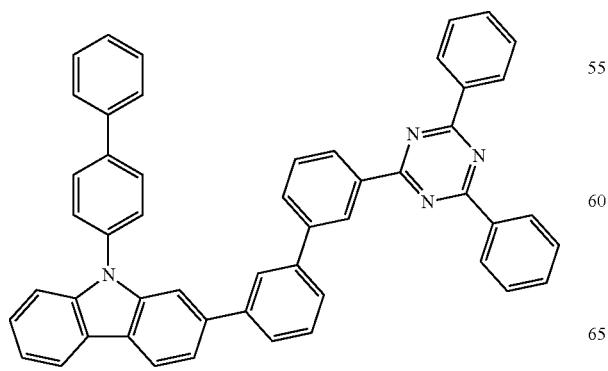

-continued

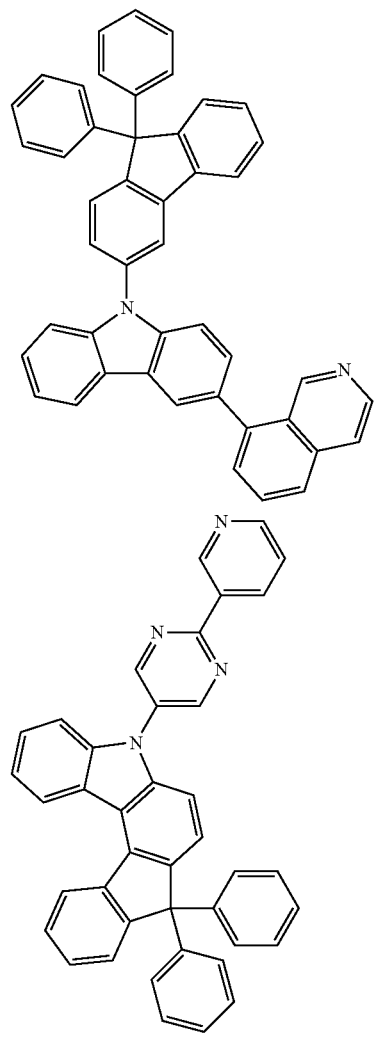

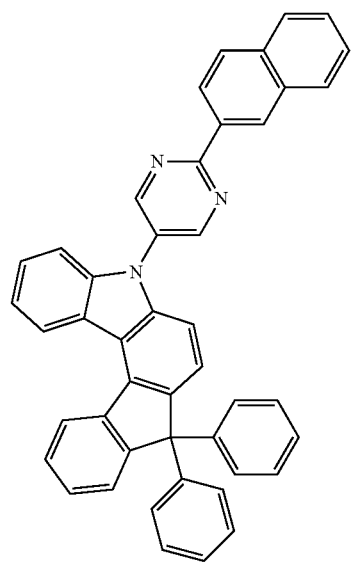

185
-continued
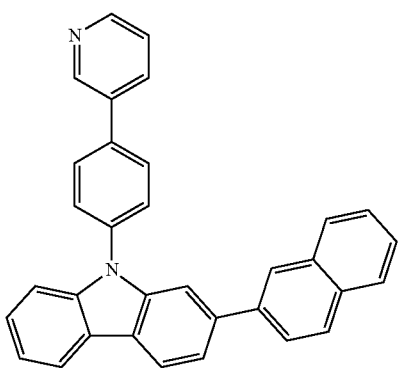
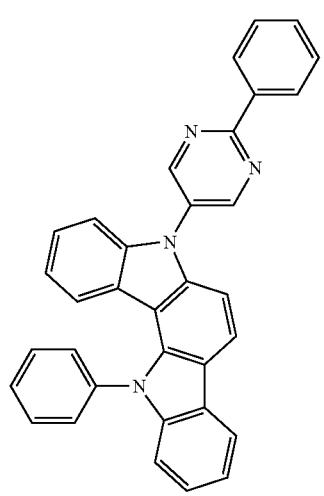
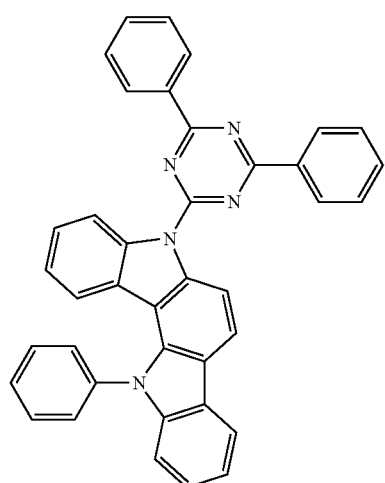
186
-continued
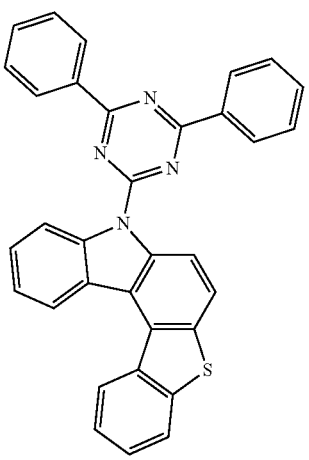
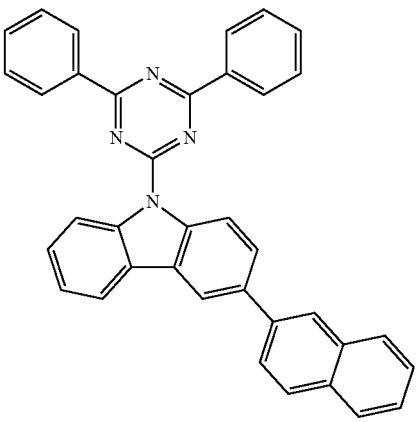

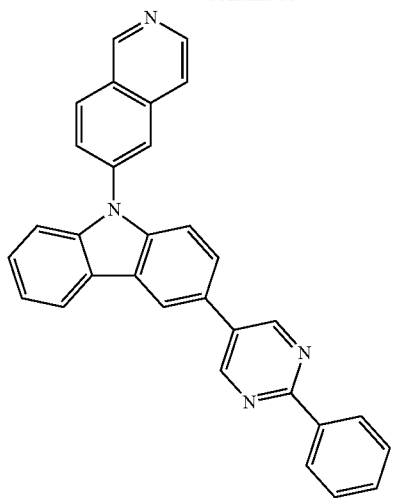
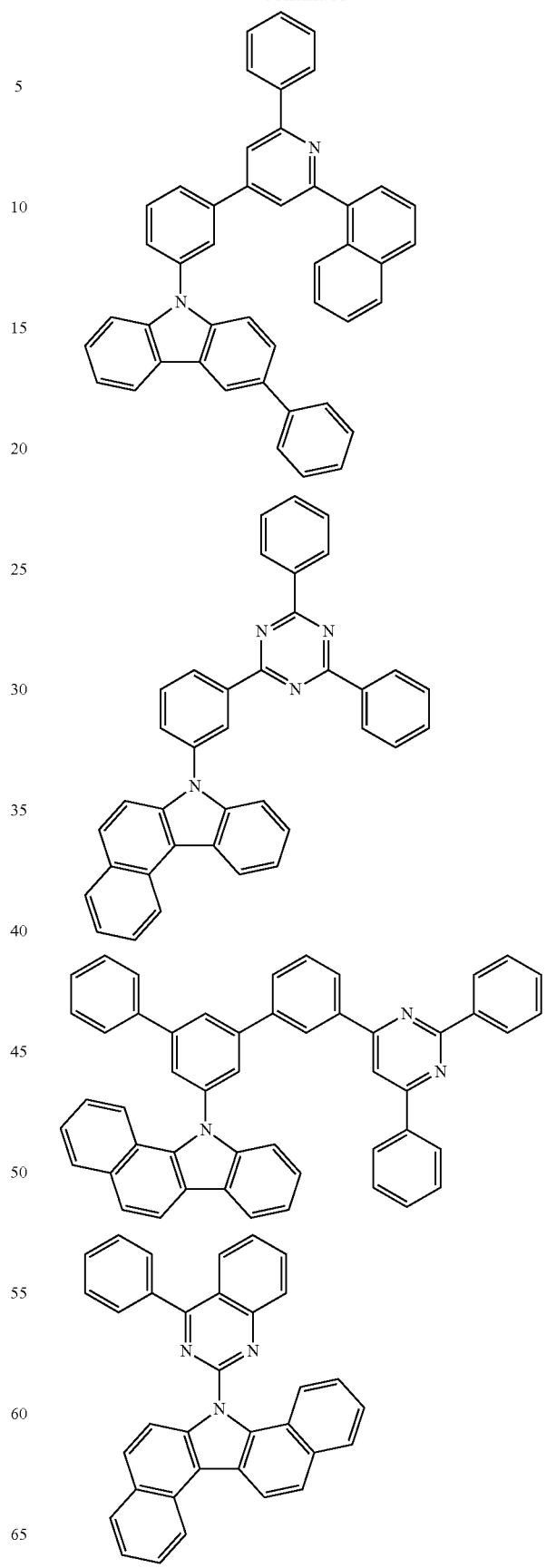

189
-continued
190
-continued
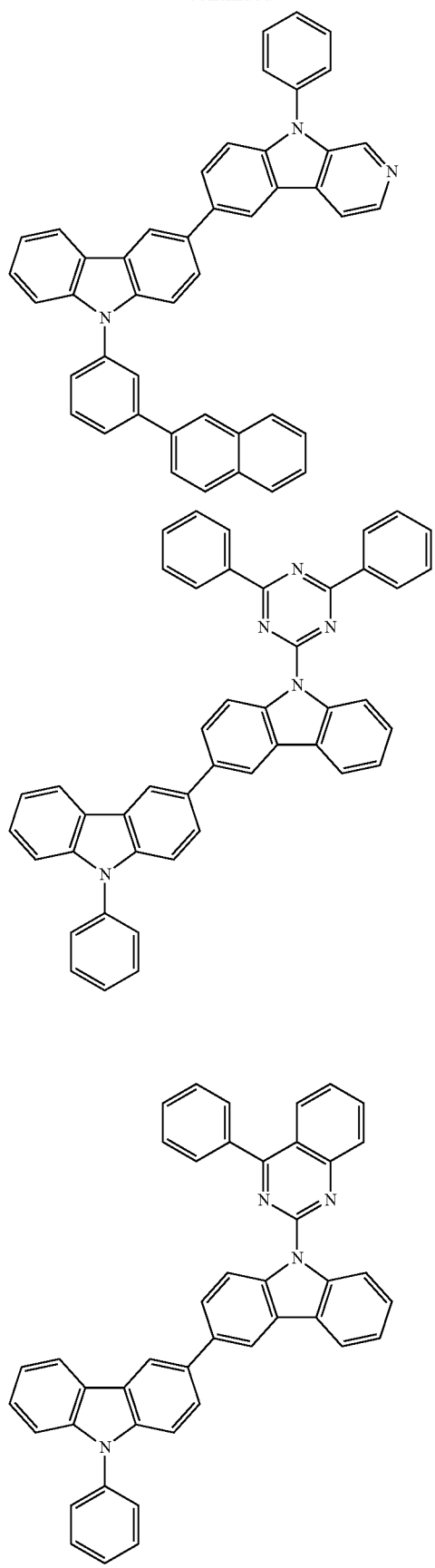
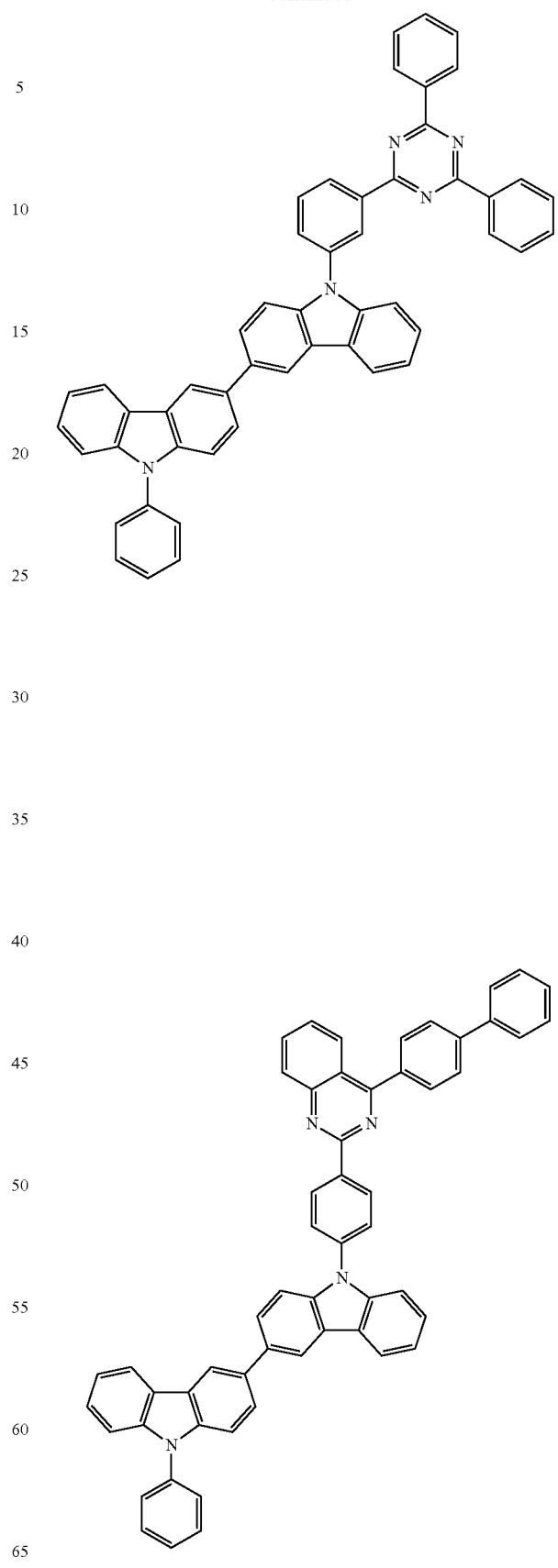

191
-continued
192
-continued
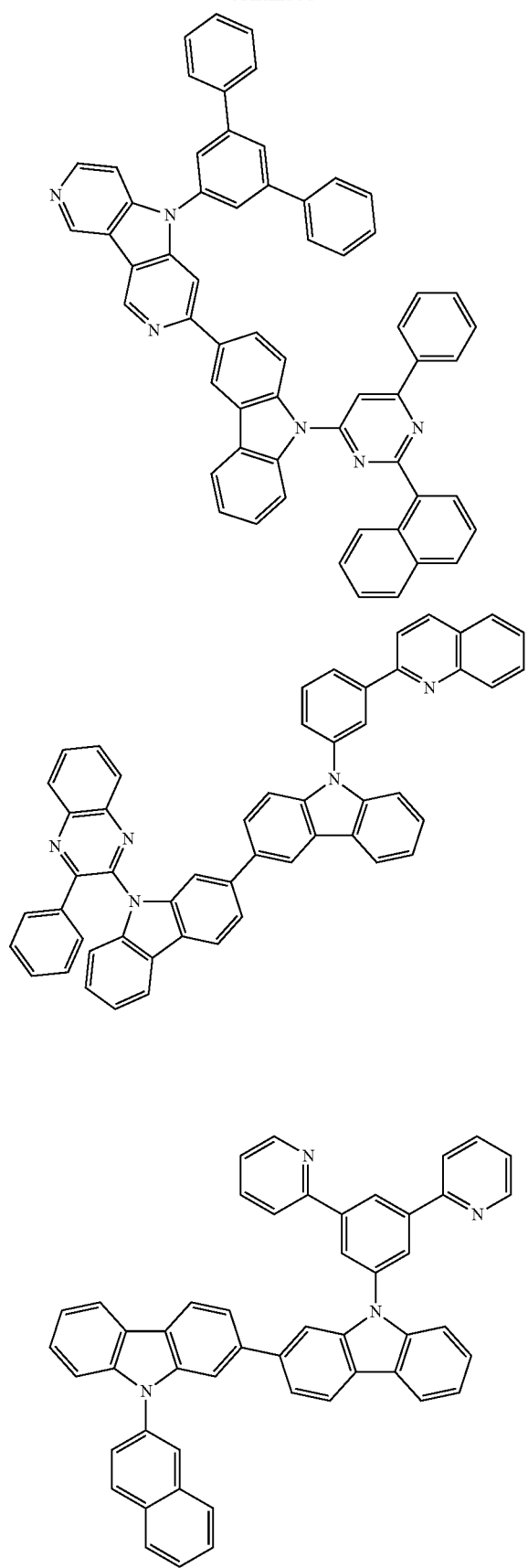
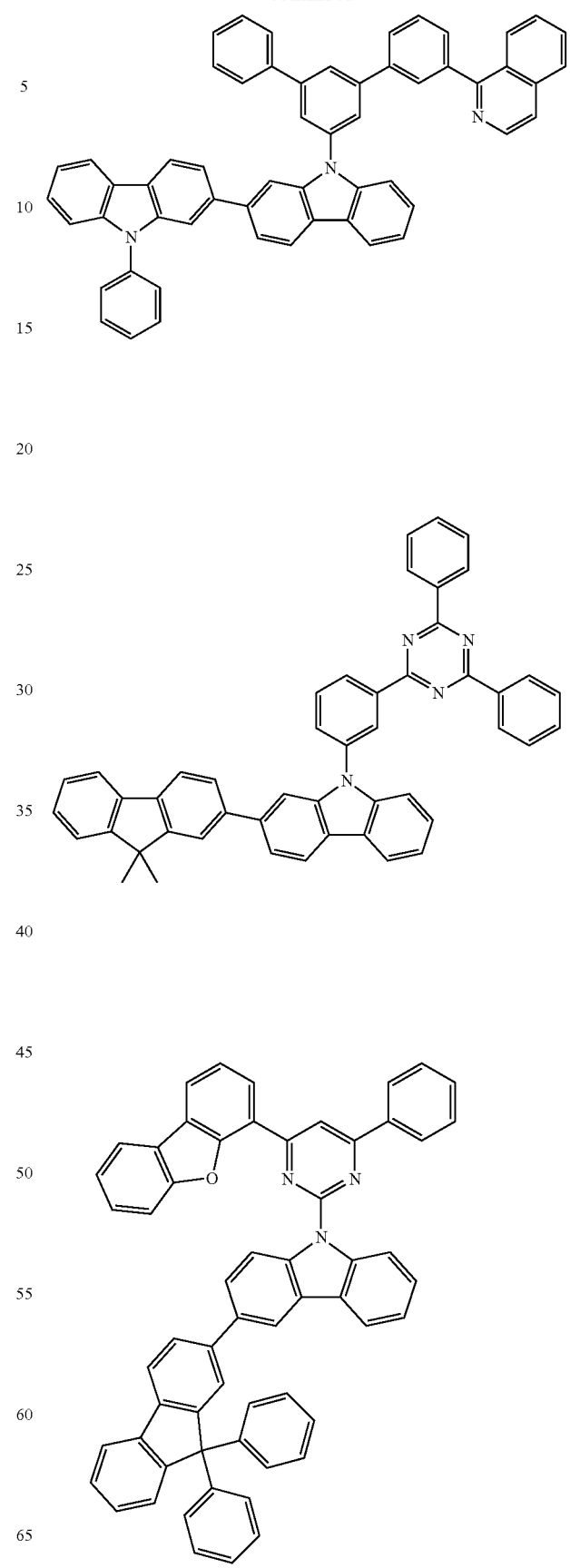

193
-continued
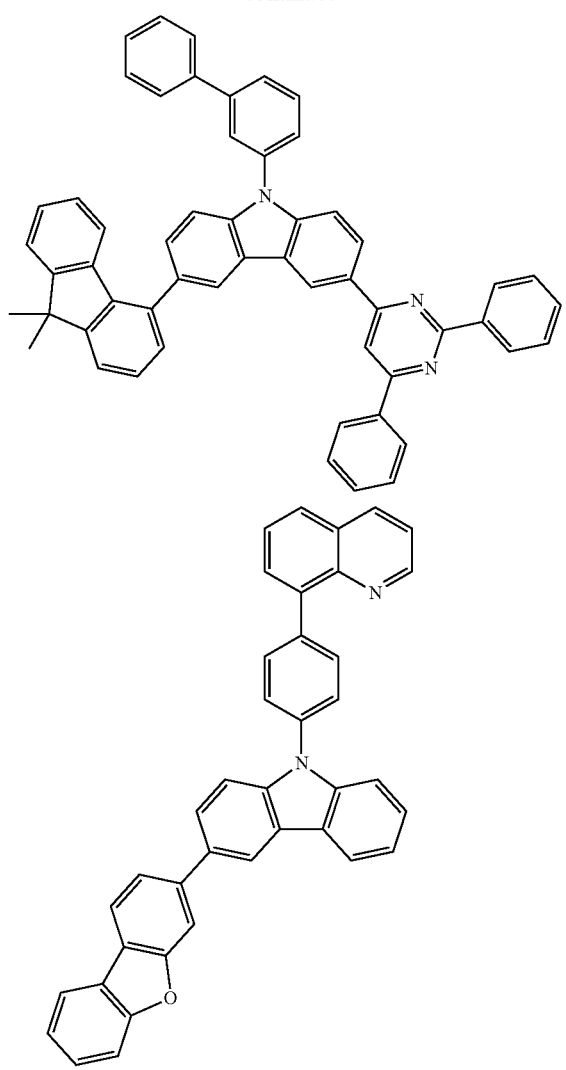
194
-continued
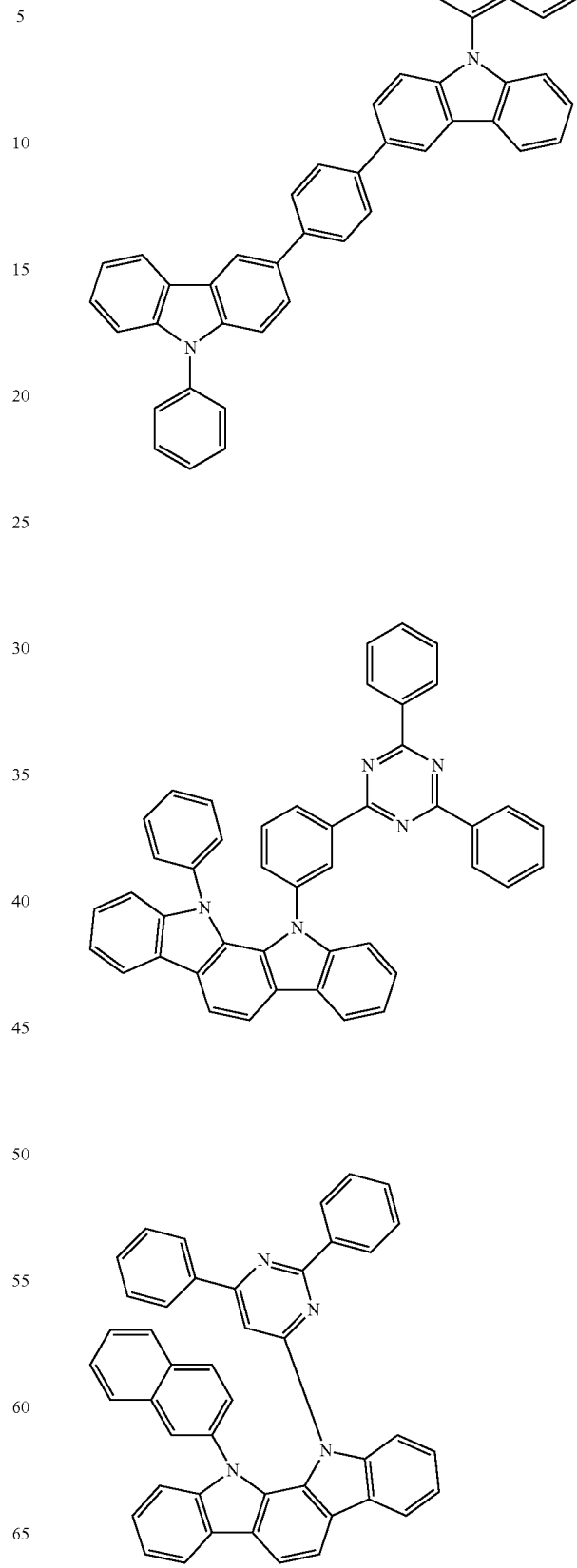

195
-continued
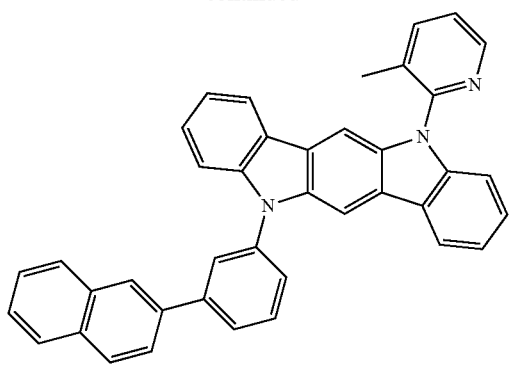
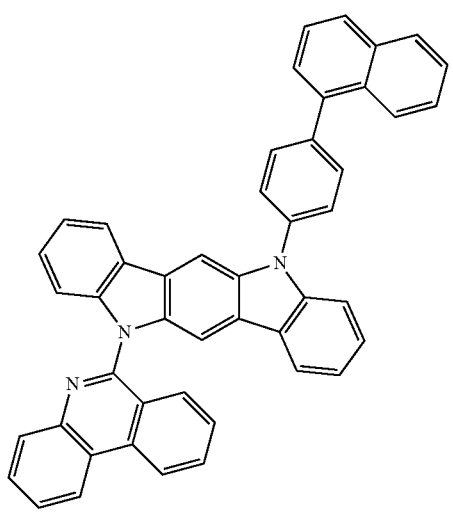
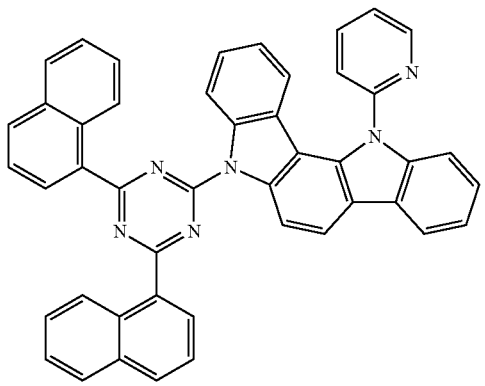
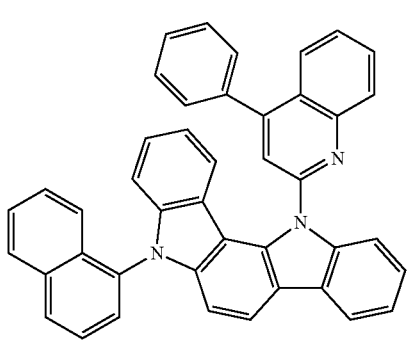
196
-continued
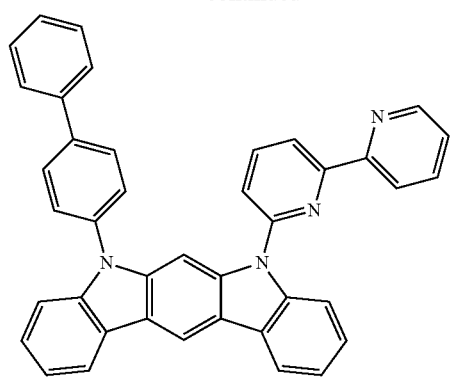
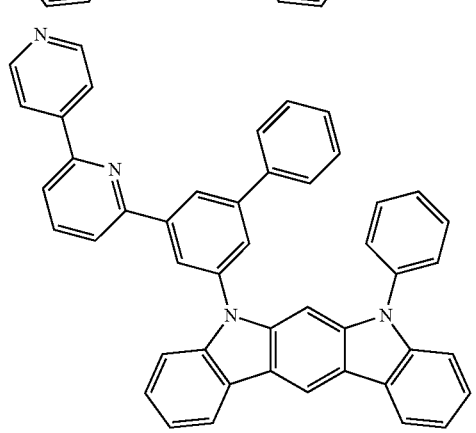
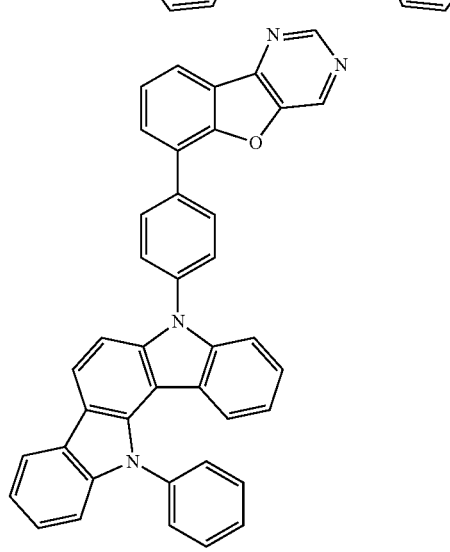
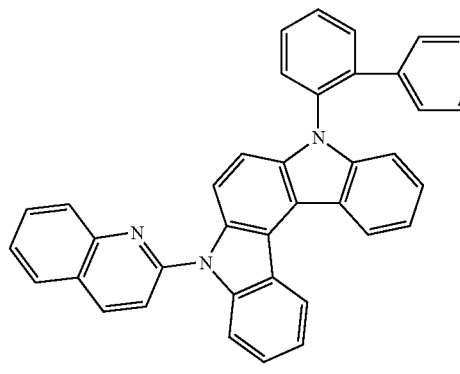

197
-continued
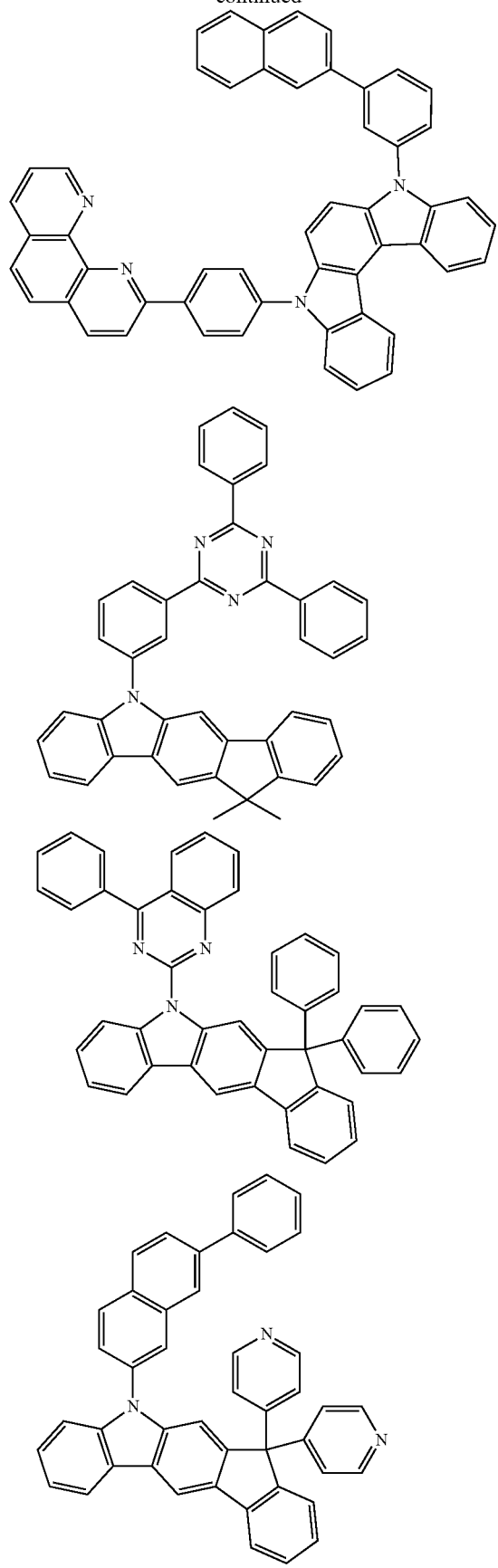
198
-continued
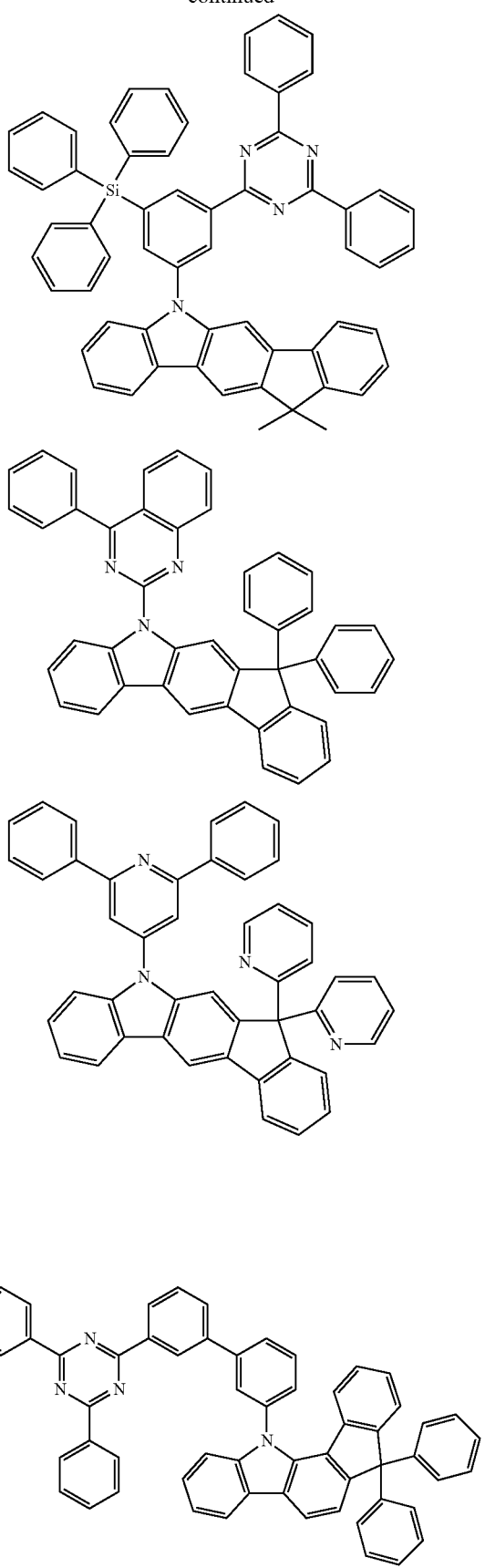

199
-continued
200
-continued
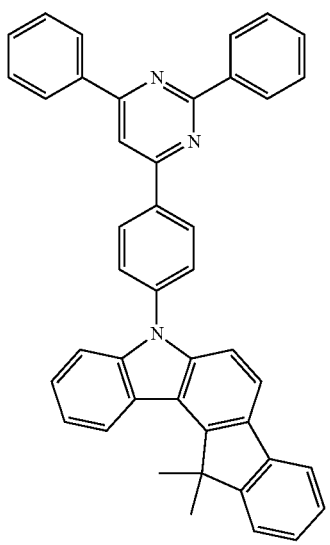
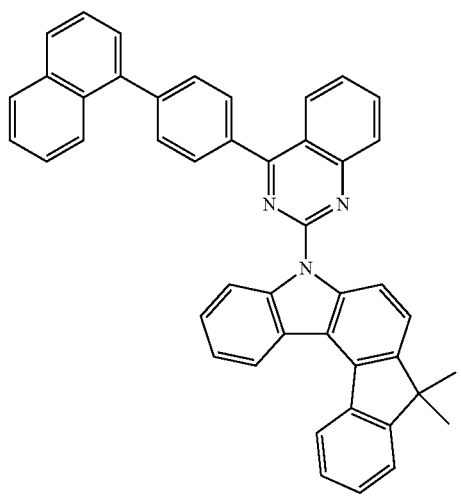
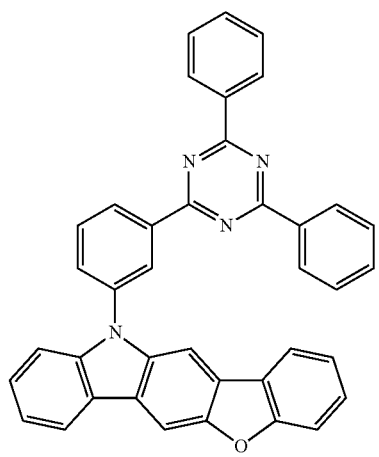
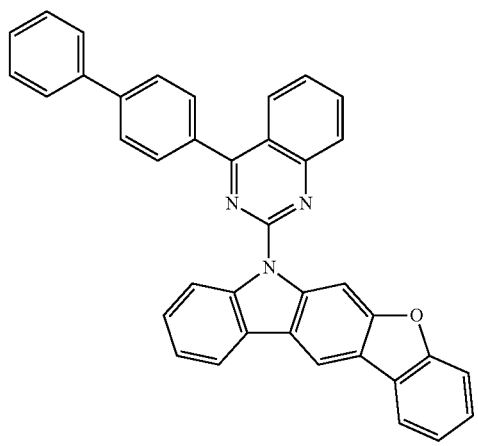
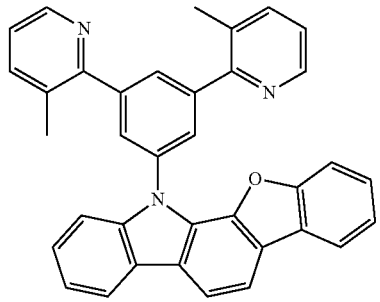

US 11,690,287 B2
201
-continued
202
-continued
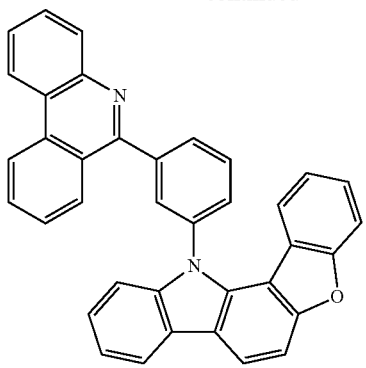
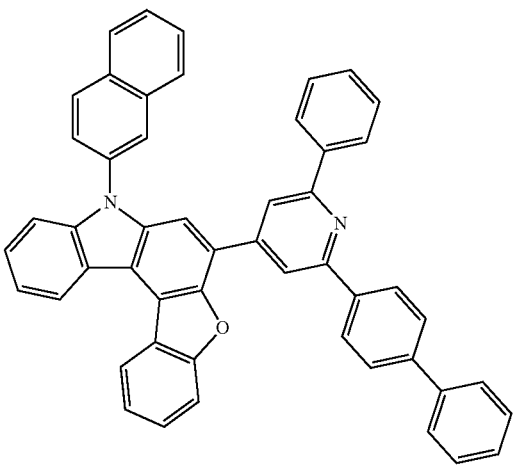
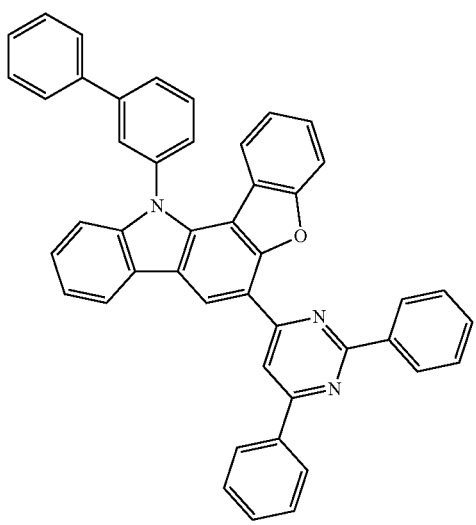
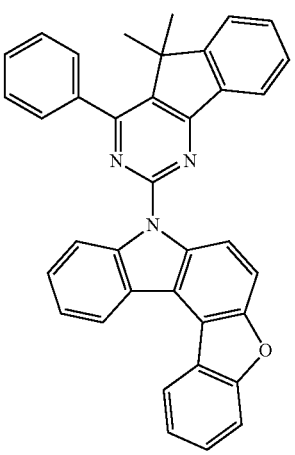
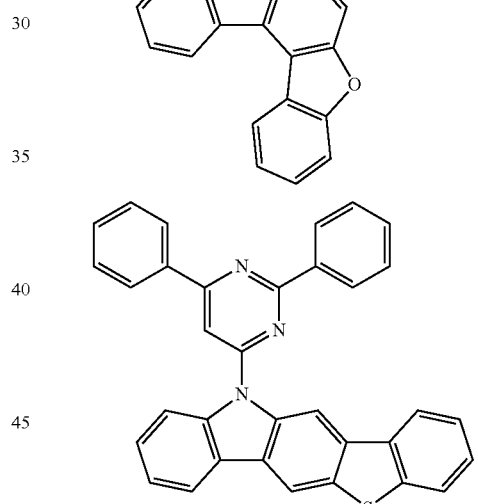
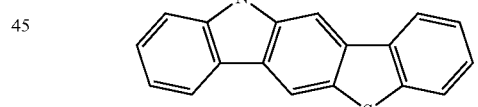
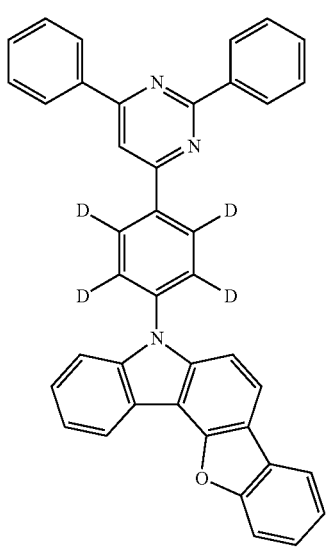
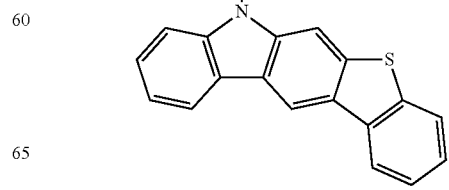

203
-continued
204
-continued
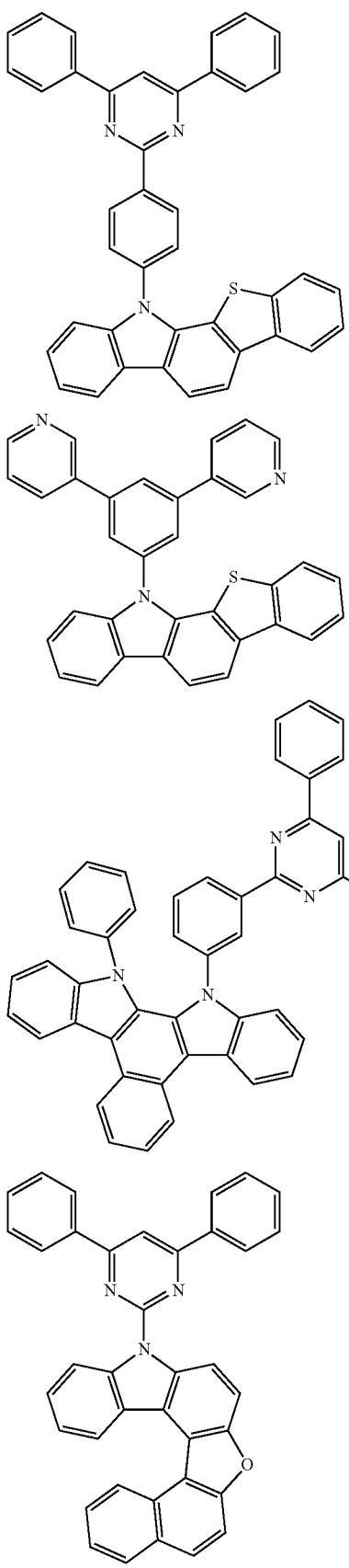
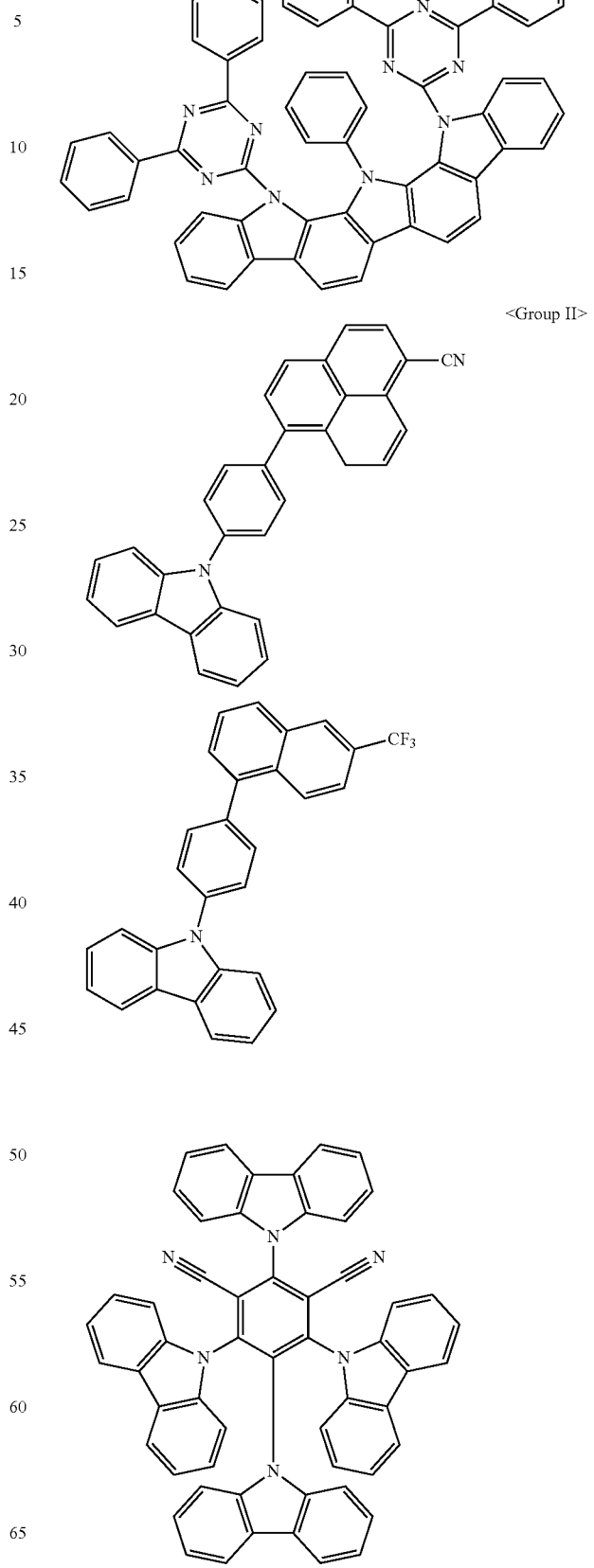
<Group II>

205
-continued
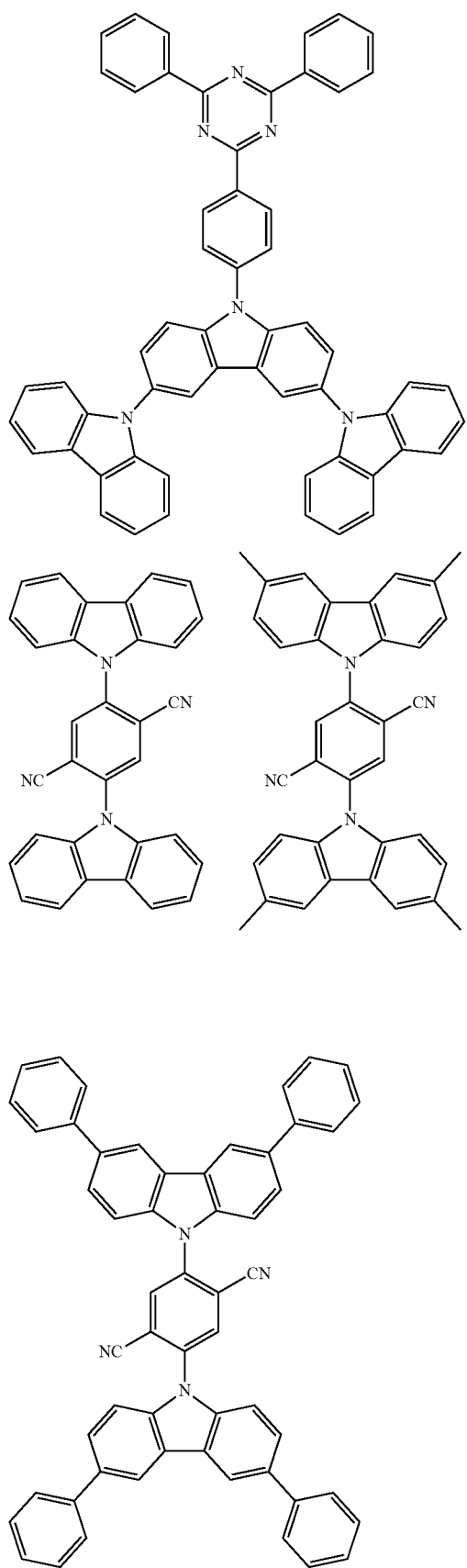
206
-continued
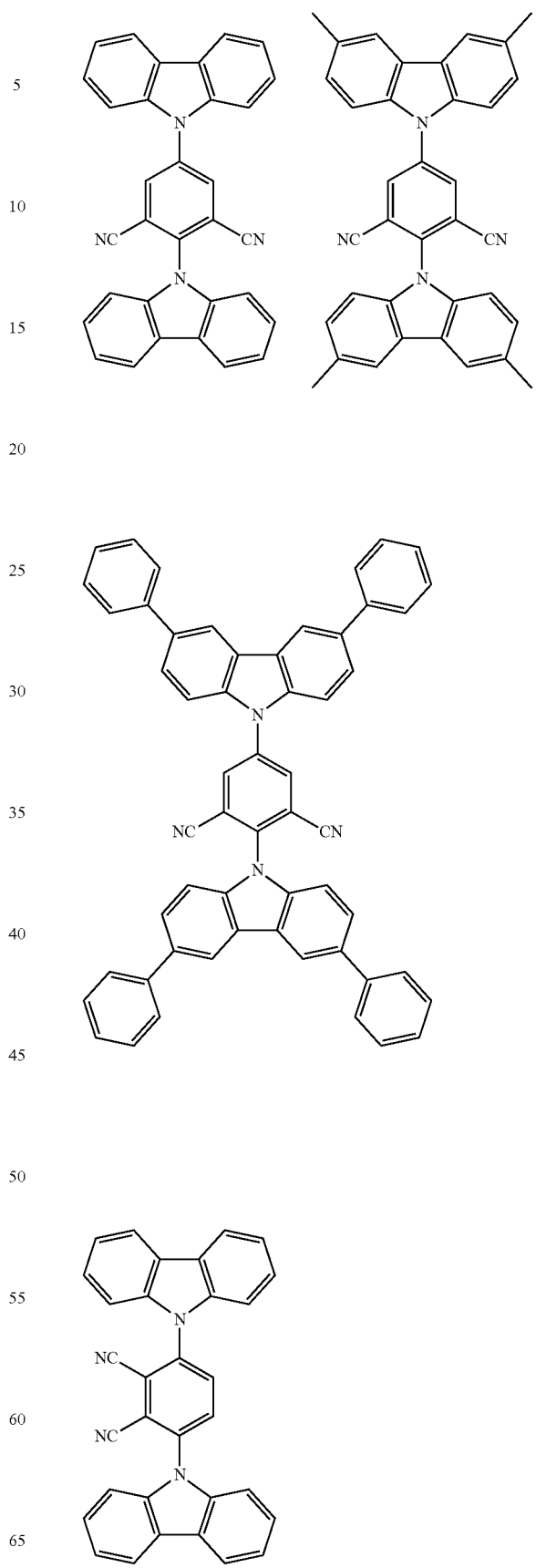

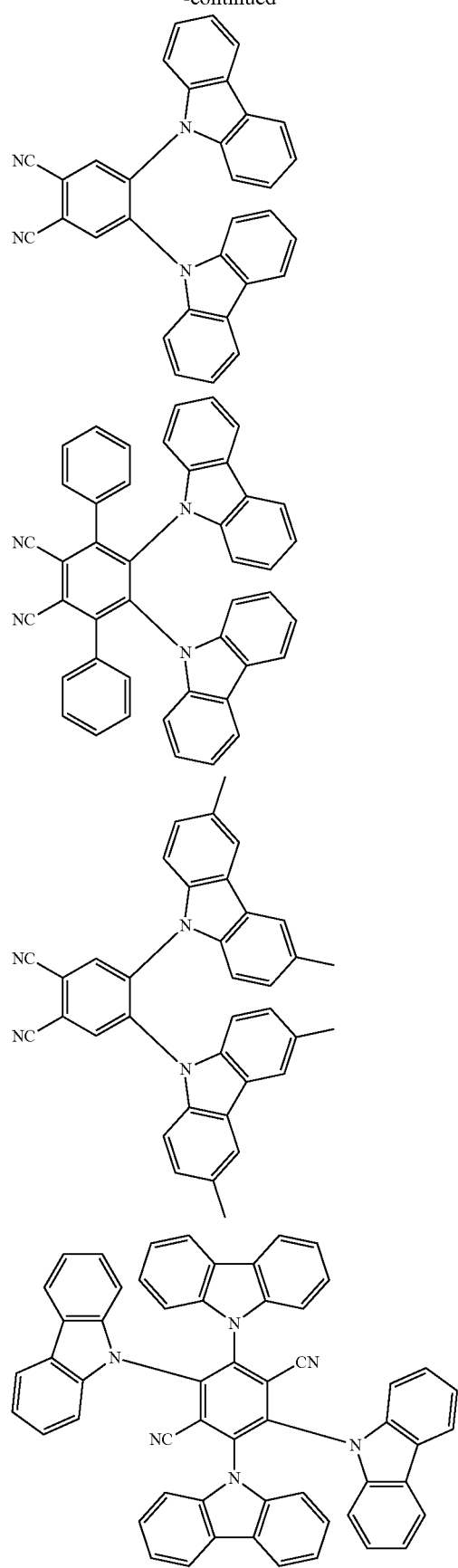
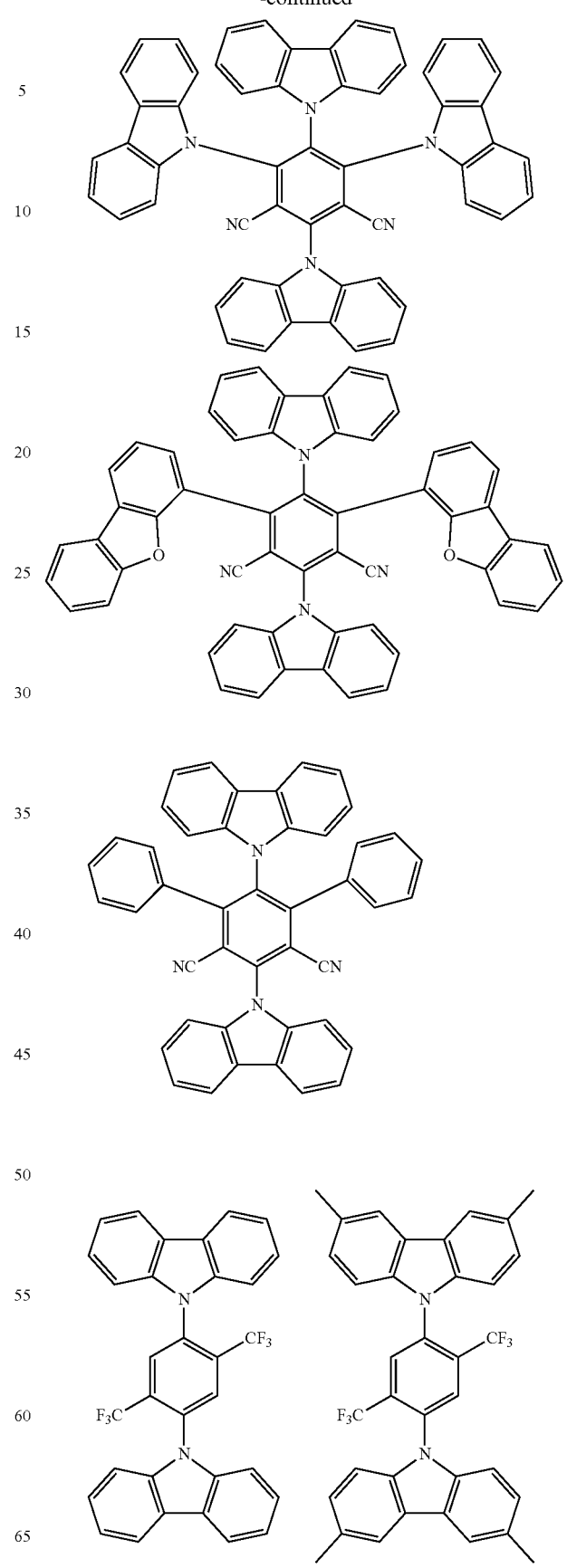

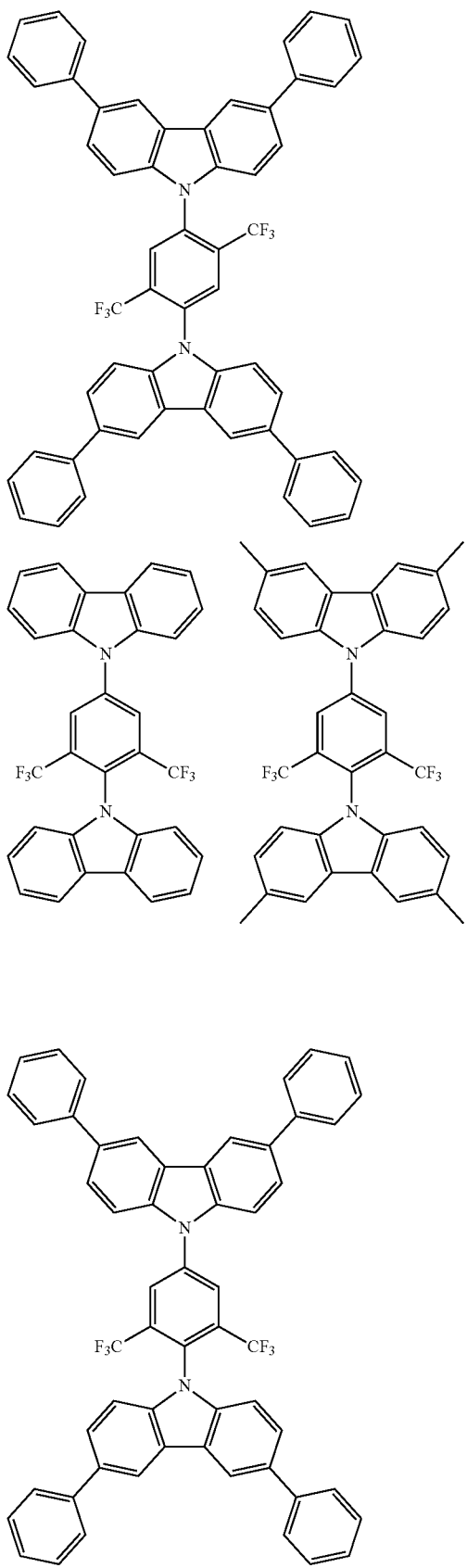
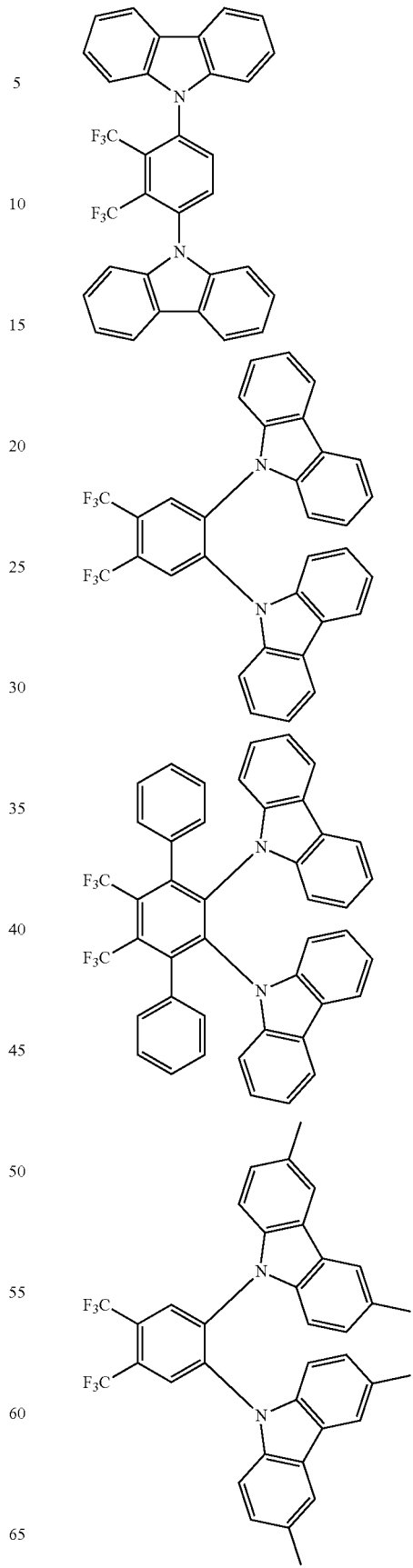

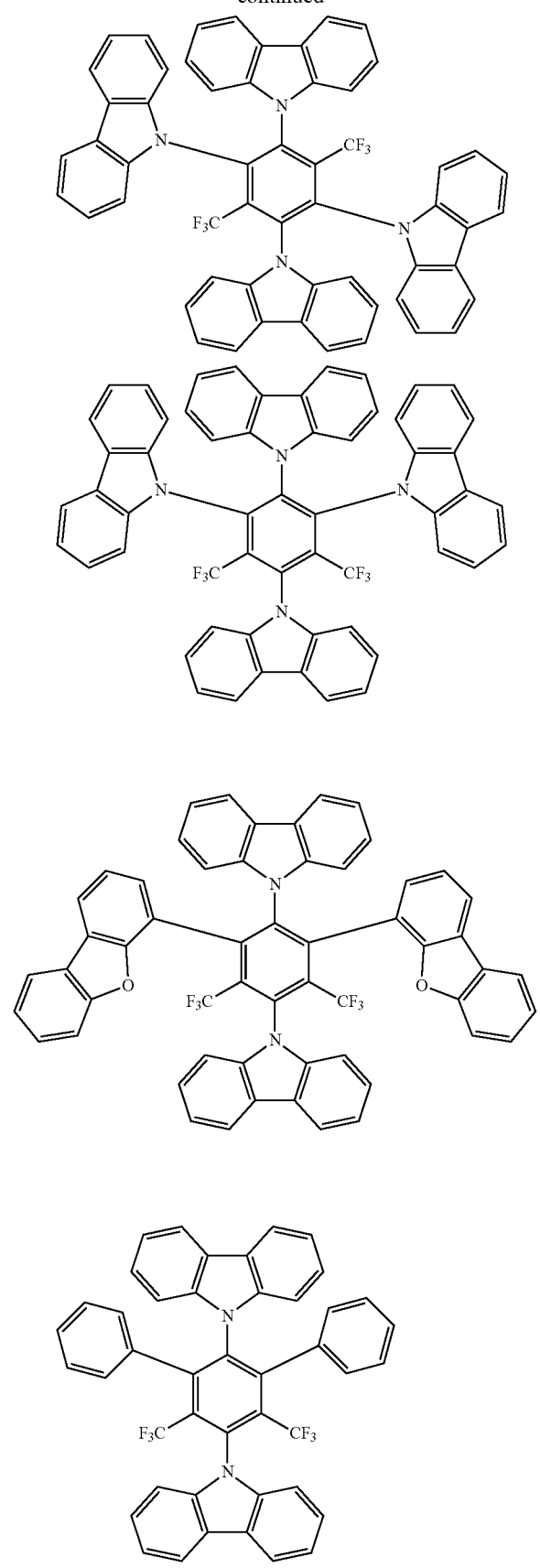

213
-continued
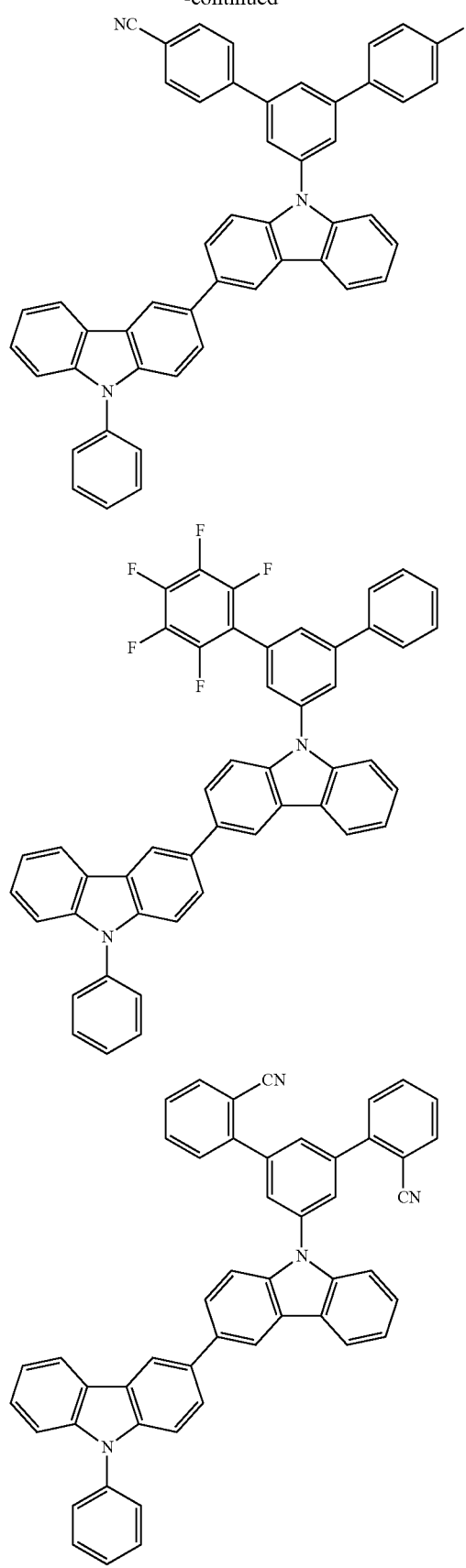
214
-continued
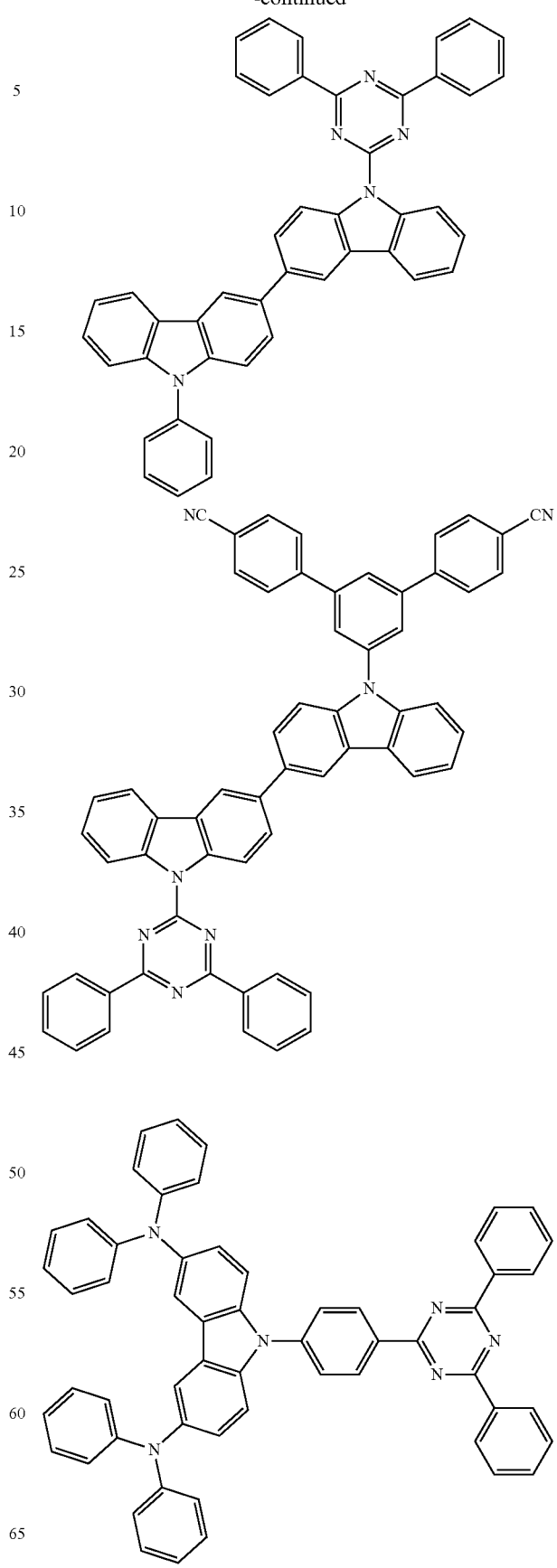

215
-continued
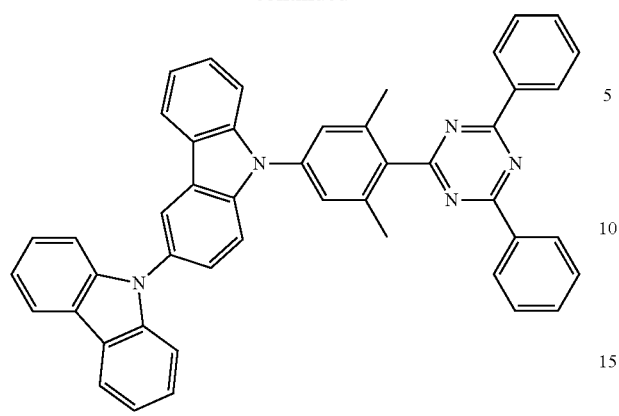
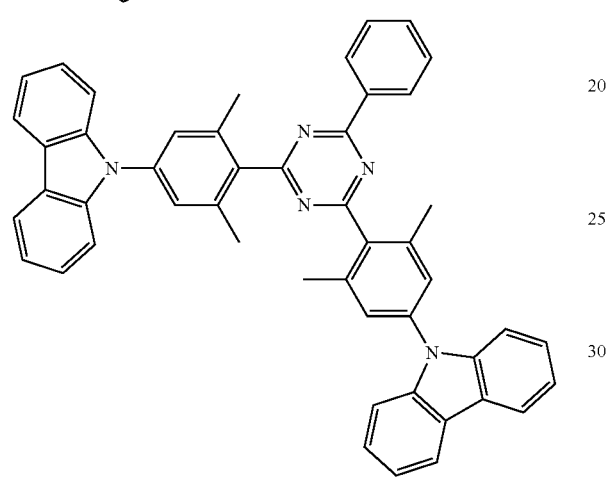
<Group III>
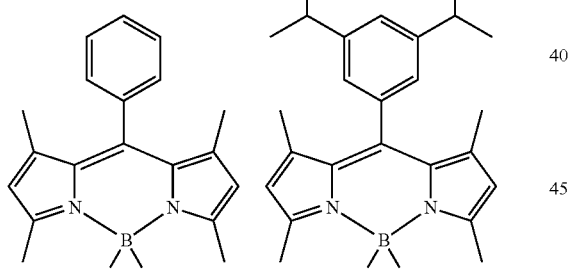
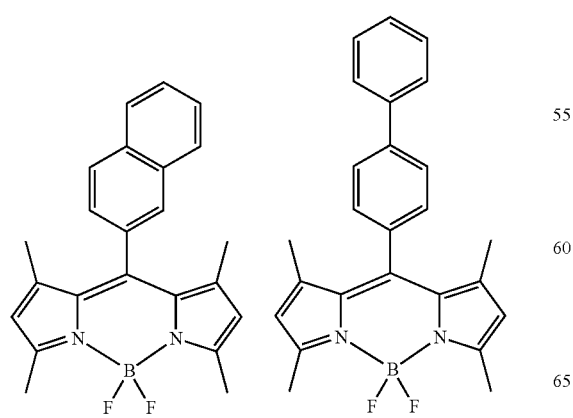
216
-continued
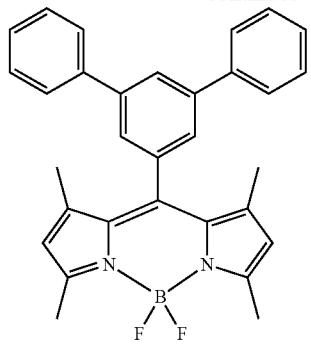
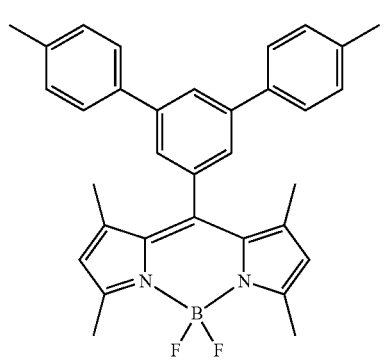
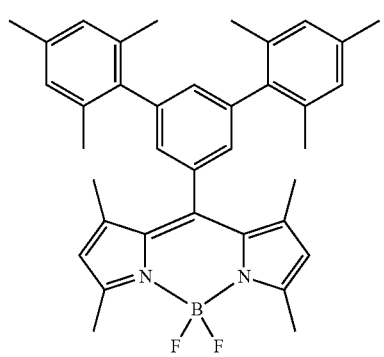
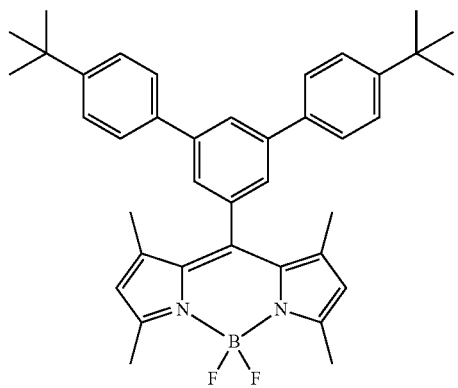

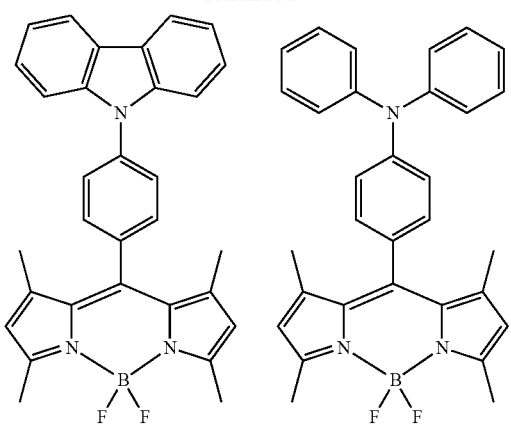
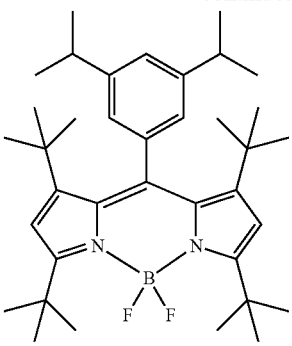
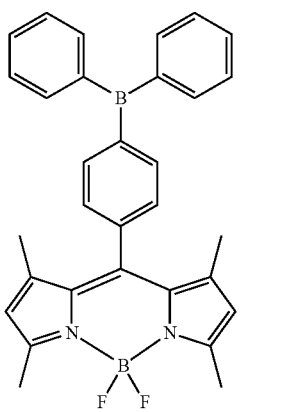
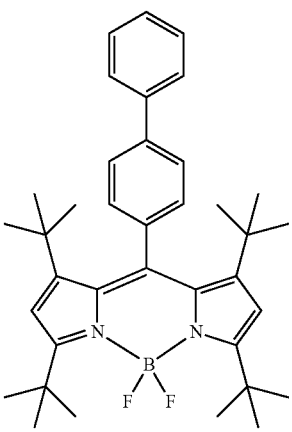
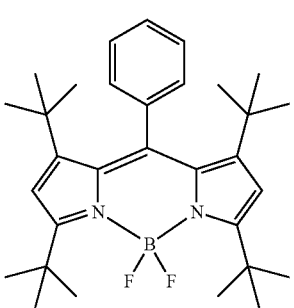
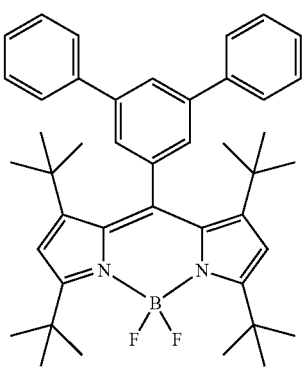

219
-continued
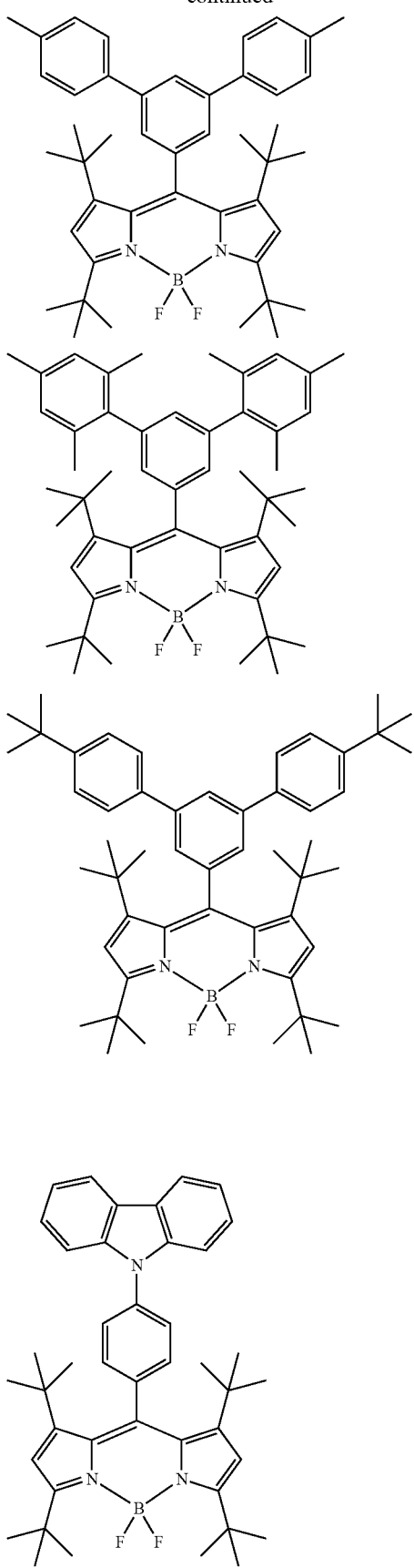
220
-continued
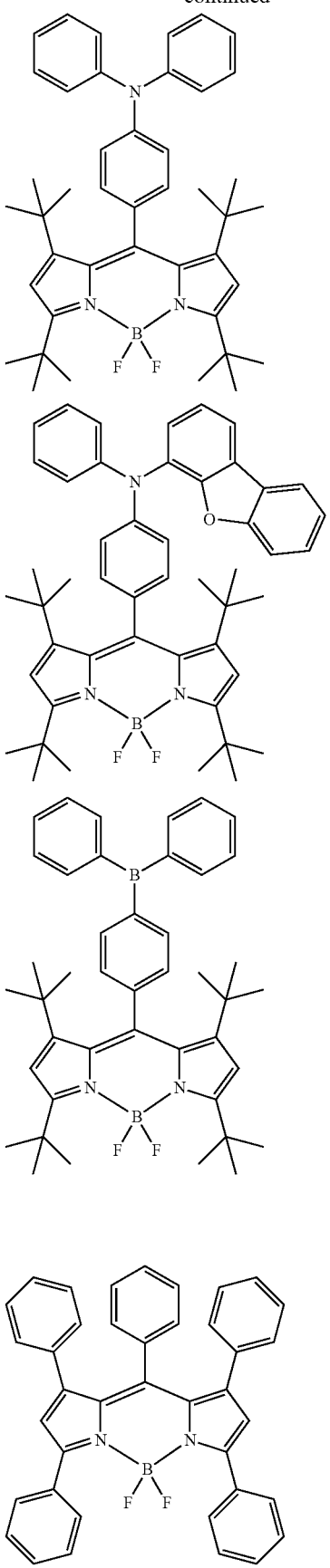

221
-continued
222
-continued
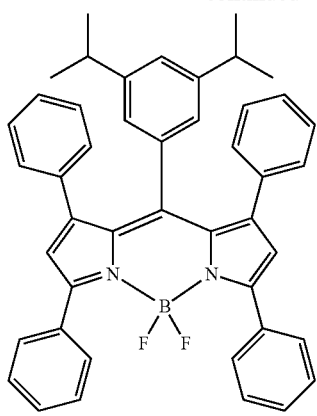
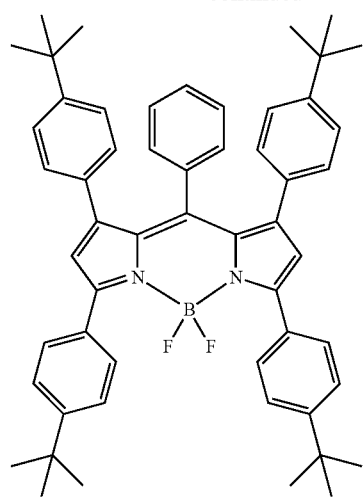
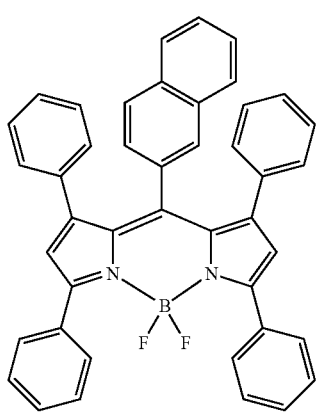
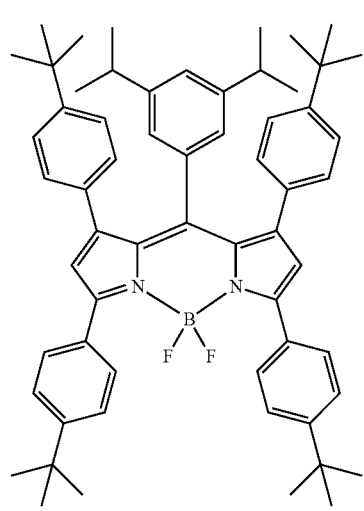
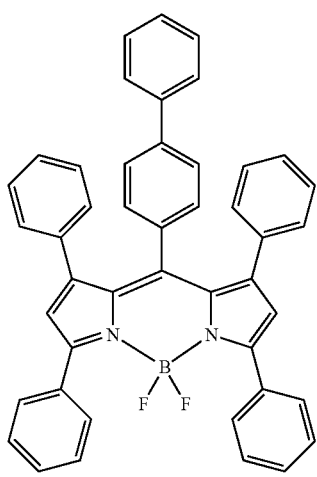
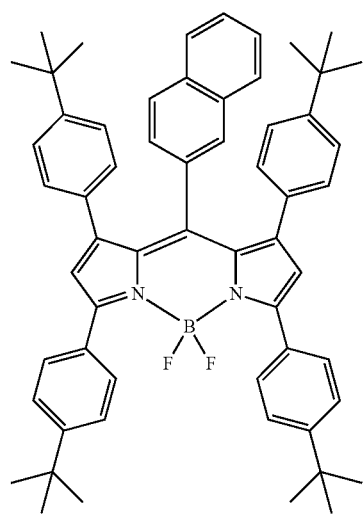

223
-continued
224
-continued
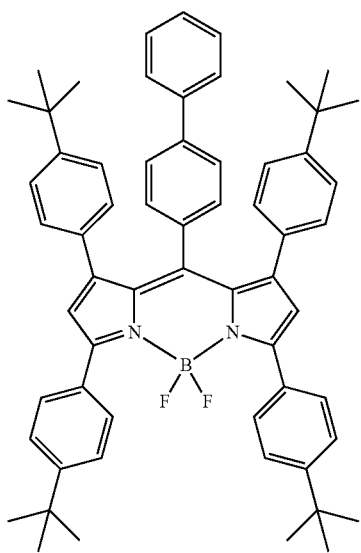
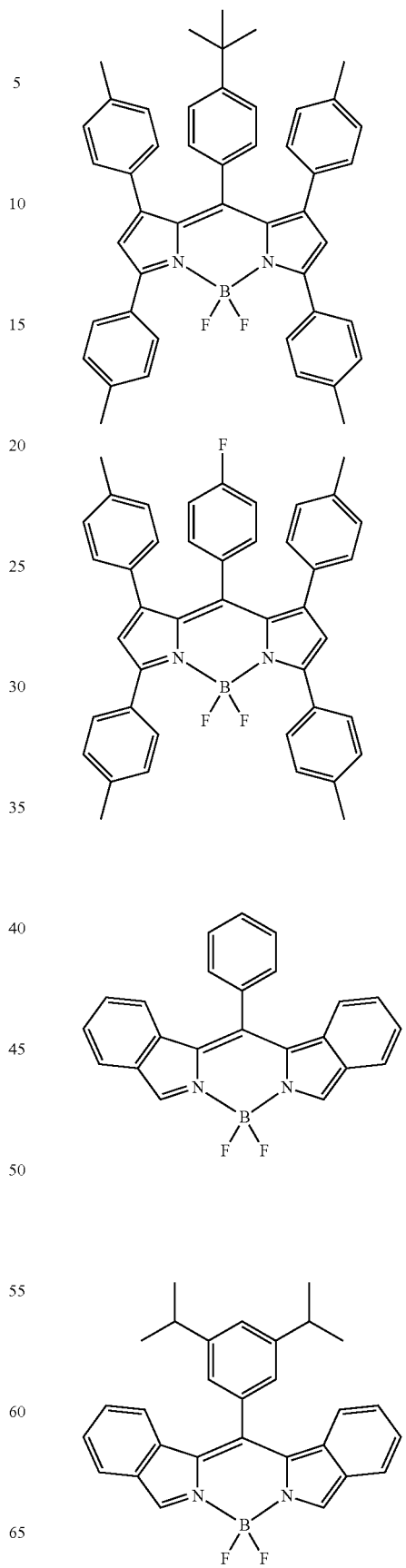

225
-continued
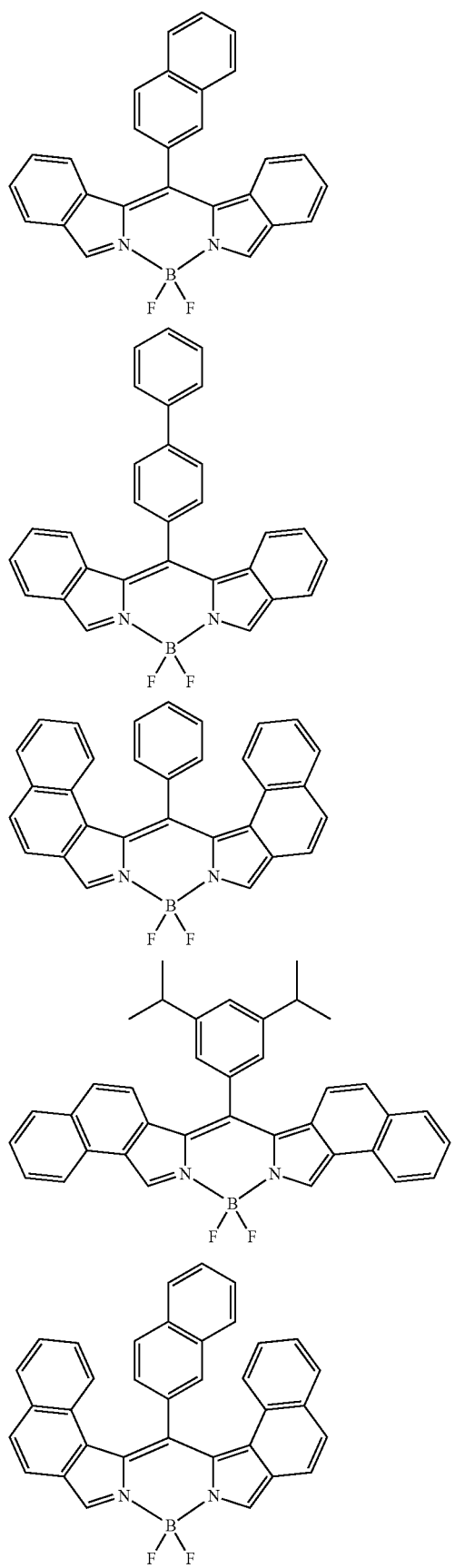
226
-continued
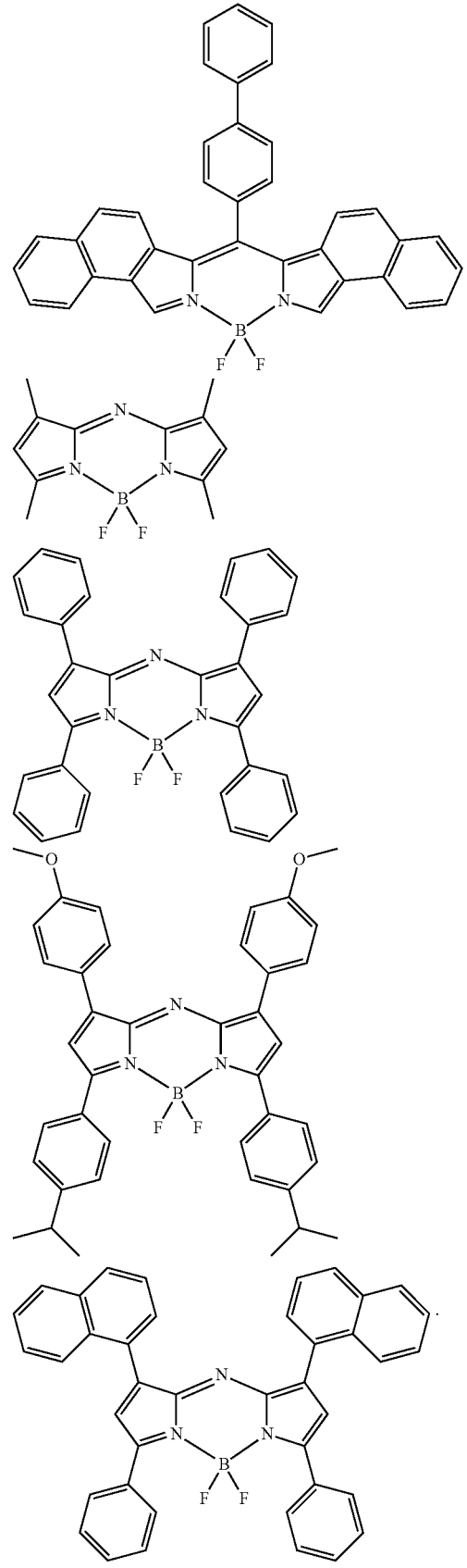

14. The organic light-emitting device of claim 1, wherein the second compound satisfies Condition 1:

$\Delta E_{ST}(C2) \leq 0.3$ eV,   Condition 1 wherein, in Condition 1,
$\Delta E_{ST}(C2)$ is a difference between a lowest excitation singlet energy level of the second compound ($E_{S_1}(C2)$) and a lowest excitation triplet energy level of the second compound ($E_{T_1}(C2)$).

15. The organic light-emitting device of claim 1, wherein the third compound has a maximum emission wavelength in a range of about 520 nm to about 780 nm.

16. The organic light-emitting device of claim 1, wherein the organic layer further comprises a hole transport region,
the hole transport region is between the first electrode and the emission layer,
the hole transport region comprises a first hole transport layer and a second hole transport layer,
the first hole transport layer comprises a first hole transport material,
the second hole transport layer comprises a second hole transport material, and
the first hole transport material and the second hole transport material are different from each other.

17. The organic light-emitting device of claim 16, wherein the first hole transport material is represented by Formula 201:

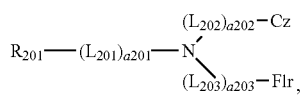

Formula 201 wherein, in Formula 201,
$L_{201}$ to $L_{203}$ are each independently selected from the group consisting of a substituted or unsubstituted $C_5$-$C_{60}$ carbocyclic group and a substituted or unsubstituted $C_1$-$C_{60}$ heterocyclic group,
a201 to a203 are each independently selected from the group consisting of 0, 1, 2, and 3,
Cz is a substituted or unsubstituted carbazolyl group,
Flr is a substituted or unsubstituted fluorenyl group, and
$R_{201}$ is selected from the group consisting of a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

18. The organic light-emitting device of claim 16, wherein the second hole transport material is represented by Formula 202:

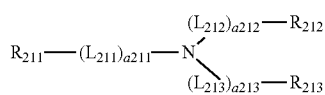

Formula 202

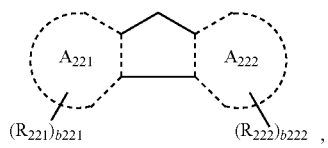

Formula 202A wherein, in Formulae 202 and 202A,
$L_{211}$ to $L_{213}$ are each independently selected from the group consisting of a substituted or unsubstituted $C_5$-$C_{60}$ carbocyclic group and a substituted or unsubstituted $C_1$-$C_{60}$ heterocyclic group,
a211 to a213 are each independently selected from the group consisting of 0, 1, 2, and 3,
$R_{211}$ to $R_{213}$ are each independently selected from the group consisting of a group represented by Formula 202A, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one selected from the group consisting of $R_{211}$ to $R_{213}$ is a group represented by Formula 202A,
$X_{221}$ is selected from the group consisting of $N(R_{223})$, $C(R_{223})(R_{224})$, O, and S,
$A_{221}$ and $A_{222}$ are each independently selected from the group consisting of i) a 6-membered ring, ii) a condensed ring in which two or more 6-membered rings are condensed with each other, and iii) a condensed ring in which at least one 6-membered ring and at least one 5-membered ring are condensed with each other,
$R_{221}$ to $R_{224}$ are each independently selected from the group consisting of a binding site, hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein one selected from the group consisting of $R_{221}$ to $R_{224}$ is a binding site, and b221 and b222 are each independently selected from the group consisting of 1, 2, 3, 4, 5, and 6.
19. The organic light-emitting device of claim 16, wherein
the first hole transport material is selected from the group consisting of compounds of Group IV, and
the second hole transport material is selected from the group consisting of compounds of Group V:
<Group IV>
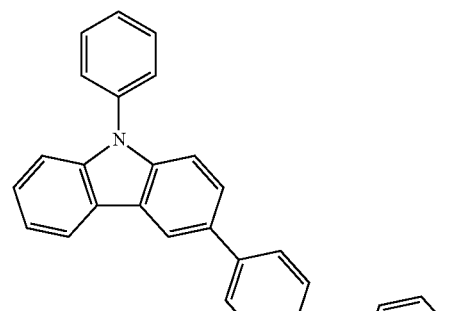
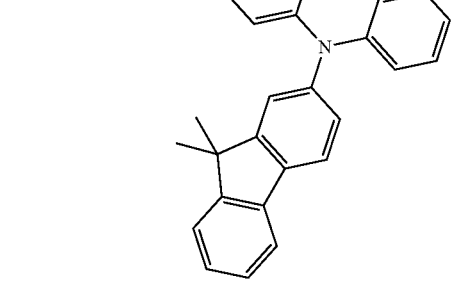
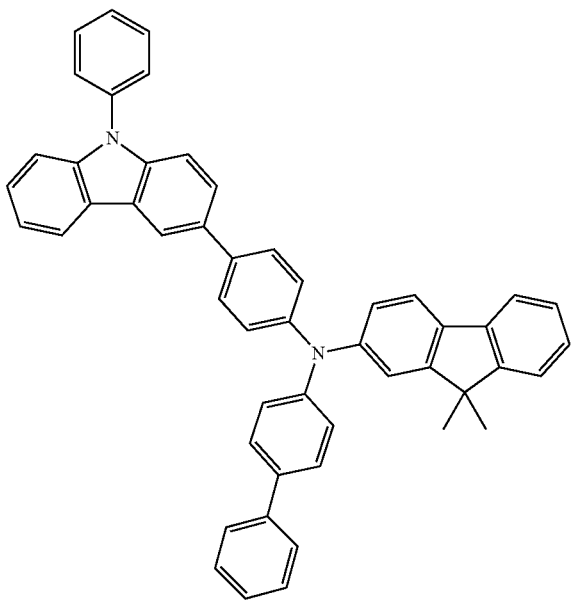
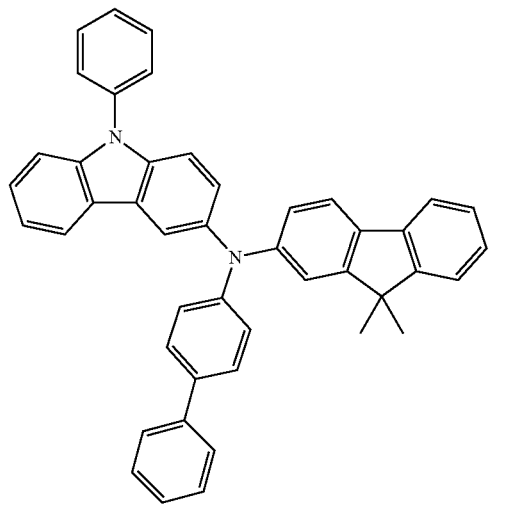
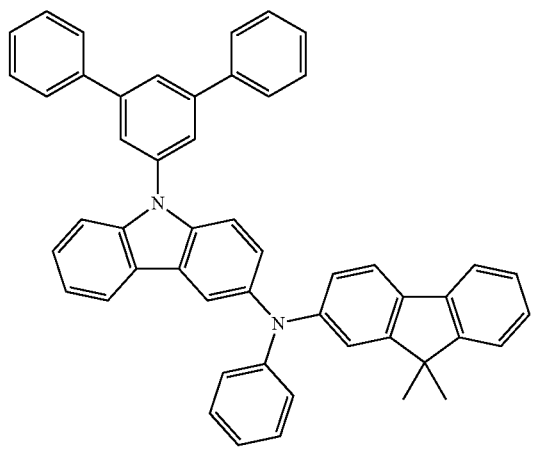
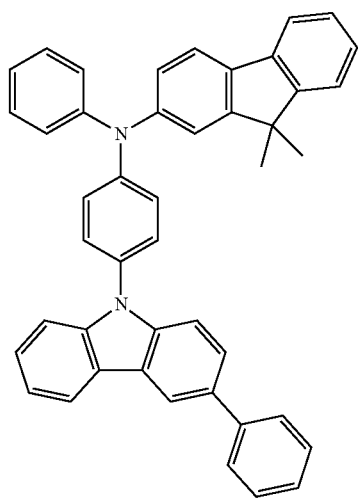

231
-continued
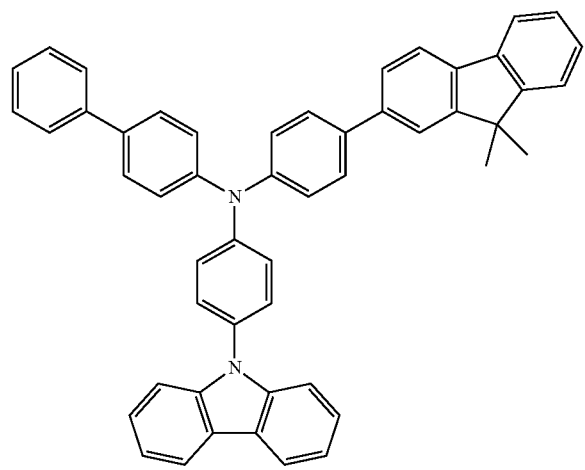
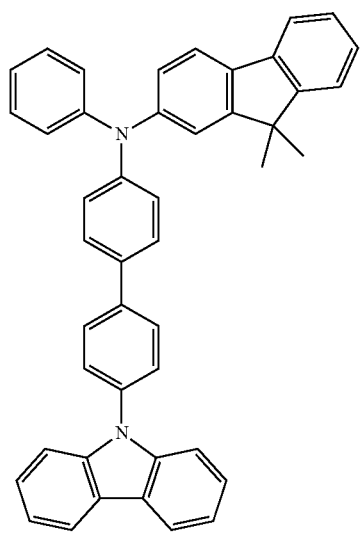
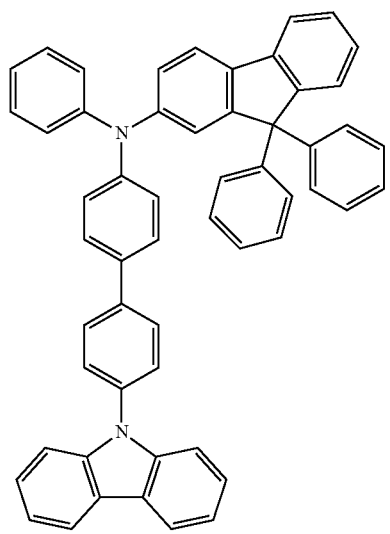
232
-continued
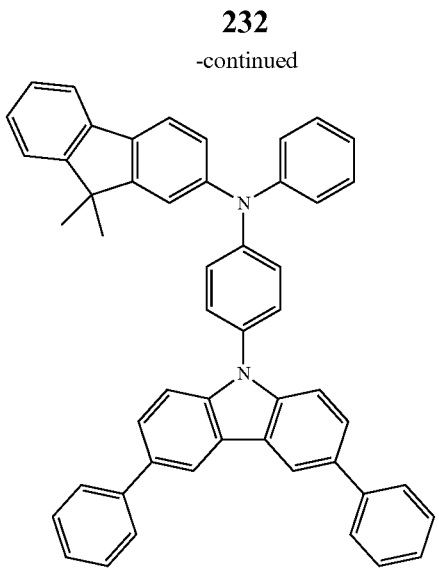
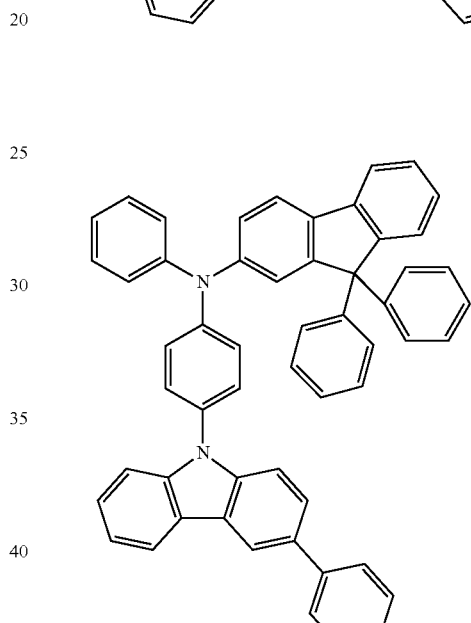
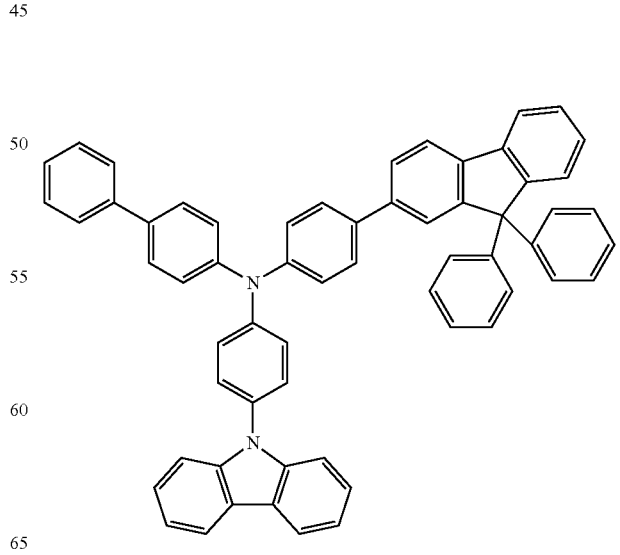

233
-continued
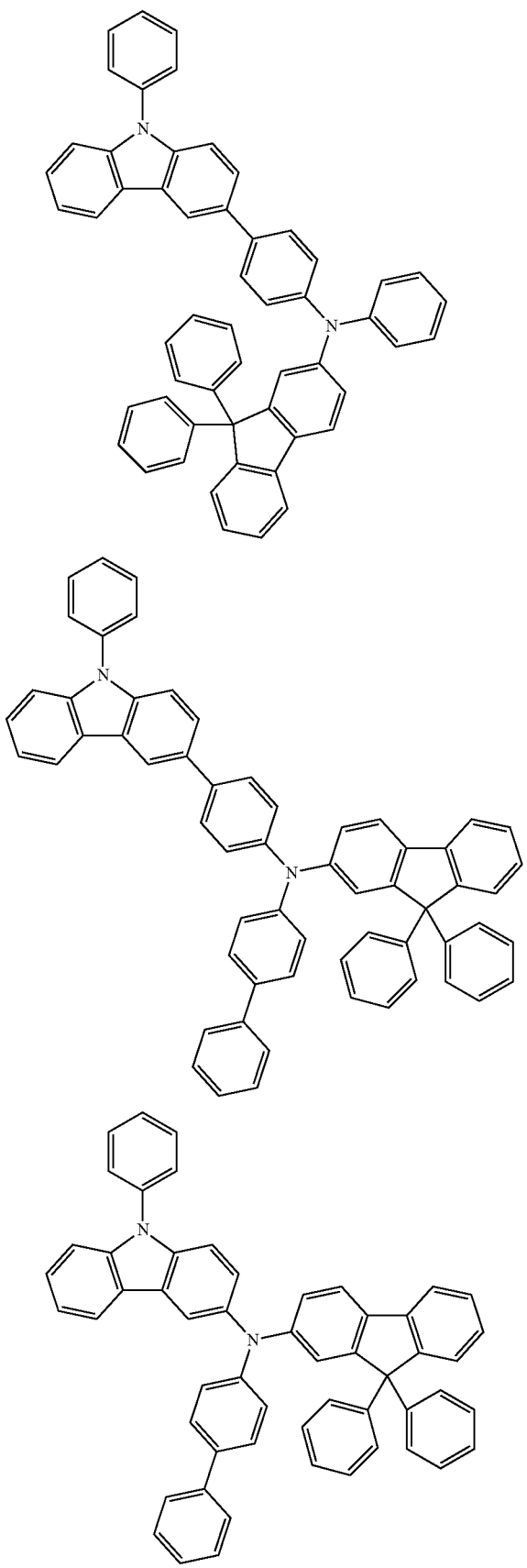
234
-continued
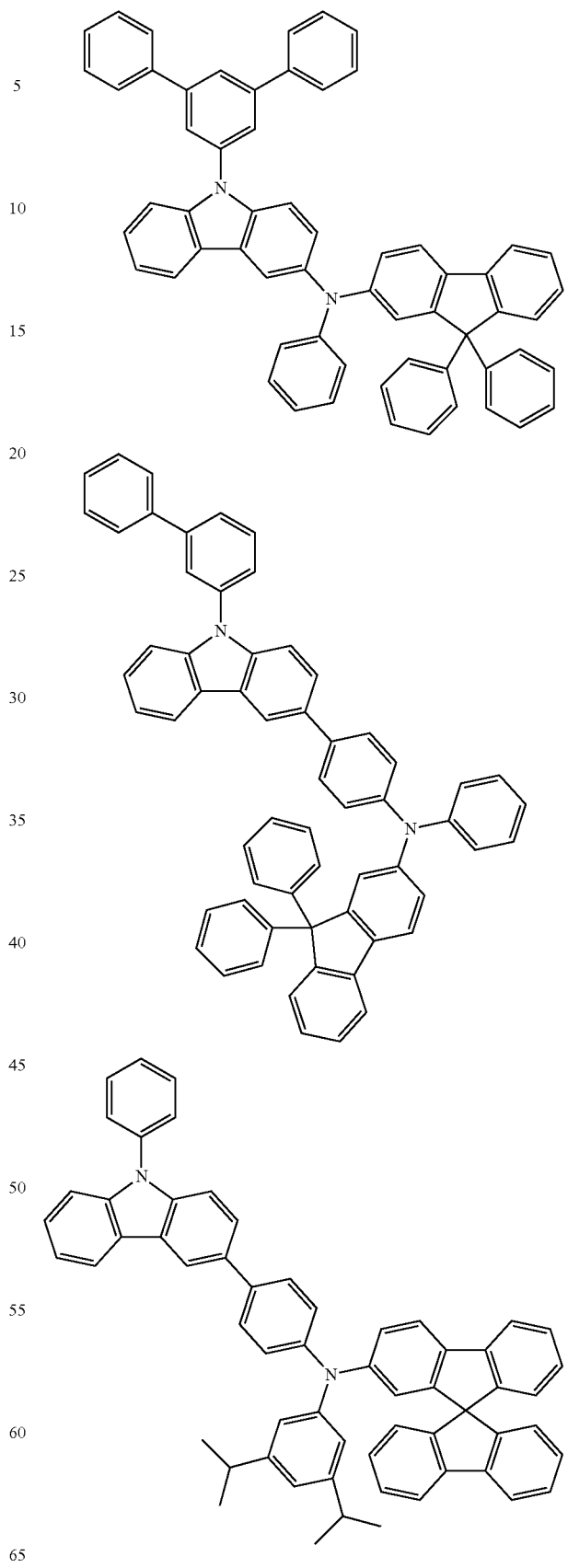

235
-continued
236
-continued
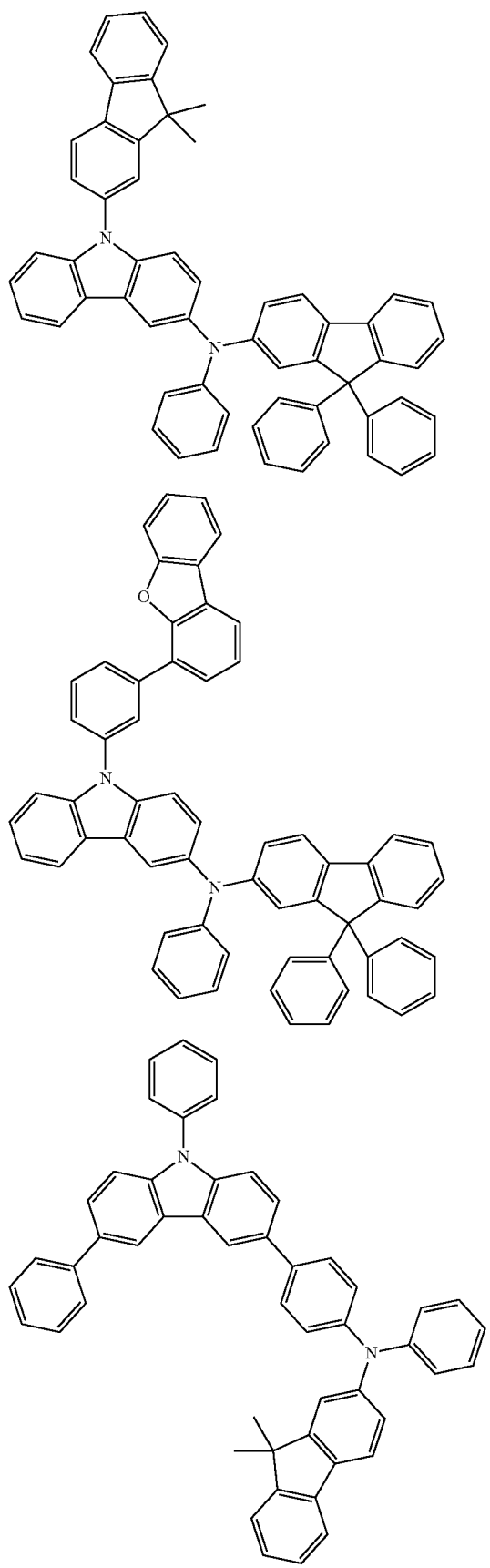
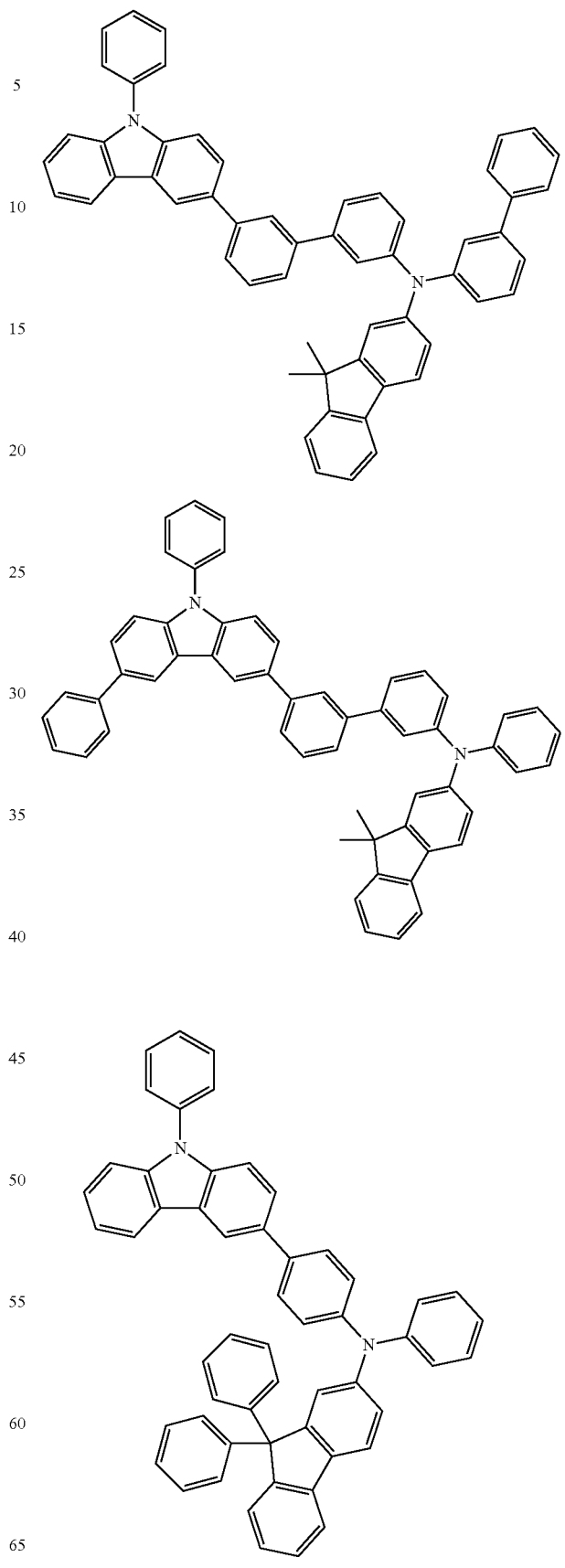

237
-continued
238
-continued
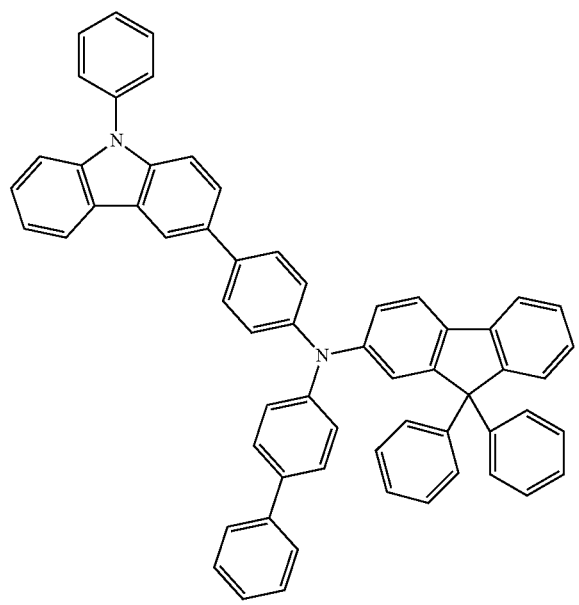
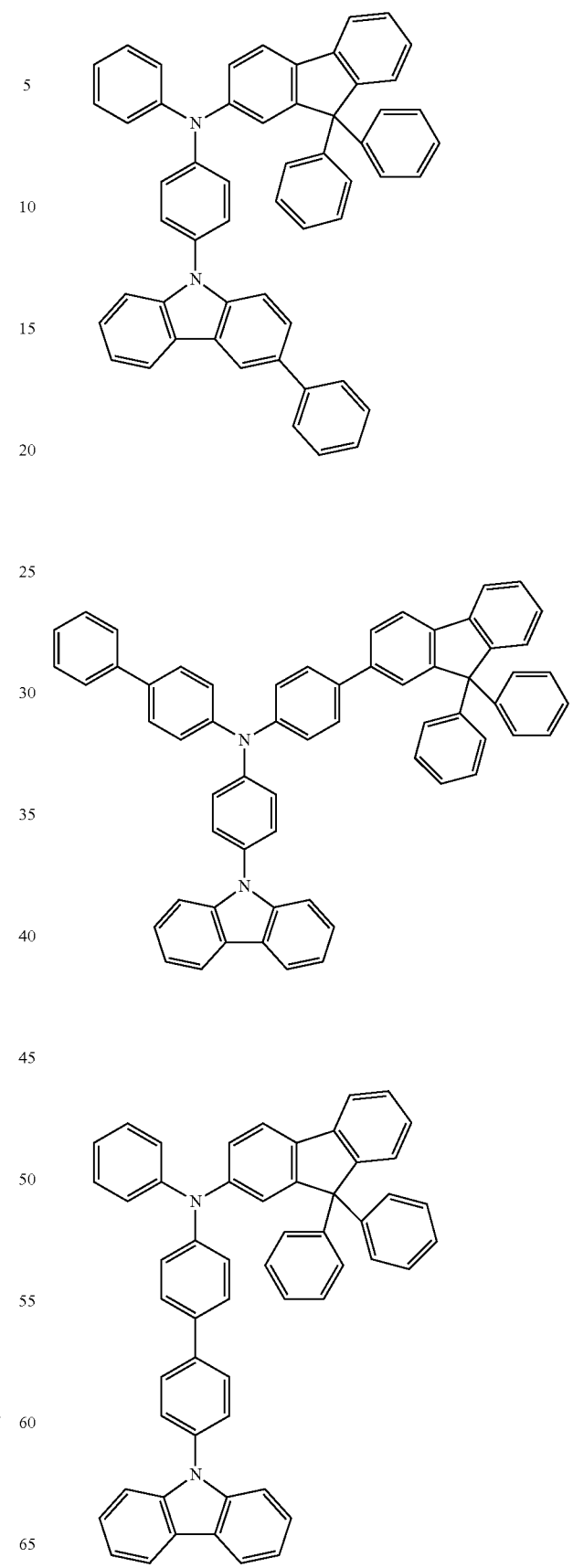

239
-continued
240
-continued
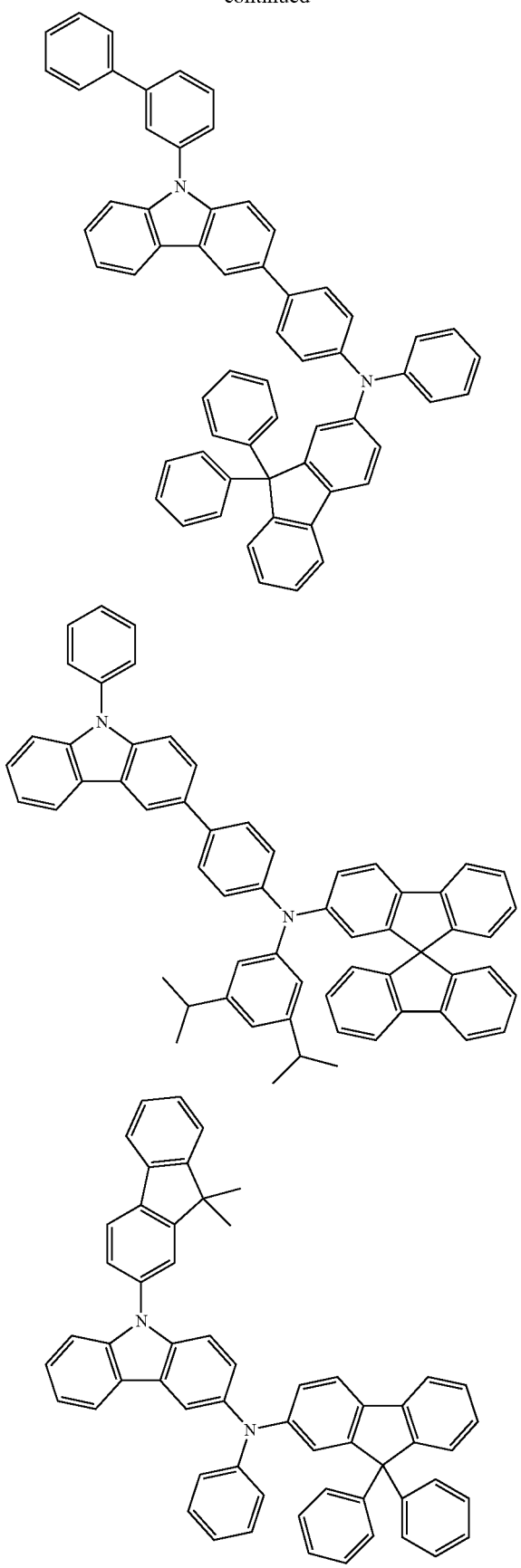
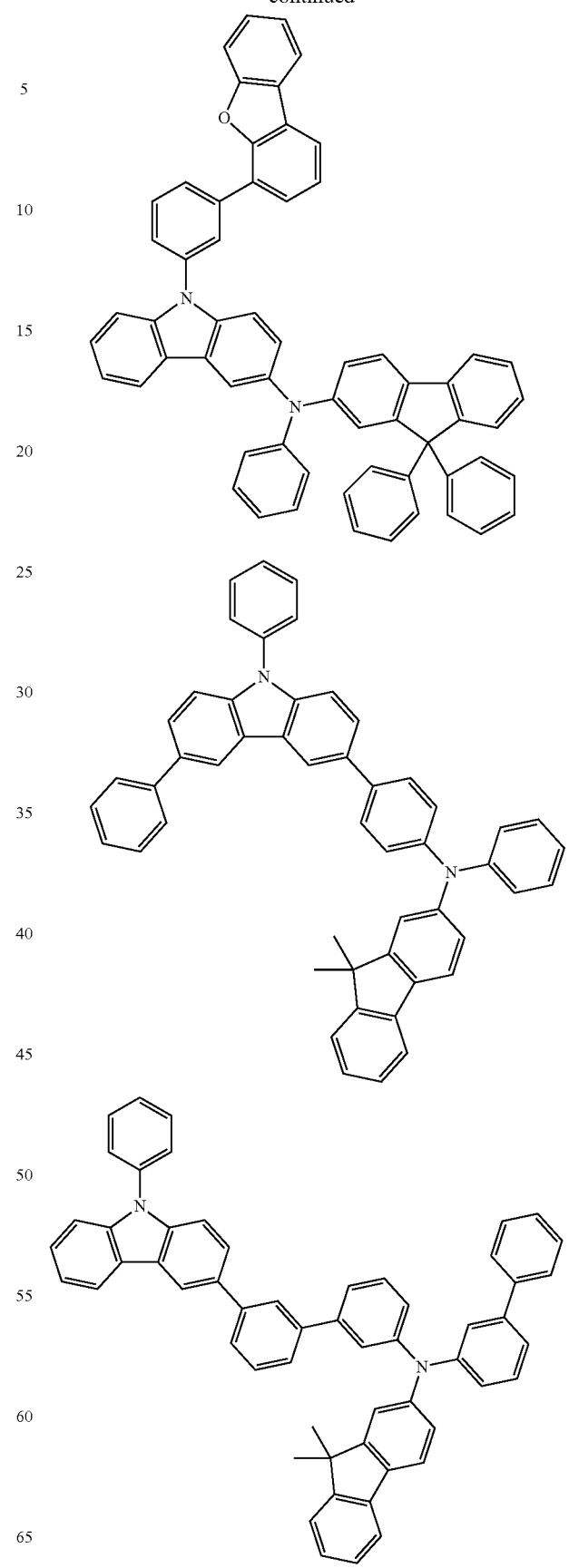

241
-continued
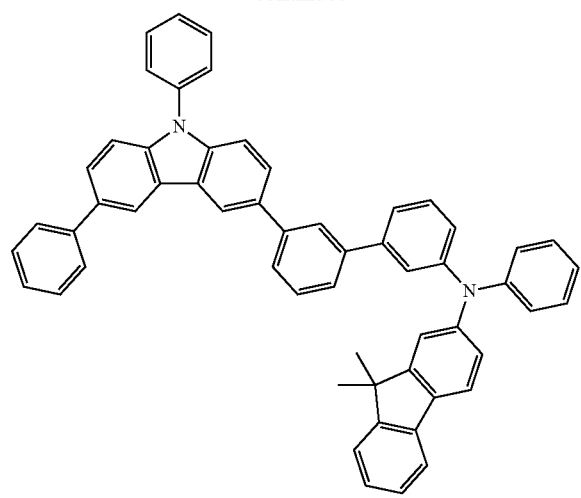
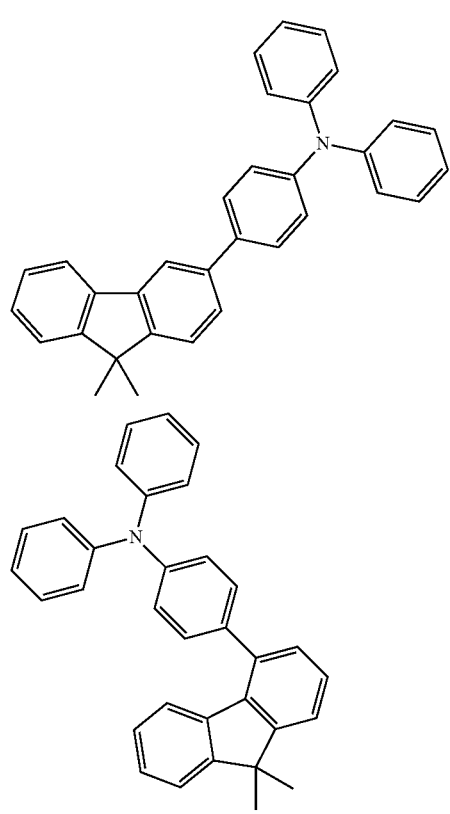
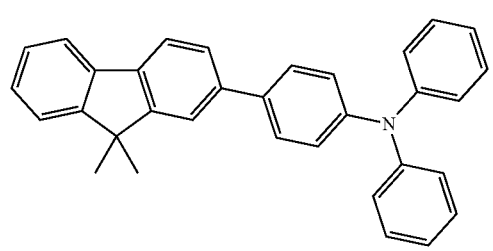
242
-continued
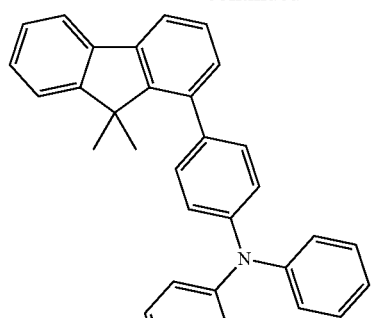
<Group V>
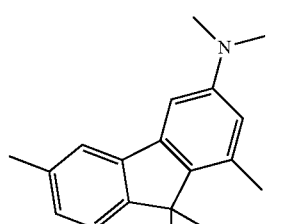
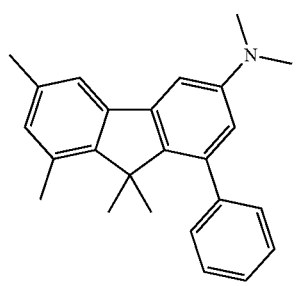
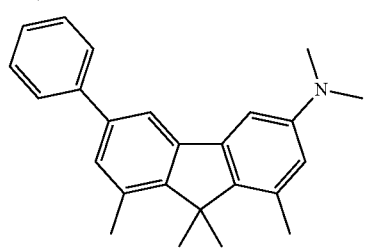
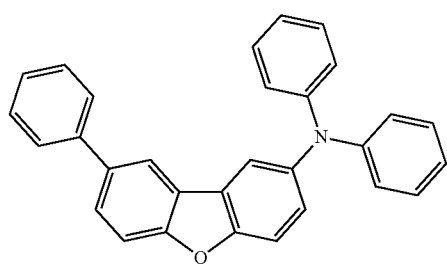

243
-continued
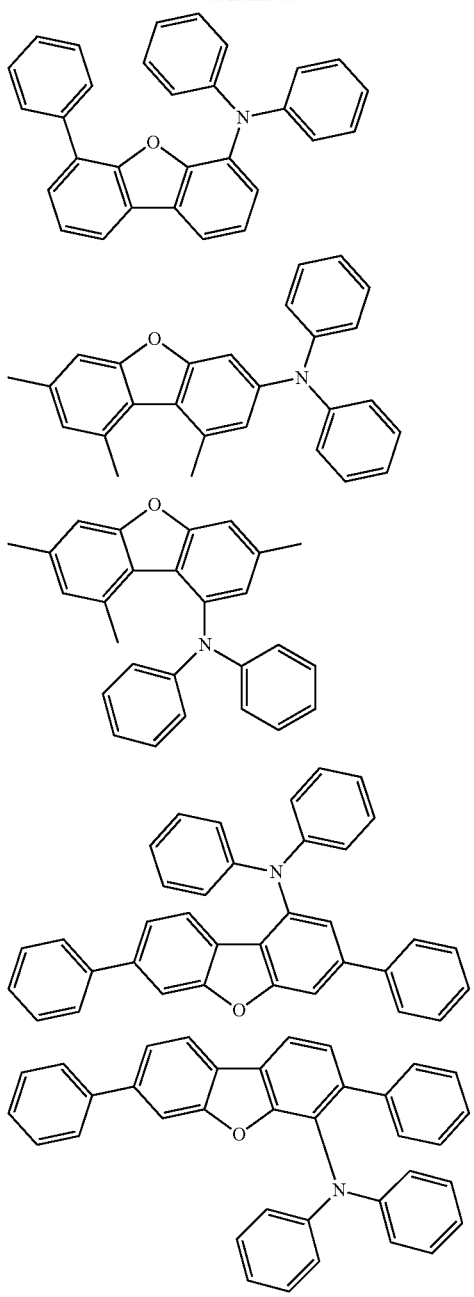
244
-continued
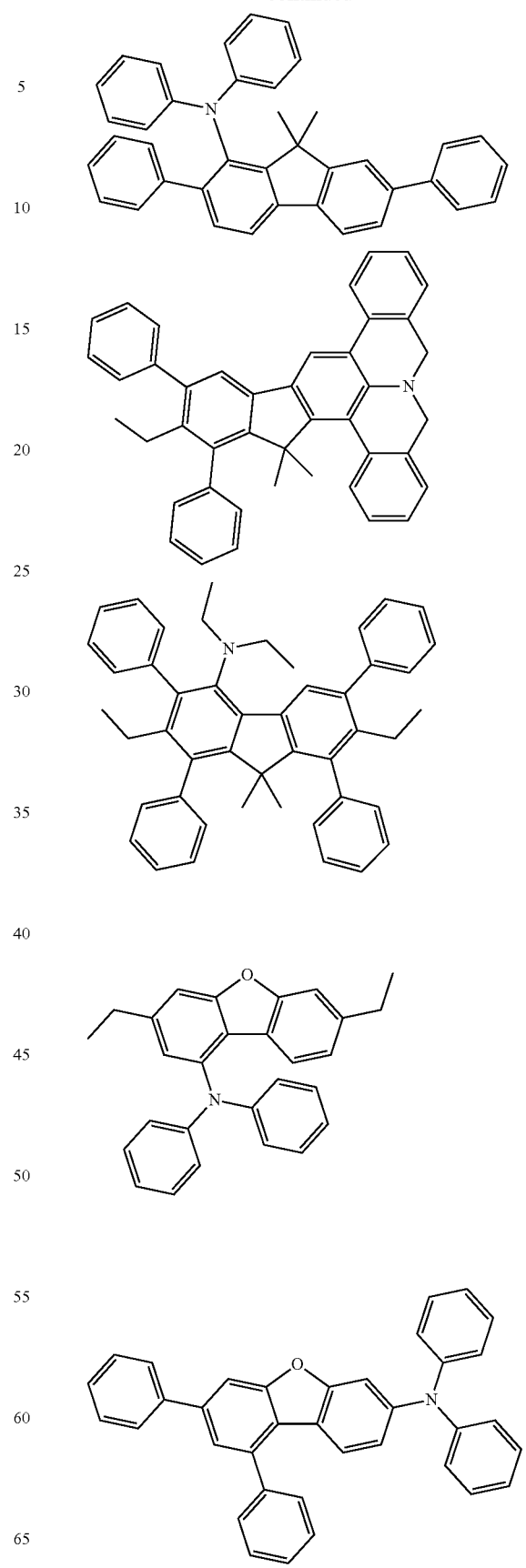

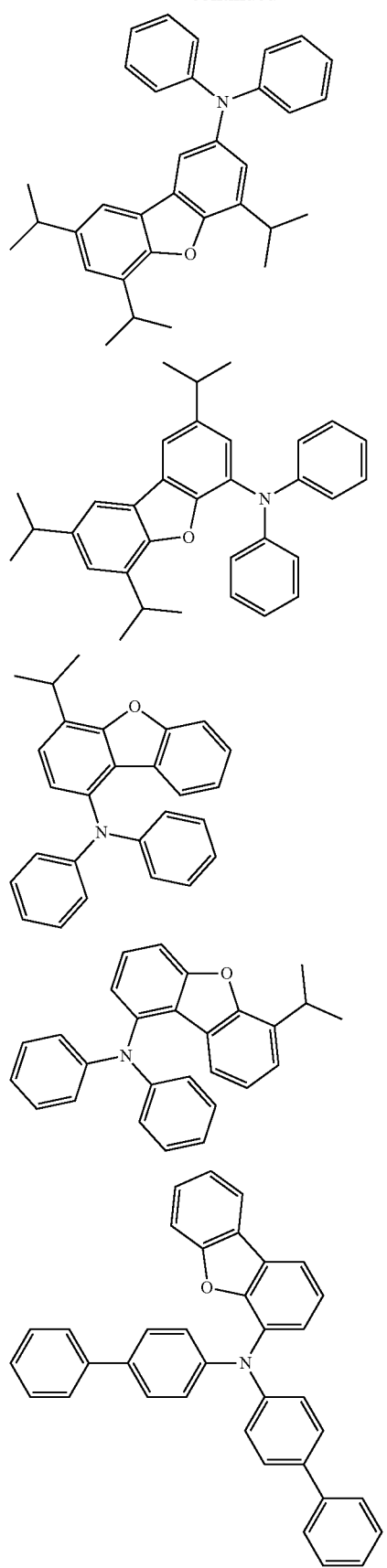
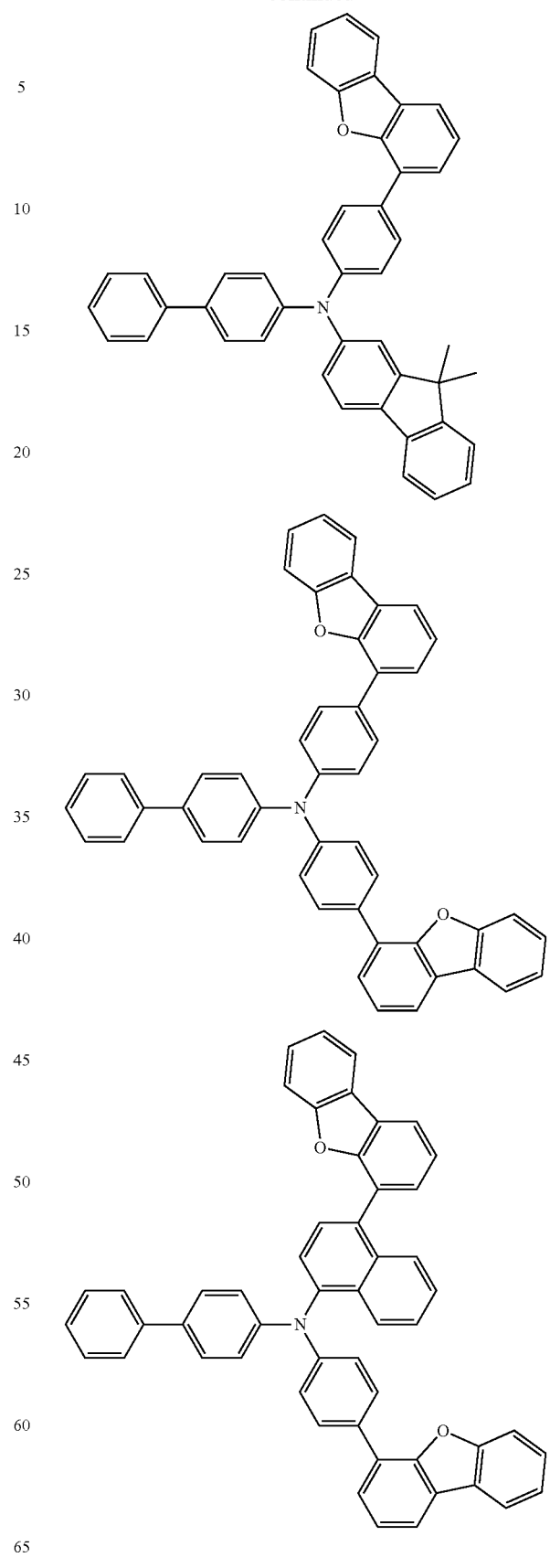

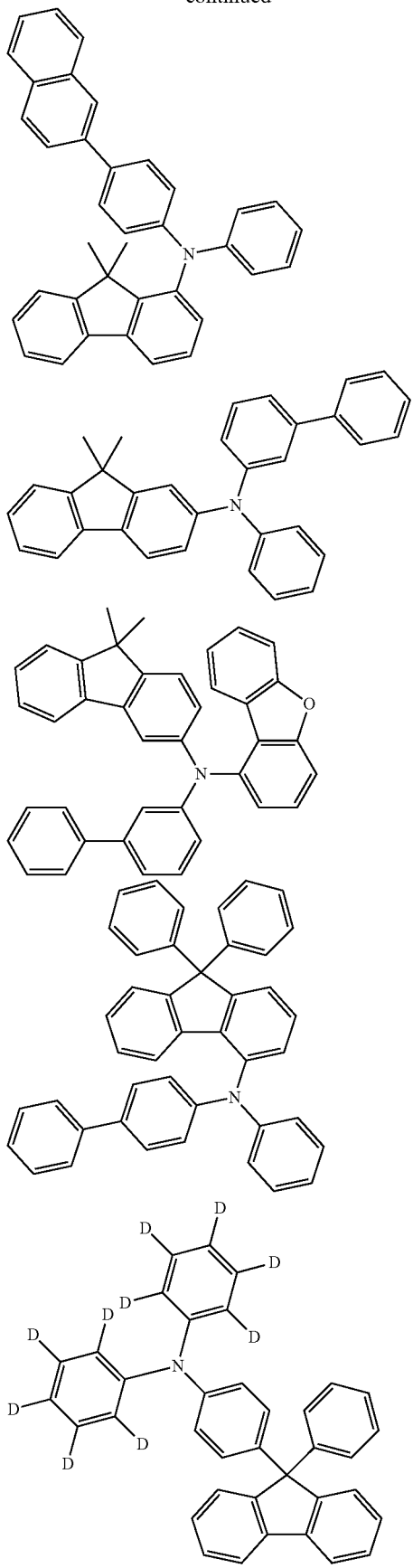

249
-continued
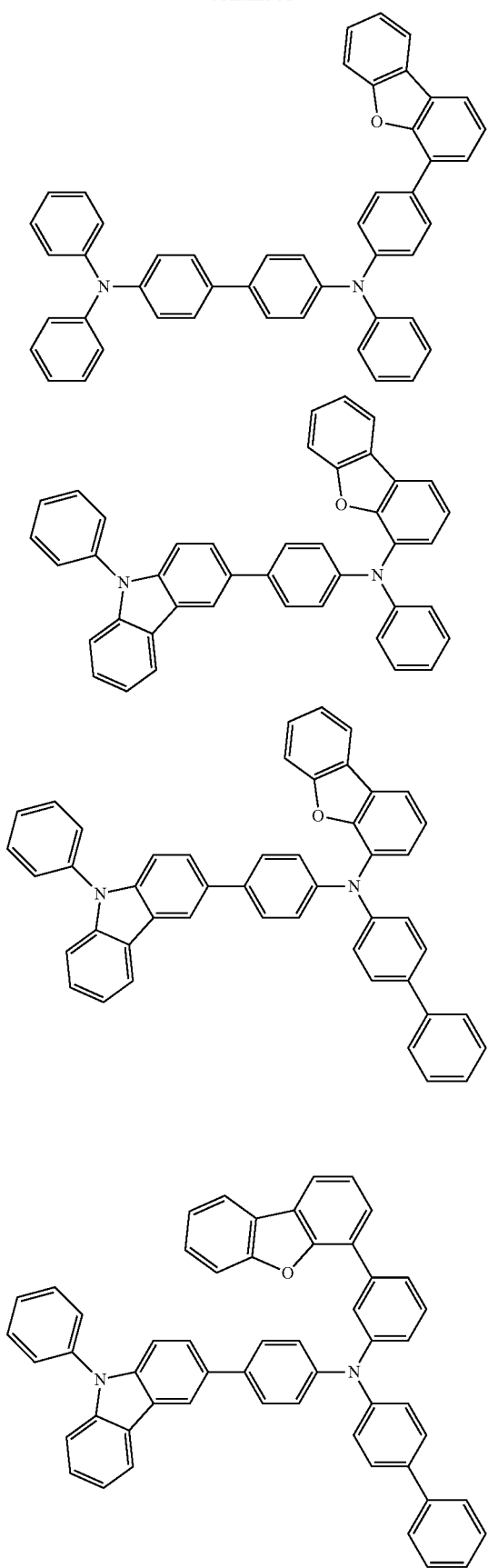
250
-continued
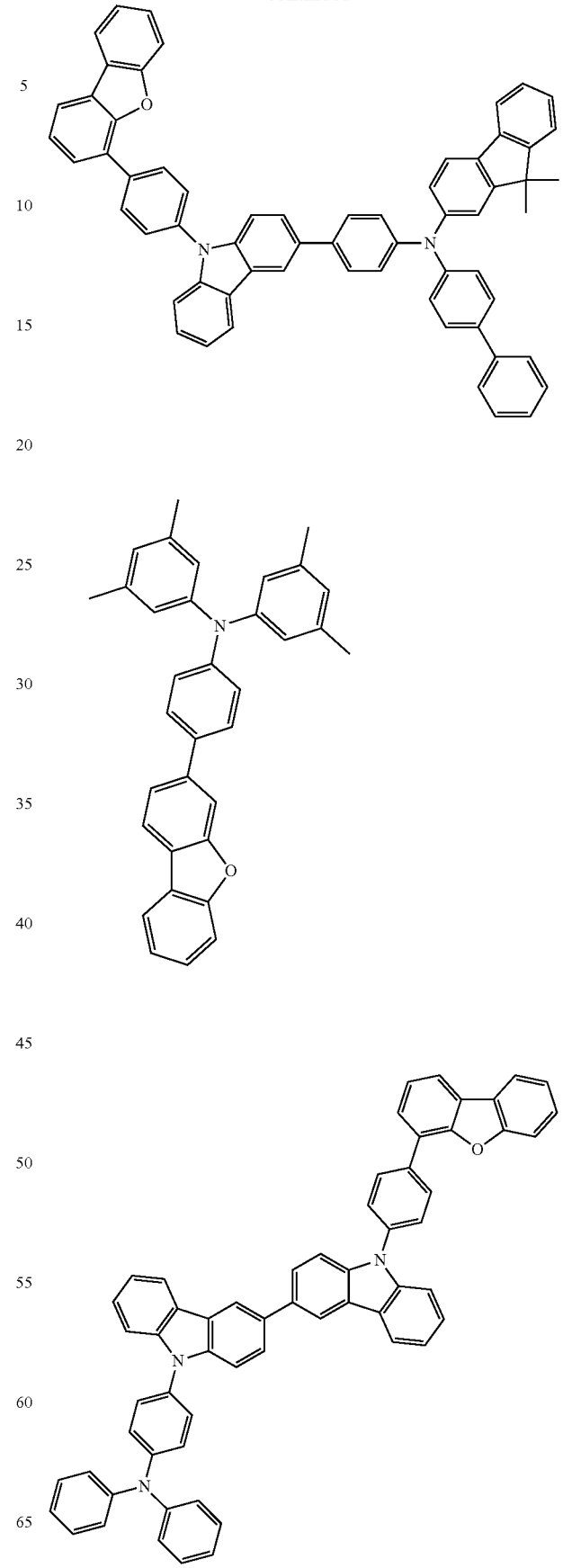

251
-continued
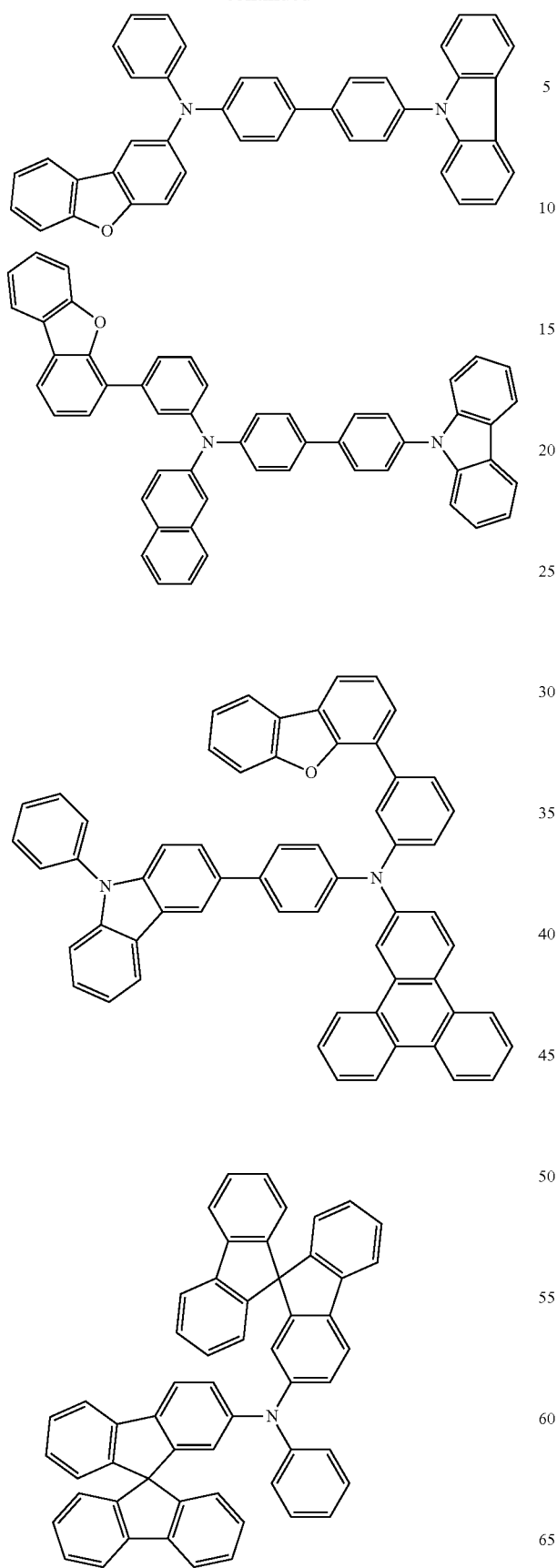
252
-continued
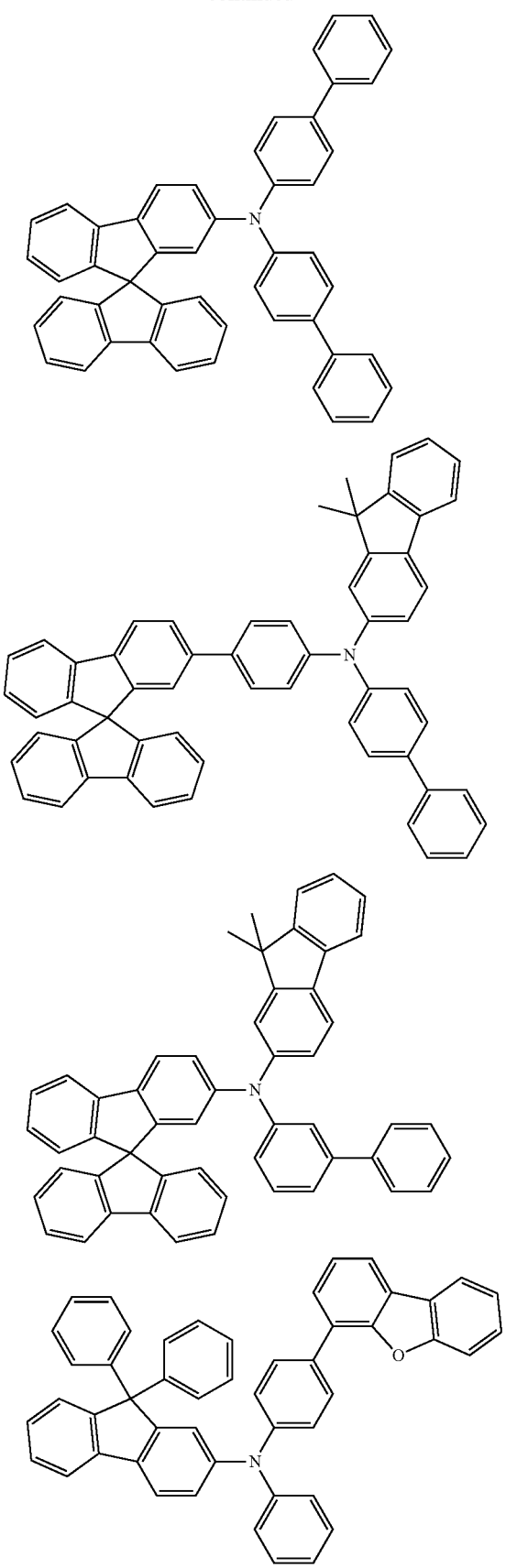

253
-continued
254
-continued
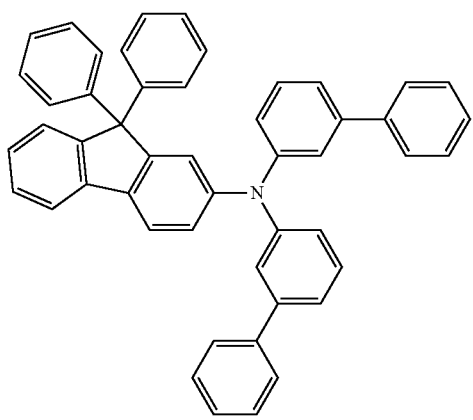
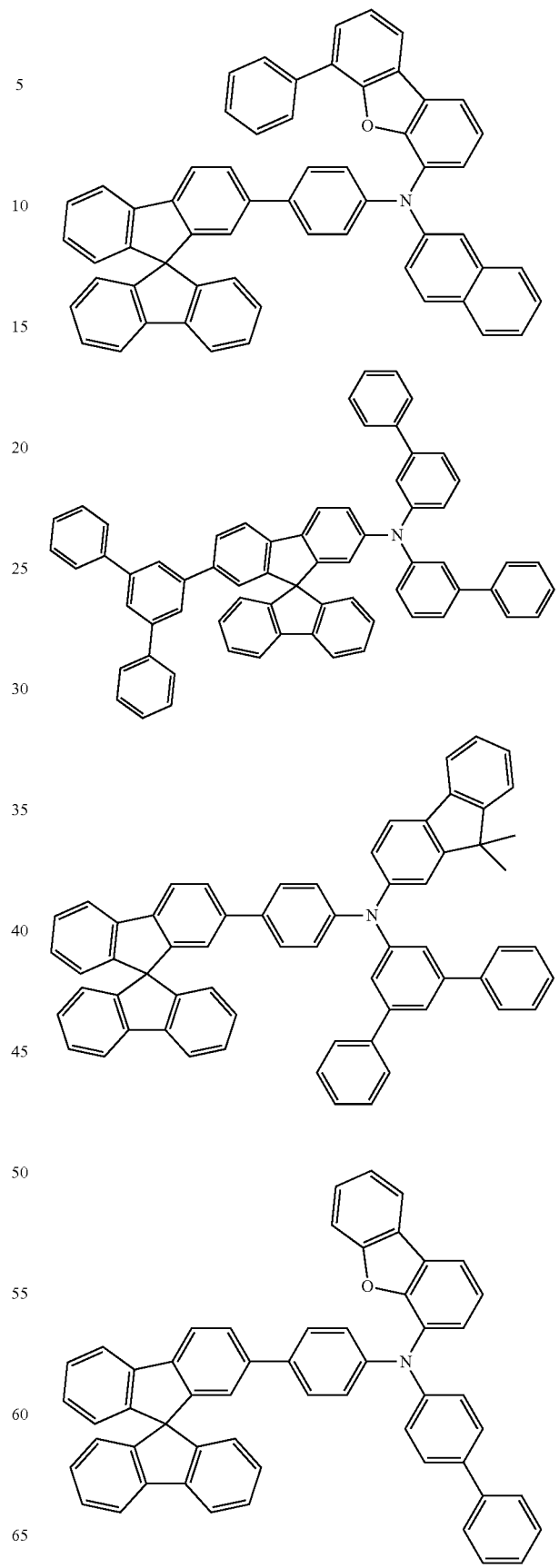

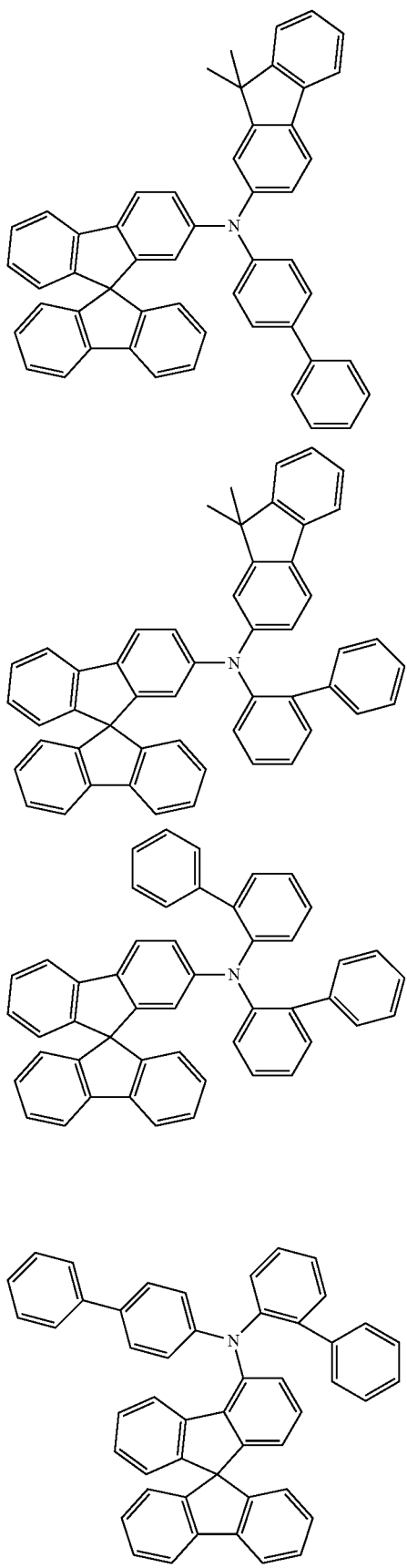
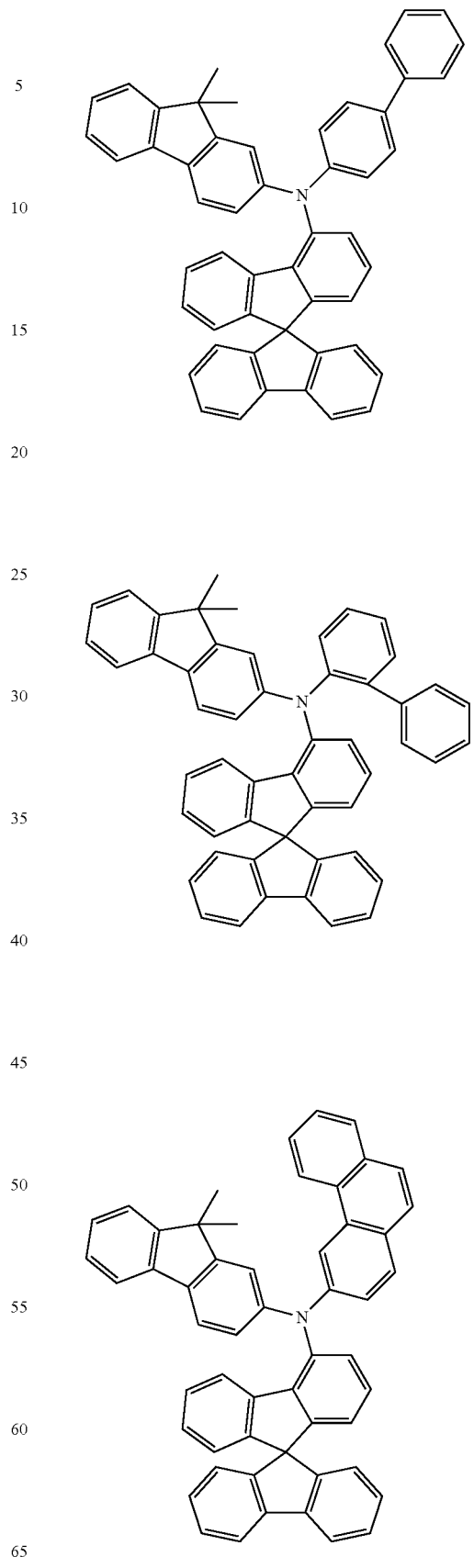

257
-continued
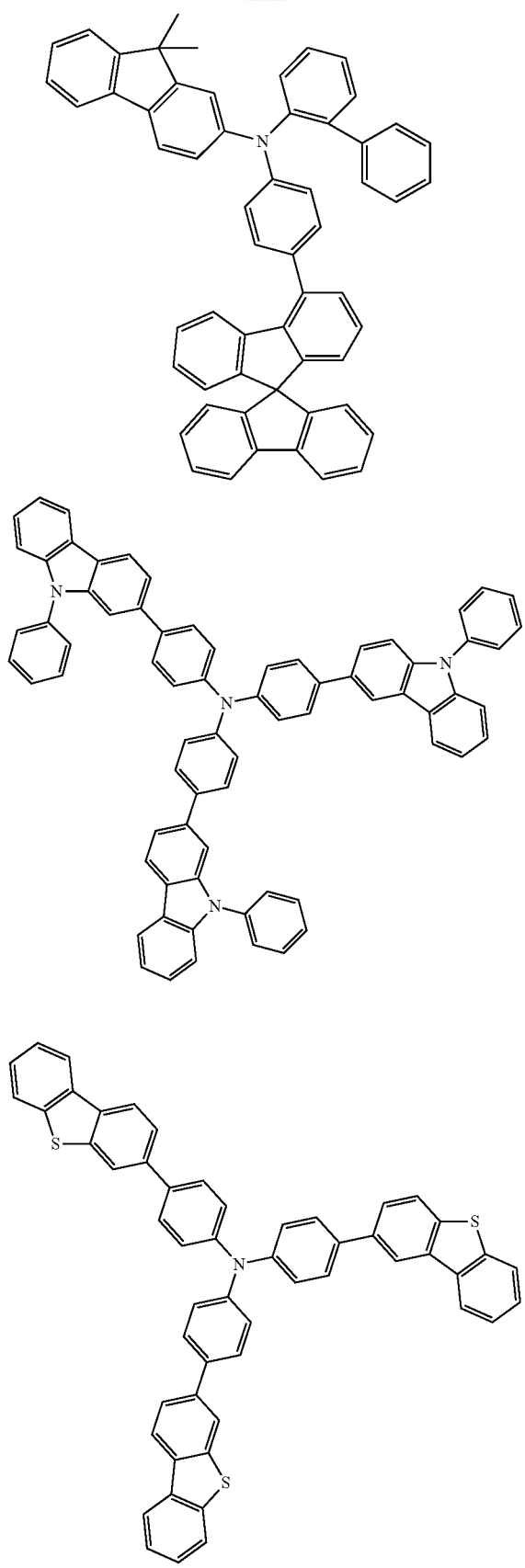
258
-continued
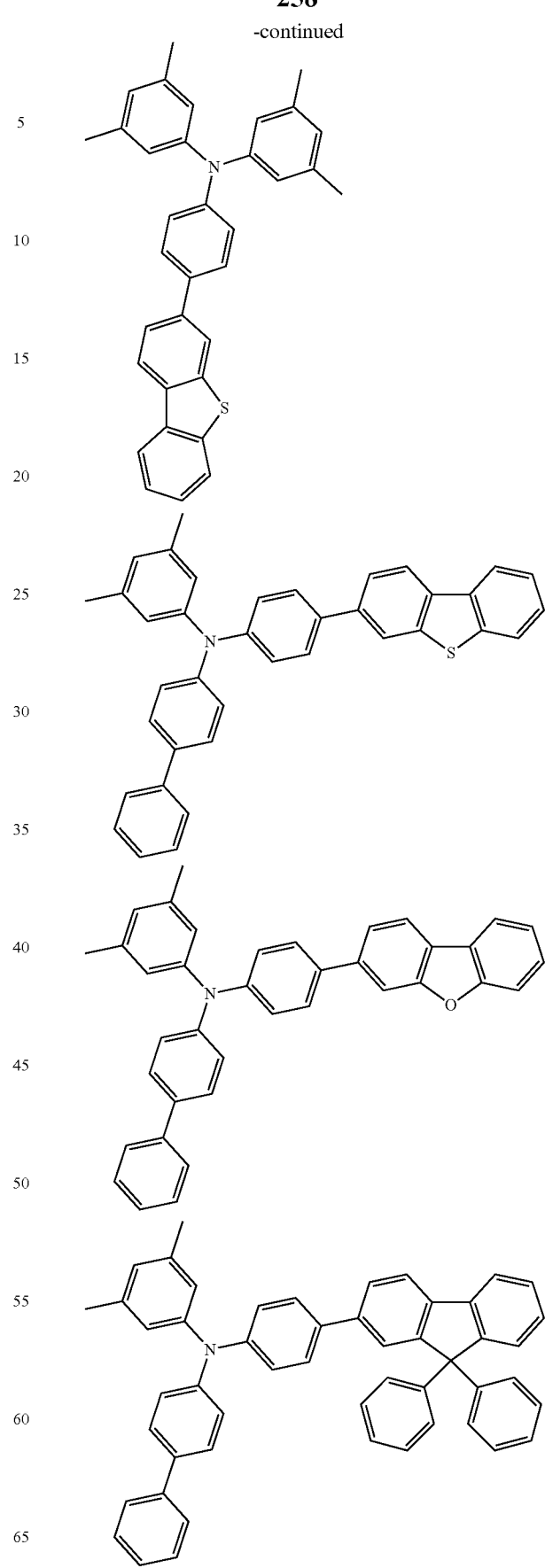

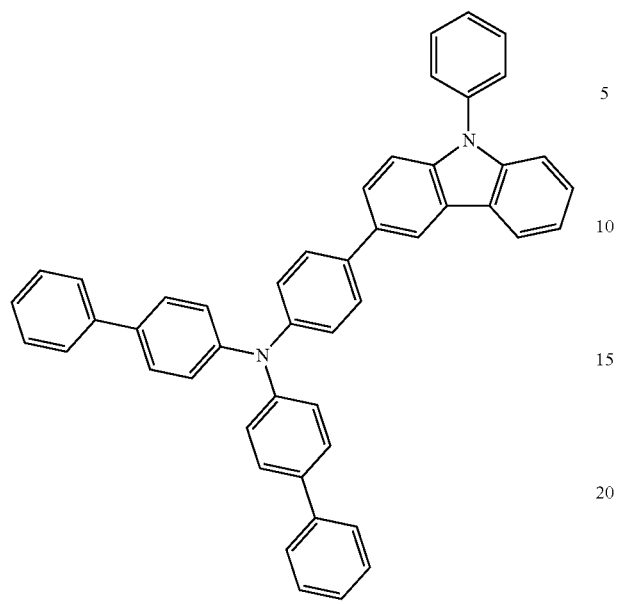
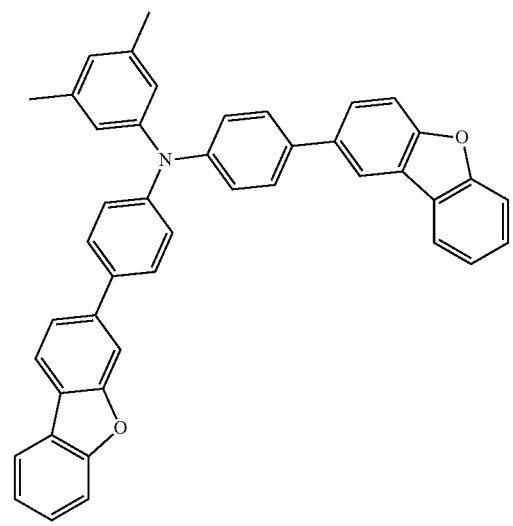
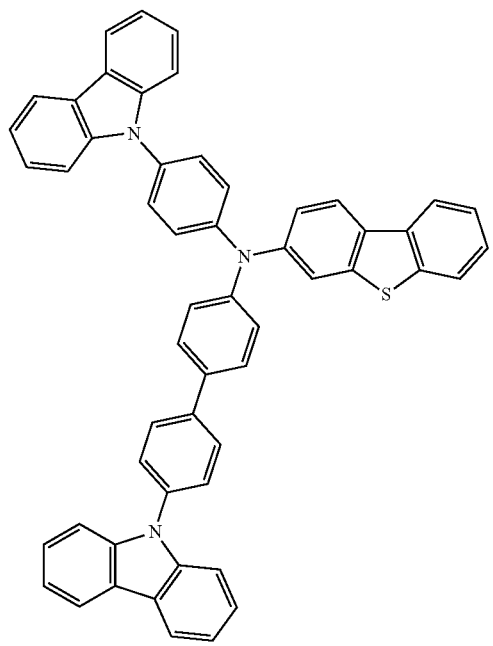

-continued

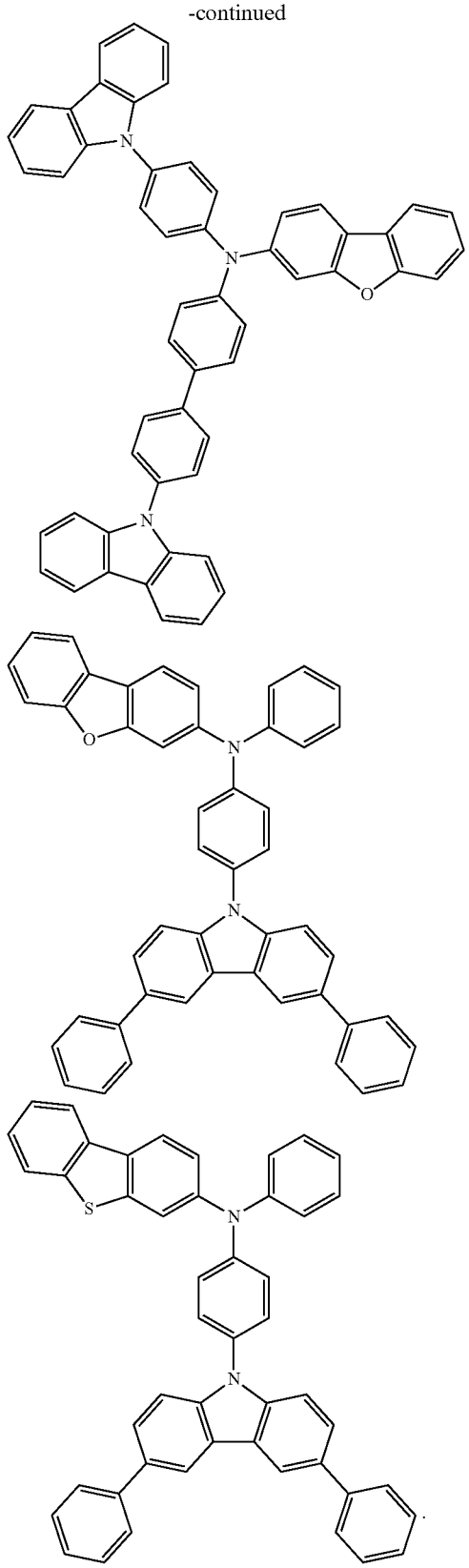

20. A display apparatus comprising:
a thin film transistor comprising a source electrode, a drain electrode, and an active layer; and
the organic light-emitting device of claim 1,
wherein the first electrode of the organic light-emitting device is electrically connected to one selected from the group consisting of the source electrode and the drain electrode of the thin film transistor.

21. An organic light-emitting device comprising:
a first electrode;
a second electrode; and
an organic layer between the first electrode and the second electrode,
wherein the organic layer comprises an emission layer,
the emission layer comprises a first compound, a second compound, and a third compound,
the first compound is represented by Formula 1,
the second compound is represented by Formula 2,
the third compound is represented by Formula 3, and
the first compound and the second compound are different from each other:

Formula 1
$$(Y_{11})_{c11}\text{—}(L_{11})_{a11}\text{—}(Y_{21})_{c12}$$

Formula 2
$$(Y_{21})_{c21}\text{—}(L_{21})_{a21}\text{—}(Y_{22})_{c22}$$

Formula 3
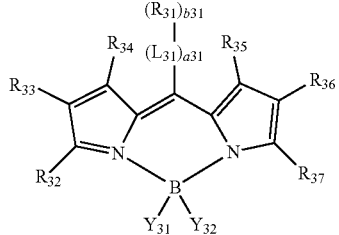

Formula 1A
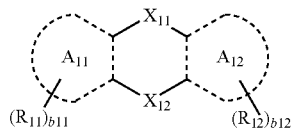

Formula 2A
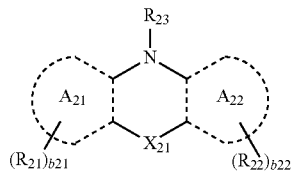

Formula 2B
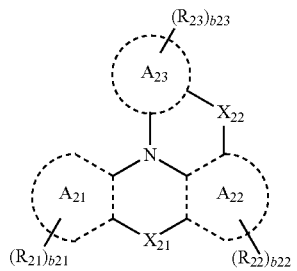

Formula 2C

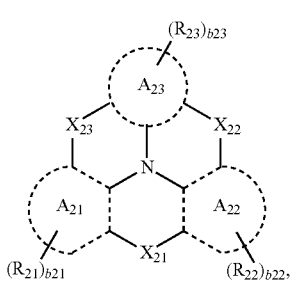

wherein, in Formulae 1 to 3, 1A, and 2A to 2C,
$L_{11}$ is selected from the group consisting of:
a π electron-depleted nitrogen-free cyclic group; and
a π electron-depleted nitrogen-free cyclic group substituted with at least one selected from the group consisting of deuterium, a $C_1$-$C_{60}$ alkyl group, a π electron-depleted nitrogen-free cyclic group, and —Si($Q_{31}$)($Q_{32}$)($Q_{33}$),
a11 is selected from the group consisting of 0, 1, 2, and 3,
$Y_{11}$ is a group represented by Formula 1A,
$Y_{12}$ is selected from the group consisting of:
—F, a cyano group, and a π electron-depleted nitrogen-containing cyclic group;
a $C_1$-$C_{60}$ alkyl group, a π electron-depleted nitrogen-containing cyclic group, and a π electron-depleted nitrogen-free cyclic group, each substituted with at least one selected from the group consisting of —F and a cyano group; and
a π electron-depleted nitrogen-containing cyclic group substituted with at least one selected from the group consisting of deuterium, a $C_1$-$C_{60}$ alkyl group, a π electron-depleted nitrogen-containing cyclic group, and a π electron-depleted nitrogen-free cyclic group,
c11 and c12 are each independently selected from the group consisting of 1, 2, and 3,
$X_{11}$ is selected from the group consisting of a single bond, N($R_{13}$), O, and S,
$X_{12}$ is selected from the group consisting of a single bond, N($R_{14}$), O, and S,
$X_{11}$ and $X_{12}$ are not a single bond at the same time,
$A_{11}$ and $A_{12}$ are each independently a π electron-depleted nitrogen-free cyclic group or a substituted or unsubstituted carbazole group,
$R_{11}$ to $R_{14}$ are each independently selected from the group consisting of:
a binding site, hydrogen, deuterium, a $C_1$-$C_{60}$ alkyl group, a π electron-depleted nitrogen-free cyclic group, and —Si($Q_1$)($Q_2$)($Q_3$);
a π electron-depleted nitrogen-free cyclic group substituted with at least one selected from the group consisting of deuterium, a $C_1$-$C_{60}$ alkyl group, a π electron-depleted nitrogen-free cyclic group, and —Si($Q_{31}$)($Q_{32}$)($Q_{33}$); and
a π electron-depleted nitrogen-free cyclic group substituted with a π electron-depleted nitrogen-free cyclic group that is substituted with at least one selected from the group consisting of deuterium, a $C_1$-$C_{60}$ alkyl group, a π electron-depleted nitrogen-free cyclic group, and —Si($Q_{21}$)($Q_{22}$)($Q_{23}$), wherein one selected from the group consisting of $R_{11}$ to $R_{14}$ is a binding site,
b11 and b12 are each independently selected from the group consisting of 1, 2, 3, 4, 5, and 6,
$L_{21}$ is selected from the group consisting of a substituted or unsubstituted $C_5$-$C_{60}$ carbocyclic group and a substituted or unsubstituted $C_1$-$C_{60}$ heterocyclic group,
a21 is selected from the group consisting of 0, 1, 2, and 3,
$Y_{21}$ is a group represented by one selected from the group consisting of Formulae 2A to 2C,
$Y_{22}$ is selected from the group consisting of:
—F, a cyano group, and a π electron-depleted nitrogen-containing cyclic group;
a $C_1$-$C_{60}$ alkyl group, a π electron-depleted nitrogen-containing cyclic group, and a π electron-depleted nitrogen-free cyclic group, each substituted with at least one selected from the group consisting of —F and a cyano group; and
a π electron-depleted nitrogen-containing cyclic group substituted with at least one selected from the group consisting of deuterium, a $C_1$-$C_{60}$ alkyl group, a π electron-depleted nitrogen-containing cyclic group, and a π electron-depleted nitrogen-free cyclic group,
c21 and c22 are each independently selected from the group consisting of 1, 2, 3, 4, 5, and 6,
$X_{21}$ is selected from the group consisting of a single bond, N($R_{24}$), O, and S,
$X_{22}$ is selected from the group consisting of a single bond, N($R_{25}$), O, and S,
$X_{23}$ is selected from the group consisting of a single bond, N($R_{26}$), O, and S,
$A_{21}$ to $A_{23}$ are each independently a π electron-depleted nitrogen-free cyclic group,
$R_{21}$ to $R_{26}$ are each independently selected from the group consisting of:
a binding site, hydrogen, deuterium, a $C_1$-$C_{60}$ alkyl group, a π electron-depleted nitrogen-free cyclic group, —N($Q_1$)($Q_2$), and —Si($Q_1$)($Q_2$)($Q_3$);
a π electron-depleted nitrogen-free cyclic group substituted with at least one selected from the group consisting of deuterium, a $C_1$-$C_{60}$ alkyl group, a π electron-depleted nitrogen-free cyclic group, —N($Q_{31}$)($Q_{32}$), and —Si($Q_{31}$)($Q_{32}$)($Q_{33}$); and
a π electron-depleted nitrogen-free cyclic group substituted with a π electron-depleted nitrogen-free cyclic group that is substituted with at least one selected from the group consisting of deuterium, a $C_1$-$C_{60}$ alkyl group, a π electron-depleted nitrogen-free cyclic group, —N($Q_{21}$)($Q_{22}$), and —Si($Q_{21}$)($Q_{22}$)($Q_{23}$), wherein one selected from the group consisting of $R_{21}$ to $R_{24}$ in Formula 2A is a binding site, one selected from the group consisting of $R_{21}$ to $R_{25}$ in Formula 2B is a binding site, and one selected from the group consisting of $R_{21}$ to $R_{26}$ in Formula 2C is a binding site,
b21 to b23 are each independently selected from the group consisting of 1, 2, 3, 4, 5, and 6,
$L_{31}$ is selected from the group consisting of a substituted or unsubstituted $C_5$-$C_{60}$ carbocyclic group and a substituted or unsubstituted $C_1$-$C_{60}$ heterocyclic group,
a31 is selected from the group consisting of 0, 1, 2, and 3,
$R_{31}$ to $R_{37}$ are each independently selected from the group consisting of hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —B$(Q_1)(Q_2)$, —N$(Q_1)(Q_2)$, —P$(Q_1)(Q_2)$, —C(=O)$(Q_1)$, —S(=O)$(Q_1)$, —S(=O)$_2(Q_1)$, —P(=O)$(Q_1)(Q_2)$, and —P(=S)$(Q_1)(Q_2)$, wherein $R_{31}$ to $R_{37}$ are optionally linked to form a substituted or unsubstituted $C_5$-$C_{60}$ carbocyclic group or a substituted or unsubstituted $C_1$-$C_{60}$ heterocyclic group, b31 is selected from the group consisting of 1, 2, 3, 4, 5, and 6, $Y_{31}$ and $Y_{32}$ are each independently selected from the group consisting of —F, —Cl, —Br, —I, a substituted or unsubstituted $C_1$-$C_{60}$ alkyl group, a substituted or unsubstituted $C_1$-$C_{60}$ alkoxy group, a substituted or unsubstituted $C_6$-$C_{60}$ aryl group, and a substituted or unsubstituted $C_6$-$C_{60}$ aryloxy group, wherein $Y_{31}$ and $Y_{32}$ are optionally linked to form a substituted or unsubstituted $C_5$-$C_{60}$ carbocyclic group or a substituted or unsubstituted $C_1$-$C_{60}$ heterocyclic group, $Q_1$ to $Q_3$, $Q_{21}$ to $Q_{23}$, and $Q_{31}$ to $Q_{33}$ are each independently selected from the group consisting of hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ hetero aryloxy group, a $C_1$-$C_{60}$ hetero arylthio group, a monovalent non-aromatic condensed polycyclic group, a monovalent non-aromatic condensed heteropolycyclic group, a biphenyl group, and a terphenyl group, and \* indicates a binding site to a neighboring atom, and wherein the first compound is about 60 wt % to about 90 wt % in amount, the second compound is about 10 wt % to about 40 wt % in amount, and the third compound is about 0.5 wt % to about 5 wt % in amount, each based on a total weight of the emission layer, and a weight ratio among the first compound, the second compound and the third compound is 70:29:1 to 80:19.5:0.5.

\* \* \* \* \*